(12) United States Patent
Bhide et al.

(10) Patent No.: US 10,787,450 B2
(45) Date of Patent: Sep. 29, 2020

(54) SPIRO-FUSED CYCLIC UREAS AS INHIBITORS OF ROCK

(71) Applicant: BRISTOL-MYERS SQUIBB COMPANY, Princeton, NJ (US)

(72) Inventors: Rajeev S. Bhide, Princeton Junction, NJ (US); Mandar Shrikrishna Bodas, Bangalore (IN); Pravin Sudhakar Shirude, Bangalore (IN); Sharanabasappa Patil, Raichur (IN); Tarun Kumar Maishal, Bangalore (IN); Kamalraj Thiyagarajan, Vellore (IN); Kumaresan Chinnakotti, Sankarankovil (IN); Peter W. Glunz, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/315,679

(22) PCT Filed: Jul. 6, 2017

(86) PCT No.: PCT/US2017/040852
§ 371 (c)(1),
(2) Date: Jan. 7, 2019

(87) PCT Pub. No.: WO2018/009627
PCT Pub. Date: Jan. 11, 2018

(65) Prior Publication Data
US 2019/0300528 A1 Oct. 3, 2019

Related U.S. Application Data

(60) Provisional application No. 62/359,363, filed on Jul. 7, 2016.

(51) Int. Cl.
| C07D 471/10 | (2006.01) |
| C07D 403/10 | (2006.01) |
| C07D 487/10 | (2006.01) |
| C07D 491/10 | (2006.01) |

(52) U.S. Cl.
CPC ......... *C07D 471/10* (2013.01); *C07D 403/10* (2013.01); *C07D 487/10* (2013.01); *C07D 491/10* (2013.01)

(58) Field of Classification Search
CPC .......................... C07D 471/10; C07D 403/10
See application file for complete search history.

(56) References Cited

U.S. PATENT DOCUMENTS 10,123,993 B2 * 11/2018 Glunz ................. C07D 401/14

FOREIGN PATENT DOCUMENTS

| WO | WO2004050039 A2 | 6/2004 |
| WO | WO2012081665 A1 | 6/2012 |
| WO | WO2014113620 A2 | 7/2014 |
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |

\* cited by examiner

*Primary Examiner* — Golam M Shameem
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

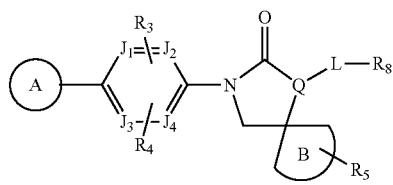

(I)

13 Claims, No Drawings
Specification includes a Sequence Listing.

US 10,787,450 B2

SPIRO-FUSED CYCLIC UREAS AS INHIBITORS OF ROCK

CROSS REFERENCE TO RELATED APPLICATIONS

This application is a 371 application of PCT/US2017/040852 filed Jul. 6, 2017 which is entitled to priority pursuant to 35 U.S.C. § 119(e) to U.S. provisional patent application No. 62/359,363, filed Jul. 7, 2016, which is incorporated herein in its entirety.

FIELD OF THE INVENTION

The present invention relates to novel spiro-fused cyclic ureas, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for µl in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

There are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005)). Reports also include WO2014/113620, WO 2014/134388, WO 2014/134391, WO2015/002915, WO2015/002926, WO2016/010950, WO2016/028971, WO2016/112236, and WO2016/144936, all of which are assigned to the present applicant. However, fasudil is the only marketed ROCK inhibitor at this time. An i.v. formulation was approved in Japan for treatment of cerebral vasospasm. Thus, there remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel spiro-fused cyclic ureas including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

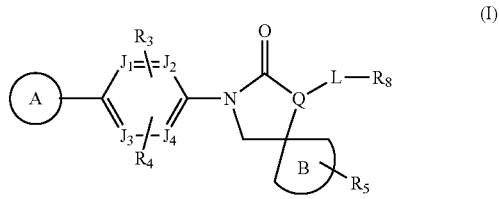

or stereoisomers, enantiomers, diastereoisomers, tautomers, pharmaceutically acceptable salts, solvates, or prodrugs thereof, wherein
Ring A is independently selected from

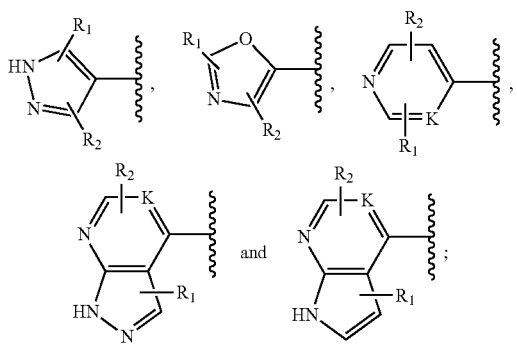

Ring B is independently selected from cycloalkyl and heterocyclyl, each substituted with 1-3 $R_5$;

$J_1$, $J_2$, $J_3$, and $J_4$ are independently selected from N, $CR_3$, and $CR_4$; provided no more than two of $J_1$, $J_2$, $J_3$, and $J_4$ are N;

Q is independently selected from N and $CR_{10}$;

L is independently selected from —$(CR_6R_7)_n$— and $NR_{10}$; provided when Q is N, L is —$(CR_6R_7)_n$— and when Q is $CR_{10}$, L is $NR_{10}$;

K, at each occurrence, is independently selected from N, $CR_1$, and $CR_2$;

$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, —$C(=O)$-heterocyclyl substituted with 0-3 $R_e$, and —$(CH_2)_r$-heterocyclyl substituted with 0-3 $R_e$;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from $C_{3-6}$ cycloalkyl, heterocyclyl, aryl and heteroaryl, each substituted with 0-5 $R_9$;

$R_9$, at each occurrence, is independently selected from F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_rC(=O)NR_aR_a$, —$(CHR_d)_rOC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_{10}$ is independently selected from H and $C_{1-4}$alkyl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-heterocyclyl, —$(CH_2)_r$-aryl, —$(CH_2)_r$-heteroaryl, F, Cl, Br, CN, $NO_2$, =O, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$ and —$(CH_2)_rNR_fR_f$;

$R_f$, at each occurrence, is independently selected from H, F, Cl, Br, CN, OH, $C_{1-5}$-alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2;

r, at each occurrence, is independently selected from zero, 1, 2, 3, 4, 5, and 6;

provided (1) when $R_9$ is —$C(=O)NR_aR_a$, one of $R_a$ is H or $C_{1-6}$ alkyl, then the other $R_a$ is not —$(CH_2)_r$-5-tetrazolyl or —$(CH_2)_r$-5-(2-oxo-1,3,4-oxadiazolyl);

(2) when $R_9$ is —$C(=O)NR_aR_a$, one of $R_a$ is H or $C_{1-6}$ alkyl, and the other $R_a$ is $C_{1-6}$ alkyl substituted with 1 $R_e$, then $R_e$ is not -5-tetrazolyl or 5-(2-oxo-1,3,4-oxadiazolyl).

In another aspect, the present invention provides compounds of Formula (I) or stereoisomers, enantiomers, diastereoisomers, tautomers, pharmaceutically acceptable salts, solvates, or prodrugs thereof, wherein $R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rNR_aC(=O)OR_b$, —$(CH_2)_rOC(=O)NR_aR_a$, —$(CH_2)_rC(=O)OR_b$, —$(CH_2)_rNR_aS(O)_pNR_aR_a$, and —$(CH_2)_rNR_aS(O)_pR_c$;

$R_3$ is independently selected from H, F, Cl, Br, CN, $C_{1-4}$ alkyl substituted with 0-3 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

R₄ is independently selected from H, F, Cl, Br, OH, CN, and C₁₋₄ alkyl substituted with 0-3 R_e;

R₅ is independently selected from H, C₁₋₄alkyl substituted with 0-4 R_e, —(CH₂)ᵣS(O)_pR_c, —(CH₂)ᵣC(=O)R_b, —(CH₂)ᵣNR_aR_a, —(CH₂)ᵣCN, —(CH₂)ᵣC(=O)NR_aR_a, —(CH₂)ᵣNR_aC(=O)R_b, —(CH₂)ᵣNR_aC(=O)NR_aR_a, —(CH₂)ᵣNR_aC(=O)OR_b, —(CH₂)ᵣOC(=O)NR_aR_a, —(CH₂)ᵣC(=O)OR_b, —(CH₂)ᵣS(O)_pNR_aR_a, —(CH₂)ᵣNR_aS(O)_pNR_aR_a, —(CH₂)ᵣNR_aS(O)_pR_c, (CH₂)ᵣ—C₃₋₆ carbocyclyl substituted with 0-3 R_e, —C(=O)-heterocyclyl substituted with 0-3 R_e, and —(CH₂)ᵣ-heterocyclyl substituted with 0-3 R_e;

R₆ and R₇ are independently selected from H, C₁₋₄alkyl substituted with 0-4 R_e, —(CH₂)ᵣOR_b, —(CH₂)ᵣC(=O)R_b, —(CH₂)ᵣNR_aR_a, —(CH₂)ᵣC(=O)NR_aR_a, —(CH₂)ᵣNR_aC(=O)R_b, —(CH₂)ᵣC(=O)OR_b, (CH₂)ᵣ—C₃₋₆ carbocyclyl substituted with 0-3 R_e, and —(CH₂)ᵣ-heterocyclyl substituted with 0-3 R_e;

R₈ is independently selected from

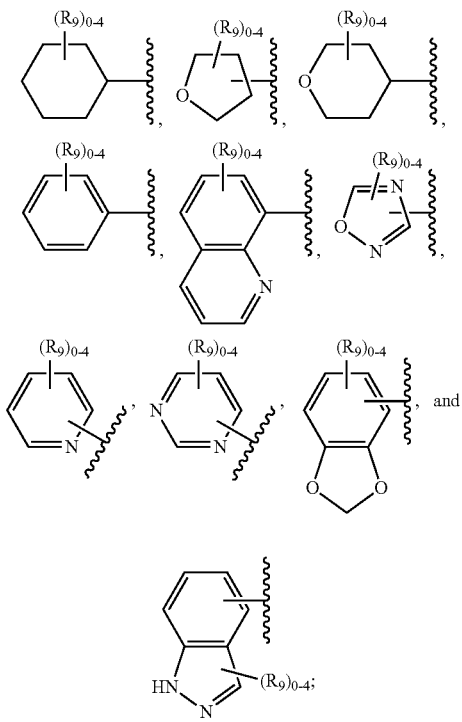

R₉, at each occurrence, is independently selected from F, Cl, Br, C₁₋₄alkyl, C₂₋₄alkenyl, C₂₋₄alkynyl, nitro, —(CHR_d)ᵣS(O)_pR_c, —(CHR_d)ᵣS(O)_pNR_aR_a, —(CHR_d)ᵣNR_aS(O)_pR_c, —(CHR_d)ᵣOR_b, —(CHR_d)ᵣCN, —(CHR_d)ᵣNR_aR_a, —(CHR_d)ᵣNR_aC(=O)R_b, —(CHR_d)ᵣNR_aC(=O)NR_aR_a, —(CHR_d)ᵣC(=O)OR_b, —(CHR_d)ᵣC(=O)R_b, —C(=O)NR_aR_a —(CHR_d)ᵣOC(=O)R_b, —(CHR_d)ᵣ-cycloalkyl, —(CHR_d)ᵣ-heterocyclyl, —(CHR_d)ᵣ-aryl, and —(CHR_d)ᵣ-heteroaryl, wherein said alkyl, cycloalkyl, heterocyclyl, aryl, or heteroaryl is substituted with 0-4 R_e, and other variables are as defined in Formula (I) above.

In another aspect, the present invention provides compounds of Formula (II):

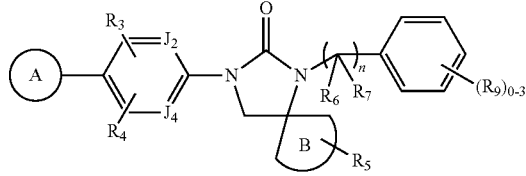

(II)

or stereoisomers, enantiomers, diastereoisomers, tautomers, pharmaceutically acceptable salts, solvates, or prodrugs thereof, wherein Ring A is independently selected from

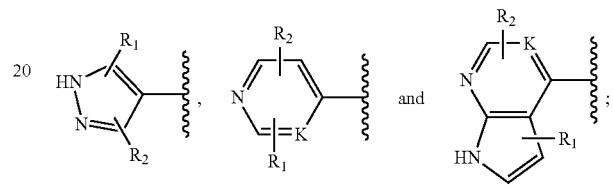

Ring B is independently selected from C₃₋₆ cycloalkyl and 4-, 5-, 6-, 7-membered heterocyclyl comprising carbon atoms and 1 heteroatom selected from N and O, and substituted with 1-3 R₅;

J₂, and J₄ are independently selected from N, CR₃, and CR₄;

R₁, at each occurrence, is independently selected from H, F, Cl, Br, CN, NR_aR_a, and C₁₋₄alkyl substituted with 0-4 R_e;

R₂, at each occurrence, is independently selected from H, F, Cl, Br, OH, CN, NR_aR_a, and C₁₋₄alkyl substituted with 0-4 R_e;

R₃ is independently selected from H, F, Cl, Br, CN, C₁₋₄ alkyl substituted with 0-3 R_e, —(CH₂)ᵣOR_b, and —C₃₋₆ cycloalkyl;

R₄ is independently selected from H, F, Cl, Br, OH, CN, OC₁₋₄ alkyl substituted with 0-3 R_e, and C₁₋₄ alkyl substituted with 0-3 R_e;

R₅ is independently selected from H, C₁₋₄alkyl substituted with 0-4 R_e, (CH₂)ᵣS(O)_pR_c, —(CH₂)ᵣC(=O)R_b, —(CH₂)ᵣC(=O)NR_aR_a, —(CH₂)ᵣNR_aC(=O)R_b, —(CH₂)ᵣNR_aC(=O)NR_aR_a, —(CH₂)ᵣNR_aC(=O)OR_b, —(CH₂)ᵣOC(=O)NR_aR_a, —(CH₂)ᵣC(=O)OR_b, —(CH₂)ᵣS(O)_pNR_aR_a, —(CH₂)ᵣNR_aS(O)_pR_c, (CH₂)ᵣ—C₃₋₆ carbocyclyl substituted with 0-3 R_e, —C(=O)-heterocyclyl substituted with 0-3 R_e, and —(CH₂)ᵣ-heterocyclyl substituted with 0-3 R_e;

R₆ and R₇ are independently selected from H, C₁₋₄alkyl substituted with 0-4 R_e, —(CH₂)ᵣOR_b, —(CH₂)ᵣC(=O)R_b, —(CH₂)ᵣNR_aR_a, —(CH₂)ᵣC(=O)NR_aR_a, —(CH₂)ᵣNR_aC(=O)R_b, —(CH₂)ᵣC(=O)OR_b, (CH₂)ᵣ—C₃₋₆ carbocyclyl substituted with 0-3 R_e, and —(CH₂)ᵣ-heterocyclyl substituted with 0-3 R_e;

R₈ is independently selected from

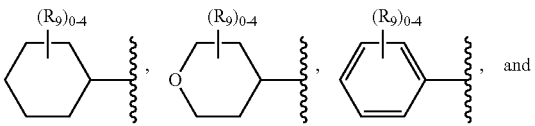

-continued

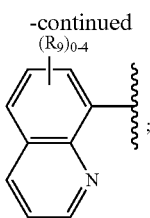

$R_9$, at each occurrence, is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$C(=O)NR_aR_a$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-heterocyclyl, —$(CH_2)_r$-aryl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;
p, at each occurrence, is independently selected from zero, 1, and 2; and
r, at each occurrence, is independently selected from zero, 1, 2, 3, and 4.

In another aspect, the present invention provides compounds of Formula (III):

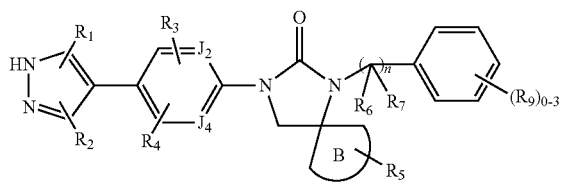

(III)

or stereoisomers, tautomers, pharmaceutically acceptable salts, solvates, or prodrugs thereof, wherein
Ring B is independently selected from cyclopropyl and 6-membered heterocyclyl comprising carbon atoms and 1 heteroatom selected from $NR_5$ and O;
$J_2$, and $J_4$ are independently selected from N, $CR_3$, and $CR_4$;
$R_1$ is independently selected from H, F, Cl, Br, CN, $NR_aR_a$, and $C_{1-4}$alkyl substituted with 0-4 $R_e$;
$R_2$ is independently selected from H and $C_{1-4}$alkyl substituted with 0-4 $R_e$;
$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, $C_{1-4}$alkyl substituted with 0-4 $R_e$, —$(CH_2)_rS(O)_pR_c$, —$(CH_2)_rC(=O)R_b$, —$(CH_2)_rC(=O)NR_aR_a$, —$(CH_2)_rC(=O)OR_b$, —$(CH_2)_rS(O)_pNR_aR_a$, $(CH_2)_r$—$C_{3-6}$ carbocyclyl substituted with 0-3 $R_e$, —$C(=O)$-heterocyclyl substituted with 0-3 $R_e$, and —$(CH_2)_r$-heterocyclyl substituted with 0-3 $R_e$;
$R_6$ is independently selected from H, $C_{1-4}$alkyl substituted with 0-4 $R_e$, —$CH_2OR_b$, —$C(=O)R_b$, $NR_aC(=O)R_b$, —$CH_2NR_aR_a$, —$C(=O)NR_aR_a$, —$_rC(=O)OR_b$, and heterocyclyl substituted with 0-3 $R_e$;
$R_7$ is independently selected from H and $C_{1-4}$alkyl;
$R_9$, at each occurrence, is independently selected from F, Cl, Br, $C_{1-4}$ alkyl, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$C(=O)NR_aR_a$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-heterocyclyl, —$(CH_2)_r$-aryl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
n is independently selected from 1 and 2;
p, at each occurrence, is independently selected from zero, 1, and 2; and r, at each occurrence, is independently selected from zero, 1, 2, 3, and 4.

In another aspect, the present invention provides compounds of Formula (IV):

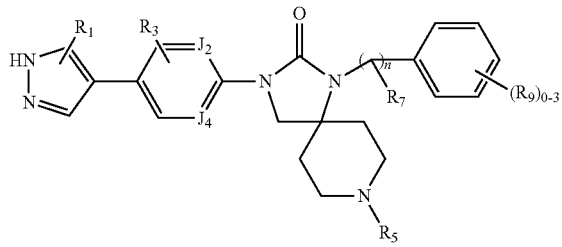

(IV)

or stereoisomers, tautomers, pharmaceutically acceptable salts, solvates, or prodrugs thereof, wherein $J_2$, and $J_4$ are independently selected from N and $CR_3$;
$R_1$ is independently selected from H and $CF_3$;
$R_3$ is independently selected from H, CN, $C_{1-4}$ alkyl, $-OC_{1-3}$ alkyl, and $-C_{3-6}$ cycloalkyl;
$R_5$ is independently selected from H, $C_{1-4}$alkyl substituted with 0-4 $R_e$, $-S(O)_pR_c$, $-(CH_2)_rC(=O)R_b$, $-(CH_2)_rC(=O)NR_aR_a$, $-(CH_2)_rC(=O)OR_b$, $-S(O)_pNR_aR_a$, $-(CH_2)_r-C_{3-6}$ carbocyclyl substituted with 0-3 $R_e$, $-C(=O)-C_{3-6}$ carbocyclyl, $-(CH_2)_r$-heterocyclyl substituted with 0-3 $R_e$, and $-C(=O)$-heterocyclyl substituted with 0-3 $R_e$;
$R_7$ is independently selected from H and $C_{1-4}$alkyl;
$R_9$, at each occurrence, is independently selected from F, Cl, $C_{1-4}$ alkyl substituted with 0-3 $R_e$, $-OR_b$, CN, $C(=O)NR_aR_a$, and heterocyclyl substituted with 0-3 $R_e$;
$R_a$, at each occurrence, is independently selected from H, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, $=O$, $CO_2H$, OH, $OC_{1-4}$alkyl, and $NR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
n is independently selected from 1 and 2; and
r, at each occurrence, is independently selected from zero, 1, 2, and 3.

In another aspect, the present invention provides compounds of Formula (IV) or stereoisomers, enantiomers, diastereoisomers, tautomers, pharmaceutically acceptable salts, solvates, or prodrugs thereof, wherein
$R_1$ is H;
$R_3$ is independently selected from H, $C_{1-4}$ alkyl, $-OC_{1-3}$ alkyl, and $-C_{3-6}$ cycloalkyl;
$R_5$ is independently selected from H, $C_{1-4}$alkyl substituted with 0-4 $R_e$, $-S(O)_pR_c$, $-(CH_2)_rC(=O)R_b$, $-(CH_2)_rC(=O)NR_aR_a$, $-(CH_2)_rC(=O)OR_b$, $-S(O)_pNR_aR_a$, $-(CH_2)_r-C_{3-6}$ cycloalkyl substituted with 0-3 $R_e$, $-C(=O)-C_{3-6}$ cycloalkyl, $-(CH_2)_r$-heterocyclyl substituted with 0-3 $R_e$, and $-C(=O)$-heterocyclyl substituted with 0-3 $R_e$; wherein the heterocyclyl is selected from

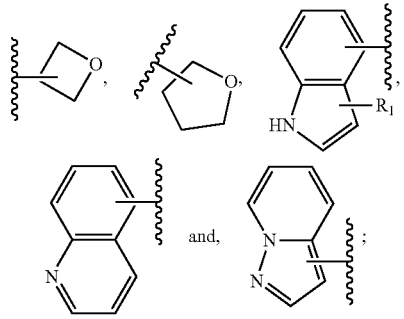

$R_7$ is independently selected from H and $C_{1-4}$alkyl;
$R_9$, at each occurrence, is independently selected from F, Cl, $CH_3$, $CF_3$, $-OH$, $OCHF_2$, $OCF_3$, CN, $-C(=O)NH_2$, $-C(=O)NHC_{1-4}$alkyl, substituted with 0-5 $R_e$, $-C(=O)N(C_{1-4}$alkyl substituted with 0-5 $R_e)_2$, $-C(=O)NH-C_{3-6}$cycloalkyl, $C(=O)NH$-heterocyclyl substituted with 0-5 $R_e$, $C(=O)N$-heterocyclyl substituted with 0-5 $R_e$;
$R_a$, at each occurrence, is independently selected from H, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, $=O$, $CO_2H$, OH, and $OC_{1-4}$alkyl and $NR_fR_f$;
$R_f$, at each occurrence, is independently selected from H, F, Cl, Br, CN, OH, $C_{1-5}$ alkyl, $C_{3-6}$ cycloalkyl, and phenyl;
n is 1;
r, at each occurrence, is independently selected from zero, 1, 2, and 3; and
other variables are as defined in Formula (IV) above.

In another aspect, the present invention provides compounds of Formula (V):

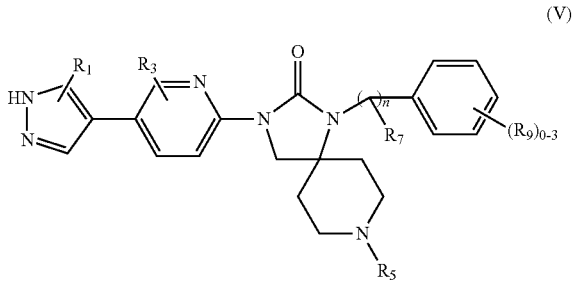

(V)

or stereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ carbocyclyl substituted with 0-3 $R_e$, —$C(=O)$—$C_{3-6}$ carbocyclyl, —$(CH_2)_r$-heterocyclyl substituted with 0-3 $R_e$, and —$C(=O)$-heterocyclyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, $C(=O)NR_aR_a$, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

In another aspect, the present invention provides compounds of Formula (VI):

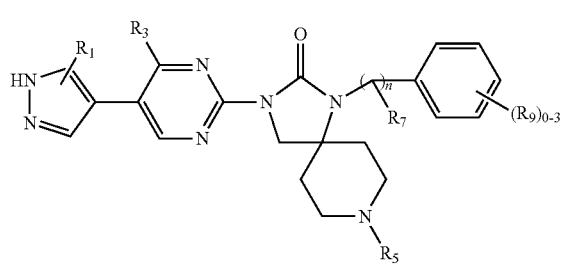

(VI)

or stereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ carbocyclyl substituted with 0-3 $R_e$, —$C(=O)$—$C_{3-6}$ carbocyclyl, —$(CH_2)_r$-heterocyclyl substituted with 0-3 $R_e$, and —$C(=O)$-heterocyclyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, —$C(=O)OR_b$, —$C(=O)R_b$, —$C(=O)NR_aR_a$, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

In another aspect, the present invention provides compounds of Formula (VII):

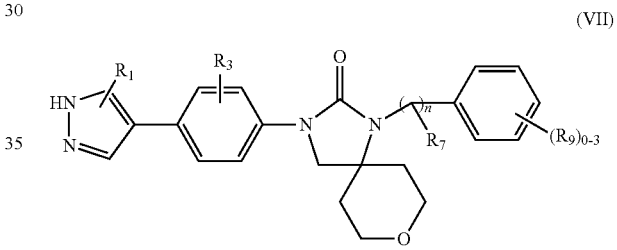

(VII)

or stereoisomers, enantiomers, diastereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ carbocyclyl substituted with 0-3 $R_e$, —$C(=O)$—$C_{3-6}$ carbocyclyl, —$(CH_2)_r$-heterocyclyl substituted with 0-3 $R_e$, and —$C(=O)$-heterocyclyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, —$C(=O)OR_b$, —$C(=O)R_b$, —$C(=O)NR_aR_a$, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, OC$_{1-4}$alkyl, and NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

In another aspect, the present invention provides compounds of Formula (VIII):

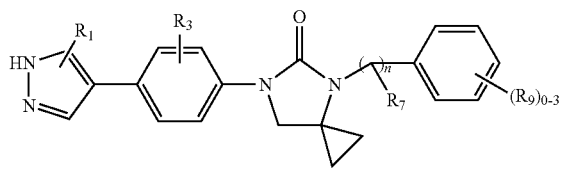

(VIII)

or stereoisomers, enantiomers, diastereoisomers, tautomers, pharmaceutically acceptable salts, solvates, or prodrugs thereof, wherein $R_1$ is independently selected from H and CF$_3$;

$R_3$ is independently selected from H, CN, $C_{1-4}$ alkyl, —OC$_{1-3}$ alkyl, and —C$_{3-6}$ cycloalkyl;

$R_7$ is independently selected from H and $C_{1-4}$alkyl;

$R_9$, at each occurrence, is independently selected from F, Cl, $C_{1-4}$ alkyl substituted with 0-3 $R_e$, —OR$_b$, CN, —C(=O)OR$_b$, —C(=O)R$_b$, —C(=O)NR$_a$R$_a$, and heterocyclyl substituted with 0-3 $R_e$;

$R_a$, at each occurrence, is independently selected from H, $C_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, and OC$_{1-4}$alkyl;

n is independently selected from 1 and 2; and r, at each occurrence, is independently selected from zero, 1, 2, and 3.

In another aspect, the present invention provides compounds of Formula (IX):

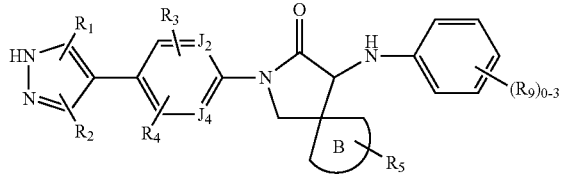

(IX)

or stereoisomers, enantiomers, diastereoisomers, tautomers, pharmaceutically acceptable salts, solvates, or prodrugs thereof, wherein Ring B is independently selected from $C_{3-6}$ cycloalkyl and 4-, 5-, 6-, 7-membered heterocyclyl comprising carbon atoms and 1 heteroatom selected from N and O, and substituted with 1-3 $R_5$;

$J_2$, and $J_4$ are independently selected from N, CR$_3$, and CR$_4$;

$R_1$ is independently selected from H, F, Cl, Br, CN, NR$_a$R$_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —(CH$_2$)$_r$OR$_b$, and —C$_{3-6}$ cycloalkyl;

$R_4$ is independently selected from H, F, Cl, Br, OH, CN, OC$_{1-4}$ alkyl substituted with 0-3 $R_e$, and $C_{1-4}$ alkyl substituted with 0-3 $R_e$;

$R_5$ is independently selected from H, $C_{1-4}$alkyl substituted with 0-4 $R_e$, —(CH$_2$)$_r$S(O)$_p$R$_c$, —(CH$_2$)$_r$C(=O)R$_b$, —(CH$_2$)$_r$C(=O)NR$_a$R$_a$, —(CH$_2$)$_r$C(=O)OR$_b$, —(CH$_2$)$_r$S(O)$_p$NR$_a$R$_a$, (CH$_2$)$_r$—C$_{3-6}$ carbocyclyl substituted with 0-3 $R_e$, —C(=O)-heterocyclyl substituted with 0-3 $R_e$, and —(CH$_2$)$_r$-heterocyclyl substituted with 0-3 $R_e$;

$R_9$, at each occurrence, is independently selected from F, Cl, Br, $C_{1-4}$ alkyl, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (X):

(X)

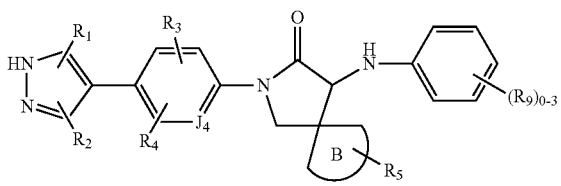

or stereoisomers, enantiomers, diastereoisomers, tautomers, pharmaceutically acceptable salts, solvates, or prodrugs thereof, wherein Ring B is independently selected from 4- and 6-membered heterocyclyl comprising carbon atoms and one nitrogen atom;

$J_4$ is independently selected from N and CH;

$R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, $C_{1-4}$alkyl substituted with 0-4 $R_e$, —C(=O)$R_b$, —C(=O)$NR_aR_a$, and —C(=O)$OR_b$;

$R_9$, at each occurrence, is independently selected from F, Cl, $C_{1-4}$ alkyl substituted with 0-3 $R_e$, —$OR_b$, CN, —C(=O)$OR_b$, —C(=O)$R_b$, —C(=O)$NR_aR_a$, and heterocyclyl substituted with 0-3 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, F, Cl, Br, CN, $NO_2$, =O, $CO_2H$, —$(CH_2)_rOR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

In another aspect, the present invention provides a compound selected from any subset list of compounds exemplified in the present application.

In another embodiment, the compounds of the present invention have ROCK $IC_{50}$ values≤10 µM.

In another embodiment, the compounds of the present invention have ROCK $IC_{50}$ values≤1 µM.

In another embodiment, the compounds of the present invention have ROCK $IC_{50}$ values≤0.1 µM.

In another embodiment, the compounds of the present invention have ROCK $IC_{50}$ values≤0.05 µM.

In another embodiment, the compounds of the present invention have ROCK $IC_{50}$ values≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

The compounds of the present invention can be used as chemical probes for capturing target proteins of bioactive low-molecular-weight compounds. Specifically, the compounds of the present invention can be converted to affinity chromatography probes, photoaffinity probes, which can covalently bind to protein targets in response to activation by light, or the like, by introducing labeling groups and linkers into portions of the compounds different from their structural portions essential for the expression of activities, using a technique described in J. Mass Spectrum. Soc. Jpn. Vol. 51, No. 5 2003, p 492-498 or WO 2007/139149, for example.

Examples of labeling groups, linkers, and the like used for chemical probes include groups shown in the group below:

(1) protein labeling groups such as photoaffinity labeling groups (for example, a benzoyl group, a benzophenone group, an azido group, a carbonylazido group, a diaziridine group, an enone group, a diazo group, and a nitro group) and chemical affinity groups (for example, a ketone group in which the alpha-carbon atom has been substituted with a halogen atom, a carbamoyl group, an ester group, an alkylthio group, an unsaturated ketone, an ester, or other Michael receptors, and an oxirane group);

(2) cleavable linkers such as —S—S—, —O—Si—O—, monosaccharides (such as a glucose group and a galactose group) or disaccharides (such as lactose), and oligopeptide linkers cleavable by enzymatic reactions;

(3) fishing tag groups such as biotin and a 3-(4,4-difluoro-5,7-dimethyl-4H-3a,4a-diaza-4-bora-s-indacen-3-yl)propion-yl group;

(4) detectable markers, for example, radiolabeling groups such as $^{125}I$, $^{32}P$, $^{3}H$ and $^{14}C$; fluorescent labeling groups such as fluorescein, rhodmine, dansyl, umbelliferone, 7-nitrofurazanyl, and a 3-(4,4-difluoro-5,7-dimethyl-4H-3a,4a-diaza-4-bora-s-indacen-3-yl)p-ropionyl group; chemiluminescent groups such as luciferin and luminol; and heavy metal ions such as lanthanoid metal ions and radium ions; or (5) groups bound to solid phase carriers such as glass beads, glass beds, microtiter plates, agarose beads, agarose beds, polystyrene beads, polystyrene beds, nylon beads, and nylon beds.

Probes prepared by introducing labeling groups selected from the group consisting of (1) to (5) above into the compounds of the present invention in accordance with a method described in the above-mentioned documents can be used as chemical probes for identification of labeled proteins useful for searching for novel drug targets, etc.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectroscopy, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^{1}H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5 S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(O)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
PyBOP benzotriazol-1-yl-oxytripyrrolidinophosphonium hexafluorophosphate
SEM-Cl 2-(trimethysilyl)ethoxymethyl chloride
2nd generation XPhos precatalyst Chloro(2-dicyclohexylphosphino-2',4',6'-triisopropyl-1,1' biphenyl)[2-(2'-amino-1,1'-biphenyl)]palladium(II), THF adduct
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P® propane phosphonic acid anhydride
TRIS tris (hydroxymethyl) aminomethane IV. Biology In Vitro Assays The effectiveness of compounds of the present invention as ROCK inhibitors can be determined in a 30 µL assay containing 20 mM HEPES, pH 7.5, 20 mM $MgCl_2$, 0.015% Brij-35, 4 mM DTT, 5 µM ATP and 1.5 µM peptide substrate (FITC-AHA-AKRRRLSSLRA-OH) (SEQ ID NO. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LAB-CHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative examples were tested in the ROCK2 assay described above and found having ROCK2 inhibitory activity. Their ROCK2 inhibitory activity ($IC_{50}$ values) of ≤3 µM (3000 nM) was observed and shown in Table A below. The ranges of the ROCK2 $IC_{50}$ values are as follows: ROCK2 $IC_{50}$: ++++ (<3 nM) +++ (3-30 nM) ++ (30-250 nM) + (250-3000 nM)

TABLE A

| Example Number | ROCK2 $IC_{50}$ |
| --- | --- |
| 1 | ++++ |
| 2 | +++ |
| 3 | ++ |
| 4 | +++ |
| 5 | ++++ |
| 6 | ++++ |
| 7 | +++ |
| 8 | ++++ |
| 9 | ++++ |
| 10 | ++++ |
| 11 | +++ |
| 12 | ++ |
| 13 | +++ |
| 14 | ++ |
| 15 | + |
| 16 | +++ |
| 17 | +++ |
| 18 | ++ |
| 19 | ++ |
| 20 | ++ |
| 21 | ++ |
| 22 | ++ |
| 23 | + |
| 24 | +++ |
| 25 | ++++ |
| 26 | ++ |
| 27 | ++ |
| 28 | ++ |
| 29 | ++ |
| 30 | ++ |
| 31 | ++ |
| 32 | ++ |
| 33 | ++++ |
| 34 | +++ |
| 35 | ++++ |
| 36 | ++++ |
| 37 | ++++ |
| 38 | ++++ |
| 39 | +++ |
| 40 | ++++ |
| 41 | ++ |
| 42 | ++ |
| 43 | + |
| 44 | ++ |
| 45 | ++++ |
| 46 | +++ |
| 47 | +++ |
| 48 | +++ |
| 49 | +++ |
| 50 | +++ |
| 51 | +++ |
| 52 | ++ |
| 53 | ++ |

TABLE A-continued

| Example Number | ROCK2 IC$_{50}$ |
|---|---|
| 54 | ++++ |
| 55 | +++ |
| 56 | +++ |
| 57 | ++++ |
| 58 | ++++ |
| 59 | ++++ |
| 60 | +++ |
| 61 | +++ |
| 62 | ++++ |
| 63 | +++ |
| 64 | +++ |
| 65 | ++ |
| 66 | ++ |
| 67 | +++ |
| 68 | +++ |
| 70 | +++ |
| 72 | + |
| 73 | +++ |
| 74 | +++ |
| 75 | ++++ |
| 76 | ++++ |
| 77 | ++ |
| 78 | ++ |
| 79 | ++ |
| 80 | +++ |
| 81 | ++ |
| 82 | +++ |
| 83 | +++ |
| 84 | ++++ |
| 85 | ++++ |
| 86 | ++++ |
| 87 | ++++ |
| 88 | ++++ |
| 89 | ++++ |
| 90 | +++ |
| 91 | ++++ |
| 91 | ++++ |
| 92 | ++++ |
| 93 | ++++ |
| 94 | ++++ |
| 95 | ++++ |
| 96 | ++++ |
| 97 | +++ |
| 98 | ++++ |
| 99 | ++++ |
| 100 | ++++ |
| 101 | +++ |
| 102 | ++++ |
| 103 | ++++ |
| 104 | ++++ |
| 105 | ++++ |
| 106 | +++ |
| 107 | ++++ |
| 108 | ++++ |
| 109 | ++++ |
| 110 | ++ |
| 111 | +++ |
| 112 | +++ |
| 113 | ++++ |
| 114 | ++++ |
| 115 | ++++ |
| 116 | ++++ |
| 117 | ++++ |
| 118 | ++++ |
| 120 | ++++ |
| 121 | ++++ |
| 122 | ++++ |
| 123 | ++++ |
| 124 | ++++ |
| 125 | +++ |
| 126 | +++ |
| 127 | +++ |
| 128 | +++ |
| 129 | +++ |
| 130 | +++ |
| 131 | ++++ |
| 132 | ++++ |

TABLE A-continued

| Example Number | ROCK2 IC$_{50}$ |
|---|---|
| 133 | +++ |
| 134 | ++ |
| 135 | ++++ |
| 136 | ++++ |
| 137 | ++++ |
| 138 | ++++ |
| 139 | ++++ |
| 140 | ++++ |
| 141 | ++++ |
| 142 | +++ |
| 143 | ++++ |
| 144 | ++++ |
| 145 | ++++ |
| 146 | ++++ |
| 147 | ++++ |
| 148 | ++++ |
| 149 | ++++ |
| 150 | ++++ |
| 151 | ++++ |
| 152 | ++++ |
| 153 | ++++ |
| 154 | ++++ |
| 155 | ++++ |
| 156 | ++++ |
| 157 | ++++ |
| 158 | ++++ |
| 159 | ++++ |
| 160 | +++ |
| 161 | ++++ |
| 162 | ++++ |
| 163 | +++ |
| 165 | ++++ |
| 166 | ++++ |
| 167 | ++++ |
| 168 | ++++ |
| 169 | ++++ |
| 170 | ++++ |
| 171 | ++++ |
| 172 | ++++ |
| 173 | ++++ |
| 174 | ++++ |
| 175 | ++++ |
| 176 | ++++ |
| 177 | ++++ |
| 178 | ++++ |
| 179 | +++ |
| 180 | +++ |
| 181 | ++++ |
| 182 | ++++ |
| 183 | ++++ |
| 184 | ++++ |
| 185 | ++++ |
| 186 | ++++ |
| 187 | ++++ |
| 188 | ++++ |
| 189 | +++ |
| 190 | ++++ |
| 191 | ++++ |
| 192 | ++++ |
| 193 | ++++ |
| 194 | +++ |
| 195 | +++ |
| 196 | +++ |
| 197 | +++ |
| 198 | +++ |
| 199 | +++ |
| 200 | ++++ |
| 201 | ++++ |
| 202 | ++++ |
| 203 | ++++ |
| 204 | ++++ |
| 205 | +++ |
| 206 | ++++ |
| 207 | ++++ |
| 208 | +++ |
| 209 | +++ |
| 210 | ++++ |

TABLE A-continued

| Example Number | ROCK2 IC$_{50}$ |
|---|---|
| 211 | ++ |
| 212 | +++ |
| 213 | +++ |
| 214 | +++ |
| 215 | ++ |
| 216 | +++ |
| 217 | ++++ |
| 218 | ++++ |
| 219 | ++++ |
| 220 | ++++ |
| 221 | ++++ |
| 222 | ++++ |
| 223 | ++++ |
| 224 | +++ |
| 225 | ++++ |
| 226 | ++++ |
| 227 | ++++ |
| 228 | ++++ |
| 229 | ++++ |
| 230 | ++++ |
| 231 | ++++ |
| 232 | ++++ |
| 233 | ++++ |
| 234 | ++++ |
| 235 | ++++ |
| 236 | ++++ |
| 237 | ++++ |
| 238 | ++++ |
| 239 | ++++ |
| 240 | ++ |
| 241 | + |
| 243 | + |
| 244 | + |
| 245 | + |
| 246 | + |
| 247 | + |
| 248 | + |
| 249 | + |
| 250 | + |
| 251 | + |
| 252 | + |
| 253 | + |
| 254 | + |
| 255 | + |
| 256 | ++ |
| 257 | + |
| 258 | ++ |
| 259 | + |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimenter or that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

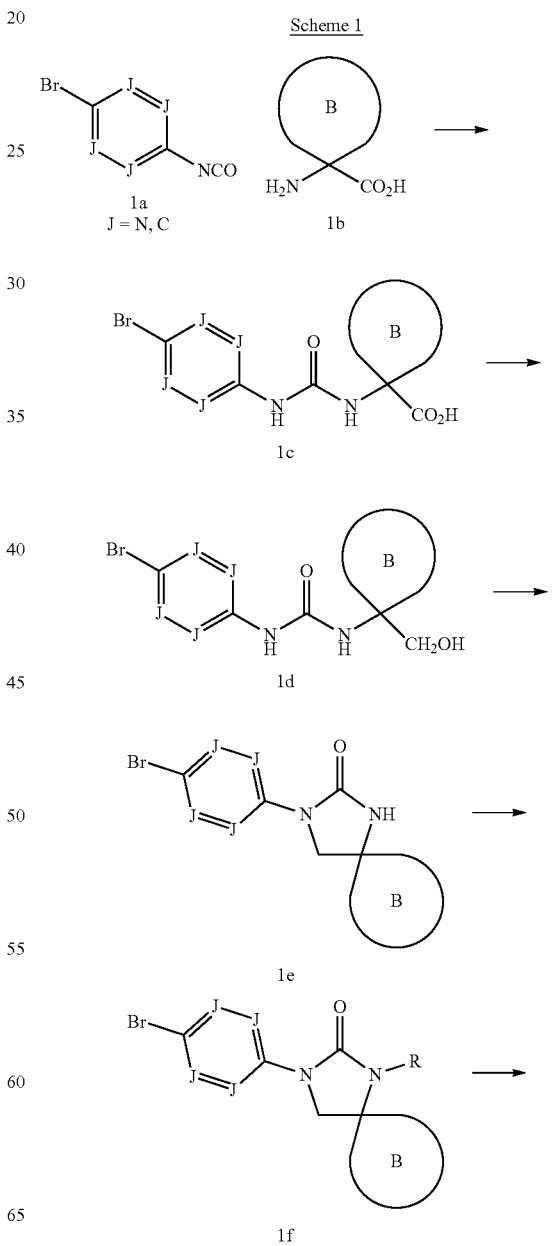

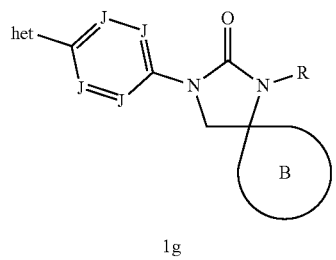

1g

Scheme 1 shows the synthesis of compound 1g from isocyanate 1a and amino acid 1b. Isocyanate 1a and amino acid 1b are either commercially available or can be prepared by known methods. Reaction of 1a with 1b affords urea 1c. Reduction of carboxylic acid 1c with a reducing agent such as borane affords alcohol 1d. Treatment of intermediate 1d with a reagent such as p-TsCl and a base, such as t-BuOK or NaH, afforded intermediate 1e. At this point, ring B may be further functionalized. Alkylation of 1e with an electrophile R—X in the presence of a base, such as NaH or t-BuOK, affords intermediate 1f. At this point, ring B may be further functionalized. Intermediate 1f is coupled with a heteroaryl boronic acid or boronate ester to afford 1g. This reaction proceeds via Suzuki coupling, using a reagent such as Pd(Ph$_3$)$_4$ or 2$^{nd}$ generation Xphos catalyst and a base such as sodium carbonate or potassium phosphate. Alternatively, compound 1f is converted to a boronic acid or boronate ester, using a boron reagent, such as bis(pinacolato)diboron, and a catalyst such as PdCl$_2$(dppf). This species is then coupled with a heteroaryl halide (het-X) via Suzuki cross-coupling to afford compound 1g.

Scheme 2 shows alternate syntheses of intermediate 1c. Aniline 2a, which is either commercially available or can be prepared by known methods, is treated with a reagent such as phosgene or triphosgene in the presence of a base such as TEA or DIEA, followed by amino acid 1b to afford urea 1c. Alternately, aniline 2a can be treated with phenyl chloroformate in the presence of a base such as TEA to afford carbamate 2b. Treatment of 2b with amino acid 1b in the presence of a base such as K$_2$CO$_3$ with heating affords urea 1c. Intermediate 1c is converted to compound 1g as depicted in Scheme 1.

Scheme 3

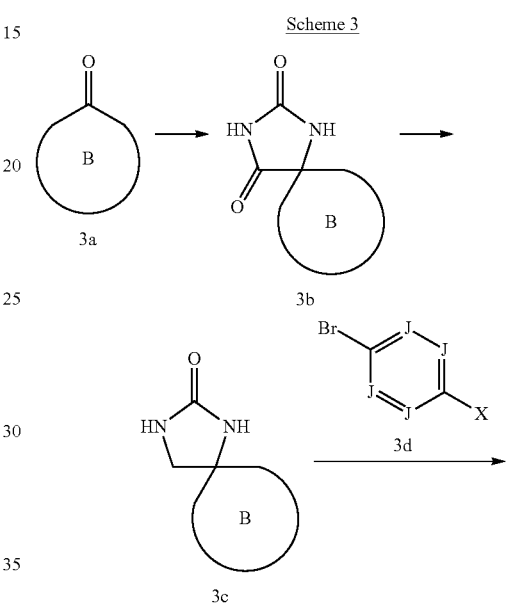

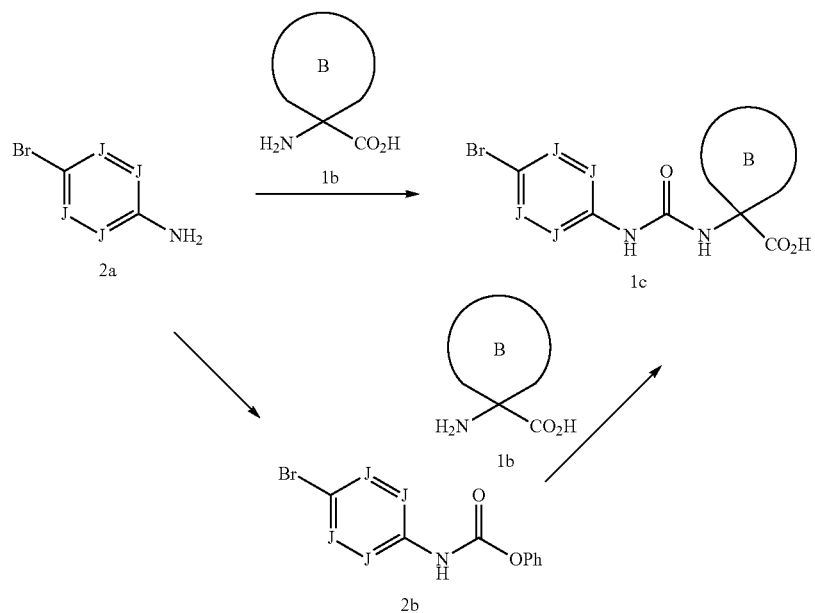

J = N, C

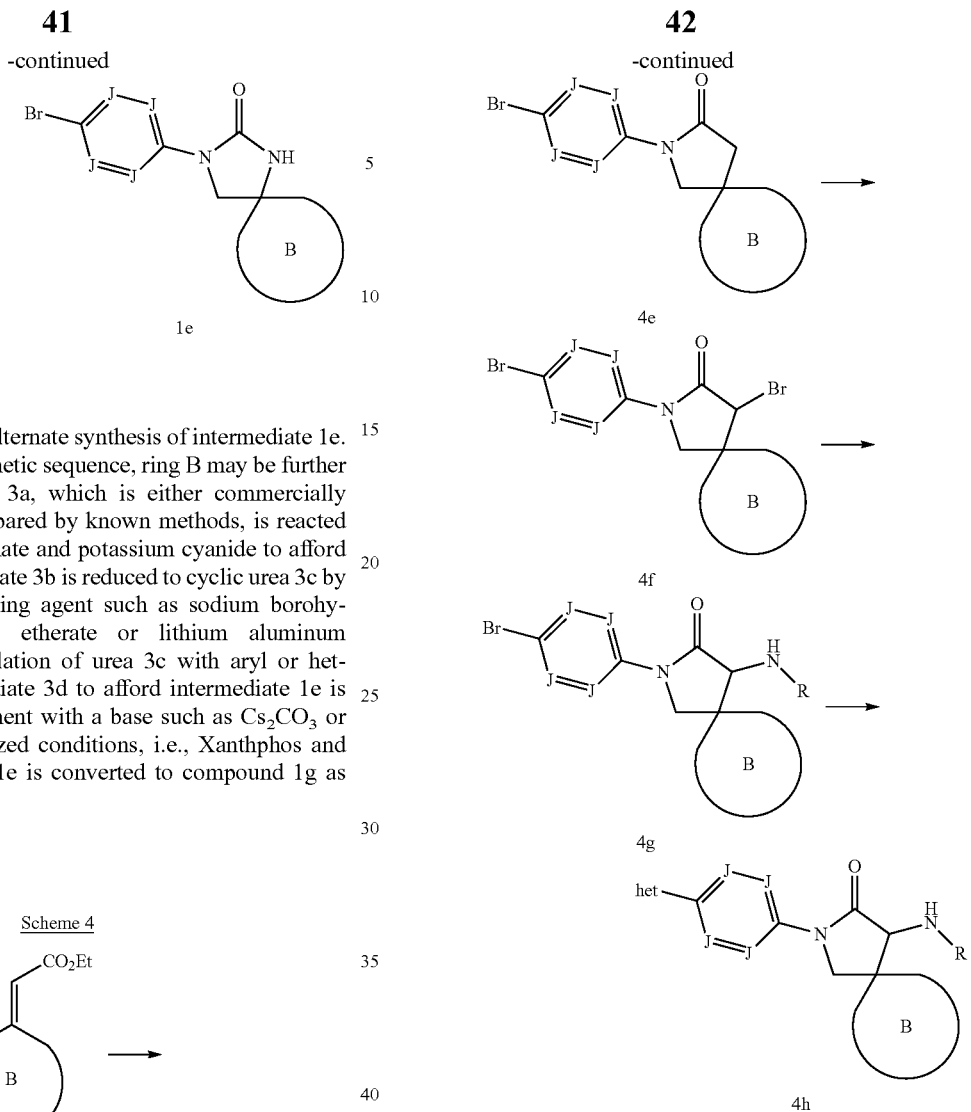

Scheme 3 shows an alternate synthesis of intermediate 1e. At each step in the synthetic sequence, ring B may be further functionalized. Ketone 3a, which is either commercially available or can be prepared by known methods, is reacted with ammonium carbonate and potassium cyanide to afford hydantoin 3b. Intermediate 3b is reduced to cyclic urea 3c by treatment with a reducing agent such as sodium borohydride-boron trifluoride etherate or lithium aluminum hydride-TMSCl. N-arylation of urea 3c with aryl or heteroaryl halide intermediate 3d to afford intermediate 1e is accomplished by treatment with a base such as $Cs_2CO_3$ or under palladium-catalyzed conditions, i.e., Xanthphos and $Pd_2dba_3$. Intermediate 1e is converted to compound 1g as depicted in Scheme 1.

Scheme 4 shows the synthesis of 4h from ketone 4a. At each step in the synthetic sequence, ring B may be further functionalized. Reaction of 4a, which is either commercially available or can be prepared by known methods, with triethylphosphonoacetate and a base such as t-BuOK affords ester 4b. Reaction of intermediate 4b with $CH_3NO_2$ and a base such as DBU or TBAF affords nitroester 4c. Reduction of nitro 4c with H2, $R_a$—Ni affords after cyclization lactam 4d. N-arylation of intermediate 4d with aryl or heteroaryl halide intermediate 3d to afford intermediate 4e is accomplished by treatment with a base such as $Cs_2CO_3$ or under palladium-catalyzed conditions, i.e., Xantphos and $Pd_2dba_3$. Intermediate 4e is treated with a base, such as LiHMDS or LDA, followed by the addition of NBS to afford bromolactam 4f. Reaction of intermediate 4f with an amine (R—$NH_2$) affords intermediate 4g. Intermediate 4g is coupled with a heteroaryl boronic acid or boronate ester to afford 4h. This reaction proceeds via Suzuki coupling, using a reagent such as $Pd(Ph_3)_4$ or $2^{nd}$ generation Xphos catalyst and a base such as sodium carbonate or potassium phosphate. Alternatively, compound 4g is converted to a boronic acid or boronate ester, using a boron reagent, such as bis(pinacolato)diboron, and a catalyst such as $PdCl_2(dppf)$. This species is then coupled with a heteroaryl halide (het-X) via Suzuki cross-coupling to afford compound 4h.

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (90% $H_2O$, 10% MeOH, 0.1% TFA) and Solvent B (10% $H_2O$, 90% MeOH, 0.1% TFA, UV 220 nm) or with gradients of Solvent A (90% $H_2O$, 10% ACN, 0.1% TFA) and Solvent B (10% $H_2O$, 90% ACN, 0.1% TFA, UV 220 nm) or with gradients of Solvent A (98% $H_2O$, 2% ACN, 0.05% TFA) and Solvent B (98% ACN, 2% $H_2O$, 0.05% TFA, UV 220 nm) (or) SunFire Prep C18 OBD 5μ 30×100 mm, 25 min gradient from 0-100% B. A=$H_2O$/ACN/TFA 90:10:0.1. B=ACN/$H_2O$/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method E:

Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method F:

Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method I:

SunFire C18 column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J:

XBridge Phenyl column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K:

SunFire C18 column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L:

XBridge Phenyl column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method M:

SunFire C18 column (3.5 μm, 4.6×150 mm). Gradient elution (1.0 mL/min) from 0-50% Solvent B over 15 min. Solvent A is 95% water, 5% acetonitrile, 0.05% TFA and Solvent B is 5% water, 95% acetonitrile, 0.05% TFA, UV 220 nm.

Method N:

XBridge Phenyl column (3.5 μm, 4.6×150 mm). Gradient elution (1.0 mL/min) from 0-50% Solvent B over 15 min. Solvent A is 95% water, 5% acetonitrile, 0.05% TFA and Solvent B is 5% water, 95% acetonitrile, 0.05% TFA, UV 220 nm.

SFC and Chiral Purity Methods

Method I:

Chiralpak AD-H, 250×4.6 mm, 5.0-μm particles; $CO_2$: 60%, Co-solvent: 40% {0.2% DEA in IPA:acetonitrile (1:1)}, Total Flow: 4.0 g/min, Back Pressure: 100 bars, Temperature: 25° C., UV: 218 nm.

Method II:

Chiralpak OD-H, 250×4.6 mm, 5.0-μm particles; $CO_2$: 60%, Co-solvent: 40% {0.2% DEA in IPA:acetonitrile (1:1)}, Total Flow: 4.0 g/min, Back Pressure: 104 bars, Temperature: 24.9° C., UV: 287 nm.

Method III:

Chiralpak OJ-H, 250×4.6 mm, 5.0-μm particles; $CO_2$: 60%, Co-solvent: 30% (0.3% DEA in methanol), Total Flow: 4.0 g/min, Back Pressure: 101 bars, Temperature: 23.6° C., UV: 272 nm.

Method IV:

Chiralpak AS-H, 250×4.6 mm, 5.0-μm particles; $CO_2$: 60%, Co-solvent: 40% (0.3% DEA in methanol), Total Flow: 4.0 g/min, Back Pressure: 102 bars, Temperature: 25.4° C., UV: 272 nm.

Method V:

Chiralcel OJ-H, 250×4.6 mm, 5.0-μm particles; $CO_2$: 60%, Co-solvent: 40% (0.2% DEA in methanol), Total Flow: 4.0 g/min, Back Pressure: 102 bars, Temperature: 24.6° C., UV: 272 nm.

Method VI:

Luxcellulose-2, 250×4.6 mm, 5.0-μm particles; $CO_2$: 60%, Co-solvent: 40% (0.2% DEA in methanol), Total Flow: 3.0 g/min, Back Pressure: 101 bars, Temperature: 23.6° C., UV: 260 nm.

Method VII:

Chiralcel AS-H, 250×4.6 mm, 5.0-μm particles; $CO_2$: 60%, Co-solvent: 40% (0.2% DEA in methanol), Total Flow: 4.0 g/min, Back Pressure: 101 bars, Temperature: 24.4° C., UV: 270 nm.

Method VIII:

Chiralpak IC, 250×4.6 mm, 5.0-μm particles; $CO_2$: 60%, Co-solvent: 40% (0.2% DEA in methanol), Total Flow: 4.0 g/min, Back Pressure: 101 bars, Temperature: 24.4° C., UV: 270 nm.

Method IX:

COLUMN: Chiralpak IF (250×4.6 mm), 5 micron, mobile phase: 0.2% DEA in ethanol, flow: 1.0 mL/min.

Method X:

COLUMN: LUX AMYLOSE 2 (250×4.6 mm), 5 micron, mobile phase: 0.2% DEA in n-hexane:ethanol (5:95), flow: 1.0 mL/min.

Method XI:

COLUMN: chiralcel OD-H (250×4.6 mm), 5 micron, MOBILE PHASE: 0.2% DEA in n-hexane:ethanol (70:30), flow: 1.0 mL/min.

Method XII:

COLUMN: CHIRAL PAK ID 250×4.6 mm), 5 micron, mobile phase: 0.1% DEA in methanol, flow: 1.0 mL/min.

VII. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

Intermediate 1

6-(4-bromophenyl)-4,6-diazaspiro[2.4]heptan-5-one

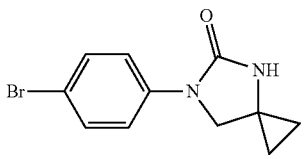 [SMILES: O=C1NC2(CC2)CN1c1ccc(Br)cc1]

Intermediate 1a

Preparation of I-(3-(4-bromophenyl)ureido)cyclopropanecarboxylic acid

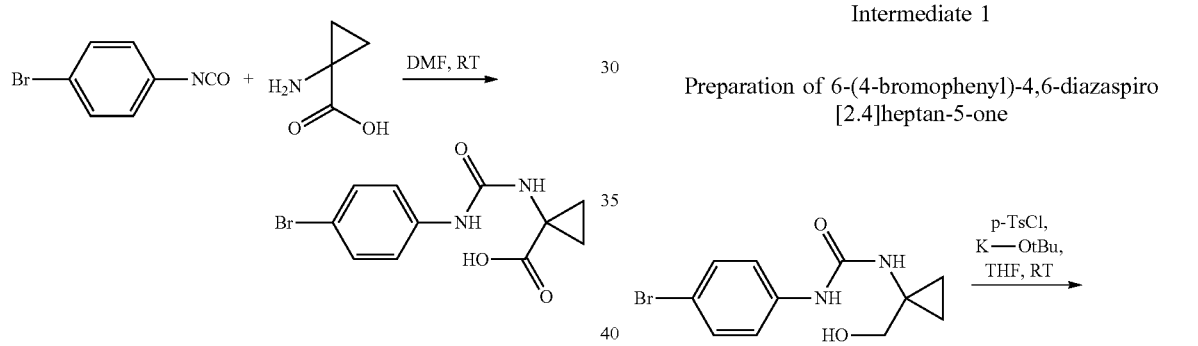

To a solution of 1-bromo-4-isocyanatobenzene (2.0 g, 10.1 mmol) in DMF (3 mL) was added 1-aminocyclopropanecarboxylic acid (2.04 g, 20.2 mmol). The reaction mixture was stirred at rt for 16 h. DMF was evaporated. Water was added to the residue, resulting in precipitation of a solid, which was collected by filtration and dried to afford 1-(3-(4-bromophenyl)ureido)cyclopropanecarboxylic acid (2.7 g, 91% yield) as a white solid. MS (ESI) m/z: 301.0 (M+H)+. 1H NMR (400 MHz, DMSO-d6) δ ppm 12.33 (br. s., 1H), 8.63 (s, 1H), 7.48-7.35 (m, 5H), 6.79 (s, 1H), 1.37-1.31 (m, 2H), 1.08-1.01 (m, 2H).

Example 1b

Preparation of 1-(4-bromophenyl)-3-(1-(hydroxymethyl)cyclopropyl)urea

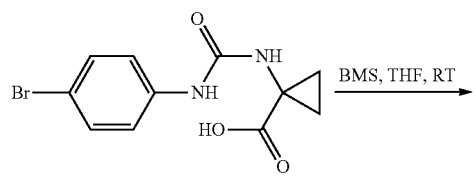

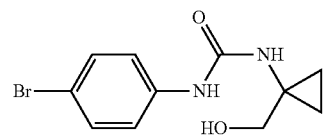

To a solution of 1-(3-(4-bromophenyl)ureido)cyclopropanecarboxylic acid (2.4 g, 8.02 mmol) in THF (60 mL) at 0° C., was added borane-methyl sulfide complex (7.62 mL, 80 mmol). The reaction mixture was allowed to cool to rt and stirred for 16 h. The reaction was quenched carefully with methanol, then stirred at rt for 30 min and concentrated to give a gummy solid. Water was added to the residue resulting in the precipitation of a solid, which was filtered and dried to afford 1-(4-bromophenyl)-3-(1-(hydroxymethyl)cyclopropyl)urea (0.8 g, 35% yield) as a white solid. MS (ESI) m/z: 287.1 (M+H)+. 1H NMR (400 MHz, DMSO-d6) δ ppm 8.65 (br. s., 1H), 7.41-7.30 (m, 4H), 6.59 (br. s., 1H), 4.84 (br. s., 1H), 3.41 (d, J=5.0 Hz, 2H), 0.71-0.57 (m, 4H).

Intermediate 1

Preparation of 6-(4-bromophenyl)-4,6-diazaspiro[2.4]heptan-5-one

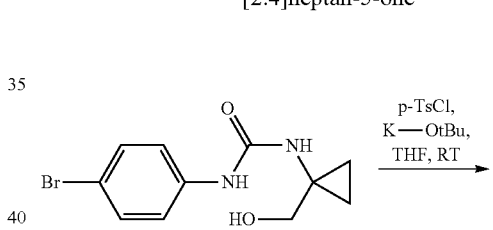

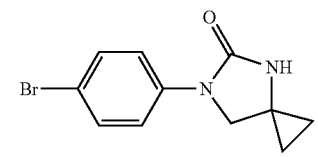

To a stirred suspension of 1-(4-bromophenyl)-3-(1-(hydroxymethyl)cyclopropyl)urea (0.8 g, 2.81 mmol) and potassium tert-butoxide (0.756 g, 6.73 mmol) in THF at 0° C., was added dropwise a solution of p-toluenesulfonyl chloride (0.642 g, 3.37 mmol) in THF (10 mL). The reaction mixture was stirred at 0° C. for 2 h. The reaction mixture was filtered and the filtrate was concentrated. The product was purified by flash chromatography (gradient elution: 0-100% EtOAc/Hexane) to afford 6-(4-bromophenyl)-4,6-diazaspiro[2.4]heptan-5-one (100 mg, 14% yield) as a white solid. MS (ESI) m/z: 287.1 (M+H)+. 1H NMR (400 MHz, DMSO-d6) δ ppm 8.65 (br. s., 1H), 7.41-7.30 (m, 4H), 6.59 (br. s., 1H), 4.84 (br. s., 1H), 3.41 (d, J=5.0 Hz, 2H), 0.71-0.57 (m, 4H).

Intermediate 2

3-(4-bromophenyl)-8-oxa-1,3-diazaspiro[4.5]decan-2-one

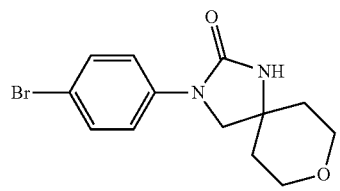 [SMILES: O=C1NC2(CCOCC2)CN1c1ccc(Br)cc1]

Intermediate 2a

Preparation of 4-(3-(4-bromophenyl) ureido)tetrahydro-2H-pyran-4-carboxylic acid

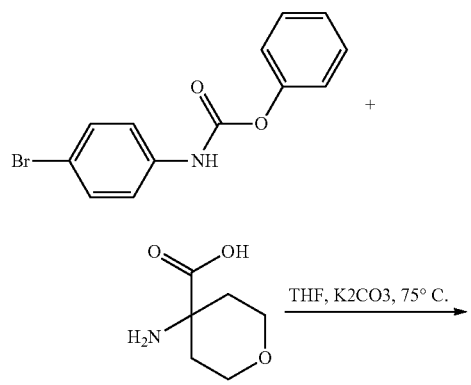

To a solution of phenyl (4-bromophenyl)carbamate (1.00 g, 3.42 mmol) in THF (25 mL), was added 4-aminotetrahydro-2H-pyran-4-carboxylic acid, HCl (0.746 g, 4.11 mmol) and $K_2CO_3$ (1.42 g, 10.3 mmol). The reaction mixture was heated at 75° C. for 4 h. The reaction was cooled to rt, then was evaporated. The residue was dissolved in water, acidified to pH 2 with 1.0 N HCl. The precipitated solid was filtered, washed with water, then hexane to afford 4-(3-(4-bromophenyl)ureido)tetrahydro-2H-pyran-4-carboxylic acid as a white solid (900 mg, 77% yield). MS(ESI) m/z: 345.2 (M+H)$^+$; $^1$H NMR (400 MHz, DMSO-d$_6$) δ ppm 12.38 (br. s., 1H) 8.59 (s, 1H) 7.29-7.40 (m, 4H) 6.68 (s, 1H) 3.71 (dt, J=11.80, 3.64 Hz, 2H) 3.49-3.59 (m, 2H) 1.90-2.01 (m, 2H) 1.80-1.90 (m, 2H).

Intermediate 2b

Preparation of 1-(4-bromophenyl)-3-(4-(hydroxymethyl)tetrahydro-2H-pyran-4-yl)urea

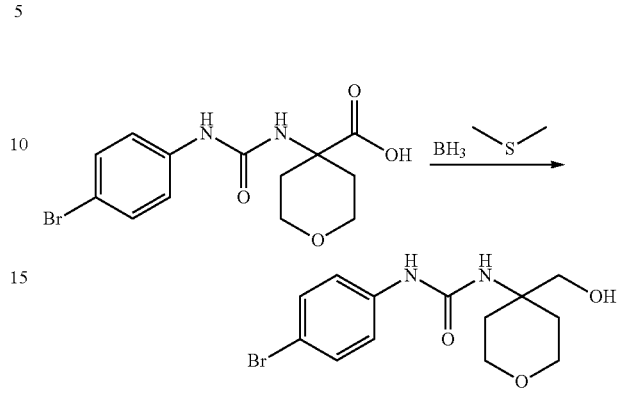

To a suspension of 4-(3-(4-bromophenyl)ureido)tetrahydro-2H-pyran-4-carboxylic acid (1.08 g, 3.15 mmol) in THF (20 mL) at 0° C., was added borane-methyl sulfide complex (1.49 mL, 15.7 mmol). The reaction mixture was stirred at that temperature, then was allowed to warm to rt and stir overnight. The reaction mixture was quenched with methanol, then concentrated. Water was added to the residue and the mixture was sonicated. The precipitated solid was collected by filtration, washed with water, then hexane and dried to afford 1-(4-bromophenyl)-3-(4-(hydroxymethyl)tetrahydro-2H-pyran-4-yl)urea as a white solid (820 mg, 79% yield). MS(ESI) m/z: 331.0 (M+H)$^+$; $^1$H NMR (400 MHz, DMSO-d$_6$) δ ppm 8.57 (s, 1H) 7.28-7.40 (m, 4H) 5.97 (s, 1H) 4.80 (t, J=5.52 Hz, 1H) 3.60-3.70 (m, 2H) 3.47-3.58 (m, 4H) 1.90 (d, J=13.05 Hz, 2H) 1.50-1.62 (m, 2H).

Intermediate 2

Preparation of 3-(4-bromophenyl)-8-oxa-1,3-diazaspiro[4.5]decan-2-one

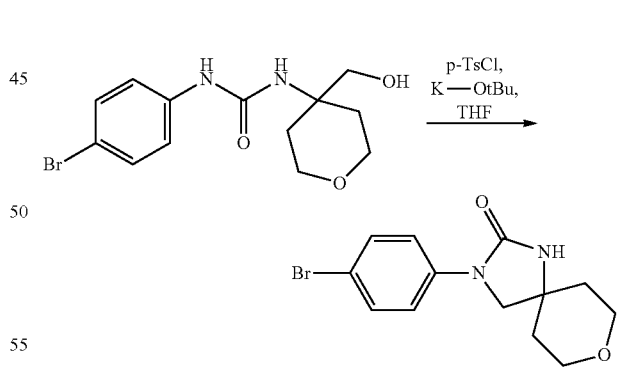

To a stirred suspension of 1-(4-bromophenyl)-3-(4-(hydroxymethyl)tetrahydro-2H-pyran-4-yl)urea (800 mg, 2.43 mmol) and potassium tert-butoxide (654 mg, 5.83 mmol) in THF (15 mL) at 0° C., was added a solution of p-toluenesulfonyl chloride (556 mg, 2.92 mmol) in THF (5 mL) dropwise. The reaction mixture was stirred at 0° C. for 30 min, then was allowed to warm to rt and was filtered. The filtrate was concentrated to a residue, which was purified by flash chromatography (gradient elution: 0-100% EtOAc/hexane) to afford 3-(4-bromophenyl)-8-oxa-1,3-diazaspiro

[4.5]decan-2-one as a white solid (210 mg, 28% yield). MS (ESI) m/z: 313.0 (M+H)$^+$; $^1$H NMR (400 MHz, DMSO-d$_6$) δ ppm 7.67 (s, 1H) 7.57 (m, J=9.04 Hz, 2H) 7.47 (m, J=9.04 Hz, 2H) 3.71-3.81 (m, 2H) 3.69 (s, 2H) 3.50-3.61 (m, 2H) 1.56-1.75 (m, 4H).

Intermediate 3

Preparation of 3-(4-bromophenyl)-1-(3-methoxybenzyl)-8-oxa-1,3-diazaspiro[4.5]decan-2-one

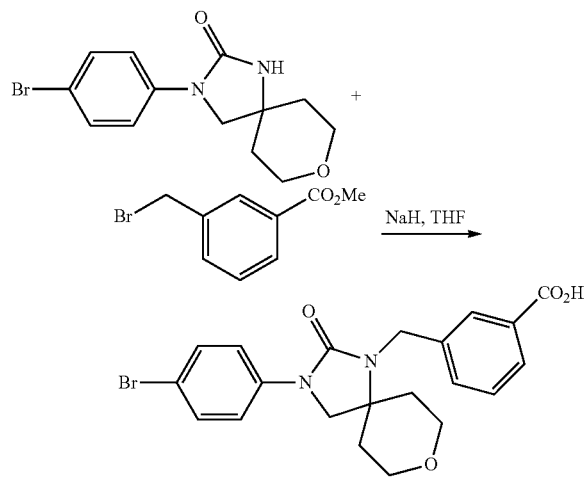

To a solution of 3-(4-bromophenyl)-8-oxa-1,3-diazaspiro [4.5]decan-2-one (50 mg, 0.161 mmol) in DMF (2.5 mL) at 0° C., was added NaH (16.1 mg, 0.402 mmol) and the reaction mixture stirred for 10 min. Methyl 3-(bromomethyl)benzoate (44.2 mg, 0.193 mmol) was added to the reaction mixture. The reaction mixture was allowed to warm to rt and stir for 3 h. Reaction mixture was quenched with water. The aqueous layer was acidified to pH 2 with 1.5 N HCl and extracted with ethyl acetate. The combined ethyl acetate was washed with water and brine, dried (Na$_2$SO$_4$) and concentrated to afford 3-((3-(4-bromophenyl)-2-oxo-8-oxa-1,3-diazaspiro[4.5]decan-1-yl)methyl)benzoic acid as an off-white solid (70 mg, 98% yield). MS(ESI) m/z: 445.0 (M+H)$^+$; $^1$H NMR (400 MHz, DMSO-d$_6$) δ ppm 7.93-7.96 (m, 1H) 7.81 (d, J=7.53 Hz, 1H) 7.63-7.67 (m, 2H) 7.61 (d, J=7.53 Hz, 1H) 7.49-7.54 (m, 2H) 7.40-7.48 (m, 1H) 4.50 (s, 2H) 3.87 (s, 2H) 3.81 (dd, J=11.80, 4.77 Hz, 2H) 3.47 (t, J=11.80 Hz, 2H) 1.81-1.94 (m, 2H) 1.41 (d, J=13.05 Hz, 2H).

Intermediate 4 tert-butyl 3-(4-bromophenyl)-2-oxo-1,3,8-triazaspiro [4.5]decane-8-carboxylate

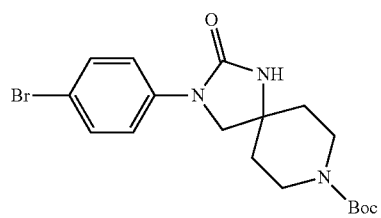 [SMILES: CC(C)(C)OC(=O)N1CCC2(CC1)CN(c1ccc(Br)cc1)C(=O)N2]

Intermediate 4a

Preparation of phenyl (4-bromophenyl)carbamate

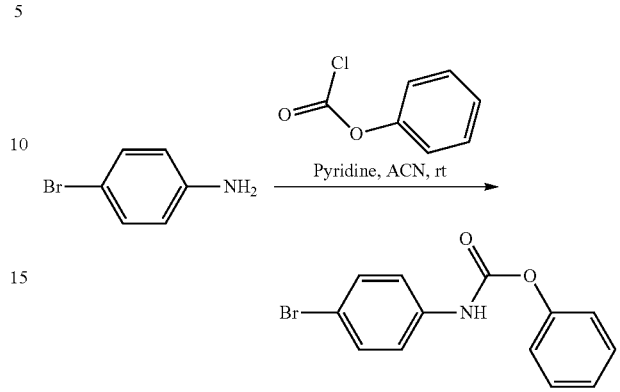

To a solution consisting of 4-bromoaniline (5.0 g, 29.1 mmol) and pyridine (2.35 mL, 29.1 mmol) in acetonitrile (100 mL) at rt, was added phenyl chloroformate (3.65 mL, 29.1 mmol), dropwise. The reaction mixture was stirred for at rt for 1 h, then was diluted with EtOAc (100 mL), washed with saturated aqueous NaHCO$_3$ (2×), water, and brine. The organic layer was dried (Na$_2$SO$_4$) and concentrated. The solid was triturated with pet. ether and collected by filtration to afford phenyl (4-bromophenyl)carbamate as a white solid (8.0 g, 94% Yield). MS (ESI) m/z: 294.3 (M+H)$^+$; $^1$H NMR (400 MHz, CHLOROFORM-d) δ ppm 7.33-7.49 (m, 6H) 7.24-7.29 (m, 1H) 7.16-7.22 (m, 2H) 6.94 (br. s., 1H).

Intermediate 4b

Preparation of 4-(3-(4-bromophenyl)ureido)-1-(tert-butoxycarbonyl)piperidine-4-carboxylic acid

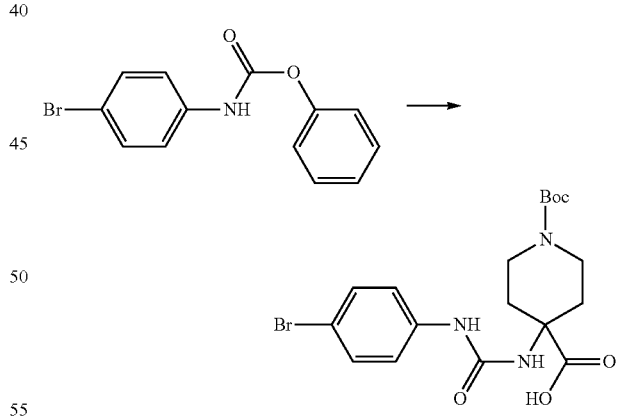

To a solution of phenyl (4-bromophenyl)carbamate (1.5 g, 5.13 mmol) in THF (60 mL), was added 4-amino-1-(tert-butoxycarbonyl)piperidine-4-carboxylic acid (1.51 g, 6.16 mmol) and K$_2$CO$_3$ (2.13 g, 15.4 mmol). The reaction mixture was heated at 75° C. for 4 h. The reaction mixture was cooled to rt, then concentrated. The resultant residue was dissolved in water. The organic phase was washed with pet. ether, then was acidified to pH 2 (1.0 N HCl). The aqueous phase was extracted with ethyl acetate. The combined ethyl acetate layers were washed with brine, dried (Na$_2$SO$_4$) and concentrated to afford 4-(3-(4-bromophenyl)ureido)-1-(tert-butoxycarbonyl)piperidine-4-carboxylic acid as a white solid (2.27 g, 100% yield). MS(ESI) m/z: 444.2 (M+H)+; 1H NMR (400 MHz, DMSO-d6) δ ppm 9.78 (br. s., 1H) 7.41 (m, J=9.04 Hz, 2H) 7.30 (m, J=8.53 Hz, 2H) 6.91 (br. s., 1H) 3.40-361 (m., 4H) 2.15-2.20 (m, 2H) 1.70 (d, J=6.53 Hz, 2H) 1.40 (s, 9H).

Intermediate 4c

Preparation of tert-butyl 4-(3-(4-bromophenyl)ureido)-4-(hydroxymethyl)piperidine-1-carboxylate

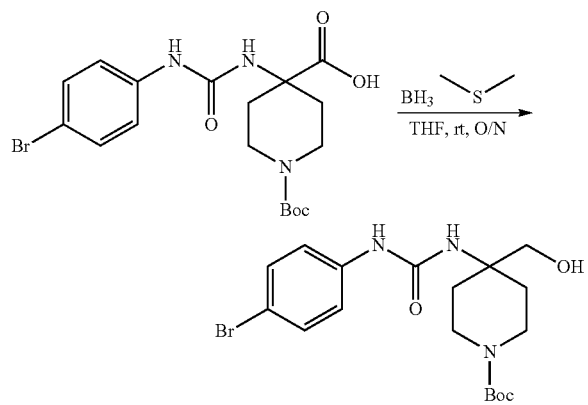

To a solution of 4-(3-(4-bromophenyl)ureido)-1-(tert-butoxycarbonyl)piperidine-4-carboxylic acid (2.5 g, 5.65 mmol) in THF (80 mL) at 0° C., was added borane-methyl sulfide complex (3.22 mL, 33.9 mmol) and. The reaction mixture was stirred for 10 min., then was stirred at rt overnight. Reaction mixture was quenched with methanol. Methanol was removed in vacuo to obtain the gummy mass. Trituration with water precipitated white solid which was filtered and washed with water, then pet. ether, and azeotroped with toluene to afford tert-butyl 4-(3-(4-bromophenyl)ureido)-4-(hydroxymethyl)piperidine-1-carboxylate as white solid (1.9 g, 78% Yield). MS(ESI) m/z: 430.0 (M+H)+; 1H NMR (400 MHz, DMSO-d6) δ ppm 8.75 (s, 1H) 7.30-7.39 (m, 4H) 6.15 (s, 1H) 4.83 (t, J=5.52 Hz, 1H) 3.67 (d, J=13.05 Hz, 2H) 3.51 (d, J=5.52 Hz, 2H) 3.01 (br. s., 2H) 1.97 (d, J=13.55 Hz, 2H) 1.42-1.50 (m, 2H) 1.40 (s, 9H).

Intermediate 4

Preparation of tert-butyl 3-(4-bromophenyl)-2-oxo-1,3,8-triazaspiro[4.5]decane-8-carboxylate

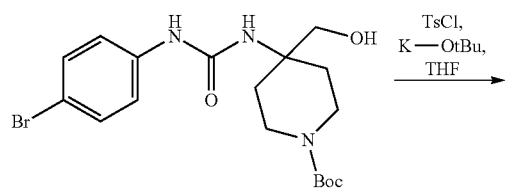

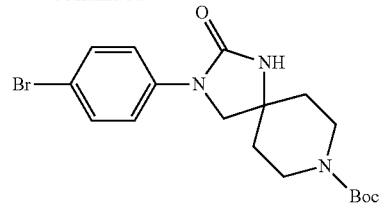

To a stirred suspension of tert-butyl 4-(3-(4-bromophenyl)ureido)-4-(hydroxymethyl)piperidine-1-carboxylate (1.9 g, 4.44 mmol) and potassium tert-butoxide (1.20 g, 10.6 mmol) at 0° C. was added a solution of p-toluenesulfonyl chloride (1.02 g, 5.32 mmol) in THF (20 mL) dropwise. The reaction mixture was stirred at 0° C. for 45 min. Reaction mixture was filtered, and the filtrate was concentrated to give gummy mass, which was purified by flash chromatography (gradient elution; 0-100% EtOAc/Hex) to afford a solid, which was recrystallized (DCM\Hexane) to afford tert-butyl 3-(4-bromophenyl)-2-oxo-1,3,8-triazaspiro[4.5]decane-8-carboxylate as a white solid (500 mg, 28% yield). MS(ESI) m/z: 412.2 (M+H)+; 1H NMR (300 MHz, DMSO-d6) δ ppm 7.64 (s, 1H) 7.54 (m, J=9.44 Hz, 2H) 7.46 (m, J=9.07 Hz, 2H) 7.37 (br. s., 1H) 3.65 (s, 2H) 3.35-3.53 (m, 4H) 1.51-1.69 (m, 4H) 1.40 (s, 9H).

Intermediate 5

3-(4-bromophenyl)-1-(3-methoxybenzyl)-1,3,8-triazaspiro[4.5]decan-2-one

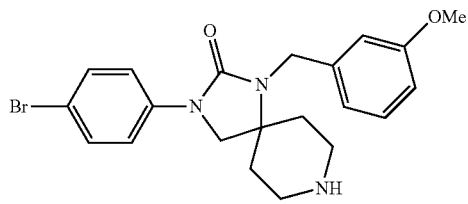 [SMILES: COc1cccc(CN2C(=O)N(c3ccc(Br)cc3)CC23CCNCC3)c1]

Intermediate 5a

Preparation of tert-butyl 3-(4-bromophenyl)-1-(3-methoxybenzyl)-2-oxo-1,3,8-triazaspiro[4.5]decane-8-carboxylate

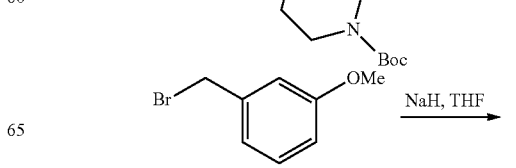

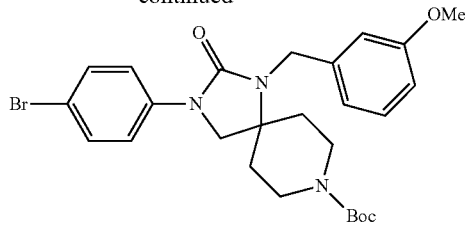

To a suspension of tert-butyl 3-(4-bromophenyl)-2-oxo-1,3,8-triazaspiro[4.5]decane-8-carboxylate (250 mg, 0.609 mmol) in THF (15 mL) at 0° C., was added NaH (73.1 mg, 1.83 mmol). After 10 min., 1-(bromomethyl)-3-methoxybenzene (172 mg, 0.853 mmol) was added dropwise. The reaction mixture was allowed to warm to rt and stir overnight. The reaction mixture was quenched with methanol, then the solvent was removed in vacuo. The residue was purified by flash chromatography (gradient elution; 0-100% EtOAc/Hex) to afford tert-butyl 3-(4-bromophenyl)-1-(3-methoxybenzyl)-2-oxo-1,3,8-triazaspiro[4.5]decane-8-carboxylate as a gummy solid (180 mg, 56% yield). MS(ESI) m/z: 530.2 (M+H)⁺; ¹H NMR (400 MHz, DMSO-d₆) δ ppm 7.59-7.65 (m, 2H) 7.48-7.54 (m, 2H) 7.22 (t, J=8.03 Hz, 1H) 6.86-6.92 (m, 2H) 6.76-6.82 (m, 1H) 4.38 (s, 2H) 3.90 (br. s., 2H) 3.81 (s, 2H) 3.72 (s, 3H) 2.87 (br. s., 2H) 1.62-1.75 (m, 2H) 1.48 (d, J=12.55 Hz, 2H) 1.37-1.40 (m, 9H).

Intermediate 5

Preparation of 3-(4-bromophenyl)-1-(3-methoxybenzyl)-1,3,8-triazaspiro[4.5]decan-2-one

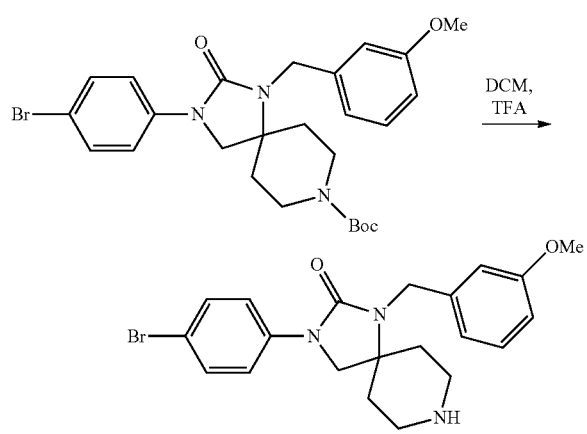

To a solution of tert-butyl 3-(4-bromophenyl)-1-(3-methoxybenzyl)-2-oxo-1,3,8-triazaspiro[4.5]decane-8-carboxylate (180 mg, 0.339 mmol) in DCM (10 mL) was added TFA (0.3 mL, 3.89 mmol). The reaction mixture stirred at rt overnight. The solvent was evaporated to give a brown gummy solid, which was basified with sat. NaHCO₃, then extracted with DCM. The combined DCM layers were washed with brine, dried (Na₂SO₄), filtered and concentrated to afford 3-(4-bromophenyl)-1-(3-methoxybenzyl)-1,3,8-triazaspiro[4.5]decan-2-one as a brown gummy solid (110 mg, 75% yield). MS(ESI) m/z: 432.2 (M+H)⁺; ¹H NMR (400 MHz, DMSO-d₆) δ ppm 7.61-7.67 (m, 2H) 7.47-7.54 (m, 2H) 7.19-7.26 (m, 1H) 6.87-6.94 (m, 2H) 6.77-6.82 (m, 1H) 4.37 (s, 2H) 3.75 (s, 2H) 3.73 (s, 3H) 2.86 (d, J=10.04 Hz, 2H) 2.55-2.61 (m, 3H) 1.62-1.74 (m, 2H) 1.39 (d, J=12.05 Hz, 2H).

Intermediate 6 tert-butyl 3-(5-bromo-4-methoxypyrimidin-2-yl)-2-oxo-1,3,8-triazaspiro[4.5]decane-8-carboxylate

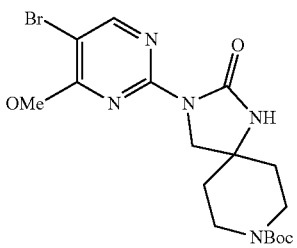 [SMILES: COc1nc(N2CC3(CCN(C(=O)OC(C)(C)C)CC3)NC2=O)ncc1Br]

Intermediate 6a

Preparation of tert-butyl 2,4-dioxo-1,3,8-triazaspiro[4.5]decane-8-carboxylate

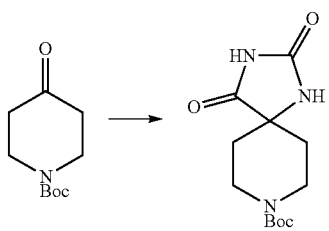 [SMILES: CC(C)(C)OC(=O)N1CCC(=O)CC1 ; CC(C)(C)OC(=O)N1CCC2(CC1)NC(=O)NC2=O]

To a stirred solution of tert-butyl 4-oxopiperidine-1-carboxylate (5.0 g, 25.1 mmol) and ammonium carbonate (4.82 g, 50.2 mmol) in a mixture of ethanol (25 mL) and water (25 mL), was added KCN (2.94 g, 45.2 mmol). The reaction mixture was heated at 60° C. for 12 h. The reaction mixture was cooled to rt and stirred for 2 h. The solid precipitate was collected by filtration, washed with water (100 mL), ethanol (20 mL) and ether (50 mL), and dried to afford tert-butyl 2,4-dioxo-1,3,8-triazaspiro[4.5]decane-8-carboxylate (3.0 g, 44% yield) as an off-white solid. MS (ESI) m/z: 268.2 (M−H)⁺.

Intermediate 6b

Preparation of tert-butyl 2-oxo-1,3,8-triazaspiro[4.5]decane-8-carboxylate

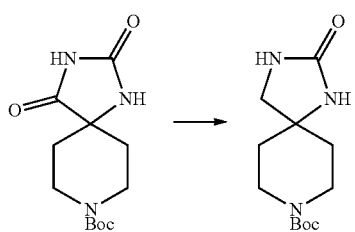 [SMILES: CC(C)(C)OC(=O)N1CCC2(CC1)NC(=O)NC2=O ; CC(C)(C)OC(=O)N1CCC2(CC1)CNC(=O)N2]

To a stirred solution of tert-butyl 2,4-dioxo-1,3,8-triazaspiro[4.5]decane-8-carboxylate (1 g, 3.71 mmol) in DCM (30 mL) at 0° C., was added dropwise TMS-Cl (0.570 mL, 4.46 mmol) over 5 min. To this mixture was added dropwise a solution of LAH [1M in THF (7.43 mL, 7.43 mmol)] over 10 min. The reaction mixture was stirred at 0° C. for 2 h. The reaction mixture was quenched with dropwise addition of 10% NaOH (10 mL) and was diluted with DCM (50 mL). The DCM layer was separated. The aqueous layer was extracted with DCM (100 mL). The combined organic extracts were evaporated under evaporated to afford tert-butyl 2-oxo-1,3,8-triazaspiro[4.5]decane-8-carboxylate (500 mg, 53% yield) as an off-white solid. $^1$H NMR (400 MHz, DMSO-$d_6$) δ ppm 6.67 (s, 1H), 6.12 (s, 1H), 3.26-3.29 (m, 4H), 3.08-3.09 (m, 2H), 1.52-1.54 (m, 4H), 1.38 (s, 9H).

Intermediate 6

Preparation of tert-butyl 3-(5-bromo-4-methoxypyrimidin-2-yl)-2-oxo-1,3,8-triazaspiro[4.5]decane-8-carboxylate

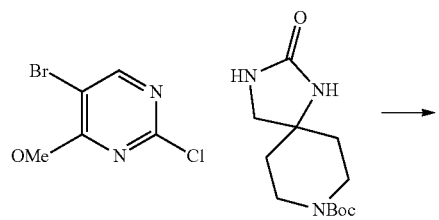

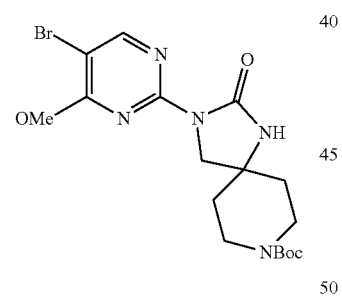

To a stirred solution of 5-bromo-2-chloro-4-methoxypyrimidine (300 mg, 1.34 mmol) and tert-butyl 2-oxo-1,3,8-triazaspiro[4.5]decane-8-carboxylate (514 mg, 2.01 mmol) in dioxane (15 mL), was added cesium carbonate (1.31 g, 4.03 mmol). The reaction mixture was heated to 105° C. for 12 h, then was cooled to rt and diluted with ethyl acetate (25 mL). The suspension was filtered through celite, rinsing with ethyl acetate (10 mL). The filtrate was concentrated. The residue was purified by flash chromatography (EtOAc/pet. ether, 1:1) to afford tert-butyl 3-(5-bromo-4-methoxypyrimidin-2-yl)-2-oxo-1,3,8-triazaspiro[4.5]decane-8-carboxylate (100 mg, 17% yield) as an off-white solid. MS (ESI) m/z: 442.1 (M+H)$^+$.

Intermediate 7 tert-butyl 8-bromo-6-(4-bromophenyl)-7-oxo-2,6-diazaspiro[3.4]octane-2-carboxylate

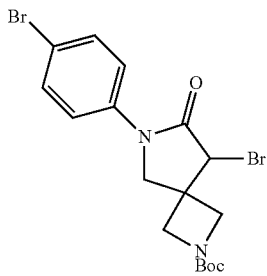 [SMILES: CC(C)(C)OC(=O)N1CC2(C1)CN(c1ccc(Br)cc1)C(=O)C2Br]

Intermediate 7a

Preparation of tert-butyl 6-(4-bromophenyl)-7-oxo-2,6-diazaspiro[3.4]octane-2-carboxylate

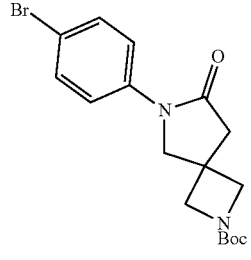

To a solution of tert-butyl 7-oxo-2,6-diazaspiro[3.4]octane-2-carboxylate (500 mg, 2.21 mmol) in Dioxane (5 mL), was added 1-bromo-4-iodobenzene (1.25 g, 4.42 mmol), followed by potassium carbonate (763 mg, 5.52 mmol) and 4,5-bis(diphenylphosphino)-9,9-dimethylxanthene (128 mg, 0.221 mmol). The reaction was degassed with nitrogen before tris(dibenzylideneacetone)dipalladium(0) (101 mg, 0.110 mmol) was added. The reaction was again degassed with nitrogen and then was heated at 100° C. overnight. The reaction was filtered through celite and the filtrate was concentrated. The crude compound was purified by flash chromatography (gradient: 0-95% EtOAc/pet ether) to afford tert-butyl 6-(4-bromophenyl)-7-oxo-2,6-diazaspiro [3.4]octane-2-carboxylate (425 mg, 1.12 mmol, 50% yield) as a light brown solid. MS (ESI) m/z: 382.2 (M+H)$^+$.

Intermediate 7

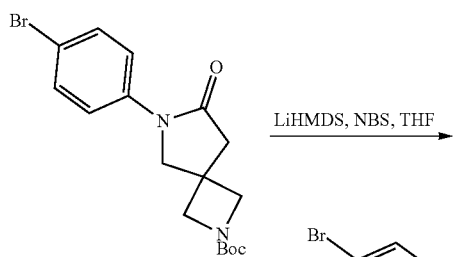

To a solution of tert-butyl 6-(4-bromophenyl)-7-oxo-2,6-diazaspiro[3.4]octane-2-carboxylate (250 mg, 0.656 mmol) in THF (5 mL) at −78° C. was added dropwise 1M LiHMDS (1.44 mL, 1.44 mmol). After 5 min, N-bromosuccinimide (140 mg, 0.787 mmol) in THF (1 mL) was added dropwise and the reaction stirred for 30 min at −78° C. The reaction was quenched with satd. aq. NH$_4$Cl. The layers were separated and the aqueous layer was extracted with EtOAc (2×15 mL). The combined organic extracts were washed with water and brine, dried (Na$_2$SO$_4$) and concentrated to afford tert-butyl 8-bromo-6-(4-bromophenyl)-7-oxo-2,6-diazaspiro[3.4]octane-2-carboxylate (290 mg, 0.630 mmol, 96% yield) as a thick yellow oil. MS (ESI) m/z: 461.1 (M+H)$^+$.

Intermediate 8 tert-butyl 4-bromo-2-(5-bromo-4-methoxypyrimidin-2-yl)-3-oxo-2,8-diazaspiro[4.5]decane-8-carboxylate

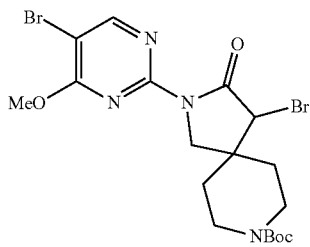 [SMILES: COc1nc(N2CC3(CCN(C(=O)OC(C)(C)C)CC3)C(Br)C2=O)ncc1Br]

Intermediate 8a

Preparation of 5-bromo-2-chloro-4-methoxypyrimidine

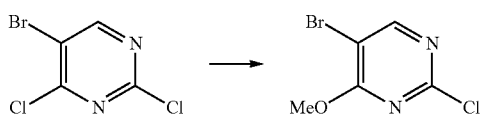 [SMILES: Clc1ncc(Br)c(Cl)n1 ; COc1nc(Cl)ncc1Br]

To a solution of 5-bromo-2,4-dichloropyrimidine (10 g, 43.9 mmol) in MeOH (100 mL) at 0° C., was added sodium methoxide (10.4 g, 48.3 mmol) over 10 min. The reaction mixture stirred at rt for 6 h, then was evaporated. Water (200 mL) was added to the residue obtained. The solid precipitated was filtered and dried to afford 5-bromo-2-chloro-4-methoxypyrimidine (8.0 g, 17.9 mmol, 41% yield) as an off-white solid. MS (ESI) m/z: 222.0 (M+H)$^+$.

Intermediate 8b

Preparation of tert-butyl 2-(5-bromo-4-methoxypyrimidin-2-yl)-3-oxo-2,8-diazaspiro[4.5]decane-8-carboxylate

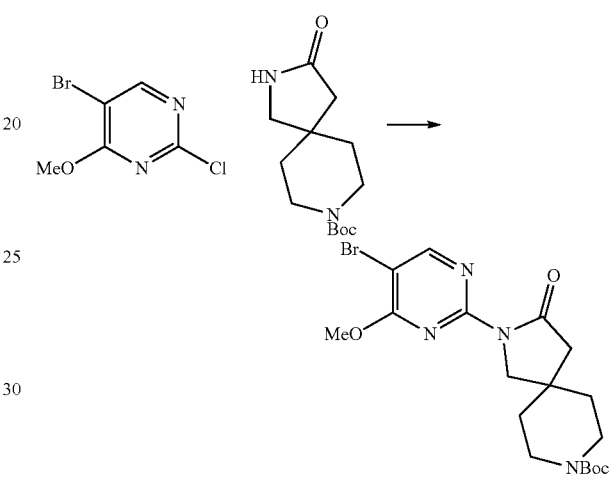

To a solution of 5-bromo-2-chloro-4-methoxypyrimidine (450 mg, 2.01 mmol) and tert-butyl 3-oxo-2,8-diazaspiro[4.5]decane-8-carboxylate (512 mg, 2.01 mmol) in dioxane (15 mL), was added cesium carbonate (1.97 g, 6.04 mmol). The reaction mixture was heated to 105° C. for 12 h, then was cooled to rt and diluted with ethyl acetate (50 mL). The suspension was filtered through celite rinsing with ethyl acetate (10 mL). The filtrate was concentrated. The residue was purified by flash chromatography (pet. ether/ethyl acetate, 3:1) to afford tert-butyl 2-(5-bromo-4-methoxypyrimidin-2-yl)-3-oxo-2,8-diazaspiro[4.5]decane-8-carboxylate (400 mg, 0.906 mmol, 45% yield) as an off-white solid. MS (ESI) m/z: 441.2 (M+H)$^+$.

Intermediate 8

Preparation of tert-butyl 4-bromo-2-(5-bromo-4-methoxypyrimidin-2-yl)-3-oxo-2,8-diazaspiro[4.5]decane-8-carboxylate

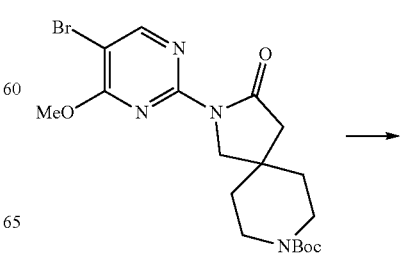

-continued

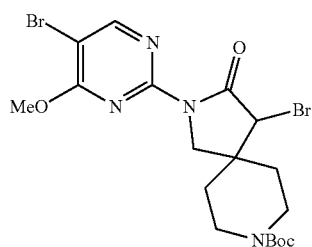

To a solution of tert-butyl 2-(5-bromo-4-methoxypyrimidin-2-yl)-3-oxo-2,8-diazaspiro[4.5]decane-8-carboxylate (320 mg, 0.725 mmol) in THF (6 mL) at −78° C., was added 1M LiHMDS (1.45 mL, 1.45 mmol). The reaction mixture was stirred at −78° C. for 30 min. N-bromosuccinimide (129 mg, 0.725 mmol) in THF (3 mL) was added dropwise and the reaction mixture stirred at −78° C. for 30 min. The reaction was quenched with sat. ammonium chloride solution (25 mL), then was extracted with ethyl acetate (50 mL). The organic layer were separated, dried (Na$_2$SO$_4$) and concentrated. The residue was purified by flash chromatography (pet. ether/ethyl acetate, 3:1) to afford tert-butyl 4-bromo-2-(5-bromo-4-methoxypyrimidin-2-yl)-3-oxo-2,8-diazaspiro[4.5]decane-8-carboxylate (300 mg, 80% yield) as a pale yellow solid. MS (ESI) m/z: 519.0 (M+H)$^+$.

Example 1

6-(4-(1H-pyrazol-4-yl)phenyl)-4-(3-methoxybenzyl)-4,6-diazaspiro[2.4]heptan-5-one

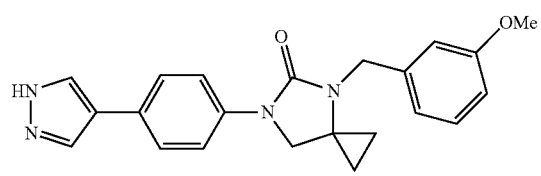 [SMILES: COc1cccc(CN2C(=O)N(c3ccc(-c4cn[nH]c4)cc3)CC23CC3)c1]

Example 1a

Preparation of 6-(4-bromophenyl)-4-(3-methoxybenzyl)-4,6-diazaspiro[2.4]heptan-5-one

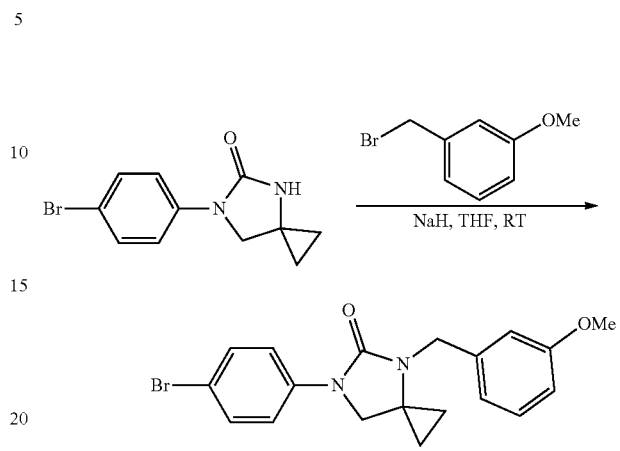

To a suspension of 6-(4-bromophenyl)-4,6-diazaspiro[2.4]heptan-5-one (100 mg, 0.374 mmol) in THF (10 mL) at 0° C., was added portion wise NaH (44.9 mg, 1.123 mmol, 60% in mineral oil). The mixture was stirred for 10 min., then 1-(bromomethyl)-3-methoxybenzene (105 mg, 0.524 mmol) was added. The mixture was stirred at rt for 16 h, then was quenched with methanol. The mixture was concentrated, and the residue was purified by flash chromatography (gradient elution; 0-100% EtOAc/Hex) to afford 6-(4-bromophenyl)-4-(3-methoxybenzyl)-4,6-diazaspiro[2.4]heptan-5-one as a yellow gummy solid. MS(ESI) m/z: 389.2 (M+H)$^+$. $^1$H NMR (400 MHz, DMSO-d$_6$) δ ppm 7.57-7.48 (m, 4H), 7.27-7.21 (m, 1H), 6.86-6.79 (m, 3H), 4.19 (s, 2H), 3.91 (s, 2H), 3.73 (s, 3H), 0.98-0.92 (m, 2H), 0.68-0.62 (m, 2H).

Example 1

Preparation of 6-(4-(1H-pyrazol-4-yl)phenyl)-4-(3-methoxybenzyl)-4,6-diazaspiro[2.4]heptan-5-one

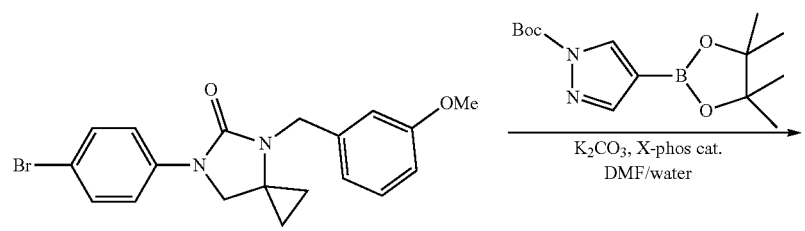

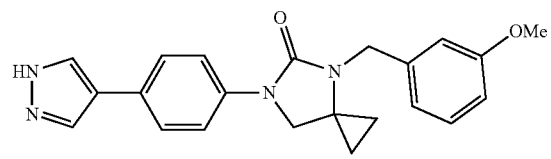

To a solution of 6-(4-bromophenyl)-4-(3-methoxybenzyl)-4,6-diazaspiro[2.4]heptan-5-one (100 mg, 0.258 mmol) in DMF (4 mL), were added tert-butyl 4-(4,4,5,5-tetramethyl-1,3,2-dioxaborolan-2-yl)-1H-pyrazole-1-carboxylate (106 mg, 0.362 mmol), K$_2$CO$_3$ (107 mg, 0.775 mmol) and water (0.4 mL). The reaction mixture was purged wit nitrogen for 5 min, then was charged with 2$^{nd}$ generation XPHOS precatalyst (12.2 mg, 0.015 mmol). The reaction mixture was again purged with nitrogen, then was heated at 90° C. for 16 h. Reaction mixture was cooled to rt and filtered through celite. The filtrate was concentrated. The crude was purified by preparative HPLC to afford 6-(4-(1H-pyrazol-4-yl)phenyl)-4-(3-methoxybenzyl)-4,6-diazaspiro[2.4]heptan-5-one (18.1 mg, 18% yield) as a yellow solid. MS (ESI) m/z: 375.2 (M+H)$^+$; $^1$H NMR (400 MHz, DMSO-d$_6$) δ ppm 12.85 (br. s., 1H) 8.11 (br. s., 1H) 7.87 (br. s., 1H) 7.51-7.60 (m, 4H) 7.24 (t, J=7.70 Hz, 1H) 6.77-6.88 (m, 3H) 4.18 (s, 2H) 3.93 (s, 2H) 3.73 (s, 3H) 0.90-0.98 (m, 2H) 0.61-0.70 (m, 2H); HPLC RT: 1.83 min (Method E) and 1.82 min (Method F).

Example 2 & Example 3

6-(4-(1H-pyrazol-4-yl)phenyl)-4-(1-(3-methoxyphenyl)ethyl)-4,6-diazaspiro[2.4]heptan-5-one (Enantiomer-1 & Enantiomer 2)

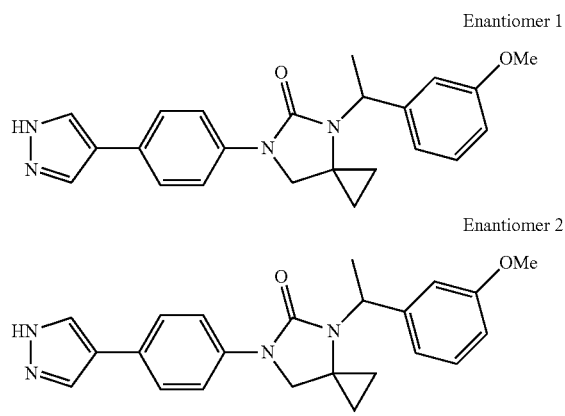

Example 2a

Preparation of 6-(4-bromophenyl)-4-(1-(3-methoxyphenyl)ethyl)-4,6-diazaspiro[2.4]heptan-5-one

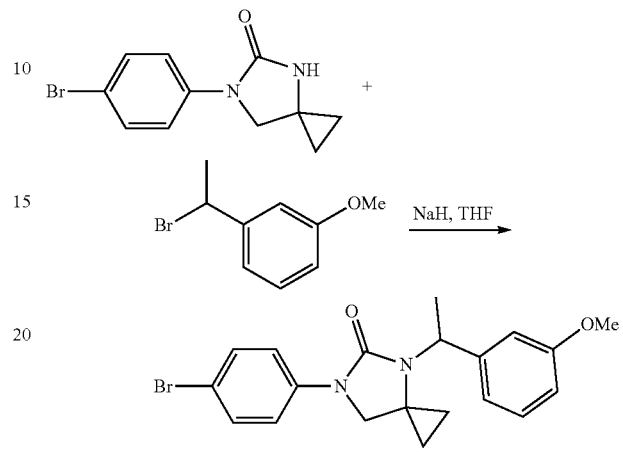

To a suspension of 6-(4-bromophenyl)-4,6-diazaspiro[2.4]heptan-5-one (300 mg, 1.123 mmol) in THF (10 mL) at 0° C., was added NaH (135 mg, 3.37 mmol). The reaction mixture stirred for 10 minutes, then 1-(1-bromoethyl)-3-methoxybenzene (338 mg, 1.57 mmol) was added. The reaction mixture was allowed to warm to rt, then was heated at 75° C. overnight. The reaction mixture was quenched with methanol, then was evaporated. The residue was purified by flash chromatography (gradient elution; 0-100% EtOAc/Hex) to give 6-(4-bromophenyl)-4-(1-(3-methoxyphenyl)ethyl)-4,6-diazaspiro[2.4]heptan-5-one (180 mg, 40%) as a white solid. MS (ESI) m/z: 403.2 (M+H)$^+$; $^1$H NMR (400 MHz, DMSO-d$_6$) δ ppm 7.43-7.54 (m, 4H) 7.18-7.28 (m, 1H) 6.87-7.00 (m, 2H) 6.81 (dd, J=8.12, 2.08 Hz, 1H) 4.20 (q, J=7.18 Hz, 1H) 3.79-3.92 (m, 2H) 3.72 (s, 3H) 1.64 (d, J=7.18 Hz, 3H) 1.00 (s, 2H) 0.71 (d, J=3.40 Hz, 2H).

Example 2 & Example 3

Preparation of 6-(4-(1H-pyrazol-4-yl)phenyl)-4-(1-(3-methoxyphenyl)ethyl)-4,6-diazaspiro[2.4]heptan-5-one (Enantiomer-1 & Enantiomer 2)

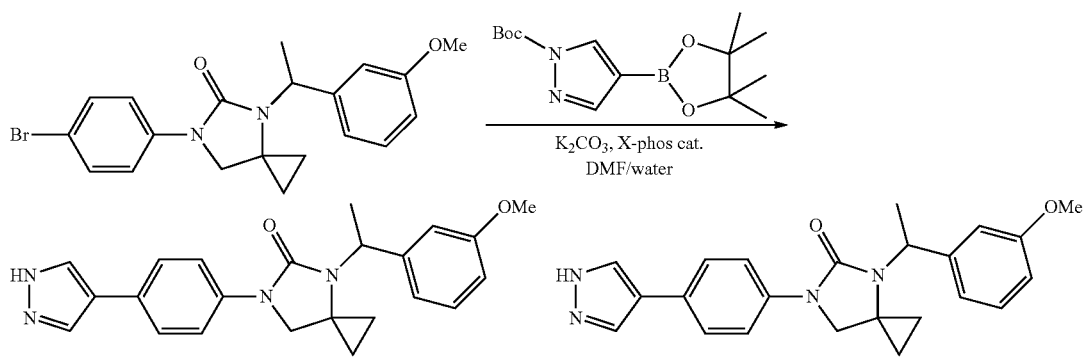

To a solution of 6-(4-bromophenyl)-4-(1-(3-methoxyphenyl)ethyl)-4,6-diazaspiro[2.4]heptan-5-one (170 mg, 0.424 mmol) in DMF (6 mL), were added tert-butyl 4-(4,4,5,5-tetramethyl-1,3,2-dioxaborolan-2-yl)-1H-pyrazole-1-carboxylate (174 mg, 0.593 mmol), $K_2CO_3$ (176 mg, 1.271 mmol) and Water (0.4 mL). The reaction mixture was purged with nitrogen for 5 min and charged with $2^{nd}$ generation XPHOS precatalyst (20.0 mg, 0.025 mmol). The reaction mixture was again purged with nitrogen, then was heated at 90° C. overnight. Reaction mixture was cooled and filtered. The filtrate concentrated and the residue was purified by preparative HPLC to afford the racemic product. Enantiomers were separated via Supercritical fluid chromatography [SFC Column: CHIRALPAK AS-H (250×21 mm), 5u, Co-solvent 30% (0.25% DEA in Methanol) to give enantiomer-1,6-(4-(1H-pyrazol-4-yl)phenyl)-4-(1-(3-methoxyphenyl)ethyl)-4,6-diazaspiro[2.4]heptan-5-one (13.5 mg, 8%) as a white solid. MS (ESI) m/z: 389.2 $(M+H)^+$; $^1$H NMR (400 MHz, DMSO-$d_6$) δ ppm 12.87 (br. s., 1H) 8.09 (br. s., 2H) 7.45-7.59 (m, 4H) 7.24 (t, J=8.03 Hz, 1H) 6.91-7.01 (m, 2H) 6.81 (dd, J=8.03, 2.51 Hz, 1H) 4.22 (q, J=7.19 Hz, 1H) 3.83-3.96 (m, 2H) 3.72-3.77 (m, 3H) 1.65 (d, J=7.03 Hz, 3H) 0.95-1.04 (m, 2H) 0.64-0.75 (m, 2H); RT=16.61 min, 98.5% [SunFire C18 (250×4.6 mm) 3.5μ; A: 5% MeCN-95% $H_2O$-0.05% TFA; B: 95% MeCN-5% $H_2O$-0.05% TFA; wavelength 220 nm; flow rate 1 mL/min; gradient time 25 minutes with 5 minute hold; 10 to 100% B]; RT=17.86 min, 98.7% [XBridge Phenyl (150×4.6 mm) 3.5μ; A: 5% MeCN-95% $H_2O$-0.05% TFA; B: 95% MeCN-5% H2O-0.05% TFA; wavelength 220 nm; flow rate 1 mL/min; gradient time 25 minutes with a 5 minute hold; 10 to 100% B]; 100% ee (RT=6.40 min), determined by chiral SFC analysis column: Chiralpak AS-H (250×4.6) mm, 5u, mobile phase: 0.2% DEA in Methanol]; $[α]^{25.1}_D$=−32.0 (c 0.05, DMSO) and enantiomer-2,6-(4-(1H-pyrazol-4-yl)phenyl)-4-(1-(3-methoxyphenyl)ethyl)-4,6-diazaspiro[2.4]heptan-5-one (12.5 mg) yellow solid. MS (ESI) m/z: 389.2 $(M+H)^+$; $^1$H NMR (400 MHz, DMSO-$d_6$) δ ppm 12.83 (br. s., 1H) 7.99 (br. s., 2H) 7.52 (m, 4H) 7.19-7.30 (m, 1H) 6.91-7.03 (m, 2H) 6.77-6.86 (m, 1H) 4.22 (q, J=7.50 Hz, 1H) 3.82-3.97 (m, 2H) 3.73 (s, 3H) 1.65 (d, J=7.03 Hz, 3H) 0.92-1.07 (m, 2H) 0.70-072 (m, 2H); 16.593 min, 99.372%; [SunFire C18 (250×4.6 mm) 3.5μ; A: 5% MeCN-95% H2O-0.05% TFA; B: 95% MeCN-5% H2O-0.05% TFA; wavelength 220 nm; flow rate 1 mL/min; gradient time 25 minutes with 5 minute hold; 10 to 100% B]; 17.85 min, 99.7% [XBridge Phenyl (150×4.6 mm) 3.5μ; A: 5% MeCN-95% H2O-0.05% TFA; B: 95% MeCN-5% H2O-0.05% TFA; wavelength 220 nm; flow rate 1 mL/min; gradient time 25 minutes with a 5 minute hold; 10 to 100% B]; 100.0% ee (RT=7.65 min), determined by chiral SFC analysis column: Chiralpak AS-H (250×4.6) mm, 5u, mobile phase: 0.2% DEA in Methanol]; $[α]^{25.2}_D$=+44.0 (c 0.05, DMSO).

The following Examples in Table 1 were made by using the same procedure as shown in Example 1.

TABLE 1

| Example | R | Name | LCMS (M + H)+ | HPLC Method, RT (min.) & Purity | NMR |
|---|---|---|---|---|---|
| 4 | (3-methoxy-5-fluorobenzyl group) | 6-(3-ethyl-4-(1H-pyrazol-4-yl)phenyl)-4-(3-fluoro-5-methoxybenzyl)-4,6-diazaspiro[2.4]heptan-5-one | 421.2 | E: 2.06 98.6%<br>F: 2.12 98.1% | ¹H NMR (400 MHz, DMSO-d6) δ ppm 12.89 (br s., 1 H) 7.84 (br s, 1 H) 7.62 (br, s, 1 H) 7.40-7.52 (m, 2 H) 7.28 (d, J = 8.4, 1 H) 6.62-6.79 (m, 3 H) 4.19 (s, 2 H) 3.97 (s, 2 H) 3.75 (s, 3 H) 3.18 (s, 2 H) 2.68 (q, 2 H) 1.08-1.19 (t, J = 7.20, 3 H) 0.89-1.02 (m, 2 H) 0.64-0.77 (m, 2 H), ¹⁹F NMR (376 MHz, DMSO-d6) δ ppm -111.563. |
| 5 | (3-methoxybenzyl group) | 6-(3-ethyl-4-(1H-pyrazol-4-yl)phenyl)-4-(3-methoxybenzyl)-4,6-diazaspiro[2.4]heptan-5-one | 403.2 | E: 2.04 96.1%<br>F: 1.94 95.9% | ¹H NMR (400 MHz, DMSO-d6) δ ppm 12.88 (br. s., 1 H) 7.83 (br. s., 1 H) 7.61 (br. s, 1 H) 7.40-7.50 (m, 2 H) 7.20-7.28 (m, 2 H) 6.77-6.87 (m, 3 H) 4.18 (s, 2 H) 3.94 (s, 2 H) 3.73 (s, 3 H) 2.67 (q, J = 7.58 Hz, 2 H) 1.12 (t, J = 7.46 Hz, 3 H) 0.92-0.98 (m, 2 H) 0.62-0.70 (m, 2 H). |
| 6 | (4-fluoro-3-methoxybenzyl group) | 6-(4-(1H-pyrazol-4-yl)phenyl)-4-(4-fluoro-3-methoxybenzyl)-4,6-diazaspiro[2.4]heptan-5-one | 393.1 | E: 1.83 98.1%<br>F: 1.89 95.9% | ¹H NMR (400 MHz, DMSO-d₆) δ ppm 12.85 (br. s., 1 H) 8.12 (br. s., 1 H) 7.87 (br. s., 1 H) 7.51-7.61 (m, 4 H) 7.05-7.21 (m, 2 H) 6.84 (ddd, J = 6.11, 4.16, 2.20 Hz, 1 H) 4.18 (s, 2 H) 3.93 (s, 2 H) 3.81 (s, 3 H) 4.16 (m, 2 H) 0.62-0.70 (m, 2 H); ¹⁹F NMR (376 MHz, DMSO-d₆) ☐ ppm -137.913 |

TABLE 1-continued

| Example | R | Name | LCMS (M + H)+ | HPLC Method, RT (min.) & Purity | NMR |
|---|---|---|---|---|---|
| 7 | (structure) | 6-(4-(1H-pyrazol-4-yl)phenyl)-4-(3-(cyclopropylmethoxy)benzyl)-4,6-diazaspiro[2.4]heptan-5-one | 415.2 | E: 2.09 97.9% F: 2.15 99.3% | ¹H NMR (400 MHz, DMSO-d₆) δ ppm 12.85 (br s, 1 H) 8.12 (br. s., 1 H) 7.88 (br. s., 1 H) 7.22 (t, J = 8.07 Hz, 1 H) 6.75-6.88 (m, 3 H) 4.18 (s, 2 H) 3.94 (s, 2 H) 3.79 (d, J = 6.85 Hz, 2 H) 1.13-1.27 (m, 1 H) 0.92-1.01 (m, 2 H) 0.61-0.71 (m, 2 H) 0.51-0.60 (m, 2 H) 0.28-0.35 (m, 2 H). |
| 8 | (structure) | 6-(4-(1H-pyrazol-4-yl)phenyl)-4-(3-fluoro-5-methoxybenzyl)-4,6-diazaspiro[2.4]heptan-5-one | 393.3 | E: 1.16 96.7% F: 1.19 94.9% | ¹H NMR (400 MHz, DMSO-d₆) δ ppm 12.87 (s, 1 H) 8.10 (s, 1 H) 7.91 (s, 1 H) 7.49-7.62 (m, 4 H) 6.63-6.75 (m, 3 H) 4.18 (s, 2 H) 3.95 (s, 2 H) 3.75 (s, 3 H) 0.90-0.99 (m, 2 H) 0.64-0.72 (m, 2 H); ¹⁹F NMR (376 MHz, DMSO-d₆) δ ppm −111.558. |

Example 9

3-(4-(1H-pyrazol-4-yl)phenyl)-1-(3-methoxybenzyl)-8-oxa-1,3-diazaspiro[4.5]decan-2-one

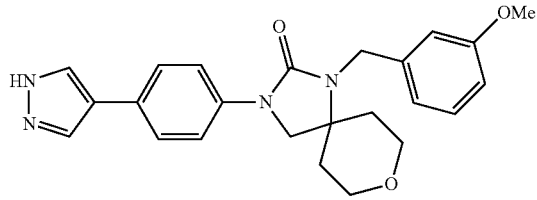 [SMILES: COc1cccc(CN2C(=O)N(c3ccc(-c4cn[nH]c4)cc3)CC23CCOCC3)c1]

Example 9a

Preparation of 3-(4-bromophenyl)-1-(3-methoxybenzyl)-8-oxa-1,3-diazaspiro[4.5]decan-2-one

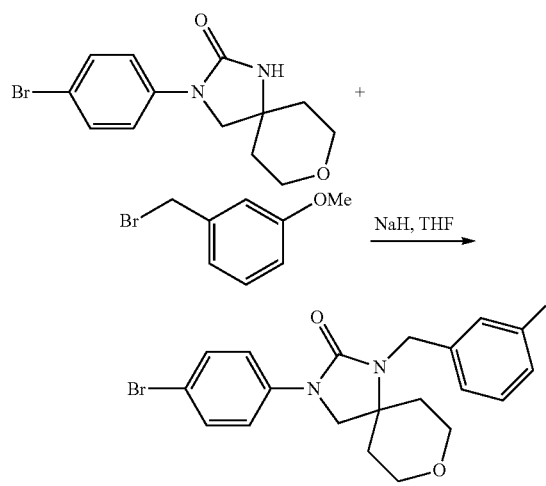

To a suspension of 3-(4-bromophenyl)-8-oxa-1,3-diazaspiro[4.5]decan-2-one (70 mg, 0.225 mmol) in THF (8 mL) at 0° C. was added NaH (27.0 mg, 0.675 mmol) and the reaction mixture stirred for 10 minutes. 1-(bromomethyl)-3-methoxybenzene (63.3 mg, 0.315 mmol) was added and the reaction mixture was allowed to warm to rt and stir overnight. The reaction mixture was quenched with methanol, then concentrated. The residue was purified by flash chromatography (gradient elution; 0-100% EtOAc/Hexanes) to afford 3-(4-bromophenyl)-1-(3-methoxybenzyl)-8-oxa-1,3-diazaspiro[4.5]decan-2-one as a gummy solid (50 mg, 52% yield). MS(ESI) m/z: 433.1 (M+H)+; 1H NMR (400 MHz, DMSO-d6) δ ppm 7.62-7.68 (m, 2H) 7.47-7.55 (m, 2H) 7.23 (t, J=8.03 Hz, 1H) 6.90-6.95 (m, 2H) 6.77-6.83 (m, 1H) 4.41 (s, 2H) 3.86 (s, 2H) 3.81 (dd, J=12.05, 4.52 Hz, 2H) 3.73 (s, 3H) 3.47 (t, J=11.55 Hz, 2H) 1.81-1.93 (m, 2H) 1.43 (d, J=13.05 Hz, 2H).

Example 9

Preparation of 3-(4-(1H-pyrazol-4-yl)phenyl)-1-(3-methoxybenzyl)-8-oxa-1,3-diazaspiro[4.5]decan-2-one

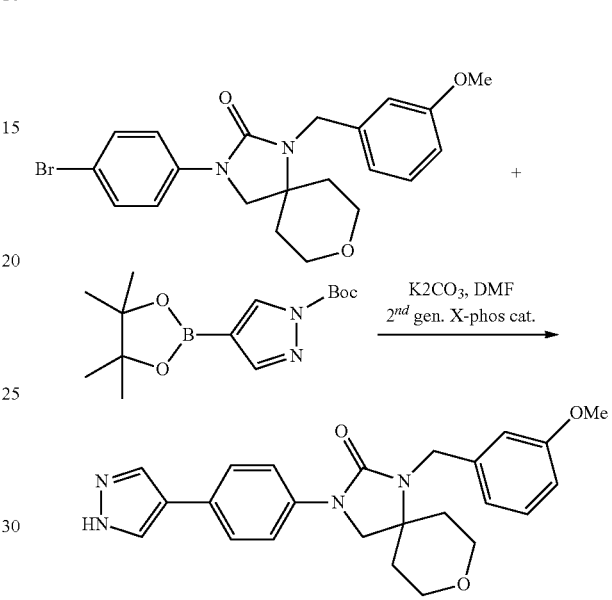

To a solution of 3-(4-bromophenyl)-1-(3-methoxybenzyl)-8-oxa-1,3-diazaspiro[4.5]decan-2-one (50 mg, 0.116 mmol) in DMF (4 mL) were added tert-butyl 4-(4,4,5,5-tetramethyl-1,3,2-dioxaborolan-2-yl)-1H-pyrazole-1-carboxylate (47.7 mg, 0.162 mmol), K2CO3 (48.1 mg, 0.348 mmol) and water (0.4 mL). The reaction mixture was purged with nitrogen for 5 min and charged with 2nd generation XPHOS precatalyst (5.5 mg, 7.0 μmol). The reaction mixture was again purged with nitrogen, then heated at 90° C. overnight. Reaction mixture was cooled to rt, then filtered. The filtrate was purified by preparative HPLC to afford 3-(4-(1H-pyrazol-4-yl)phenyl)-1-(3-methoxybenzyl)-8-oxa-1,3-diazaspiro[4.5]decan-2-one as pale yellow solid (12 mg, 24% yield). MS(ESI) m/z: 419.2 (M+H)+; 1H NMR (400 MHz, DMSO-d6) δ ppm 12.86 (br. s., 1H) 8.13 (br. s., 1H) 7.88 (br. s., 1H) 7.64 (d, J=8.80 Hz, 2H) 7.57 (d, J=8.56 Hz, 2H) 7.23 (t, J=7.95 Hz, 1H) 6.88-6.97 (m, 2H) 6.75-6.82 (m, 1H) 4.40 (s, 2H) 3.87 (s, 2H) 3.81 (dd, J=11.86, 4.77 Hz, 2H) 3.73 (s, 3H) 3.48 (t, J=12.10 Hz, 2H) 1.87 (td, J=12.84, 4.65 Hz, 2H) 1.43 (d, J=12.23 Hz, 2H). LCMS RT=1.58 min, 96.7% (Method E), 1.71 min, 96.0% (Method F).

The following Examples in Table 2 were made by using the same procedure as shown in Example 9.

TABLE 2

| Example | R | Name | LCMS (M + H)+ | HPLC Method, RT (min.) & Purity | NMR |
|---|---|---|---|---|---|
| 10 | (structure with OMe, F substituents) | 3-(4-(1H-pyrazol-4-yl)phenyl)-1-(3-fluoro-5-methoxybenzyl)-8-oxa-1,3-diazaspiro[4.5]decan-2-one | 437.20 | E: 1.66 min, 100%  F: .179 min, 99.7% | 1H NMR (400 MHz, DMSO-d6) δ ppm 12.86 (br. s., 1 H) 8.12 (br. s., 1 H) 7.89 (br. s., 1 H) 7.63 (d, J = 8.80 Hz, 2 H) 7.57 (d, J = 8.80 Hz, 2 H) 6.64-6.82 (m, 3 H) 4.39 (s, 2 H) 3.89 (s, 2 H) 3.82 (dd, J = 11.37, 4.28 Hz, 2 H) 3.74 (s, 3 H) 3.49 (t, J = 11.74 Hz, 2 H) 1.86 (td, J = 12.90, 5.26 Hz, 2 H) 1.45 (d, J = 12.47 Hz, 2 H); 19F NMR (376 MHz, METHANOL-d4) δ –111.871 |
| 11 | (structure with cyclopropylmethoxy) | 3-(4-(1H-pyrazol-4-yl)phenyl)-1-(3-(cyclopropylmethoxy)benzyl)-8-oxa-1,3-diazaspiro[4.5]decan-2-one | 459.20 | E: 1.86 min, 97.2%  F: 1.98 min, 96.4% | 1H NMR (400 MHz, DMSO-d6) δ ppm 12.86 (br. s., 1 H) 8.14 (br. s., 1 H) 7.89 (br. s., 1 H) 7.64 (d, J = 8.80 Hz, 2 H) 7.58 (d, J = 8.80 Hz, 2 H) 7.20 (t, J = 7.95 Hz, 1 H) 6.87-6.95 (m, 2 H) 6.78 (d, J = 8.56 Hz, 1 H) 4.39 (s, 2 H) 3.88 (s, 2 H) 3.75-3.84 (m, 4 H) 3.49 (t, J = 12.23 Hz, 2 H) 1.80-1.95 (m, 2 H) 1.43 (d, J = 12.72 Hz, 2 H) 1.12-1.26 (m, 1 H) 0.51-0.59 (m, 2 H) 0.26-0.35 (m, 2 H) |
| 12 | (structure with 2-fluorobenzyl) | 3-(4-(1H-pyrazol-4-yl)phenyl)-1-(2-fluorobenzyl)-8-oxa-1,3-diazaspiro[4.5]decan-2-one | 407.30 | F: 1.55 min, 95.2% | 1H NMR (400 MHz, DMSO-d6) δ ppm 13.13 (br. s., 1 H) 8.40 (br. s., 1 H) 7.86-7.96 (m, 3 H) 7.79-7.86 (m, 2 H) 7.67-7.74 (m, 1 H) 7.52-7.61 (m, 1 H) 7.35-7.49 (m, 2 H) 4.72 (s, 2 H) 4.17 (s, 2 H) 4.09 (dd, J = 11.74, 4.65 Hz, 2 H) 3.77 (t, J = 11.74 Hz, 3 H) 2.12 (td, J = 12.66, 5.01 Hz, 2 H) 1.76 (d, J = 12.47 Hz, 2 H) |
| 13 | (structure with 3-fluorobenzyl) | 3-(4-(1H-pyrazol-4-yl)phenyl)-1-(3-fluorobenzyl)-8-oxa-1,3-diazaspiro[4.5]decan-2-one | 407.30 | F: 1.55 min, 95.6% | 1H NMR (400 MHz, DMSO-d6) δ ppm 13.14 (br. s., 1 H) 8.41 (br. s., 1 H) 8.15 (br. s., 1 H) 7.79-8.03 (m, 4 H) 7.63 (br. s., 1 H) 7.40-7.56 (m, 2 H) 7.32 (br. s., 1 H) 4.71 (br. s., 2 H) 4.31-4.42 (m, 1 H) 4.16 (br. s., 2 H) 4.09 (d, J = 11.49 Hz, 2 H) 3.76 (t, J = 11.98 Hz, 2 H) 3.44 (t, J = 4.77 Hz, 2 H) 2.14 (br. s., 2 H) 1.73 (d, J = 11.74 Hz, 2 H) |

TABLE 2-continued

| Example | R | Name | LCMS (M + H)+ | HPLC Method, RT (min.) & Purity | NMR |
|---|---|---|---|---|---|
| 14 | (3-CN benzyl) | 3-((3-(4-(1H-pyrazol-4-yl)phenyl)-2-oxo-8-oxa-1,3-diazaspiro[4.5]decan-1-yl)methyl)benzonitrile | 414.30 | E: 1.32 min, 95.1% | 1H NMR (400 MHz, DMSO-d6) δ ppm 13.13 (br. s., 1 H) 8.40 (br. s., 1 H) 8.08 (s, 1 H) 7.98 (dd, J = 7.83, 1.47 Hz, 2 H) 7.87-7.95 (m, 2 H) 7.74-7.87 (m, 3 H) 4.75 (s, 2 H) 4.17 (s, 2 H) 4.09 (dd, J = 11.74, 4.65 Hz, 2 H) 3.76 (t, J = 11.86 Hz, 2 H) 2.13 (td, J = 12.72, 5.14 Hz, 2H) 1.74 (d, J = 12.72 Hz, 2 H) |
| 16 | (3-OH benzyl) | 3-(4-(1H-pyrazol-4-yl)phenyl)-1-(3-chlorobenzyl)-8-oxa-1,3-diazaspiro[4.5]decan-2-one | 423.20 | E: 1.61 min, 94.4% | 1H NMR (400 MHz, DMSO-d6) δ ppm 13.13 (br. s., 1 H) 8.40 (s, 1 H) 8.15 (s, 1 H) 7.87-7.96 (m, 2 H) 7.78-7.87 (m, 2 H) 7.69 (s, 1 H) 7.52-7.65 (m, 3 H) 4.70 (s, 2 H) 4.16 (s, 2 H) 4.09 (dd, J = 11.74, 4.65 Hz, 2 H) 3.76 (t, J = 11.49 Hz, 2 H) 2.14 (td, J = 12.72, 4.65 Hz, 2 H) 1.71 (d, J = 12.72 Hz, 2 H) |
| 17 | (3,4-diF benzyl) | 3-(4-(1H-pyrazol-4-yl)phenyl)-1-(3,4-difluorobenzyl)-8-oxa-1,3-diazaspiro[4.5]decan-2-one | 425.30 | F: 1.56 min, 96.1% | 1H NMR (400 MHz, DMSO-d6) δ ppm 13.13 (br. s., 1 H) 8.40 (s, 1 H) 8.15 (s, 1 H) 7.86-7.94 (m, 2 H) 7.79-7.86 (m, 2 H) 7.59-7.72 (m, 2 H) 7.49 (dd, J = 5.62, 3.42 Hz, 1 H) 4.68 (s, 2 H) 4.15 (s, 2 H) 4.09 (dd, J = 11.86, 4.52 Hz, 2 H) 3.76 (t, J = 11.62 Hz, 2 H) 2.13 (td, J = 12.84, 5.14 Hz, 2 H) 1.72 (d, J = 12.96 Hz, 2 H) |
| 18 | (3-CF3 benzyl) | 3-(4-(1H-pyrazol-4-yl)phenyl)-1-(3-(trifluoromethyl)benzyl)-8-oxa-1,3-diazaspiro[4.5]decan-2-one | 457.30 | E: 1.69 min, 95.8% | 1H NMR (400 MHz, DMSO-d6) δ ppm 13.13 (br. s., 1 H) 8.40 (s, 1 H) 8.15 (s, 1 H) 7.98 (s, 1 H) 7.95 (d, J = 6.85 Hz, 1 H) 7.78-7.93 (m, 6 H) 4.80 (s, 2 H) 4.17 (s, 2 H) 4.10 (d, J = 11.25 Hz, 2 H) 3.76 (t, J = 11.86 Hz, 2 H) 2.17 (d, J = 7.34 Hz, 2 H) 1.72 (d, J = 13.21 Hz, 2 H) |

TABLE 2-continued

| Example | R | Name | LCMS (M + H)+ | HPLC Method, RT (min.) & Purity | NMR |
|---|---|---|---|---|---|
| 19 | (3,4-dichlorobenzyl structure) | 3-(4-(1H-pyrazol-4-yl)phenyl)-1-(3,4-dichlorobenzyl)-8-oxa-1,3-diazaspiro[4.5]decan-2-one | 457.20 | E: 1.77 min, 95.2% | 1H NMR (400 MHz, DMSO-d6) δ ppm 13.13 (br. s., 1 H) 8.40 (s, 1 H) 8.15 (s, 1 H) 7.87-7.95 (m, 3 H) 7.77-7.87 (m, 3 H) 7.63 (dd, J = 8.31, 2.20 Hz, 1 H) 4.70 (s, 2 H) 4.16 (s, 2 H) 4.10 (dd, J = 11.86, 4.52 Hz, 2 H) 3.76 (t, J = 11.98 Hz, 2 H) 2.14 (td, J = 12.78, 5.01 Hz, 2 H) 1.72 (d, J = 12.72 Hz, 2 H) |
| 20 | (3-trifluoromethoxybenzyl structure) | 3-(4-(1H-pyrazol-4-yl)phenyl)-1-(3-(trifluoromethoxy)benzyl)-8-oxa-1,3-diazaspiro[4.5]decan-2-one | 473.30 | E: 1.75 min, 97.0% | 1H NMR (400 MHz, DMSO-d6) δ ppm 13.13 (br. s., 1 H) 8.39 (br. s., 1 H) 8.15 (br. s., 1 H) 7.87-7.95 (m, 2 H) 7.79-7.87 (m, 2 H) 7.63-7.77 (m, 2 H) 7.61 (s, 1 H) 7.49 (dt, J = 7.95, 1.04 Hz, 1 H) 4.75 (s, 2 H) 4.16 (s, 2 H) 4.09 (dd, J = 11.49, 4.65 Hz, 2 H) 3.76 (t, J = 11.74 Hz, 2 H) 2.14 (td, J = 12.72, 5.14 Hz, 2 H) 1.71 (d, J = 12.72 Hz, 2 H) |
| 21 | (quinoline structure) | 3-(4-(1H-pyrazol-4-yl)phenyl)-1-(quinolin-8-ylmethyl)-8-oxa-1,3-diazaspiro[4.5]decan-2-one | 440.30 | E: 0.96 min, 97.0% | 1H NMR (400 MHz, DMSO-d6) δ ppm 13.13 (br. s., 1 H) 9.27 (dd, J = 4.16, 1.71 Hz, 1 H) 8.68 (dd, J = 8.44, 1.83 Hz, 1 H) 8.15 (d, J = 6.85 Hz, 2 H) 8.01 (d, J = 5.87 Hz, 1 H) 7.91-7.97 (m, 2 H) 7.75-7.91 (m, 4 H) 5.35 (s, 2 H) 4.24 (s, 2 H) 4.05 (dd, J = 12.10, 4.28 Hz, 2 H) 3.77 (t, J = 11.49 Hz, 2 H) 2.09 (td, J = 12.78, 5.01 Hz, 2 H) 1.82 (d, J = 12.72 Hz, 2 H) |
| 22 | (2,4-difluorobenzyl structure) | 3-(4-(1H-pyrazol-4-yl)phenyl)-1-(2,4-difluorobenzyl)-8-oxa-1,3-diazaspiro[4.5]decan-2-one | 425.30 | E: 1.55 min, 97.2% | 1H NMR (400 MHz, DMSO-d6) δ ppm 13.13 (br. s., 1 H) 8.40 (br. s., 1 H) 8.15 (br. s., 1 H) 7.86-7.94 (m, 2 H) 7.80-7.86 (m, 2 H) 7.75 (td, J = 8.80, 6.85 Hz, 1 H) 7.49 (ddd, J = 10.76, 9.29, 2.45 Hz, 1 H) 7.22-7.37 (m, 1 H) 4.68 (s, 2 H) 4.16 (s, 2 H) 4.10 (dd, J = 11.49, 4.65 Hz, 2 H) 3.77 (t, J = 11.62 Hz, 2 H) 2.12 (td, J = 12.59, 4.89 Hz, 2 H) 1.76 (d, J = 12.96 Hz, 2 H) |

TABLE 2-continued

| Example | R | Name | LCMS (M + H)+ | HPLC Method, RT (min.) & Purity | NMR |
|---|---|---|---|---|---|
| 23 | 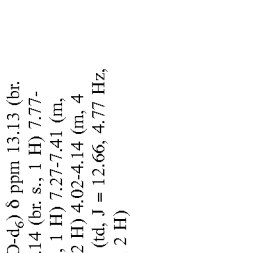 | 3-(4-(1H-pyrazolo-4-yl)phenyl)-1-(2,6-difluorobenzyl)-8-oxa-1,3-diazaspiro[4.5]decan-2-one | 425.20 | E: 1.48 min, 97.5% | 1H NMR (400 MHz, DMSO-d6) δ ppm 13.13 (br. s., 1 H) 8.39 (s, 1 H) 8.14 (br. s., 1 H) 7.77-7.93 (m, 4 H) 7.58-7.71 (m, 1 H) 7.27-7.41 (m, 2 H) 6.80 (s, 2 H) 4.75 (s, 2 H) 4.02-4.14 (m, 4 H) 3.74-3.80 (m, 2 H) 2.16 (td, J = 12.66, 4.77 Hz, 2 H) 1.73 (d, J = 12.72 Hz, 2 H) |
| 24 | 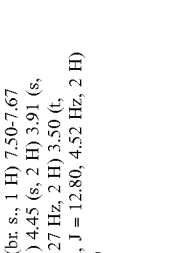 | 3-(4-(1H-pyrazol-4-yl)phenyl)-1-(3,5-difluorobenzyl)-8-oxa-1,3-diazaspiro[4.5]decan-2-one | 425.30 | | 1H NMR (400 MHz, DMSO-d6) δ ppm 12.85 (br. s., 1 H) 8.13 (s, 1 H) 7.88 (br. s., 1 H) 7.50-7.67 (m, 4 H) 7.00-7.15 (m, 3 H) 4.45 (s, 2 H) 3.91 (s, 2 H) 3.84 (dd, J = 11.29, 4.27 Hz, 2 H) 3.50 (t, J = 11.80 Hz, 2 H) 1.86 (td, J = 12.80, 4.52 Hz, 2 H) 1.49 (d, J = 12.05 Hz, 2 H) |
| 25 | 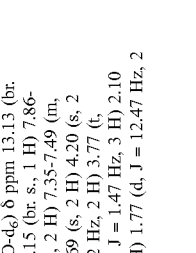 | 3-(4-(1H-pyrazol-4-yl)phenyl)-1-(3-fluoro-2-methylbenzyl)-8-oxa-1,3-diazaspiro[4.5]decan-2-one | 421.30 | E: 1.60 min, 95.3% | 1H NMR (400 MHz, DMSO-d6) δ ppm 13.13 (br. s., 1 H) 8.15 (br. s., 1 H) 7.86-7.95 (m, 2 H) 7.78-7.86 (m, 2 H) 7.35-7.49 (m, 2 H) 7.23-7.33 (m, 1 H) 4.69 (s, 2 H) 4.20 (s, 2 H) 4.08 (dd, J = 11.86, 4.52 Hz, 2 H) 3.77 (t, J = 11.74 Hz, 2 H) 2.51 (d, J = 1.47 Hz, 3 H) 2.10 (td, J = 12.66, 5.01 Hz, 2 H) 1.77 (d, J = 12.47 Hz, 2 H) |
| 26 | 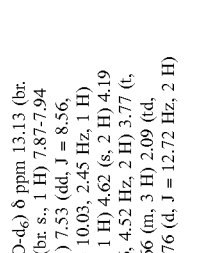 | 3-(4-(1H-pyrazol-4-yl)phenyl)-1-(4-fluoro-2-methylbenzyl)-8-oxa-1,3-diazaspiro[4.5]decan-2-one | 421.30 | E: 1.63 min, 97.4% | 1H NMR (400 MHz, DMSO-d6) δ ppm 13.13 (br. s., 1 H) 8.40 (s, 1 H) 8.15 (br. s., 1 H) 7.87-7.94 (m, 2 H) 7.73-7.87 (m, 2 H) 7.53 (dd, J = 8.56, 6.11 Hz, 1 H) 7.29 (dd, J = 10.03, 2.45 Hz, 1 H) 7.21 (td, J = 8.56, 2.69 Hz, 1 H) 4.62 (s, 2 H) 4.19 (s, 2 H) 4.08 (dd, J = 11.86, 4.52 Hz, 2 H) 3.77 (t, J = 11.62 Hz, 2 H) 2.59-2.66 (m, 3 H) 2.09 (td, J = 12.84, 5.14 Hz, 2 H) 1.76 (d, J = 12.72 Hz, 2 H) |

TABLE 2-continued

| Example | R | Name | LCMS (M + H)+ | HPLC Method, RT (min.) & Purity | NMR |
|---|---|---|---|---|---|
| 27 | 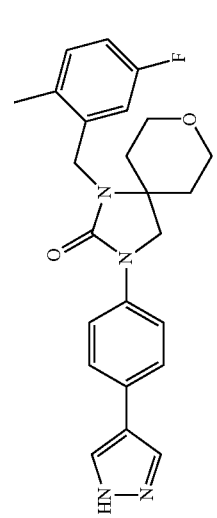 | 3-(4-(1H-pyrazol-4-yl)phenyl)-1-(5-fluoro-2-methylbenzyl)-8-oxa-1,3-diazaspiro[4.5]decan-2-one | 421.30 | E: 1.58 min, 95.5% | 1H NMR (400 MHz, DMSO-d6) δ ppm 13.13 (br. s., 1 H) 8.40 (br. s., 1 H) 8.15 (br. s., 1 H) 7.88-7.95 (m, 2 H) 7.79-7.88 (m, 2 H) 7.45 (dd, J = 8.56, 6.11 Hz, 1 H) 7.31 (dd, J = 10.39, 2.57 Hz, 1 H) 7.21 (td, J = 8.44, 2.93 Hz, 1 H) 4.62 (s, 2 H) 4.23 (s, 2 H) 4.09 (dd, J = 11.49, 4.65 Hz, 2 H) 3.78 (t, J = 11.62 Hz, 2 H) 2.57 (s, 3 H) 2.10 (td, J = 12.72, 4.65 Hz, 2 H) 1.81 (d, J = 12.23 Hz, 2 H) |
| 28 | 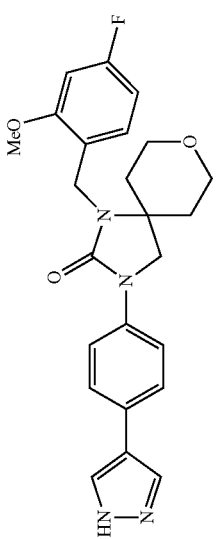 | 3-(4-(1H-pyrazol-4-yl)phenyl)-1-(4-fluoro-2-methoxybenzyl)-8-oxa-1,3-diazaspiro[4.5]decan-2-one | 437.3 | F: 1.58 min, 99.9% | 1H NMR (400 MHz, DMSO-d6) δ ppm 13.13 (br. s., 1 H) 7.89 (m, J = 9.05 Hz, 2 H) 7.83 (m, J = 8.80 Hz, 2 H) 7.47-7.58 (m, 1 H) 7.17 (dd, J = 11.25, 2.45 Hz, 1 H) 6.97 (td, J = 8.56, 2.45 Hz, 1 H) 4.56 (s, 2 H) 4.16 (s, 2 H) 4.13 (s, 3 H) 4.08 (dd, J = 12.01, 4.77 Hz, 2 H) 3.71-3.80 (m, 3 H) 1.97-2.12 (m, 3 H) 1.74 (d, J = 13.45 Hz, 3 H) |
| 29 | 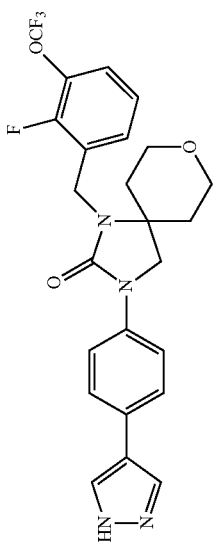 | 3-(4-(1H-pyrazol-4-yl)phenyl)-1-(2-fluoro-3-methoxybenzyl)-8-oxa-1,3-diazaspiro[4.5]decan-2-one | 437.30 | F: 1.49 min, 98.6% | 1H NMR (400 MHz, DMSO-d6) δ ppm 13.13 (br. s., 1 H) 8.39 (br. s., 1 H) 8.15 (br. s., 1 H) 7.86-7.94 (m, 2 H) 7.75-7.86 (m, 2 H) 7.26-7.39 (m, 2 H) 7.22 (td, J = 6.66, 2.57 Hz, 1 H) 6.79 (s, 1 H) 4.70 (s, 2 H) 4.15 (s, 2 H) 3.97-4.12 (m, 5 H) 3.71-3.82 (m, 2 H) 2.11 (td, J = 12.78, 5.01 Hz, 2 H) 1.75 (d, J = 12.47 Hz, 2 H) |
| 30 | 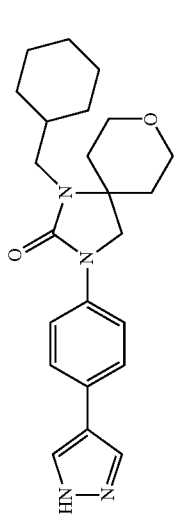 | 3-(4-(1H-pyrazol-4-yl)phenyl)-1-(cyclohexylmethyl)-8-oxa-1,3-diazaspiro[4.5]decan-2-one | 395.30 | F: 1.77 min, 97.8% | 1H NMR (400 MHz, DMSO-d6) δ ppm 13.12 (br. s., 1 H) 8.36 (br. s., 1 H) 8.16 (br. s., 1 H) 7.74-7.92 (m, 4 H) 4.12 (dd, J = 11.74, 4.65 Hz, 2 H) 4.05 (s, 2 H) 3.77 (t, J = 11.62 Hz, 2 H) 3.18 (d, J = 7.34 Hz, 2 H) 2.15 (td, J = 12.78, 5.01 Hz, 2 H) 1.91-2.04 (m, 4 H) 1.79-1.91 (m, 2 H) 1.75 (d, J = 12.96 Hz, 2 H) 1.31-1.54 (m, 3 H) 1.02-1.25 (m, 2 H) |

Example 31

3-((3-(4-(1H-pyrazol-4-yl)phenyl)-2-oxo-8-oxa-1,3-diazaspiro[4.5]decan-1-yl)methyl)-N-methylbenzamide

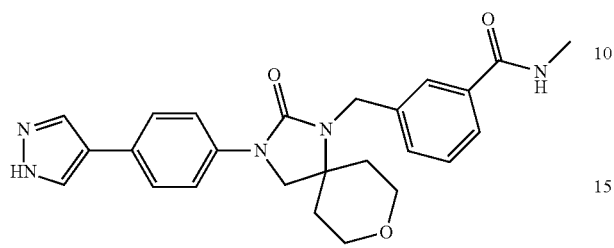

Example 31a

Preparation of 3-((3-(4-bromophenyl)-2-oxo-8-oxa-1,3-diazaspiro[4.5]decan-1-yl)methyl)-N-methylbenzamide

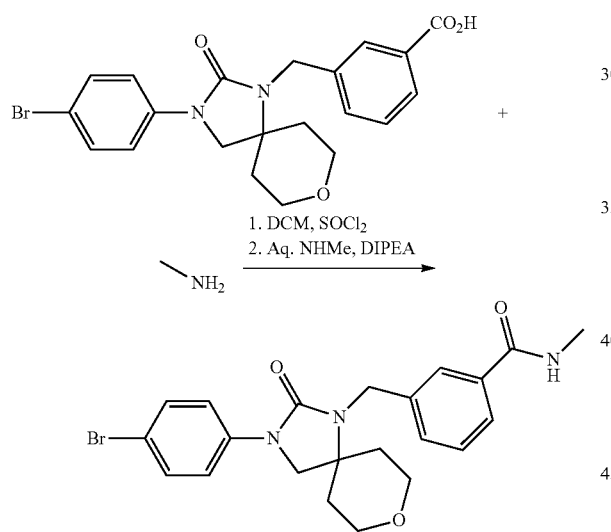

To a solution of 3-((3-(4-bromophenyl)-2-oxo-8-oxa-1,3-diazaspiro[4.5]decan-1-yl)methyl)benzoic acid (70 mg, 0.16 mmol) in DCM (8 mL), was added thionyl chloride (0.017 mL, 0.24 mmol) and a drop of DMF. The reaction mixture was stirred at rt for 2 h. DCM and excess thionyl chloride was removed via evaporation to obtain the 3-((3-(4-bromophenyl)-2-oxo-8-oxa-1,3-diazaspiro[4.5]decan-1-yl)methyl)benzoyl chloride as crude product. A solution of 3-((3-(4-bromophenyl)-2-oxo-8-oxa-1,3-diazaspiro[4.5]decan-1-yl)methyl)benzoyl chloride (35 mg, 0.075 mmol) was added dropwise to methylamine (aqueous, 40%) and DIPEA (33 μL, 0.19 mmol) at 0° C. The mixture was stirred for 5 min, then was allowed to warm to rt and stir for 2.5 h. Reaction mixture was diluted with water, then was extracted with ethyl acetate. The combined ethyl acetate layers were washed with water, brine, dried over $Na_2SO_4$, filtered and concentrated to afford 3-((3-(4-bromophenyl)-2-oxa-1,3-diazaspiro[4.5]decan-1-yl)methyl)-N-methylbenzamide as an off-white solid (50 mg). MS(ESI) m/z: 456.0 (M+H)$^+$; $^1$H NMR (400 MHz, DMSO-$d_6$) δ ppm 7.79 (s, 1H) 7.62-7.68 (m, 2H) 7.50-7.54 (m, 2H) 7.45-7.49 (m, 1H) 7.42-7.45 (m, 1H) 7.36-7.42 (m, 1H) 4.47 (s, 2H) 3.87 (s, 2H) 3.81 (dd, J=12.30, 4.77 Hz, 2H) 3.47 (t, J=11.80 Hz, 2H) 2.77 (d, J=4.52 Hz, 3H) 1.82-1.91 (m, 2H) 1.43 (d, J=12.05 Hz, 2H).

Example 31

Preparation of 3-((3-(4-(1H-pyrazol-4-yl)phenyl)-2-oxo-8-oxa-1,3-diazaspiro[4.5]decan-1-yl)methyl)-N-methylbenzamide

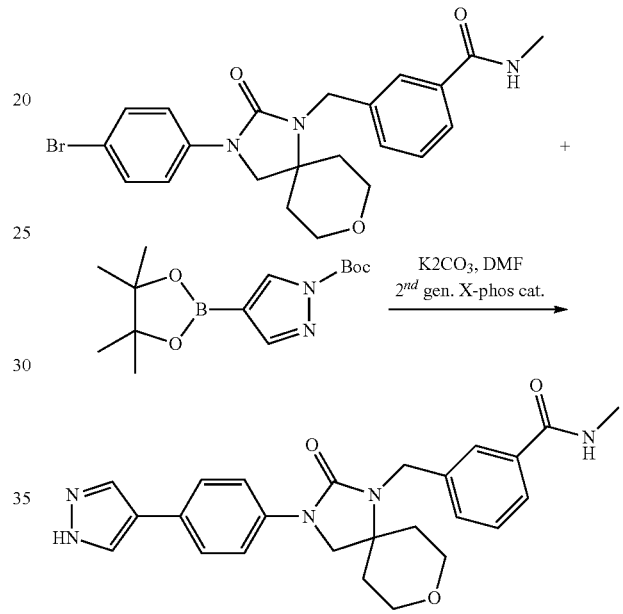

To a solution of 3-((3-(4-bromophenyl)-2-oxo-8-oxa-1,3-diazaspiro[4.5]decan-1-yl)methyl)-N-methylbenzamide (50 mg, 0.109 mmol) in DMF (4 mL) were added tert-butyl 4-(4,4,5,5-tetramethyl-1,3,2-dioxaborolan-2-yl)-1H-pyrazole-1-carboxylate (44.9 mg, 0.153 mmol), $K_2CO_3$ (45.2 mg, 0.327 mmol) and water (0.4 mL). The reaction mixture was purged with nitrogen for 5 min and charged with $2^{nd}$ generation XPHOS precatalyst (5.2 mg, 6.6 μmol). The reaction mixture was again purged with nitrogen for 3 min and heated at 90° C. overnight. The reaction mixture was cooled to rt and filtered. The filtrate was purified by preparative HPLC to afford 3-((3-(4-(1H-pyrazol-4-yl)phenyl)-2-oxo-8-oxa-1,3-diazaspiro[4.5]decan-1-yl)methyl)-N-methylbenzamide as pale yellow solid (7.0 mg, 14% yield). MS(ESI) m/z: 446.1 (M+H)$^+$; $^1$H NMR (400 MHz, DMSO-$d_6$) δ ppm 12.88 (br. s., 1H) 8.43 (d, J=4.40 Hz, 1H) 8.15 (br. s., 1H) 7.89 (br. s., 1H) 7.81 (s, 1H) 7.63-7.71 (m, 3H) 7.59 (d, J=8.80 Hz, 2H) 7.51 (d, J=7.58 Hz, 1H) 7.40 (t, J=7.46 Hz, 1H) 4.48 (s, 2H) 3.90 (s, 2H) 3.82 (dd, J=11.62, 4.52 Hz, 2H) 3.50 (t, J=11.86 Hz, 2H) 2.78 (d, J=4.65 Hz, 3H) 1.80-1.94 (m, 2H) 1.44 (d, J=13.45 Hz, 2H). LCMS RT=1.28 min, 100.0% (Method E), 1.31 min, 100.0% (Method F).

The following Examples in Table 3 were made by using the same procedure as shown in Example 31.

TABLE 3

| Example | R | Name | LCMS (M + H)+ | HPLC Method, RT (min.) & Purity | NMR |
|---|---|---|---|---|---|
| 32 | | 3-((3-(4-(1H-pyrazol-4-yl)phenyl)-2-oxo-8-oxa-1,3-diazaspiro[4.5]decan-1-yl)methyl)benzamide | 432.10 | E: 1.28 min, 100% F: 1.24 min, 100% | ¹H NMR (400 MHz, DMSO-d6) δ ppm 12.88 (br. s., 1 H) 8.15 (br. s., 1 H) 7.98 (s, 1 H) 7.90 (br. s., 1 H) 7.85 (s, 1 H) 7.74 (d, J = 7.83 Hz, 1 H) 7.66 (m, J = 8.56 Hz, 2 H) 7.59 (m, J = 8.80 Hz, 2 H) 7.52 (d, J = 7.58 Hz, 1 H) 7.40 (t, J = 7.70 Hz, 2 H) 4.48 (s, 2 H) 3.90 (s, 2 H) 3.82 (dd, J = 11.49, 4.16 Hz, 2 H) 3.50 (t, J = 12.10 Hz, 2 H) 1.88 (td, J = 12.84, 4.89 Hz, 2 H) 1.45 (d, J = 12.47 Hz, 2 H) |
| 33 | | 3-((3-(4-(1H-pyrazol-4-yl)phenyl)-2-oxo-8-oxa-1,3-diazaspiro[4.5]decan-1-yl)methyl)-N-cyclobutylbenzamide | 486.10 | F: 1.56 min, 98.6% | ¹H NMR (400 MHz, DMSO-d6) δ ppm 12.85 (br. s., 1 H) 8.57 (d, J = 7.53 Hz, 1 H) 8.13 (br. s., 1 H) 7.88 (s, 1 H) 7.81 (s, 1 H) 7.70 (d, J = 8.03 Hz, 1 H) 7.60-7.68 (m, 2 H) 7.52-7.60 (m, 2 H) 7.50 (d, J = 8.03 Hz, 1 H) 7.39 (t, J = 7.78 Hz, 1 H) 4.48 (s, 2 H) 4.33-4.46 (m, 1 H) 3.88 (s, 2 H) 3.81 (dd, J = 12.05, 4.52 Hz, 2 H) 3.49 (t, J = 11.80 Hz, 2 H) 2.14-2.26 (m, 2 H) 1.98-2.11 (m, 2 H) 1.88 (td, J = 12.55, 4.52 Hz, 2 H) 1.58-1.75 (m, 2 H) 1.43 (d, J = 13.05 Hz, 2 H) |
| 34 | | 3-((3-(4-(1H-pyrazol-4-yl)phenyl)-2-oxo-8-oxa-1,3-diazaspiro[4.5]decan-1-yl)methyl)-N-isopropylbenzamide | 474.40 | F: 1.27 min, 96.5% | ¹H NMR (400 MHz, DMSO-d6) δ ppm 12.86 (br. s., 1 H) 8.18 (d, J = 7.53 Hz, 1 H) 8.13 (br. s., 1 H) 7.88 (br. s., 1 H) 7.82 (s, 1 H) 7.70 (d, J = 8.03 Hz, 1 H) 7.61-7.67 (m, 2 H) 7.53-7.61 (m, 2 H) 7.49 (d, J = 8.03 Hz, 1 H) 7.38 (t, J = 7.53 Hz, 1 H) 4.48 (s, 2 H) 4.02-4.16 (m, 1 H) 3.89 (s, 2 H) 3.82 (dd, J = 11.55, 4.52 Hz, 2 H) 3.50 (t, J = 11.55 Hz, 2 H) 1.88 (td, J = 12.80, 5.02 Hz, 2 H) 1.44 (d, J = 12.55 Hz, 2 H) 1.16 (d, J = 6.53 Hz, 6 H) |
| 35 | | 3-((3-(4-(1H-pyrazol-4-yl)phenyl)-2-oxo-8-oxa-1,3-diazaspiro[4.5]decan-1-yl)methyl)-N-isobutylbenzamide | 488.10 | F: 1.62 min, 98.7% | ¹H NMR (400 MHz, DMSO-d6) δ ppm 12.85 (br. s., 1 H) 8.42 (t, J = 6.02 Hz, 1 H) 8.13 (s, 1 H) 7.88 (br. s., 1 H) 7.82 (s, 1 H) 7.70 (d, J = 8.03 Hz, 1 H) 7.60-7.67 (m, 2 H) 7.52-7.60 (m, 2 H) 7.50 (d, J = 8.03 Hz, 1 H) 7.39 (t, J = 7.53 Hz, 1 H) 4.48 (s, 2 H) 3.89 (s, 2 H) 3.75-3.85 (m, 2 H) 3.50 (t, J = 11.80 Hz, 2 H) 3.03-3.13 (m, 2 H) 1.86 (tt, J = 13.68, 7.15 Hz, 3 H) 1.44 (d, J = 13.05 Hz, 2 H) 0.88 (d, J = 6.53 Hz, 6 H) |

TABLE 3-continued

| Example | R | Name | LCMS (M + H)+ | HPLC Method, RT (min.) & Purity | NMR |
|---|---|---|---|---|---|
| 36 | (structure with hydroxyethyl amide) | 3-((3-(4-(1H-pyrazol-4-yl)phenyl)-2-oxo-8-oxa-1,3-diazaspiro[4.5]decan-1-yl)methyl)-N-(2-hydroxyethyl)benzamide | 476.10 | E: 1.18 min, 99.6% | $^1$H NMR (400 MHz, DMSO-d$_6$) δ ppm 12.86 (br. s., 1 H) 8.41 (t, J = 5.77 Hz, 1 H) 8.14 (br. s., 1 H) 7.89 (br. s., 1 H) 7.84 (s, 1 H) 7.72 (d, J = 7.53 Hz, 1 H) 7.62-7.69 (m, 2 H) 7.55-7.61 (m, 2 H) 7.51 (d, J = 8.03 Hz, 1 H) 7.40 (t, J = 7.53 Hz, 1 H) 4.48 (s, 2 H) 3.90 (s, 2 H) 3.82 (dd, J = 11.55, 4.52 Hz, 2 H) 3.45-3.55 (m, 4 H) 3.33-3.37 (m, 2 H) 1.83-1.94 (m, 2 H) 1.45 (d, J = 13.05 Hz, 2 H) |
| 37 | (structure with cyclopropylmethyl amide) | 3-((3-(4-(1H-pyrazol-4-yl)phenyl)-2-oxo-8-oxa-1,3-diazaspiro[4.5]decan-1-yl)methyl)-N-(cyclopropylmethyl)benzamide | 486.10 | F: 1.54 min, 98.8% | $^1$H NMR (400 MHz, DMSO-d$_6$) δ ppm 12.85 (br. s., 1 H) 8.52 (s, 1 H) 8.13 (s, 1 H) 7.88 (br. s., 1 H) 7.83 (s, 1 H) 7.71 (d, J = 8.03 Hz, 1 H) 7.65 (d, J = 9.04 Hz, 2 H) 7.57 (d, J = 9.04 Hz, 2 H) 7.50 (d, J = 8.03 Hz, 1 H) 7.40 (t, J = 7.78 Hz, 1 H) 4.48 (s, 2 H) 3.89 (s, 2 H) 3.82 (s, 2 H) 3.50 (t, J = 12.05 Hz, 2 H) 3.14 (t, J = 6.27 Hz, 2 H) 1.81-1.93 (m, 2 H) 1.44 (d, J = 13.05 Hz, 2 H) 1.02 (d, J = 5.02 Hz, 1 H) 0.36-0.46 (m, 2 H) 0.15-0.27 (m, 2 H) |
| 38 | (structure with trifluoroethyl amide) | 3-((3-(4-(1H-pyrazol-4-yl)phenyl)-2-oxo-8-oxa-1,3-diazaspiro[4.5]decan-1-yl)methyl)-N-(2,2,2-trifluoroethyl)benzamide | 514.0 | F: 1.58 min, 99.6% | $^1$H NMR (400 MHz, DMSO-d$_6$) δ ppm 12.85 (br. s., 1 H) 9.06 (t, J = 6.27 Hz, 1 H) 8.13 (s, 1 H) 7.87 (s, 2 H) 7.75 (d, J = 8.03 Hz, 1 H) 7.61-7.69 (m, 2 H) 7.49-7.61 (m, 3 H) 7.39-7.47 (m, 1 H) 4.49 (s, 2 H) 4.00-4.14 (m, 2 H) 3.89 (s, 2 H) 3.82 (dd, J = 11.80, 4.77 Hz, 2 H) 3.50 (t, J = 11.80 Hz, 2 H) 1.80-1.97 (m, 2 H) 1.44 (d, J = 12.55 Hz, 2 H) |
| 39 | (structure with 1-methylcyclopropyl amide) | 3-((3-(4-(1H-pyrazol-4-yl)phenyl)-2-oxo-8-oxa-1,3-diazaspiro[4.5]decan-1-yl)methyl)-N-(1-methylcyclopropyl)benzamide | 486.10 | E: 1.470 min, 99.0% | $^1$H NMR (400 MHz, DMSO-d$_6$) δ ppm 12.85 (br. s., 1 H) 8.61 (s, 1 H) 8.13 (s, 1 H) 7.88 (br. s., 1 H) 7.79 (s, 1 H) 7.61-7.68 (m, 3 H) 7.55-7.61 (m, 2 H) 7.48 (d, J = 1.53 Hz, 1 H) 7.36 (t, J = 7.78 Hz, 1 H) 4.46 (s, 2 H) 3.89 (s, 2 H) 3.75-3.85 (m, 2 H) 3.49 (t, J = 12.30 Hz, 2 H) 1.88 (t, J = 12.80 Hz, 2 H) 1.43 (d, J = 13.05 Hz, 2 H) 1.36 (s, 3 H) 0.68-0.78 (m, 2 H) 0.53-0.62 (m, 2 H) |

TABLE 3-continued

| Example | R | | LCMS (M + H)+ | HPLC Method, RT (min.) & Purity | Name | NMR |
|---|---|---|---|---|---|---|
| 40 | 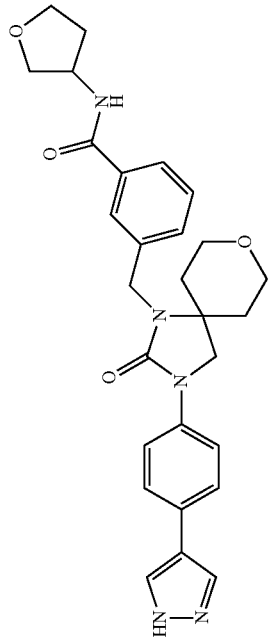 | | 502.1 | F: 1.34 min, 99.0% | 3-((3-(4-(1H-pyrazol-4-yl)phenyl)-2-oxo-8-oxa-1,3-diazaspiro[4.5]decan-1-yl)methyl)-N-(tetrahydrofuran-3-yl)benzamide | $^{1}$H NMR (400 MHz, DMSO-$d_6$) δ ppm 8.51 (d, J = 6.53 Hz, 1 H) 8.02 (br. s., 2 H) 7.84 (s, 1 H) 7.73 (d, J = 7.53 Hz, 1 H) 7.62-7.70 (m, 2 H) 7.54-7.62 (m, 2 H) 7.51 (d, J = 8.03 Hz, 1 H) 7.40 (t, J = 7.78 Hz, 1 H) 4.39-4.55 (m, 3 H) 4.08 (br. s., 1 H) 3.77-3.94 (m, 7 H) 3.72 (td, J = 8.03, 6.02 Hz, 1 H) 3.59 (dd, J = 8.78, 4.27 Hz, 1 H) 3.47-3.54 (m, 2 H) 3.18 (s, 2 H) 2.08-2.22 (m, 1 H) 1.79-1.99 (m, 6 H) 1.44 (d, J = 12.55 Hz, 2 H) |
| 41 | 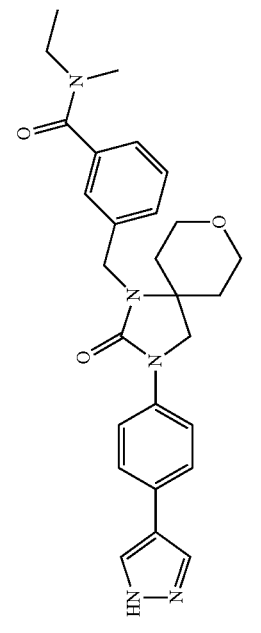 | | 474.10 | F: 1.46 min, 99.1% | 3-((3-(4-(1H-pyrazol-4-yl)phenyl)-2-oxo-8-oxa-1,3-diazaspiro[4.5]decan-1-yl)methyl)-N-ethyl-N-methylbenzamide | $^{1}$H NMR (400 MHz, DMSO-$d_6$) δ ppm 12.86 (br. s., 1 H) 8.14 (br. s., 1 H) 7.89 (br. s., 2 H) 7.62-7.69 (m, 2 H) 7.51-7.62 (m, 2 H) 7.30-7.49 (m, 3 H) 7.23 (d, J = 6.53 Hz, 1 H) 4.48 (s, 2 H) 3.89 (s, 2 H) 3.82 (dd, J = 11.80, 4.27 Hz, 2 H) 3.50 (t, J = 11.80 Hz, 3 H) 3.18 (d, J = 5.02 Hz, 1 H) 2.92 (br. s., 2 H) 2.87 (br. s., 1 H) 1.81-1.98 (m, 2 H) 1.37-1.51 (m, 2 H) 1.12 (br. s., 1 H) 1.04 (br. s., 2 H) |
| 42 | 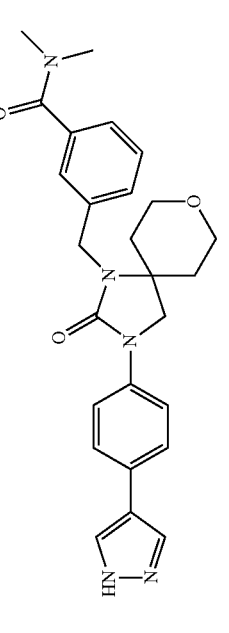 | | 460.10 | E: 1.33 min, 98.3% | 3-((3-(4-(1H-pyrazol-4-yl)phenyl)-2-oxo-8-oxa-1,3-diazaspiro[4.5]decan-1-yl)methyl)-N,N-dimethylbenzamide | $^{1}$H NMR (400 MHz, DMSO-$d_6$) δ ppm 12.85 (br. s., 1 H) 8.13 (br. s., 1 H) 7.88 (br. s., 1 H) 7.64 (m, J = 9.04 Hz, 2 H) 7.57 (m, J = 9.04 Hz, 2 H) 7.41-7.48 (m, 1 H) 7.32-7.41 (m, 2 H) 7.25 (d, J = 7.53 Hz, 1 H) 4.47 (s, 2 H) 3.89 (s, 2 H) 3.82 (d, J = 6.53 Hz, 2 H) 3.49 (t, J = 11.29 Hz, 2 H) 2.97 (br. s., 3 H) 2.88 (br. s., 3 H) 1.78-1.94 (m, 2 H) 1.44 (d, J = 13.05 Hz, 2 H) |
| 43 | 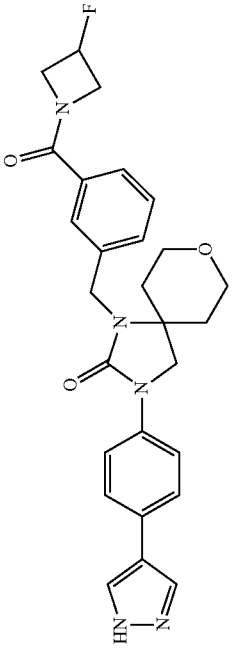 | | 490.40 | E: 1.19 min, 97.6% | 3-(4-(1H-pyrazol-4-yl)phenyl)-1-(3-(3-fluoroazetidine-1-carbonyl)benzyl)-8-oxa-1,3-diazaspiro[4.5]decan-2-one | $^{1}$H NMR (400 MHz, DMSO-$d_6$) δ ppm 12.85 (br. s., 1 H) 8.13 (br. s., 1 H) 7.89 (br. s., 1 H) 7.61-7.70 (m, 3 H) 7.55-7.61 (m, 2 H) 7.46-7.55 (m, 2 H) 7.35-7.46 (m, 3 H) 5.34 (tt, J = 6.02, 3.01 Hz, 1 H) 4.48 (s, 3 H) 4.37 (dd, J = 6.02, 4.05 Hz, 2 H) 3.89 (s, 2 H) 3.82 (dd, J = 11.55, 4.52 Hz, 2 H) 3.50 (t, J = 11.80 Hz, 2 H) 1.78-2.01 (m, 2 H) 1.43 (d, J = 12.55 Hz, 2 H) |

TABLE 3-continued

| Example | R | Name | LCMS (M + H)+ | HPLC Method, RT (min.) & Purity | NMR |
|---|---|---|---|---|---|
| 44 | | (S)-3-(4-(1H-pyrazol-4-yl)phenyl)-1-(3-(3-hydroxypyrrolidine-1-carbonyl)benzyl)-8-oxa-1,3-diazaspiro[4.5]decan-2-one | 502.10 | F: 1.22 min, 99.0% | $^1$H NMR (400 MHz, DMSO-d$_6$) δ ppm 12.87 (br. s., 1 H) 8.12 (br. s., 1 H) 7.91 (br. s., 1 H) 7.65 (m, J = 9.04 Hz, 2 H) 7.58 (m, J = 9.04 Hz, 2 H) 7.46 (d, J = 6.53 Hz, 1 H) 7.50 (d, J = 6.53 Hz, 1 H) 7.28-7.42 (m, 2 H) 4.99 (d, J = 3.51 Hz, 1 H) 4.92 (d, J = 3.51 Hz, 1 H) 4.48 (s, 2 H) 4.32 (br. s., 1 H) 4.21 (br. s., 1 H) 3.89 (s, 2 H) 3.83 (d, J = 8.03 Hz, 2 H) 3.45-3.62 (m, 5 H) 1.83-1.97 (m, 4 H) 1.78 (br. s., 1 H) 1.44 (d, J = 12.55 Hz, 2H) |
| 45 | | 3-((3-(4-(1H-pyrazol-4-yl)phenyl)-2-oxo-8-oxa-1,3-diazaspiro[4.5]decan-1-yl)methyl)-N-cyclopropyl-N-methylbenzamide | 486.10 | E: 1.49 min, 96.9% | $^1$H NMR (400 MHz, DMSO-d$_6$) δ ppm 12.86 (br. s., 1 H) 8.58 (d, J = 7.53 Hz, 1 H) 8.14 (br. s., 1 H) 7.89 (m, 3 H) 7.82 (s, 1 H) 7.71 (d, J = 7.53 Hz, 1 H) 7.62-7.68 (m, 2 H) 7.53-7.62 (m, 2 H) 7.50 (d, J = 8.03 Hz, 1 H) 7.40 (t, J = 7.53 Hz, 1 H) 4.48 (s, 2 H) 4.41 (q, J = 8.20 Hz, 1 H) 3.89 (s, 2 H) 3.82 (dd, J = 12.55, 4.52 Hz, 2 H) 3.50 (t, J = 11.55 Hz, 2 H) 2.15-2.27 (m, 2 H) 1.98-2.14 (m, 2 H) 1.81-1.94 (m, 2 H) 1.61-1.74 (m, 2 H) 1.44 (d, J = 12.55 Hz, 2 H) |
| 46 | | 3-(4-(1H-pyrazol-4-yl)phenyl)-1-(3-(3-(dimethylamino)azetidine-1-carbonyl)benzyl)-8-oxa-1,3-diazaspiro[4.5]decan-2-one | 515.10 | F: 1.33 min, 95.8% | $^1$H NMR (400 MHz, DMSO-d$_6$) δ ppm 12.86 (br. s., 1 H) 7.89 (br. s., 1 H) 7.60-7.70 (m, 3 H) 7.54-7.60 (m, 2 H) 7.46-7.54 (m, 2 H) 7.36-7.44 (m, 1 H) 4.49 (s, 2 H) 4.20-4.32 (m, 1 H) 3.98-4.13 (m, 2 H) 3.89 (s, 2 H) 3.70-3.86 (m, 3 H) 3.50 (t, J = 11.80 Hz, 2 H) 3.04 (br. s., 1 H) 2.05 (s, 6 H) 1.83-1.96 (m, 2 H) 1.44 (d, J = 13.05 Hz, 2 H) |
| 47 | | 3-(4-(1H-pyrazol-4-yl)phenyl)-1-(3-(4-(hydroxymethyl)piperidine-1-carbonyl)benzyl)-8-oxa-1,3-diazaspiro[4.5]decan-2-one | 530.40 | F: 1.11 min, 95.7% | $^1$H NMR (400 MHz, DMSO-d$_6$) δ ppm 12.86 (br. s., 1 H) 8.11 (br. s., 1 H) 7.89 (m, 2 H) 7.59-7.71 (m, 2 H) 7.48-7.59 (m, 2 H) 7.43-7.48 (m, 1 H) 7.27-7.43 (m, 2 H) 7.14-7.26 (m, 1 H) 4.47 (s, 4 H) 3.88 (s, 2 H) 3.82 (dd, J = 11.80, 4.77 Hz, 2 H) 3.49 (t, J = 11.55 Hz, 3 H) 3.23 (t, J = 5.27 Hz, 2 H) 2.98 (d, J = 13.05 Hz, 1 H) 2.66-2.83 (m, 1 H) 1.80-1.96 (m, 2 H) 1.76 (br. s., 1 H) 1.61 (d, J = 3.01 Hz, 2 H) 1.43 (d, J = 13.05 Hz, 2 H) 1.08 (br. s., 2H) |

Example 48 tert-butyl 3-(4-(1H-pyrazol-4-yl)phenyl)-1-(3-methoxybenzyl)-2-oxo-1,3,8-triazaspiro[4.5]decane-8-carboxylate

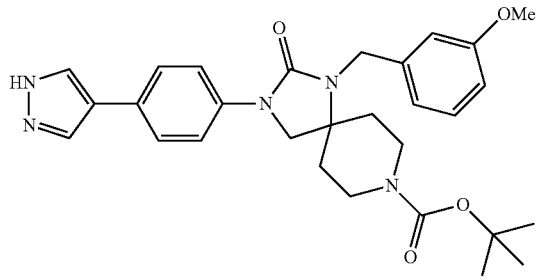 [SMILES: COc1cccc(CN2C(=O)N(c3ccc(-c4cn[nH]c4)cc3)CC23CCN(C(=O)OC(C)(C)C)CC3)c1]

Preparation of tert-butyl 3-(4-(1H-pyrazol-4-yl)phenyl)-1-(3-methoxybenzyl)-2-oxo-1,3,8-triazaspiro[4.5]decane-8-carboxylate

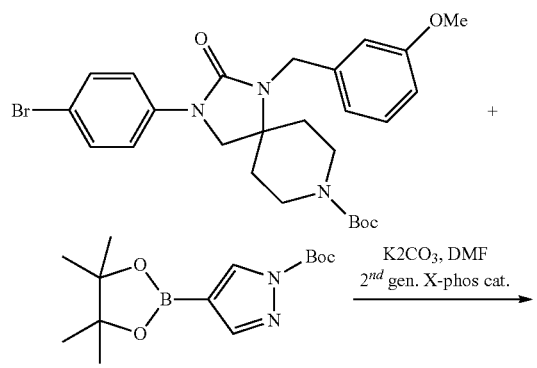

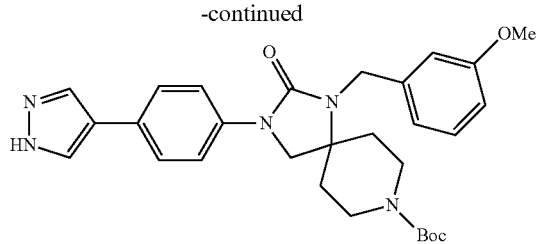

-continued

To a solution of tert-butyl 3-(4-bromophenyl)-1-(3-methoxybenzyl)-2-oxo-1,3,8-triazaspiro[4.5]decane-8-carboxylate (25 mg, 0.047 mmol) in DMF (2 mL) were added tert-butyl 4-(4,4,5,5-tetramethyl-1,3,2-dioxaborolan-2-yl)-1H-pyrazole-1-carboxylate (19.4 mg, 0.066 mmol), $K_2CO_3$ (19.5 mg, 0.141 mmol) and water (0.4 mL). The reaction mixture was purged with nitrogen for 5 min and charged with $2^{nd}$ generation XPHOS precatalyst (2.2 mg, 2.8 µmol). The reaction mixture was again purged with nitrogen for 3 min and heated at 90° C. overnight. The reaction mixture was cooled to rt and evaporated. The crude material was purified by preparative HPLC to afford tert-butyl 3-(4-(1H-pyrazol-4-yl)phenyl)-1-(3-methoxybenzyl)-2-oxo-1,3,8-triazaspiro[4.5]decane-8-carboxylate as pale yellow solid (13.8 mg, 55% yield). MS(ESI) m/z: 518.3 $(M+H)^+$; $^1H$ NMR (400 MHz, DMSO-$d_6$) δ ppm 12.86 (br. s., 1H) 8.12 (br. s., 1H) 7.89 (br. s., 1H) 7.63 (d, J=9.05 Hz, 2H) 7.58 (d, J=8.80 Hz, 2H) 7.23 (t, J=7.95 Hz, 1H) 6.85-6.96 (m, 2H) 6.75-6.84 (m, 1H) 4.38 (s, 2H) 3.87-4.00 (m, 2H) 3.83 (s, 2H) 3.73 (s, 3H) 2.90 (br. s., 2H) 1.60-1.75 (m, 2H) 1.49 (d, J=12.47 Hz, 2H) 1.39 (s, 9H). LCMS RT=2.18 min, 98.1% (Method E), 2.14 min, 97.7% (Method F).

The following Examples in Table 4 were made by using the same procedure as shown in Example 48.

TABLE 4

| Example | R | Name | LCMS (M + H)+ | HPLC Method, RT (min.) & Purity | NMR |
|---|---|---|---|---|---|
| 49 | (structure) | tert-butyl 3-(4-(1H-pyrazol-4-yl)phenyl)-1-(3-fluoro-2-methylbenzyl)-2-oxo-1,3,8-triazaspiro[4.5]decane-8-carboxylate | 520.10 | E: 2.23 min, 100% F: 2.29 min, 100% | $^1$H NMR (400 MHz, DMSO-d6) δ ppm 12.86 (br. s., 1 H) 8.13 (br. s., 1 H) 7.89 (br. s., 1 H) 7.64 (m, J = 9.05 Hz, 2 H) 7.58 (m, J = 8.80 Hz, 2 H) 7.09-7.21 (m, 2 H) 7.00-7.07 (m, 1 H) 4.41 (s, 2 H) 3.89 (s, 4 H) 2.92 (br. s., 2 H) 2.23 (s, 3 H) 1.62-1.75 (m, 2 H) 1.57 (d, J = 11.98 Hz, 2 H) 1.39 (s, 9 H). $^{19}$F NMR (376 MHz, DMSO-d6) d ppm −118.264 |
| 50 | (structure) | 3-(5-(1H-pyrazol-4-yl)pyridin-2-yl)-8-acetyl-1-(3-methoxybenzyl)-1,3,8-triazaspiro[4.5]decan-2-one | 461.10 | E: 1.22 min, 96.0% F: 1.41 min, 97.4% | $^1$H NMR (400 MHz, DMSO-d6) δ ppm 12.96 (s, 1 H) 8.59 (d, J = 2.45 Hz, 1 H) 8.13-8.32 (m, 1 H) 7.98 (dd, J = 8.68, 2.32 Hz, 2 H) 7.15-7.28 (m, 1 H) 6.88-6.95 (m, 2 H) 6.81 (d, J = 9.05 Hz, 1 H) 4.36-4.46 (m, 2 H) 4.03 (s, 2 H) 3.82 (d, J = 16.63 Hz, 1 H) 3.74 (s, 3 H) 3.19 (t, J = 13.57 Hz, 1 H) 2.59-2.70 (m, 1 H) 2.00 (s, 3 H) 1.77-1.90 (m, 2 H) 1.66 (d, J = 12.23 Hz, 1H) 1.45-1.60 (m, 2H) |
| 51 | (structure) | tert-butyl 3-(5-(1H-pyrazol-4-yl)pyridin-2-yl)-1-(3-methoxybenzyl)-2-oxo-1,3,8-triazaspiro[4.5]decane-8-carboxylate | 519.10 | E: 1.82 min, 100% F: 2.06 min, 100% | $^1$H NMR (400 MHz, DMSO-d6) δ ppm 12.98 (br. s., 1 H) 8.58 (d, J = 1.96 Hz, 1 H) 8.19 (d, J = 8.80 Hz, 2 H) 7.90-8.02 (m, 2 H) 7.19-7.28 (m, 1 H) 6.86-6.95 (m, 2 H) 6.81 (d, J = 9.05 Hz, 1 H) 4.41 (s, 2 H) 3.98 (s, 2 H) 3.92 (d, J = 11.74 Hz, 2 H) 3.73 (s, 3 H) 2.86 (d, J = 4.89 Hz, 2 H) 1.61-1.77 (m, 2 H) 1.51 (d, J = 12.72 Hz, 2 H) 1.39 (s, 9 H) |

| Example | R | Name | LCMS (M + H)+ | HPLC Method, RT (min.) & Purity | NMR |
|---|---|---|---|---|---|
| 52 | 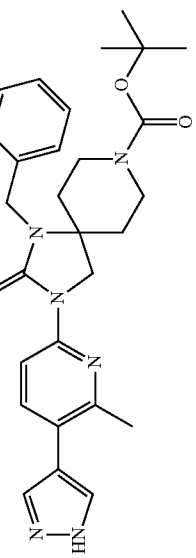 | tert-butyl 1-(3-methoxybenzyl)-3-(6-methyl-5-(1H-pyrazol-4-yl)pyridin-2-yl)-2-oxo-1,3,8-triazaspiro[4.5]decane-8-carboxylate | 533.3 | E: 1.81 min, 100% F: 2.22 min, 100% | 1H NMR (400 MHz, DMSO-d6) δ ppm 13.01 (br. s., 1H), 8.04 (d, J = 8.6 Hz, 1H), 8.01-7.95 (m, 1H), 7.76 (d, J = 8.6 Hz, 2H), 7.23 (t, J = 8.1 Hz, 1H), 6.96-6.87 (m, 2H), 6.85-6.76 (m, 1H), 4.41 (s, 2H), 3.98 (s, 2H), 3.91 (br. s., 2H), 3.73 (s, 3H), 2.87 (br. s., 2H), 2.54 (s, 3H), 1.76-1.63 (m, 2H), 1.56-1.46 (m, 2H), 1.40 (s, 9H) |
| 53 | 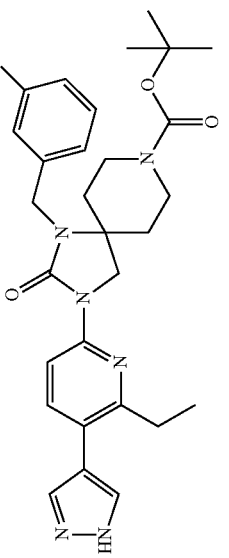 | tert-butyl 3-(6-ethyl-5-(1H-pyrazol-4-yl)pyridin-2-yl)-1-(3-methoxybenzyl)-2-oxo-1,3,8-triazaspiro[4.5]decane-8-carboxylate | 547.3 | E: 1.89 min, 100% F: 2.36 min, 100% | 1H NMR (400 MHz, DMSO-d6) δ ppm 12.99 (br. s., 1H), 8.02 (d, J = 8.6 Hz, 1H), 7.93 (br. s., 1H), 7.69 (d, J = 8.6 Hz, 2H), 7.23 (t, J = 7.9 Hz, 1H), 6.96-6.88 (m, 2H), 6.85-6.77 (m, 1H), 4.42 (s, 2H), 4.00 (s, 2H), 3.97-3.84 (m, 2H), 3.73 (s, 3H), 2.82 (q, J = 7.4 Hz, 4H), 1.72 (d, J = 4.6 Hz, 2H), 1.52 (d, J = 12.2 Hz, 2H), 1.40 (s, 9H), 1.24 (t, J = 7.5 Hz, 3H) |
| 54 | 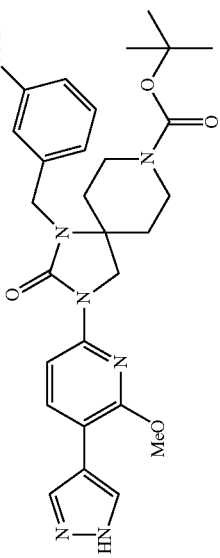 | tert-butyl 3-(6-methoxy-5-(1H-pyrazol-4-yl)pyridin-2-yl)-1-(3-methoxybenzyl)-2-oxo-1,3,8-triazaspiro[4.5]decane-8-carboxylate | 549.3 | E: 2.26 min, 100% F: 2.26 min, 100% | 1H NMR (400 MHz, DMSO-d6) δ ppm 12.88 (br. s., 1 H), 8.09 (br. s., 1 H), 8.04-7.90 (m, 2 H), 7.75 (d, J = 8.3 Hz, 1 H), 7.26-7.20 (m, 1 H), 6.93-6.88 (m, 2 H), 6.80 (d, J = 6.8 Hz, 1 H), 4.41 (s, 2 H), 4.01 (s, 5 H), 3.91 (br. s., 2 H), 3.73 (s, 3 H), 2.95-2.85 (m, 2 H), 1.78-1.67 (m, 2 H), 1.55-1.44 (m, 2 H), 1.39 (s, 9 H) |

TABLE 4-continued

| Example | R | Name | LCMS (M + H)+ | HPLC Method, RT (min.) & Purity | NMR |
|---|---|---|---|---|---|
| 55 | (structure with F, methyl, pyridine-OMe, pyrazole, Boc-piperidine spiro) | tert-butyl 1-(3-fluoro-2-methylbenzyl)-3-(6-methoxy-5-(1H-pyrazol-4-yl)pyridin-2-yl)-2-oxo-1,3,8-triazaspiro[4.5]decane-8-carboxylate | 551.3 | E: 1.35 min, 94.8% F: 1.83 min, 94.1% | $^1$H NMR (400 MHz, DMSO-d6) δ ppm 12.88 (br. s., 1 H), 8.09 (br. s., 1 H), 7.99 (d, J = 8.3 Hz, 1 H), 7.95 (br. s., 1 H), 7.73 (d, J = 8.3 Hz, 1 H), 7.18-7.13 (m, 1 H), 7.12-7.08 (m, 1 H), 7.07-7.00 (m, 1 H), 4.43 (s, 2 H), 4.08 (s, 2 H), 4.03 (s, 3 H), 3.92 (br. s., 2 H), 2.91 (br. s., 2 H), 2.22 (s, 3 H), 1.76-1.64 (m, 2 H), 1.62-1.54 (m, 2 H), 1.39 (s, 9 H); $^{19}$F NMR (376 MHz, DMSO-d6) δ ppm -118.25 |
| 56 | (structure with OMe, pyrimidine-OMe, pyrazole, Boc-piperidine spiro) | tert-butyl 3-(4-methoxy-5-(1H-pyrazol-2-yl)pyrimidin-2-yl)-1-(3-methoxybenzyl)-2-oxo-1,3,8-triazaspiro[4.5]decane-8-carboxylate | 550.3 | E: 1.35 min, 96.5% F: 1.50 min, 95.2% | $^1$H NMR (400 MHz, DMSO-d$_6$) δ ppm 13.01 (br. s., 1 H) 8.70 (s, 1 H) 8.16 (br. s., 1 H) 8.00 (br. s., 1 H) 7.18-7.28 (m, 1 H) 6.96 (m, 2 H) 6.81 (d, J = 8.31 Hz, 1 H) 4.40 (s, 2 H) 4.05-4.13 (m, 3 H) 3.85-4.02 (m, 4 H) 3.73 (s, 3 H) 2.76-2.99 (m, 2 H) 1.63-1.77 (m, 2 H) 1.51 (d, J = 12.47 Hz, 2 H) 1.39 (s, 9 H) |

Example 57

3-(4-(1H-pyrazol-4-yl)phenyl)-1-(3-methoxybenzyl)-1,3,8-triazaspiro[4.5]decan-2-one

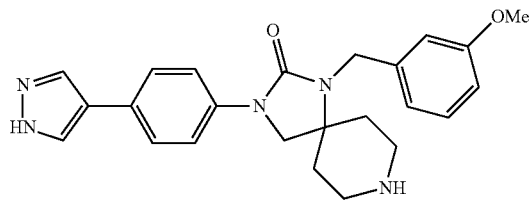 [SMILES: COc1cccc(CN2C(=O)N(c3ccc(-c4cn[nH]c4)cc3)CC23CCNCC3)c1]

Preparation of 3-(4-(H-pyrazol-4-yl)phenyl)-1-(3-methoxybenzyl)-1,3,8-triazaspiro[4.5]decan-2-one

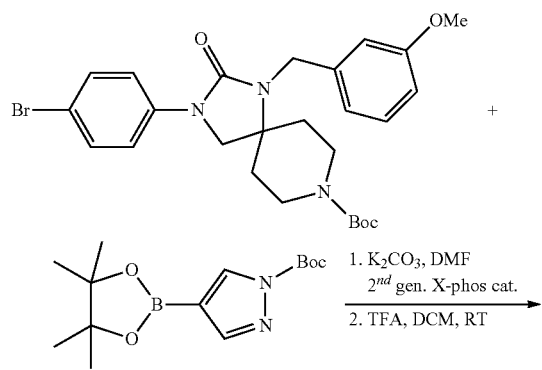

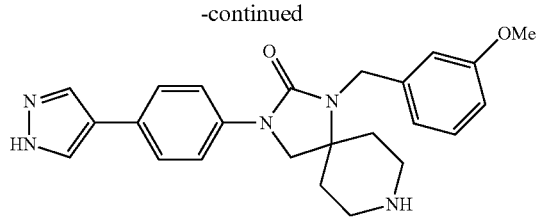

To a solution of tert-butyl 3-(4-bromophenyl)-1-(3-methoxybenzyl)-2-oxo-1,3,8-triazaspiro[4.5]decane-8-carboxylate (40 mg, 0.075 mmol) in DMF (4 mL) were added tert-butyl 4-(4,4,5,5-tetramethyl-1,3,2-dioxaborolan-2-yl)-1H-pyrazole-1-carboxylate (31.1 mg, 0.106 mmol), $K_2CO_3$ (31.3 mg, 0.226 mmol) and Water (0.4 mL). The reaction mixture was purged with nitrogen for 5 min and charged with $2^{nd}$ generation XPHOS precatalyst (3.6 mg, 4.5 μmol). The reaction mixture was again purged with nitrogen for 3 min and heated at 90° C. overnight. The reaction mixture was cooled to rt and concentrated. The residue was partitioned between water and ethyl acetate. Aqueous layer was extracted with ethyl acetate. The combined ethyl acetate layers were washed with brine solution, dried by $Na_2SO_4$, filtered and concentrated. The solid was dissolved DCM (3 mL), then TFA (0.2 mL, 2.6 mmol) was added. The reaction mixture was stirred at rt for 3 h, then was concentrated. The crude product was purified by preparative HPLC to afford 3-(4-(1H-pyrazol-4-yl)phenyl)-1-(3-methoxybenzyl)-1,3,8-triazaspiro[4.5]decan-2-one as a white solid (11.4 mg, 35% yield). MS(ESI) m/z: 418.2 (M+H)$^+$; $^1$H NMR (400 MHz, DMSO-d$_6$) δ ppm 8.00 (br. s., 2H) 7.60-7.67 (m, 2H) 7.52-7.59 (m, 2H) 7.19-7.27 (m, 1H) 6.88-6.94 (m, 2H) 6.79 (dd, J=7.53, 2.51 Hz, 1H) 4.37 (s, 2H) 3.77 (s, 2H) 3.73 (s, 3H) 2.86 (d, J=11.04 Hz, 2H) 2.58 (t, J=11.80 Hz, 2H) 1.68 (td, J=12.42, 4.77 Hz, 2H) 1.40 (d, J=12.05 Hz, 2H); RT=1.08 min, 97.4% (Method E), RT=1.03 min, 100% (Method F).

The following Examples in Table 5 were made by using the same procedure as shown in Example 57.

TABLE 5

| Example | R | Name | LCMS (M + H)+ | HPLC Method, RT (min.) & Purity | NMR |
|---|---|---|---|---|---|
| 58 | OMe, F (3-methoxy-5-fluorophenyl) | 3-(4-(1H-pyrazol-4-yl)phenyl)-1-(3-fluoro-5-methoxybenzyl)-1,3,8-triazaspiro[4.5]decan-2-one, TFA | 436.10 | E: 1.15 min, 99.6% F: 1.18 min, 99.6% | ¹H NMR (400 MHz, DMSO-d6) δ ppm 12.88 (br. s., 1 H) 8.14 (br. s., 1 H) 7.90 (br. s., 1 H) 7.55-7.67 (m, 4 H) 6.69-6.81 (m, 3 H) 4.37 (s, 2 H) 3.93 (s, 2 H) 3.77 (s, 3 H) 2.98-3.14 (m, 2 H) 2.53-2.58 (m, 2 H) 1.89-2.05 (m, 2 H) 1.74 (d, J = 13.55 Hz, 2 H). ¹⁹F NMR (376 MHz, METHANOL-d4) δ ppm -73.430 and -111.569 |
| 59 | OMe, F (4-fluoro-3-methoxyphenyl) | 3-(4-(1H-pyrazol-4-yl)phenyl)-1-(4-fluoro-3-methoxybenzyl)-1,3,8-triazaspiro[4.5]decan-2-one | 436.20 | E: 1.21 min, 99.8% F: 1.10 min, 99.7% | ¹H NMR (400 MHz, DMSO-d6) δ ppm 8.00 (br. s., 2 H) 7.63 (m, J = 8.80 Hz, 2 H) 7.56 (m, J = 8.56 Hz, 2 H) 7.08-7.18 (m, 2 H) 6.85-6.94 (m, 1 H) 4.37 (s, 2 H) 3.99 (s, 2 H) 3.78 (s, 3 H) 2.91 (d, J = 12.23 Hz, 2 H) 2.65 (d, J = 13.94 Hz, 2 H) 1.66-1.79 (m, 2 H) 1.44 (d, J = 12.23 Hz, 2 H); ¹⁹F NMR (376 MHz, DMSO-d6) δ ppm -138.256 |
| 60 | cyclopropylmethoxy phenyl | 3-(4-(1H-pyrazol-4-yl)phenyl)-1-(3-(cyclopropylmethoxy)benzyl)-1,3,8-triazaspiro[4.5]decan-2-one, TFA | 458.30 | E: 1.39 min, 100% F: 1.32 min, 100% | ¹H NMR (400 MHz, DMSO-d6) δ ppm 7.99 (br. s., 2 H) 7.62 (m, J = 8.80 Hz, 2 H) 7.56 (m, J = 8.80 Hz, 2 H) 7.15-7.26 (m, 1 H) 6.84-6.92 (m, 2 H) 6.73-6.80 (m, 1 H) 4.35 (s, 2 H) 3.73-3.81 (m, 5 H) 2.95 (d, J = 11.74 Hz, 2 H) 2.59-2.73 (m, 2 H) 1.75 (td, J = 12.59, 3.91 Hz, 2 H) 1.45 (d, J = 12.23 Hz, 2 H) 1.13-1.25 (m, 1 H) 0.51-0.59 (m, 2 H) 0.26-0.34 (m, 2 H); ¹⁹F NMR (376 MHz, DMSO-d6) d ppm -73.431 |
| 61 | OCHF₂ | 3-(4-(1H-pyrazol-4-yl)phenyl)-1-(3-(difluoromethoxy)benzyl)-1,3,8-triazaspiro[4.5]decan-2-one | 454.20 | E: 1.27 min, 100% F: 1.22 min, 100% | ¹H NMR (400 MHz, DMSO-d6) δ ppm 8.01 (br. s., 2 H) 7.60-7.68 (m, 2 H) 7.52-7.60 (m, 2 H) 7.33-7.43 (m, 1 H) 7.19-7.26 (m, 2 H) 7.14 (s, 1 H) 7.01-7.08 (m, 1 H) 4.41 (s, 2 H) 3.78 (s, 2 H) 2.87 (d, J = 11.04 Hz, 2 H) 2.59 (t, J = 11.80 Hz, 2 H) 1.68 (td, J = 12.55, 4.52 Hz, 2 H) 1.42 (d, J = 12.05 Hz, 2 H). ¹⁹F NMR (376 MHz, DMSO-d6) δ ppm -81.715 |

TABLE 5-continued

| Example | R | Name | LCMS (M + H)+ | HPLC Method, RT (min.) & Purity | NMR |
|---|---|---|---|---|---|
| 62 | (3-hydroxybenzyl structure) | 3-(4-(1H-pyrazol-4-yl)phenyl)-1-(3-hydroxybenzyl)-1,3,8-triazaspiro[4.5]decan-2-one | 404.20 | E: 0.94 min, 100% F: 0.87 min, 99.7% | 1H NMR (400 MHz, DMSO-d6) δ ppm 9.30 (br. s., 1 H) 8.00 (br. s., 2 H) 7.60-7.69 (m, 2 H) 7.52-7.60 (m, 2 H) 7.02-7.13 (m, 1 H) 6.68-6.80 (m, 2 H) 6.60 (dt, J = 8.03, 1.25 Hz, 1 H) 4.31 (s, 2 H) 3.77 (s, 2 H) 2.90 (d, J = 12.55 Hz, 2 H) 2.54-2.65 (m, 2 H) 1.63-1.79 (m, 2 H) 1.41 (d, J = 12.05 Hz, 2 H) |
| 63 | (2-fluorobenzyl structure) | 3-(4-(1H-pyrazol-4-yl)phenyl)-1-(2-fluorobenzyl)-1,3,8-triazaspiro[4.5]decan-2-one | 406.20 | F: 1.04 min, 98.4% | 1H NMR (400 MHz, METHANOL-d4) δ ppm 7.95 (s, 2 H) 7.56-7.69 (m, 4 H) 7.37 (td, J = 8.03, 6.02 Hz, 1 H) 7.22 (d, J = 7.53 Hz, 1 H) 7.15 (dt, J = 9.91, 1.82 Hz, 1 H) 7.01 (td, J = 8.28, 2.01 Hz, 1 H) 4.54 (s, 2 H) 3.99 (s, 2 H) 3.36 (br. s., 1 H) 3.10 (td, J = 13.55, 2.51 Hz, 2 H) 2.06 (td, J = 13.80, 4.52 Hz, 2 H) 1.97 (s, 1 H) 1.83 (d, J = 13.55 Hz, 2 H) |
| 64 | (2,3-difluorobenzyl structure) | 3-(4-(1H-pyrazol-4-yl)phenyl)-1-(3-fluorobenzyl)-1,3,8-triazaspiro[4.5]decan-2-one | 424.20 | F: 1.08 min, 97.1% | 1H NMR (400 MHz, DMSO-d6) δ ppm 13.12 (br. s., 1 H) 8.38 (br. s., 1 H) 8.15 (br. s., 1 H) 7.75-7.95 (m, 4 H) 7.52-7.64 (m, 1 H) 7.45-7.52 (m, 1 H) 7.36-7.45 (m, 1 H) 4.72 (s, 2 H) 4.07 (s, 2 H) 3.15 (d, J = 11.25 Hz, 2 H) 2.87 (t, J = 12.23 Hz, 3 H) 1.85-2.03 (m, 2 H) 1.74 (d, J = 11.49 Hz, 2 H) |
| 65 | (3,5-difluorobenzyl structure) | 3-(4-(1H-pyrazol-4-yl)phenyl)-1-(2,3-difluorobenzyl)-1,3,8-triazaspiro[4.5]decan-2-one | 424.20 | F: 1.08 min, 97.9% | 1H NMR (400 MHz, DMSO-d6) δ ppm 8.30 (s, 2 H) 7.78-7.92 (m, 4 H) 7.69-7.78 (m, 1 H) 7.42-7.54 (m, 1 H) 7.25-7.36 (m, 1 H) 4.65 (s, 2 H) 4.09 (s, 2 H) 3.25 (d, J = 11.98 Hz, 2 H) 2.95-3.04 (m, 1 H) 1.92-2.07 (m, 2 H) 1.79 (d, J = 12.72 Hz, 2 H) |

TABLE 5-continued

| Example | R | Name | LCMS (M + H)+ | HPLC Method, RT (min.) & Purity | NMR |
|---|---|---|---|---|---|
| 66 | (structure: 2,4-difluorobenzyl) | 3-(4-(1H-pyrazol-4-yl)phenyl)-1-(2,4-difluorobenzyl)-1,3,8-triazaspiro[4.5]decan-2-one | 424.20 | F: 1.25 min, 96.7% | $^1$H NMR (400 MHz, METHANOL-d$_4$) δ ppm 7.95 (s, 2 H) 7.52-7.69 (m, 4 H) 7.23 (ddd, J = 8.91, 5.90, 3.26 Hz, 1 H) 7.15 (td, J = 9.29, 4.52 Hz, 1 H) 6.95-7.10 (m, 1 H) 4.56 (s, 2 H) 4.03 (s, 2 H) 3.36-3.49 (m, 2 H) 3.19 (td, J = 13.55, 3.01 Hz, 2 H) 2.12 (td, J = 13.68, 4.77 Hz, 2 H) 1.85-2.03 (m, 2 H) |
| 67 | (structure: 2,5-difluorobenzyl) | 3-(4-(1H-pyrazol-4-yl)phenyl)-1-(2,5-difluorobenzyl)-1,3,8-triazaspiro[4.5]decan-2-one | 394.20 | F: 1.34 min, 97.5% | $^1$H NMR (400 MHz, METHANOL-d$_4$) δ ppm 7.93 (s, 1 H) 7.57 (s, 2 H) 3.87 (s, 1 H) 3.36 (br. s., 1 H) 2.91-3.13 (m, 2 H) 2.08 (td, J = 13.55, 4.52 Hz, 1 H) 1.95 (s, 2 H) 1.62-1.90 (m, 4 H) 1.15-1.39 (m, 2 H) 0.86-1.06 (m, 1 H) |
| 68 | (structure: cyclohexylmethyl) | 3-(4-(1H-pyrazol-4-yl)phenyl)-1-(cyclohexylmethyl)-1,3,8-triazaspiro[4.5]decan-2-one | 424.2 | F: 1.12 min, 95.4% | $^1$H NMR (400 MHz, DMSO-d$_6$) δ ppm 8.38 (s, 1 H) 7.89 (m, J = 8.80 Hz, 2 H) 7.83 (m, J = 9.05 Hz, 2 H) 7.25-7.41 (m, 3 H) 4.68 (s, 2 H) 4.07 (s, 2 H) 3.14 (d, J = 11.98 Hz, 2 H) 2.83-2.90 (m, 3 H) 2.08 (s, 2 H) 1.87-1.98 (m, 2 H) 1.72 (br. s., 2 H) |
| 70 | (structure: 3-fluoro-2-methylbenzyl) | 3-(4-(1H-pyrazol-4-yl)phenyl)-1-(3-fluoro-2-methylbenzyl)-1,3,8-triazaspiro[4.5]decan-2-one | 420.30 | E: 1.32 min, 98.1% | $^1$H NMR (400 MHz, METHANOL-d$_4$) δ ppm 7.95 (s, 2 H) 7.54-7.71 (m, 4 H) 7.31 (dd, J = 8.53, 6.02 Hz, 1 H) 6.86-7.01 (m, 2 H) 4.50 (s, 2 H) 4.03 (s, 2 H) 3.38 (d, J = 15.06 Hz, 2 H) 3.08-3.22 (m, 2 H) 2.43 (s, 3 H) 2.05 (td, J = 13.68, 4.27 Hz, 2 H) 1.97 (s, 1 H) 1.85-1.93 (m, 2 H) |
| 72 | (structure: tetrahydro-2H-pyran-4-ylmethyl) | 3-(4-(1H-pyrazol-4-yl)phenyl)-1-((tetrahydro-2H-pyran-4-yl)methyl)-1,3,8-triazaspiro[4.5]decan-2-one | 396.30 | E: 0.75 min, 94.5%; F: 0.77 min, 99.1% | $^1$H NMR (400 MHz, DMSO-d6) δ ppm 8.71 (br. s., 1 H) 8.25 (br. s., 1 H) 7.56 (s, 4 H) 3.79-3.91 (m, 4 H) 3.36 (d, J = 12.05 Hz, 2 H) 3.24 (t, J = 10.79 Hz, 2 H) 3.00-3.15 (m, 2 H) 2.93 (d, J = 7.53 Hz, 2 H) 1.98-2.11 (m, 2 H) 1.86 (br. s., 1 H) 1.77 (d, J = 14.06 Hz, 2 H) 1.60 (d, J = 12.55 Hz, 3 H) 1.06-1.20 (m, 3 H) |

TABLE 5-continued

| Example | R | Name | LCMS (M + H)+ | HPLC Method, RT (min.) & Purity | NMR |
|---|---|---|---|---|---|
| 73 | (structure with OMe phenyl, pyridine, pyrazole, triazaspirodecane) | 3-(5-(1H-pyrazol-4-yl)pyridin-2-yl)-1-(3-methoxybenzyl)-1,3,8-triazaspiro[4.5]decan-2-one | 419.10 | E: 1.03 min, 97.9%<br>F: 1.11 min, 95.3% | $^1$H NMR (400 MHz, DMSO-d6) δ ppm 12.97 (brs, 1 H) 8.58 (d, J = 1.83 Hz, 1 H) 8.20 (d, J = 8.68 Hz, 2 H) 7.96 (dd, J = 8.62, 2.14 Hz, 2 H) 7.23 (t, J = 7.70 Hz, 1 H) 6.88-6.97 (m, 2 H) 6.80 (d, J = 8.56 Hz, 1 H) 4.40 (s, 2 H) 3.92 (s, 2 H) 3.73 (s, 3 H) 2.89 (d, J = 8.93 Hz, 2 H) 2.49-2.70 (m, 2 H) 1.64-1.77 (m, 2 H) 1.42 (d, J = 13.08 Hz, 2 H) |
| 74 | (structure with OMe phenyl, 6-methylpyridine, pyrazole, triazaspirodecane) | 1-(3-methoxybenzyl)-5-(1H-pyrazol-4-yl)pyridin-2-yl)-1,3,8-triazaspiro[4.5]decan-2-one | 433.8 | E: 1.02, 100%<br>F: 1.19, 100% | $^1$H NMR (400 MHz, DMSO-d$_6$) δ ppm 13.00 (br. s., 1H), 8.05 (d, J = 8.6 Hz, 1H), 7.96 (br. s., 1H), 7.90-7.79 (m, 1H), 7.75 (d, J = 8.6 Hz, 1H), 7.24 (t, J = 7.9 Hz, 1H), 6.95-6.89 (m, 2H), 6.81 (d, J = 8.6 Hz, 1H), 4.40 (s, 2H), 3.94 (s, 2H), 3.74 (s, 3H), 2.92 (d, J = 16.9 Hz, 2H), 2.70-2.56 (m, 2H), 2.54 (s, 3H), 1.78-1.66 (m, 2H), 1.44 (d, J = 12.2 Hz, 2H) |
| 75 | (structure with OMe phenyl, 6-ethylpyridine, pyrazole, triazaspirodecane) | 3-(6-ethyl-5-(1H-pyrazol-4-yl)pyridin-2-yl)-1-(3-methoxybenzyl)-1,3,8-triazaspiro[4.5]decan-2-one, TFA | 447.3 | E: 1.10, 100%<br>F: 1.28, 100% | $^1$H NMR (400 MHz, DMSO-d$_6$) δ ppm = 12.99 (br. s., 1H), 8.02 (d, J = 8.6 Hz, 1H), 7.97-7.73 (m, 2H), 7.67 (d, J = 8.8 Hz, 1H), 7.23 (t, J = 7.9 Hz, 1H), 6.97-6.70 (m, 3H), 4.40 (s, 2H), 4.03-3.89 (m, 2H), 3.73 (s, 3H), 2.95 (d, J = 11.2 Hz, 2H), 2.82 (q, J = 7.6 Hz, 2H), 2.69-2.55 (m, 2H), 1.84-1.63 (m, 2H), 1.53-1.36 (m, 2H), 1.23 (t, J = 7.5 Hz, 3H) |

Example 76

3-(4-(1H-pyrazol-4-yl)phenyl)-8-acetyl-1-(3-methoxybenzyl)-1,3,8-triazaspiro[4.5]decan-2-one

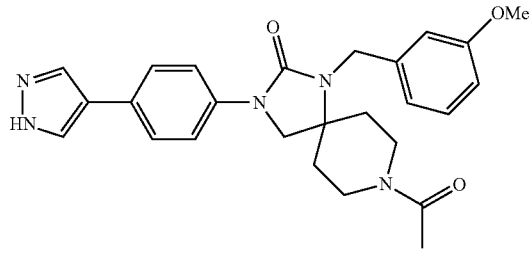 [SMILES: COc1cccc(CN2C(=O)N(c3ccc(-c4cn[nH]c4)cc3)CC23CCN(C(C)=O)CC3)c1]

Example 76a

Preparation of 8-acetyl-3-(4-bromophenyl)-1-(3-methoxybenzyl)-1,3,8-triazaspiro[4.5]decan-2-one

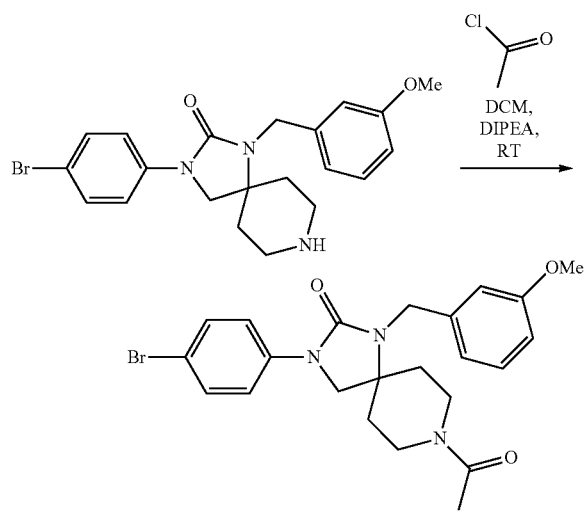

To a solution of 3-(4-bromophenyl)-1-(3-methoxybenzyl)-1,3,8-triazaspiro[4.5]decan-2-one (140 mg, 0.325 mmol) in DCM (8 mL) at 0° C., was added DIPEA (0.142 mL, 0.813 mmol). Acetyl chloride (0.035 mL, 0.488 mmol) was added dropwise and the reaction mixture was allowed to warm to rt and stirred overnight. The reaction mixture was diluted with DCM, washed with sat. NaHCO$_3$ and brine, dried over Na$_2$SO$_4$, filtered and concentrated to afford 8-acetyl-3-(4-bromophenyl)-1-(3-methoxybenzyl)-1,3,8-triazaspiro[4.5]decan-2-one as a brown gummy solid (140 mg, 91% yield). MS(ESI) m/z: 474.0 (M+H)$^+$; $^1$H NMR (300 MHz, DMSO-d$_6$) δ ppm 7.63 (d, J=9.07 Hz, 2H) 7.51 (d, J=9.07 Hz, 2H) 7.22 (t, J=8.12 Hz, 1H) 6.84-6.92 (m, 2H) 6.79 (d, J=9.07 Hz, 1H) 4.37 (s, 3H) 3.86 (s, 2H) 3.72 (s, 3H) 3.16 (t, J=12.84 Hz, 1H) 2.73 (s, 1H) 1.99 (s, 3H) 1.80 (d, J=8.69 Hz, 1H) 1.51 (t, J=11.71 Hz, 2H) 1.21-1.28 (m, 2H).

Example 76

Preparation of 3-(4-(1H-pyrazol-4-yl)phenyl)-8-acetyl-1-(3-methoxybenzyl)-1,3,8-triazaspiro[4.5]decan-2-one

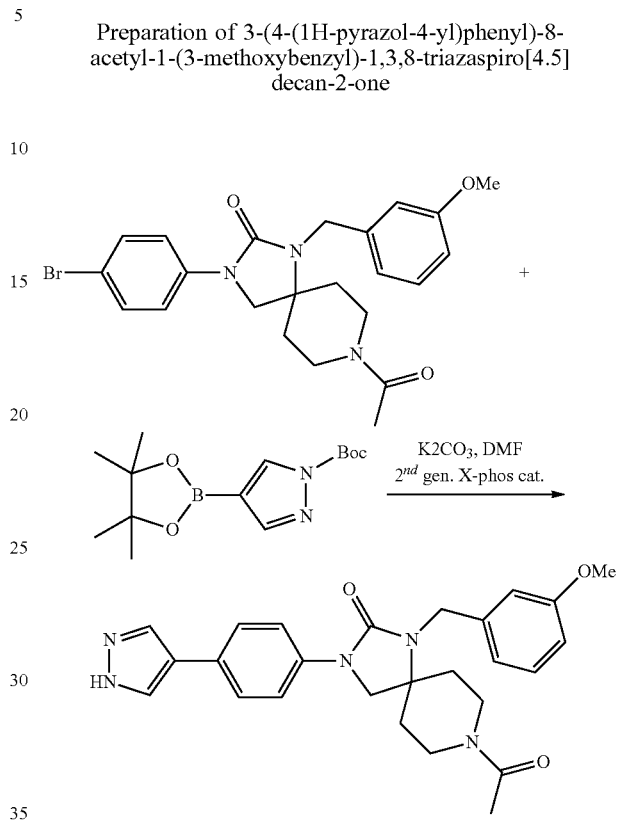

To a solution of 8-acetyl-3-(4-bromophenyl)-1-(3-methoxybenzyl)-1,3,8-triazaspiro[4.5]decan-2-one (140 mg, 0.296 mmol) in DMF (4 mL) were added tert-butyl 4-(4,4,5,5-tetramethyl-1,3,2-dioxaborolan-2-yl)-1H-pyrazole-1-carboxylate (122 mg, 0.415 mmol), K$_2$CO$_3$ (123 mg, 0.889 mmol) and water (0.4 mL). The reaction mixture was purged with nitrogen for 5 min and charged with 2$^{nd}$ generation XPHOS precatalyst (14 mg, 0.018 mmol). The reaction mixture was again purged with nitrogen for 3 min and heated at 90° C. overnight. The reaction mixture was cooled to rt and filtered. The filtrate was concentrated and the residue was purified by preparative HPLC to afford 3-(4-(1H-pyrazol-4-yl)phenyl)-8-acetyl-1-(3-methoxybenzyl)-1,3,8-triazaspiro[4.5]decan-2-one as a white solid (54 mg, 39% yield). MS(ESI) m/z: 460.4 (M+H)$^+$; $^1$H NMR (400 MHz, DMSO-d$_6$) δ ppm 12.86 (br. s., 1H) 8.12 (br. s., 1H) 7.89 (br. s., 1H) 7.60-7.69 (m, 2H) 7.53-7.60 (m, 2H) 7.18-7.28 (m, 1H) 6.87-6.95 (m, 2H) 6.79 (dd, J=7.28, 1.76 Hz, 1H) 4.41 (br. s., 1H) 4.37 (s, 2H) 3.88 (s, 2H) 3.81 (d, J=13.05 Hz, 1H) 3.73 (s, 3H) 3.19 (t, J=12.80 Hz, 1H) 2.61-2.72 (m, 1H) 2.00 (s, 3H) 1.75-1.89 (m, 1H) 1.65 (td, J=12.80, 4.52 Hz, 1H) 1.46-1.59 (m, 2H). HPLC RT=6.33 min, 99.17% (Method I), 7.68 min, 99.11% (Method J).

The following Examples in Table 6 were made by using the same procedure as shown in Example 76.

TABLE 6

| Example | R | Name | LCMS (M + H)+ | HPLC Method, RT (min.) & Purity | NMR |
|---|---|---|---|---|---|
| 77 | 2,3-difluorobenzyl group on spiro scaffold | 3-(4-(1H-pyrazol-4-yl)phenyl)-8-acetyl-1-(2,3-difluorobenzyl)-1,3,8-triazaspiro[4.5]decan-2-one | 466.30 | E: 1.30 min, 93.5% | $^1$H NMR (400 MHz, METHANOL-$d_4$) δ ppm 7.94 (s, 2 H) 7.51-7.70 (m, 4 H) 7.22-7.30 (m, 1 H) 7.07-7.21 (m, 2 H) 4.58 (s, 3 H) 3.91-4.05 (m, 3 H) 3.37 (d, J = 2.51 Hz, 1 H) 2.71-2.84 (m, 1 H) 2.14 (s, 3 H) 1.89-2.02 (m, 2 H) 1.79-1.89 (m, 1 H) 1.67-1.79 (m, 2 H) |
| 78 | 2,5-difluorobenzyl group on spiro scaffold | 3-(4-(1H-pyrazol-4-yl)phenyl)-8-acetyl-1-(2,5-difluorobenzyl)-1,3,8-triazaspiro[4.5]decan-2-one | 466.3 | E: 1.29 min, 97.3% | $^1$H NMR (400 MHz, METHANOL-$d_4$) δ ppm 7.94 (br. s., 2 H) 7.54-7.70 (m, 4 H) 7.21 (ddd, J = 8.91, 5.65, 3.01 Hz, 1 H) 7.13 (td, J = 9.29, 4.52 Hz, 1 H) 6.97-7.07 (m, 1 H) 4.55-4.65 (m, 1 H) 4.53 (s, 2 H) 3.92-4.07 (m, 3 H) 3.37 (d, J = 2.51 Hz, 1 H) 2.73-2.85 (m, 1 H) 2.14 (s, 3 H) 1.96 (td, J = 13.05, 4.52 Hz, 1 H) 1.68-1.87 (m, 3 H) |
| 79 | cyclohexylmethyl group on spiro scaffold | 3-(4-(1H-pyrazol-4-yl)phenyl)-8-acetyl-1-(cyclohexylmethyl)-1,3,8-triazaspiro[4.5]decan-2-one | 436.40 | F: 1.50 min, 98.4% | $^1$H NMR (400 MHz, DMSO-$d_6$) δ ppm 8.01 (br. s., 2 H) 7.49-7.67 (m, 4 H) 7.18 (br. s., 4 H) 4.45 (d, J = 12.05 Hz, 1 H) 3.70-3.90 (m, 3 H) 3.17-3.24 (m, 1 H) 2.89 (d, J = 7.53 Hz, 2 H) 2.04 (s, 3 H) 1.78-1.89 (m, 1 H) 1.46-1.76 (m, 9 H) 1.03-1.22 (m, 3 H) 0.87 (d, J = 9.54 Hz, 2 H) |

TABLE 6-continued

| Example | R | Name | LCMS (M + H)+ | HPLC Method, RT (min.) & Purity | NMR |
|---|---|---|---|---|---|
| 80 | (structure) | 3-(4-(1H-pyrazol-4-yl)phenyl)-8-acetyl-1-(4-fluoro-2-methylbenzyl)-1,3,8-triazaspiro[4.5]decan-2-one | 432.30 | F: 1.39 min, 95.9% | $^1$H NMR (400 MHz, METHANOL-d$_4$) δ ppm 7.95 (br. s., 2 H) 7.52-7.69 (m, 4 H) 7.30 (dd, J = 8.53, 6.02 Hz, 1 H) 6.83-6.98 (m, 2 H) 4.58 (d, J = 14.56 Hz, 1 H) 4.47 (s, 2 H) 3.99-4.07 (m, 2 H) 3.95 (d, J = 14.56 Hz, 1 H) 2.73-2.86 (m, 1 H) 2.39 (s, 3 H) 2.07-2.16 (m, 3 H) 1.89 (td, J = 12.93, 4.77 Hz, 1 H) 1.67-1.82 (m, 3 H) |
| 81 | (structure) | 3-(4-(1H-pyrazol-4-yl)phenyl)-8-acetyl-1-(2,4-difluorobenzyl)-1,3,8-triazaspiro[4.5]decan-2-one | 466.30 | E: 1.31 min, 97.6% | $^1$H NMR (400 MHz, METHANOL-d$_4$) δ ppm 7.94 (br. s., 2 H) 7.55-7.69 (m, 4 H) 7.44-7.55 (m, 1 H) 6.86-7.04 (m, 2 H) 4.56-4.66 (m, 1 H) 4.52 (s, 2 H) 3.87-4.05 (m, 3 H) 3.34-3.39 (m, 1 H) 2.70-2.86 (m, 1 H) 2.14 (s, 3 H) 1.90-2.01 (m, 1 H) 1.63-1.88 (m, 3 H) |
| 82 | (structure) | 3-(4-(1H-pyrazol-4-yl)phenyl)-8-acetyl-1-(3-fluoro-2-methylbenzyl)-1,3,8-triazaspiro[4.5]decan-2-one | 462.20 | I: 8.16 min, 99.5% J: 7.08 min, 99.5% | $^1$H NMR (400 MHz, DMSO-d6) δ ppm 12.86 (br. s., 1 H) 8.13 (br. s., 1 H) 7.90 (br. s., 1 H) 7.61-7.69 (m, 2 H) 7.55-7.60 (m, 2 H) 7.14-7.22 (m, 1 H) 7.07-7.12 (m, 1 H) 6.98-7.05 (m, 1 H) 4.34-4.46 (m, 3 H) 3.95 (s, 2 H) 3.81 (d, J = 13.05 Hz, 1 H) 3.21 (t, J = 12.80 Hz, 2 H) 2.23 (d, J = 1.51 Hz, 3 H) 1.99 (s, 3 H) 1.74-1.85 (m, 1 H) 1.56-1.69 (m, 3 H). $^{19}$F NMR (376 MHz, DMSO-d6) d ppm −118.962 |

TABLE 6-continued

| Example | Name | R | LCMS (M + H)+ | HPLC Method, RT (min.) & Purity | NMR |
|---|---|---|---|---|---|
| 83 | 3-(4-(1H-pyrazol-4-yl)phenyl)-8-acetyl-1-(5-fluoro-2-methylbenzyl)-1,3,8-triazaspiro[4.5]decan-2-one | 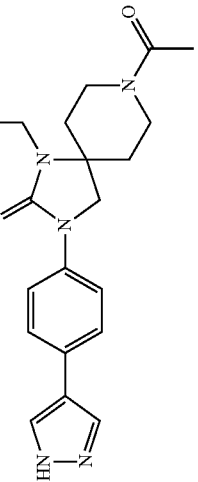 | 462.30 | F: 1.38 min, 93.7% | ¹H NMR (400 MHz, METHANOL-d₄) δ ppm 7.99 (br. s., 1 H) 7.91 (br. s., 1 H) 7.53-7.72 (m, 4 H) 7.17 (dd, J = 8.53, 6.02 Hz, 1 H) 7.03 (dd, J = 10.29, 2.76 Hz, 1 H) 6.88 (td, J = 8.41, 2.76 Hz, 1 H) 4.58 (s, 1 H) 4.46 (s, 2 H) 4.05 (s, 2 H) 3.97 (d, J = 14.56 Hz, 1 H) 2.73-2.86 (m, 1 H) 2.35 (s, 3 H) 2.08-2.16 (m, 3 H) 1.86-1.97 (m, 1 H) 1.71-1.85 (m, 3 H) |
| 84 | 3-(5-(1H-pyrazol-4-yl)pyridin-2-yl)-8-acetyl-1-(3-methoxybenzyl)-1,3,8-triazaspiro[4.5]decan-2-one | 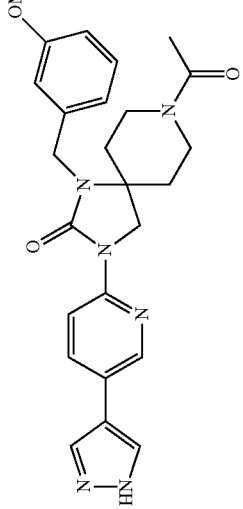 | 461.10 | E: 1.22 min, 96.0%<br>F: 1.41 min, 97.4% | ¹H NMR (400 MHz, DMSO-d6) δ ppm 12.96 (s, 1 H) 8.59 (d, J = 2.45 Hz, 1 H) 8.13-8.32 (m, 2 H) 7.98 (dd, J = 8.68, 2.32 Hz, 1 H) 7.15-7.28 (m, 1 H) 6.88-6.95 (m, 2 H) 6.81 (d, J = 9.05 Hz, 1 H) 4.36-4.46 (m, 2 H) 4.03 (s, 2 H) 3.82 (d, J = 16.63 Hz, 1 H) 3.74 (s, 3 H) 3.19 (t, J = 13.57 Hz, 1 H) 2.59-2.70 (m, 1 H) 2.00 (s, 3 H) 1.77-1.90 (m, 2 H) 1.66 (d, J = 12.23 Hz, 1 H) 1.45-1.60 (m, 2 H) |
| 85 | 8-acetyl-3-(6-methoxy-5-(1H-pyrazol-4-yl)pyridin-2-yl)-1-(3-methoxybenzyl)-1,3,8-triazaspiro[4.5]decan-2-one | 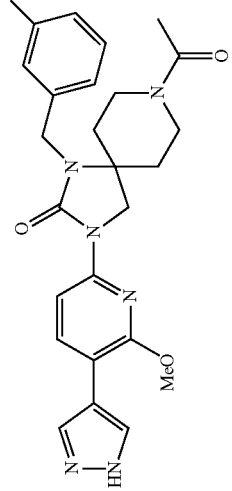 | 491.2 | E: 1.57 min, 99.6%<br>F: 1.60 min, 99.6% | ¹H NMR (400 MHz, DMSO-d6) δ ppm 12.87 (br. s., 1 H), 8.09 (br. s., 1 H), 8.00 (d, J = 8.3 Hz, 1 H), 7.95 (br. s., 1 H), 7.75 (d, J = 8.3 Hz, 1 H), 7.27-7.20 (m, 1 H), 6.95-6.88 (m, 2 H), 6.83-6.77 (m, 1 H), 4.48-3.36 (m, 3 H), 4.06 (s, 2 H), 4.02 (s, 3 H), 3.83 (d, J = 11.2 Hz, 1 H), 3.73 (s, 3 H), 3.24-3.13 (m, 1 H), 2.71-2.61 (m, 1 H), 2.00 (s, 3 H), 1.91-1.78 (m, 1 H), 1.72-1.60 (m, 1 H), 1.59-1.47 (m, 2 H) |

TABLE 6-continued

| Example | R | Name | LCMS (M + H)+ | HPLC Method, RT (min.) & Purity | NMR |
|---|---|---|---|---|---|
| 86 | (structure with 3-fluoro-2-methylphenyl, methoxy-pyridine-pyrazole) | 8-acetyl-1-(3-fluoro-2-methylbenzyl)-3-(6-methoxy-5-(1H-pyrazol-4-yl)pyridin-2-yl)-1,3,8-triazaspiro[4.5]decan-2-one | 493.2 | E: 1.72 min, 100% F: 1.75 min, 100% | ¹H NMR (400 MHz, DMSO-d6) δ ppm 12.88 (br. s., 1 H), 8.09 (br. s., 1 H), 7.98 (d, J = 8.4 Hz, 1 H), 7.95 (br. s., 1 H), 7.72 (d, J = 8.3 Hz, 1 H), 7.21-7.13 (m, 1 H), 7.12-7.07 (m, 1 H), 7.03 (t, J = 8.9 Hz, 1 H), 4.41 (br. s., 3 H), 4.14 (d, J = 2.9 Hz, 2 H), 4.04 (s, 3 H), 3.87-3.77 (m, 1 H), 3.24-3.14 (m, 1 H), 2.72-2.61 (m, 1 H), 2.23 (s, 3 H), 1.99 (s, 3 H), 1.85-1.75 (m, 1 H), 1.70-1.58 (m, 3 H); ¹⁹F NMR (376 MHz, DMSO-d6) δ ppm −118.51 |
| 87 | (structure with 3-fluoro-2-methylphenyl, ethyl-pyridine-pyrazole) | 8-acetyl-3-(6-ethyl-5-(1H-pyrazol-4-yl)pyridin-2-yl)-1-(3-fluoro-2-methylbenzyl)-1,3,8-triazaspiro[4.5]decan-2-one | 491.3 | E: 1.55 min, 97.7% | ¹H NMR (400 MHz, DMSO-d6) d ppm 7.99 (d, J = 8.53 Hz, 1 H) 7.92 (br. s., 1 H) 7.68 (d, J = 8.53 Hz, 2 H) 7.12-7.21 (m, 1 H) 7.07-7.12 (m, 1 H) 6.96-7.07 (m, 1 H) 4.42 (s, 3 H) 4.11 (s, 2 H) 3.82 (d, J = 12.05 Hz, 1 H) 3.11-3.24 (m, 1 H) 2.84 (q, J = 7.36 Hz, 2 H) 2.64 (d, J = 10.54 Hz, 1 H) 2.23 (s, 3 H) 1.99 (s, 3 H) 1.73-1.86 (m, 1 H) 1.65 (d, J = 15.56 Hz, 3 H) 1.25 (t, J = 7.53 Hz, 3 H) |
| 88 | (structure with 3-methoxyphenyl, ethyl-pyridine-pyrazole) | 8-acetyl-3-(6-ethyl-5-(1H-pyrazol-4-yl)pyridin-2-yl)-1-(3-methoxybenzyl)-1,3,8-triazaspiro[4.5]decan-2-one | 489.3 | E: 1.43 min, 98.5% | ¹H NMR (400 MHz, METHANOL-d4) d ppm 8.04 (d, J = 8.53 Hz, 1 H) 7.83 (s, 2 H) 7.67 (d, J = 8.53 Hz, 1 H) 7.25 (t, J = 8.03 Hz, 1 H) 6.91-6.99 (m, 2H) 6.83 (d, J = 10.54 Hz, 1 H) 4.58 (s, 2 H) 4.52 (s, 2 H) 4.18 (d, J = 2.51 Hz, 2 H) 3.80 (s, 3 H) 3.66 (s, 1 H) 2.88 (q, J = 7.53 Hz, 3 H) 2.79 (br. s., 2 H) 2.13 (s, 3 H) 1.63-1.71 (m, 2 H) 1.25-1.38 (m, 12 H) 0.86-0.96 (m, 3 H) |

TABLE 6-continued

| Example | R | Name | LCMS (M + H)+ | HPLC Method, RT (min.) & Purity | NMR |
|---|---|---|---|---|---|
| 89 | (structure with OMe, F, pyridine-ethyl, pyrazole) | 8-acetyl-3-(6-ethyl-5-(1H-pyrazol-4-yl)pyridin-2-yl)-1-(3-fluoro-5-methoxybenzyl)-1,3,8-triazaspiro[4.5]decan-2-one | 507. | F: 1.21 min, 98.8% | $^1$H NMR (400 MHz, METHANOL-d4) d ppm 8.04 (d, J = 8.53 Hz, 1 H) 7.82 (br. s., 1 H) 7.70 (br. s., 1 H) 7.67 (d, J = 8.53 Hz, 1 H) 6.78 (s, 1 H) 6.68-6.75 (m, 1 H) 6.59 (dt, J = 10.79, 2.13 Hz, 1 H) 4.56-4.66 (m, 1 H) 4.50 (s, 2 H) 4.15-4.24 (m, 2 H) 3.98 (d, J = 14.06 Hz, 1 H) 3.80 (s, 3 H) 2.88 (q, J = 7.53 Hz, 2 H) 2.71-2.84 (m, 1 H) 2.14 (s, 3 H) 1.97 (td, J = 12.93, 4.77 Hz, 1 H) 1.85 (td, J = 13.05, 5.02 Hz, 1 H) 1.62-1.76 (m, 2 H) 1.25-1.38 (m, 5 H) |
| 90 | (structure with OMe, pyrimidine-methoxy, pyrazole) | 8-acetyl-3-(4-methoxy-5-(1H-pyrazol-4-yl)pyrimidin-2-yl)-1-(3-methoxybenzyl)-1,3,8-triazaspiro[4.5]decan-2-one | 492.3 | F: 1.12 min, 96.2% | $^1$H NMR (400 MHz, METHANOL-d4) d ppm 8.63 (br. s., 1 H) 8.11 (s, 2 H) 7.26 (t, J = 8.03 Hz, 1 H) 6.97 (br. s., 2 H) 6.85 (d, J = 8.03 Hz, 1 H) 4.62 (br. s., 1 H) 4.56 (s, 2 H) 4.25 (s, 3 H) 4.20 (s, 2 H) 3.98 (d, J = 9.04 Hz, 1 H) 3.80 (s, 3 H) 2.73-2.85 (m, 1 H) 2.07-2.18 (m, 3 H) 1.94-2.05 (m, 1 H) 1.83-1.94 (m, 1 H) 1.63-1.78 (m, 2 H) |

Example 91

3-(4-(1H-pyrazol-4-yl)phenyl)-1-(3-methoxybenzyl)-N-methyl-2-oxo-1,3,8-triazaspiro[4.5]decane-8-carboxamide

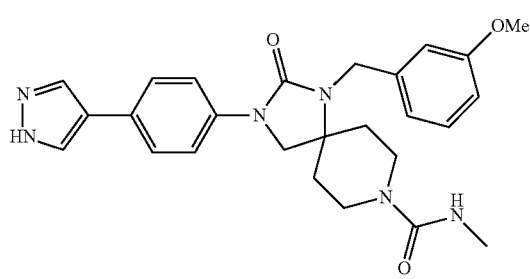 [SMILES: CNC(=O)N1CCC2(CC1)CN(c1ccc(-c3cn[nH]c3)cc1)C(=O)N2Cc1cccc(OC)c1]

Example 91a

Preparation of 3-(4-bromophenyl)-1-(3-methoxybenzyl)-N-methyl-2-oxo-1,3,8-triazaspiro[4.5]decane-8-carboxamide

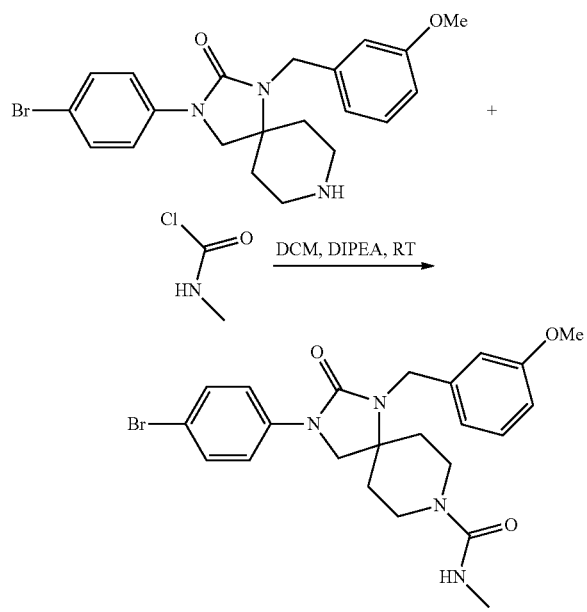

To a solution of 3-(4-bromophenyl)-1-(3-methoxybenzyl)-1,3,8-triazaspiro[4.5]decan-2-one (50 mg, 0.116 mmol) in DCM (5 mL) at 0° C., was added DIPEA (0.051 mL, 0.290 mmol). Methylcarbamic chloride (16.3 mg, 0.174 mmol) was added dropwise and reaction mixture was allowed to warm to rt and stir for 16 h. Reaction mixture was diluted with DCM, washed with sat. NaHCO₃, brine, dried over Na₂SO₄, filtered and concentrated to afford 3-(4-bromophenyl)-1-(3-methoxybenzyl)-N-methyl-2-oxo-1,3,8-triazaspiro[4.5]decane-8-carboxamide as a brown gummy solid (60 mg). MS(ESI) m/z: 487.0 (M+H)⁺; ¹H NMR (400 MHz, DMSO-d₆) δ ppm 7.61-7.68 (m, 2H) 7.49-7.56 (m, 2H) 7.23 (t, J=8.03 Hz, 1H) 6.86-6.93 (m, 2H) 6.77-6.83 (m, 1H) 6.40-6.47 (m, 1H) 4.37 (s, 2H) 3.93 (d, J=13.05 Hz, 2H) 3.82 (s, 2H) 3.73 (s, 3H) 2.79 (t, J=12.55 Hz, 2H) 2.55 (d, J=4.52 Hz, 3H) 1.66 (td, J=12.67, 4.27 Hz, 2H) 1.45 (d, J=12.55 Hz, 2H).

Example 91

Preparation of 3-(4-(1H-pyrazol-4-yl)phenyl)-1-(3-methoxybenzyl)-N-methyl-2-oxo-1,3,8-triazaspiro[4.5]decane-8-carboxamide

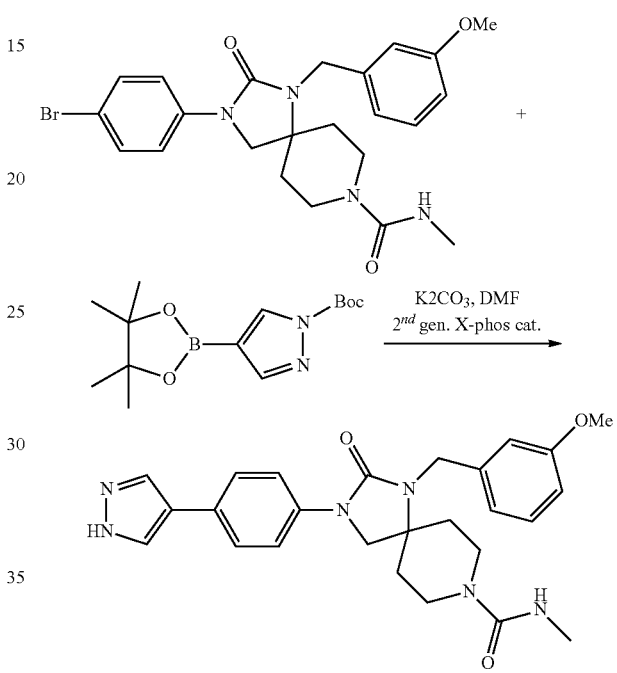

To a solution of 3-(4-bromophenyl)-1-(3-methoxybenzyl)-N-methyl-2-oxo-1,3,8-triazaspiro[4.5]decane-8-carboxamide (60 mg, 0.123 mmol) in DMF (3 mL) were added tert-butyl 4-(4,4,5,5-tetramethyl-1,3,2-dioxaborolan-2-yl)-1H-pyrazole-1-carboxylate (50.7 mg, 0.172 mmol), K₂CO₃ (51.0 mg, 0.369 mmol) and water (0.5 mL). The reaction mixture was purged with nitrogen for 5 min and charged with 2$^{nd}$ generation XPHOS precatalyst (5.81 mg, 7.39 μmol). The reaction mixture was again purged with nitrogen for 3 min and heated at 90° C. overnight. The reaction mixture was cooled to rt and filtered. The filtrate was concentrated and the residue was purified by preparative HPLC to afford 3-(4-(1H-pyrazol-4-yl)phenyl)-1-(3-methoxybenzyl)-N-methyl-2-oxo-1,3,8-triazaspiro[4.5]decane-8-carboxamide as a white solid (16.5 mg, 28% yield). MS(ESI) m/z: 475.3 (M+H)⁺; ¹H NMR (400 MHz, METHANOL-d₄) δ ppm 7.98 (s, 2H) 7.57-7.68 (m, 4H) 7.19-7.28 (m, 1H) 6.91-6.98 (m, 2H) 6.82 (dd, J=7.28, 2.26 Hz, 1H) 4.48 (s, 2H) 4.02 (d, J=14.05 Hz, 2H) 3.93 (s, 2H) 3.79 (s, 3H) 2.94 (t, J=12.55 Hz, 2H) 2.73 (s, 3H) 1.87 (td, J=12.93, 4.27 Hz, 2H) 1.60 (d, J=13.05 Hz, 2H). HPLC RT=6.11 min, 98.7% (Method I), 7.47 min, 98.5% (Method J).

The following Examples in Table 7 were made by using the same procedure as shown in Example 91.

TABLE 7

| Example | R | Name | LCMS (M + H)+ | HPLC Method, RT (min.) & Purity | NMR |
|---|---|---|---|---|---|
| 92 | 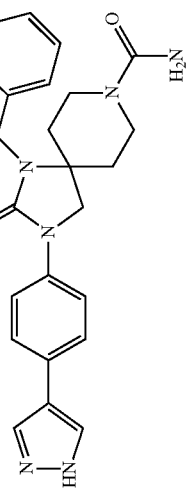 | 3-(4-(1H-pyrazol-4-yl)phenyl)-1-(3-methoxybenzyl)-2-oxo-1,3,8-triazaspiro[4.5]decane-8-carboxamide | 461.30 | E: 1.32 min, 95.2%<br>F: 1.39 min, 95.6% | ¹H NMR (400 MHz, DMSO-d6) δ ppm 8.27 (s, 2 H) 7.87-7.93 (m, 2 H) 7.80-7.86 (m, 2 H) 7.44-7.52 (m, 1 H) 7.13-7.20 (m, 2 H) 7.02-7.08 (m, 1 H) 6.21 (s, 2 H) 4.63 (s, 2 H) 4.22 (d, J = 12.00 Hz, 2 H) 4.11 (s, 2 H) 3.99 (s, 3 H) 3.08 (t, J = 12.72 Hz, 2 H) 1.87-1.99 (m, 2 H) 1.66-1.79 (m, 2 H) |
| 93 | 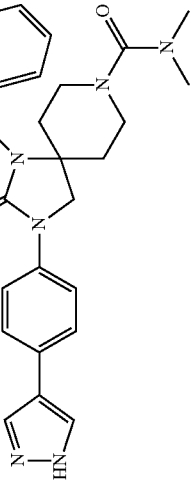 | 3-(4-(1H-pyrazol-4-yl)phenyl)-1-(3-methoxybenzyl)-N,N-dimethyl-2-oxo-1,3,8-triazaspiro[4.5]decane-8-carboxamide | 489.10 | E: 1.60 min, 100%<br>F: 1.64 min, 100% | ¹H NMR (400 MHz, DMSO-d6) δ ppm 12.86 (br. s., 1 H) 8.13 (br. s., 1 H) 7.89 (br. s., 1 H) 7.64 (d, J = 8.80 Hz, 2 H) 7.58 (d, J = 9.05 Hz, 2 H) 7.19-7.28 (m, 1 H) 6.87-6.96 (m, 2 H) 6.77-6.83 (m, 1 H) 4.39 (s, 2 H) 3.85 (s, 2 H) 3.74 (s, 3 H) 3.51 (d, J = 12.47 Hz, 2 H) 2.88 (t, J = 12.59 Hz, 2 H) 2.74 (s, 6 H) 1.72-1.86 (m, 2 H) 1.51 (d, J = 12.72 Hz, 2 H) |

Example 94

Methyl 3-(4-(1H-pyrazol-4-yl)phenyl)-1-(3-methoxybenzyl)-2-oxo-1,3,8-triazaspiro[4.5]decane-8-carboxylate

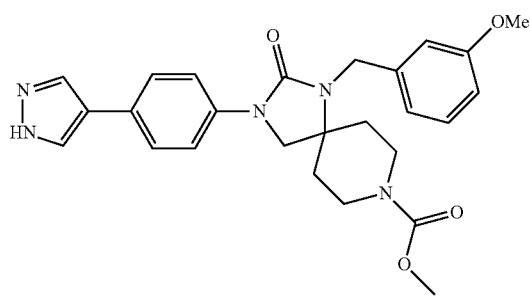 [SMILES: COC(=O)N1CCC2(CC1)CN(c1ccc(-c3cn[nH]c3)cc1)C(=O)N2Cc1cccc(OC)c1]

Example 94a

Preparation of Methyl 3-(4-bromophenyl)-1-(3-methoxybenzyl)-2-oxo-, 3,8-triazaspiro[4.5]decane-8-carboxylate

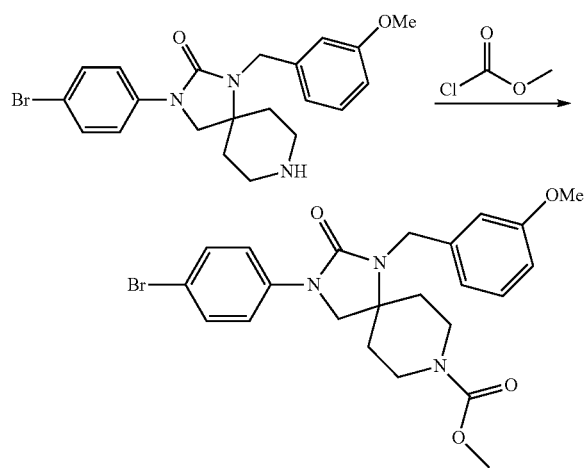

To a solution of 3-(4-bromophenyl)-1-(3-methoxybenzyl)-1,3,8-triazaspiro[4.5]decan-2-one (50 mg, 0.116 mmol) in DCM (5 mL) at 0° C., were added TEA (0.040 mL, 0.29 mmol) and methyl chloroformate (0.011 mL, 0.139 mmol). The reaction mixture was stirred at 0° C. for 10 min, then was allowed to warm to rt and stir for 3 h. The reaction mixture was diluted with DCM, washed with sat. aq. NaHCO$_3$ and brine, dried over Na$_2$SO$_4$, filtered and concentrated to afford methyl 3-(4-bromophenyl)-1-(3-methoxybenzyl)-2-oxo-1,3,8-triazaspiro[4.5]decane-8-carboxylate as a gummy solid (45 mg, 79% yield) MS(ESI) m/z: 491.6 (M+H)$^+$; $^1$H NMR (400 MHz, DMSO-d$_6$) δ ppm 7.58-7.66 (m, 2H) 7.47-7.55 (m, 2H) 7.22 (t, J=8.03 Hz, 1H) 6.87-6.94 (m, 2H) 6.76-6.83 (m, 1H) 4.38 (s, 2H) 3.95 (br. s., 2H) 3.83 (s, 2H) 3.72 (s, 3H) 3.58 (s, 3H) 2.94 (br. s., 2H) 1.74 (td, J=12.93, 4.77 Hz, 2H) 1.49 (d, J=13.05 Hz, 2H).

Example 94

Preparation of methyl 3-(4-(1H-pyrazol-4-yl)phenyl)-1-(3-methoxybenzyl)-2-oxo-1,3,8-triazaspiro[4.5]decane-8-carboxylate

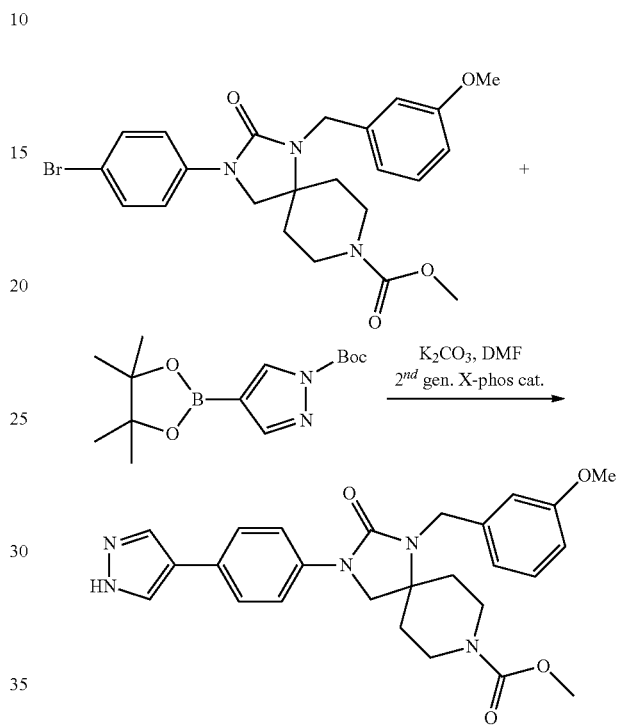

To a solution of methyl 3-(4-bromophenyl)-1-(3-methoxybenzyl)-2-oxo-1,3,8-triazaspiro[4.5]decane-8-carboxylate (45 mg, 0.092 mmol) in DMF (2 mL) were added tert-butyl 4-(4,4,5,5-tetramethyl-1,3,2-dioxaborolan-2-yl)-1H-pyrazole-1-carboxylate (37.9 mg, 0.129 mmol), K$_2$CO$_3$ (38.2 mg, 0.276 mmol) and water (0.4 mL). The reaction mixture was purged with nitrogen for 5 min and charged with 2$^{nd}$ generation XPHOS precatalyst (4.4 mg, 5.5 μmol). The reaction mixture was again purged with nitrogen for 3 min and heated at 90° C. for 16 h. Reaction mixture was cooled to rt and filtered. The filtrate was concentrated and the residue was purified by preparative HPLC to afford methyl 3-(4-(1H-pyrazol-4-yl)phenyl)-1-(3-methoxybenzyl)-2-oxo-1,3,8-triazaspiro[4.5]decane-8-carboxylate as off white solid (16.3 mg, 37% yield). MS(ESI) m/z: 476.2 (M+H)$^+$; $^1$H NMR (400 MHz, DMSO-d$_6$) δ ppm 12.86 (br. s., 1H) 8.13 (br. s., 1H) 7.88 (br. s., 1H) 7.60-7.65 (m, 2H) 7.53-7.59 (m, 2H) 7.22 (t, J=8.07 Hz, 1H) 6.87-6.95 (m, 2H) 6.76-6.82 (m, 1H) 4.38 (s, 2H) 3.96 (br. s., 2H) 3.85 (s, 2H) 3.73 (s, 3H) 3.59 (s, 3H) 2.97 (br. s., 2H) 1.66-1.81 (m, 2H) 1.50 (d, J=13.94 Hz, 2H). LCMS RT=1.79 min, 99.89% (Method E), 1.82 min, 100.0% (Method F).

The following Examples in Table 8 were made by using the same procedure as shown in Example 94.

TABLE 8

| Example | R | Name | LCMS (M + H)+ | HPLC Method, RT (min.) & Purity | NMR |
|---|---|---|---|---|---|
| 95 | | isobutyl 3-(4-(1H-pyrazol-4-yl)phenyl)-1-(3-methoxybenzyl)-2-oxo-1,3,8-triazaspiro[4.5]decane-8-carboxylate | 518.40 | E: 1.91 min, 98.9% | ¹H NMR (400 MHz, DMSO-d₆) δ ppm 7.52-7.67 (m, 4 H) 7.17-7.26 (m, 1 H) 6.86-6.96 (m, 2 H) 6.79 (d, J = 5.02 Hz, 1 H) 4.38 (s, 2 H) 3.99 (br. s., 3 H) 3.85 (s, 3 H) 3.78 (d, J = 6.53 Hz, 3 H) 3.72 (s, 4 H) 3.45 (dd, J = 12.05, 6.02 Hz, 2 H) 1.86 (d, J = 6.53 Hz, 2H) 1.74 (br. s., 3 H) 1.51 (d, J = 11.55 Hz, 3 H) 0.87 (d, J = 6.53 Hz, 8 H) |
| 96 | | ethyl 3-(4-(1H-pyrazol-4-yl)phenyl)-1-(3-methoxybenzyl)-2-oxo-1,3,8-triazaspiro[4.5]decane-8-carboxylate | 490.30 | F: 1.66 min, 99.0% | ¹H NMR (400 MHz, DMSO-d₆) δ ppm 12.84 (br. s., 1 H) 8.11 (br. s., 1 H) 7.90 (br. s., 1 H) 7.50-7.66 (m, 4 H) 7.22 (t, J = 8.03 Hz, 1 H) 6.85-6.95 (m, 2 H) 6.72-6.83 (m, 1 H) 4.38 (s, 2 H) 4.03 (q, J = 7.03 Hz, 2 H) 3.95 (br. s., 2 H) 3.84 (s, 2 H) 3.72 (s, 3 H) 2.95 (br. s., 2 H) 1.66-1.79 (m, 2 H) 1.50 (d, J = 13.05 Hz, 2 H) 1.17 (t, J = 7.03 Hz, 3 H) |
| 97 | | neopentyl 3-(4-(1H-pyrazol-4-yl)phenyl)-1-(3-methoxybenzyl)-2-oxo-1,3,8-triazaspiro[4.5]decane-8-carboxylate | 532.40 | F: 2.01 min, 98.9% | ¹H NMR (400 MHz, DMSO-d₆) δ ppm 12.84 (s, 1 H) 8.14 (br. s., 1 H) 7.89 (s, 1 H) 7.53-7.67 (m, 4 H) 7.22 (t, J = 7.78 Hz, 1 H) 6.85-6.94 (m, 2 H) 6.79 (d, J = 9.54 Hz, 1 H) 4.38 (s, 2 H) 3.98 (d, J = 13.05 Hz, 2 H) 3.85 (s, 2 H) 3.72 (s, 3 H) 3.70 (s, 3 H) 1.75 (br. s., 2 H) 1.52 (d, J = 13.05 Hz, 2 H) 0.89 (s, 10 H) |

TABLE 8-continued

| Example | R | Name | LCMS (M + H)+ | HPLC Method, RT (min.) & Purity | NMR |
|---|---|---|---|---|---|
| 98 | (structure with OMe phenyl, spiro imidazolidinone-piperidine, 4-(1H-pyrazol-4-yl)phenyl, 2-methoxyethyl carbamate) | 2-methoxyethyl 3-(4-(1H-pyrazol-4-yl)phenyl)-1-(3-methoxybenzyl)-2-oxo-1,3,8-triazaspiro[4.5]decane-8-carboxylate | 520.40 | F: 1.51 min, 98.3% | ¹H NMR (400 MHz, DMSO-d₆) δ ppm 12.87 (s, 1 H) 8.13 (s, 1 H) 7.89 (s, 1 H) 7.54-7.65 (m, 4 H) 7.22 (t, J = 8.03 Hz, 1 H) 6.86-6.94 (m, 2 H) 6.80 (d, J = 9.54 Hz, 1 H) 4.38 (s, 2 H) 4.11 (br. s., 2 H) 3.98 (br. s., 2 H) 3.85 (s, 2 H) 3.72 (s, 3 H) 3.51 (t, J = 4.52 Hz, 2 H) 1.74 (br. s., 2 H) 1.51 (d, J = 13.05 Hz, 2 H) |
| 99 | (structure with OMe phenyl, spiro imidazolidinone-piperidine, 4-(1H-pyrazol-4-yl)phenyl, isopropyl carbamate) | isopropyl 3-(4-(1H-pyrazol-4-yl)phenyl)-1-(3-methoxybenzyl)-2-oxo-1,3,8-triazaspiro[4.5]decane-8-carboxylate | 504.40 | E: 1.76 min, 98.6% | ¹H NMR (400 MHz, DMSO-d₆) δ ppm 12.86 (s, 1 H) 8.14 (s, 1 H) 7.88 (br. s., 1 H) 7.52-7.67 (m, 4 H) 7.22 (t, J = 8.03 Hz, 1 H) 6.84-6.95 (m, 2 H) 6.80 (d, J = 9.04 Hz, 1 H) 4.76 (t, J = 6.27 Hz, 1 H) 4.38 (s, 2 H) 3.96 (br. s., 4 H) 3.84 (s, 2 H) 3.72 (s, 5 H) 1.71 (br. s., 3 H) 1.50 (d, J = 12.05 Hz, 3 H) 1.17 (d, J = 6.02 Hz, 7 H) |
| 100 | (structure with OMe phenyl, spiro imidazolidinone-piperidine, 4-(1H-pyrazol-4-yl)phenyl, propyl carbamate) | propyl 3-(4-(1H-pyrazol-4-yl)phenyl)-1-(3-methoxybenzyl)-2-oxo-1,3,8-triazaspiro[4.5]decane-8-carboxylate | 504.4 | F: 1.78 min, 99.2% | ¹H NMR (400 MHz, DMSO-d₆) δ ppm 12.85 (s, 1 H) 8.11 (br. s., 1 H) 7.89 (s, 1 H) 7.50-7.72 (m, 4 H) 7.22 (t, J = 8.03 Hz, 1 H) 6.84-6.96 (m, 2 H) 6.69-6.84 (m, 1 H) 4.38 (s, 2 H) 3.94 (t, J = 6.53 Hz, 5 H) 3.85 (s, 2 H) 3.72 (s, 4 H) 2.96 (br. s., 2 H) 1.65-1.82 (m, 2 H) 1.39-1.62 (m, 5 H) 0.87 (t, J = 7.28 Hz, 4 H) |

TABLE 8-continued

| Example | R | Name | LCMS (M + H)+ | HPLC Method, RT (min.) & Purity | NMR |
|---|---|---|---|---|---|
| 101 | 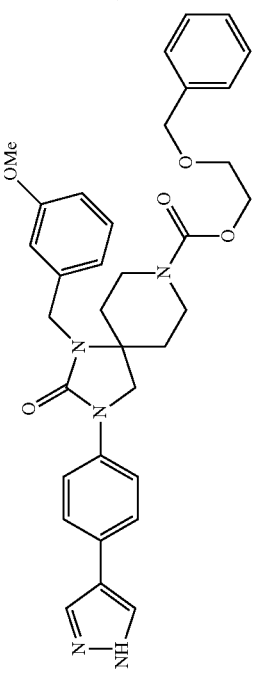 | 2-(benzyloxy)ethyl 3-(4-(1H-pyrazol-4-yl)phenyl)-1-(3-methoxybenzyl)-2-oxo-1,3,8-triazaspiro[4.5]decane-8-carboxylate | 596.40 | F: 1.880 min, 97.8 | $^1$H NMR (400 MHz, DMSO-d$_6$) δ ppm 8.00 (br. s., 1 H) 7.48-7.68 (m, 3 H) 7.24-7.37 (m, 4 H) 7.17-7.24 (m, 1 H) 6.82-6.94 (m, 2 H) 6.70-6.82 (m, 1 H) 4.50 (s, 2 H) 4.36 (s, 2 H) 4.10-4.24 (m, 2 H) 3.98 (d, J = 12.05 Hz, 2 H) 3.86 (s, 2 H) 3.66-3.77 (m, 3 H) 3.53-3.66 (m, 2 H) 2.97 (br. s., 2 H) 1.66-1.81 (m, 2 H) 1.52 (d, J = 12.55 Hz, 2 H) |
| 102 | 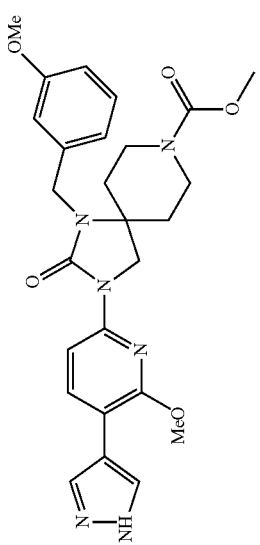 | methyl 3-(6-methoxy-5-(1H-pyrazol-4-yl)pyridin-2-yl)-1-(3-methoxybenzyl)-2-oxo-1,3,8-triazaspiro[4.5]decane-8-carboxylate | 507.2 | E: 1.87 min, 100% F: 1.90 min, 100% | $^1$H NMR (400 MHz, DMSO-d6) δ ppm 12.87 (br. s., 1 H), 8.09 (br. s., 1 H), 7.99 (d, J = 8.4 Hz, 1 H), 7.95 (br. s., 1 H), 7.74 (d, J = 8.3 Hz, 1 H), 7.23 (t, J = 7.9 Hz, 1 H), 6.95-6.88 (m, 2 H), 6.80 (dd, J = 7.1, 2.0 Hz, 1 H), 4.41 (s, 2 H), 4.03 (s, 2 H), 4.01 (s, 3 H), 4.00-3.93 (m, 2 H), 3.73 (s, 3 H), 3.59 (s, 3 H), 2.95 (br. s., 2 H), 1.84-1.71 (m, 2 H), 1.58-1.47 (m, 2 H) |
| 103 | 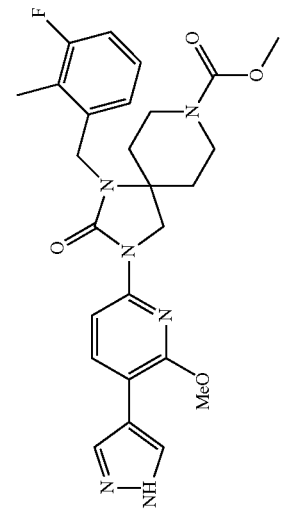 | methyl 1-(3-fluoro-2-methylbenzyl)-3-(6-methoxy-5-(1H-pyrazol-4-yl)pyridin-2-yl)-2-oxo-1,3,8-triazaspiro[4.5]decane-8-carboxylate | 509.2 | E: 2.02 min, 100% F: 2.04 min, 100% | $^1$H NMR (400 MHz, DMSO-d6) δ ppm 12.87 (br. s., 1 H), 8.09 (br. s., 1 H), 7.99 (d, J = 8.1 Hz, 1 H), 7.95 (br. s., 1 H), 7.72 (d, J = 8.3 Hz, 1 H), 7.20-7.13 (m, 1 H), 7.12-7.07 (m, 1 H), 7.06-6.97 (m, 1 H), 4.42 (s, 2 H), 4.10 (s, 2 H), 4.03 (s, 3 H), 3.98 (br. s., 2 H), 3.58 (s, 3 H), 2.98 (br. s., 2 H), 2.22 (s, 3 H), 1.80-1.69 (m, 2 H), 1.64-1.53 (m, 2 H); $^{19}$F NMR (376 MHz, DMSO-d6) δ ppm –118.42 |

TABLE 8-continued

| Example | R | Name | LCMS (M + H)+ | HPLC Method, RT (min.) & Purity | NMR |
|---|---|---|---|---|---|
| 104 | (3-fluoro-2-methylbenzyl) | methyl 3-(6-ethyl-5-(1H-pyrazol-4-yl)pyridin-2-yl)-1-(3-fluoro-2-methylbenzyl)-2-oxo-1,3,8-triazaspiro[4.5]decane-8-carboxylate | 507.3 | E: 1.42 min, 98.3% | ¹H NMR (400 MHz, DMSO-d6) d ppm 13.00 (br. s., 1 H) 7.99 (d, J = 8.53 Hz, 1 H) 7.92 (br. s., 1 H) 7.68 (d, J = 8.53 Hz, 2 H) 7.12-7.21 (m, 1 H) 7.06-7.12 (m, 1 H) 6.94-7.06 (m, 1 H) 4.43 (s, 2 H) 4.08 (s, 2 H) 3.96 (br. s., 2 H) 3.59 (s, 3 H) 2.97 (br. s., 2 H) 2.83 (q, J = 7.53 Hz, 2 H) 2.23 (d, J = 1.51 Hz, 3 H) 1.66-1.80 (m, 2 H) 1.61 (d, J = 12.55 Hz, 2 H) 1.25 (t, J = 7.53 Hz, 4 H) |
| 105 | (3-methoxybenzyl) | methyl 3-(6-ethyl-5-(1H-pyrazol-4-yl)pyridin-2-yl)-1-(3-methoxybenzyl)-2-oxo-1,3,8-triazaspiro[4.5]decane-8-carboxylate | 505.3 | E: 1.71 min, 98.3% | ¹H NMR (400 MHz, DMSO-d6) d ppm 13.00 (s, 1 H) 8.03 (s, 1 H) 7.93 (s, 1 H) 7.69 (d, J = 8.56 Hz, 2 H) 7.23 (t, J = 8.07 Hz, 1 H) 6.85-6.97 (m, 2 H) 6.81 (d, J = 9.78 Hz, 1 H) 4.42 (s, 2 H) 4.01 (s, 4 H) 3.73 (s, 3 H) 3.60 (s, 3 H) 2.95 (s, 2 H) 2.82 (q, J = 7.66 Hz, 2 H) 1.69-1.84 (m, 2 H) 1.53 (d, J = 11.00 Hz, 2 H) 1.20-1.28 (m, 4 H) |
| 106 | (3-fluoro-5-methoxybenzyl) | ethyl 3-(6-ethyl-5-(1H-pyrazol-4-yl)pyridin-2-yl)-1-(3-fluoro-5-methoxybenzyl)-2-oxo-1,3,8-triazaspiro[4.5]decane-8-carboxylate | 537.3 | E: 1.87 min, 92.0% | ¹H NMR (400 MHz, METHANOL-d4) d ppm 8.03 (d, J = 8.53 Hz, 1 H) 7.82 (br. s., 2 H) 7.67 (d, J = 8.53 Hz, 1 H) 6.78 (s, 1 H) 6.72 (d, J = 9.54 Hz, 1 H) 6.55-6.63 (m, 1 H) 4.49 (s, 2 H) 4.11-4.23 (m, 6 H) 3.80 (s, 3 H) 3.02 (br. s., 3 H) 2.88 (q, J = 7.53 Hz, 2 H) 1.89 (br. s., 2 H) 1.64 (d, J = 13.05 Hz, 2 H) 1.24-1.35 (m, 11 H) |

TABLE 8-continued

| Example | R | Name | LCMS (M + H)+ | HPLC Method, RT (min.) & Purity | NMR |
|---|---|---|---|---|---|
| 107 | | methyl 3-(6-ethyl-5-(1H-pyrazol-4-yl)pyridin-2-yl)-1-(3-fluoro-5-methoxybenzyl)-2-oxo-1,3,8-triazaspiro[4.5]decane-8-carboxylate | 523.3 | F: 1.35 min, 97.4% | 1H NMR (400 MHz, DMSO-d6) d ppm 13.00 (s, 1 H) 8.01 (d, J = 8.56 Hz, 1 H) 7.93 (br. s., 1 H) 7.69 (d, J = 8.56 Hz, 2 H) 6.65-6.80 (m, 3 H) 4.42 (s, 2 H) 4.03 (s, 4 H) 3.75 (s, 3 H) 3.60 (s, 3 H) 2.95 (br. s., 2 H) 2.82 (q, J = 7.42 Hz, 2 H) 1.67-1.83 (m, 2 H) 1.55 (d, J = 12.47 Hz, 2 H) 1.24 (t, J = 7.34 Hz, 4 H) |
| 108 | | methyl 3-(4-(1H-pyrazol-4-yl)phenyl)-1-(3-fluoro-2-methylbenzyl)-2-oxo-1,3,8-triazaspiro[4.5]decane-8-carboxylate | 478.3 | F: 1.55 min, 98.7% | 1H NMR (400 MHz, DMSO-d6) d ppm 12.86 (br. s., 1 H) 8.13 (s, 1 H) 7.88 (s, 1 H) 7.53-7.66 (m, 4 H) 7.12-7.21 (m, 1 H) 7.07-7.12 (m, 1 H) 7.03 (t, J = 8.78 Hz, 1 H) 4.40 (s, 2 H) 3.85-4.05 (m, 4 H) 3.59 (s, 3 H) 2.99 (br. s., 2 H) 2.23 (d, J = 1.51 Hz, 3 H) 1.66-1.80 (m, 2 H) 1.59 (d, J = 12.05 Hz, 2 H) |
| 109 | | methyl 3-(4-(1H-pyrazol-4-yl)phenyl)-1-(3-fluoro-5-methoxybenzyl)-2-oxo-1,3,8-triazaspiro[4.5]decane-8-carboxylate | 494.3 | F: 1.48 min, 96.7% | 1H NMR (400 MHz, DMSO-d6) d ppm 12.86 (br. s., 1 H) 8.14 (s, 1 H) 7.88 (s, 1 H) 7.60-7.66 (m, 2 H) 7.54-7.60 (m, 2 H) 6.77 (s, 1 H) 6.74 (d, J = 9.54 Hz, 1 H) 6.69 (dt, J = 11.04, 2.51 Hz, 1 H) 4.38 (s, 2 H) 3.97 (br. s., 2 H) 3.87 (s, 2 H) 3.75 (s, 3 H) 3.60 (s, 3 H) 2.98 (br. s., 2 H) 1.75 (td, J = 12.80, 5.52 Hz, 2 H) 1.53 (d, J = 12.55 Hz, 2H) |

TABLE 8-continued

| Example | R | Name | LCMS (M + H)+ | HPLC Method, RT (min.) & Purity | NMR |
|---|---|---|---|---|---|
| 110 | | ethyl 3-(5-(1H-pyrazol-4-yl)pyridin-2-yl)-1-(3-methoxybenzyl)-2-oxo-1,3,8-triazaspiro[4.5]decane-8-carboxylate | 491.3 | E: 1.56 min, 98.4% | $^1$H NMR (400 MHz, DMSO-d6) d ppm 12.96 (br. s., 1 H) 8.59 (dd, J = 2.51, 1.00 Hz, 1 H) 8.17-8.24 (m, 1 H) 7.92-8.01 (m, 1 H) 7.23 (t, J = 8.03 Hz, 1 H) 6.86-6.97 (m, 2 H) 6.76-6.85 (m, 1 H) 6.52 (s, 1 H) 4.42 (s, 2 H) 3.88-4.09 (m, 6 H) 3.73 (s, 3 H) 2.94 (br. s., 2 H) 1.75 (td, J = 12.93, 4.77 Hz, 2 H) 1.52 (d, J = 12.05 Hz, 2 H) 1.18 (t, J = 7.03 Hz, 3 H) |
| 111 | | methyl 3-(4-methoxy-5-(1H-pyrazol-4-yl)pyrimidin-2-yl)-1-(3-methoxybenzyl)-2-oxo-1,3,8-triazaspiro[4.5]decane-8-carboxylate | 508.3 | F: 1.14 min, 93.7% | $^1$H NMR (400 MHz, DMSO-d6) d ppm 13.01 (s, 1 H) 8.71 (s, 1 H) 8.16 (s, 1 H) 8.00 (s, 1 H) 7.20-7.27 (m, 1 H) 6.87-6.96 (m, 2 H) 6.81 (d, J = 10.04 Hz, 1 H) 4.41 (s, 2 H) 4.07 (s, 3 H) 4.00 (s, 3 H) 3.74 (s, 3 H) 3.59 (s, 3 H) 2.92 (s, 2 H) 1.76 (s, 2 H) 1.53 (d, J = 13.05 Hz, 2 H) |
| 112 | | ethyl 3-(4-methoxy-5-(1H-pyrazol-4-yl)pyrimidin-2-yl)-1-(3-methoxybenzyl)-2-oxo-1,3,8-triazaspiro[4.5]decane-8-carboxylate | 522.3 | E: 1.49 min, 97.8% | $^1$H NMR (400 MHz, DMSO-d6) d ppm 13.01 (br. s., 1 H) 8.71 (s, 1 H) 8.16 (s, 1 H) 8.00 (br. s., 1 H) 7.19-7.27 (m, 1 H) 6.86-6.95 (m, 2 H) 6.81 (d, J = 5.52 Hz, 1 H) 4.41 (s, 2 H) 4.05-4.09 (m, 3 H) 3.94-4.05 (m, 6 H) 3.74 (s, 3 H) 2.95 (s, 2 H) 1.74 (s, 2 H) 1.53 (d, J = 14.05 Hz, 2 H) 1.18 (t, J = 7.28 Hz, 3 H) |

Example 113

3-(4-(1H-pyrazol-4-yl)phenyl)-1-(3-methoxybenzyl)-8-methyl-1,3,8-triazaspiro[4.5]decan-2-one

Example 113a

Preparation of 3-(4-bromophenyl)-1-(3-methoxybenzyl)-8-methyl-1,3,8-triazaspiro[4.5]decan-2-one

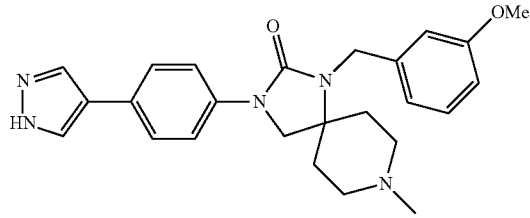 [SMILES: COc1cccc(CN2C(=O)N(c3ccc(-c4cn[nH]c4)cc3)CC23CCN(C)CC3)c1]

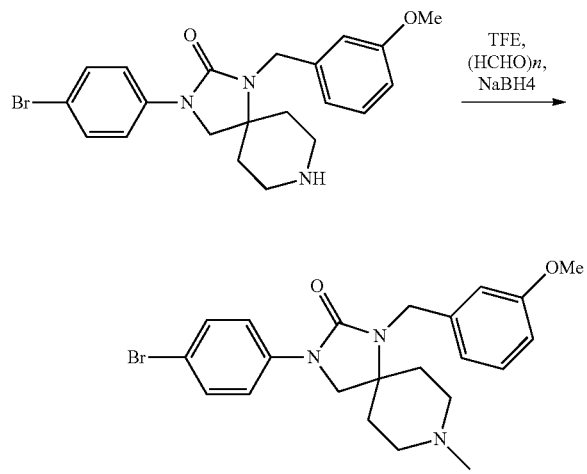

To a solution of 3-(4-bromophenyl)-1-(3-methoxybenzyl)-1,3,8-triazaspiro[4.5]decan-2-one (60 mg, 0.139 mmol) in 2,2,2-trifluoroethanol (1 mL), was added paraformaldehyde (20.93 mg, 0.697 mmol). NaBH$_4$ (10.6 mg, 0.279 mmol) was added and the mixture was stirred at 75° C. for 3 h. The reaction mixture was filtered, rinsing with TFE. The solvent was evaporated. The residue was partitioned between water and ethyl acetate. The ethyl acetate layer was washed with brine, dried over Na$_2$SO$_4$, filtered and concentrated to afford 3-(4-bromophenyl)-1-(3-methoxybenzyl)-8-methyl-1,3,8-triazaspiro[4.5]decan-2-one as gummy solid (60 mg, 97% yield). MS(ESI) m/z: 446.2 (M+H)$^+$; $^1$H NMR (300 MHz, DMSO-d$_6$) δ ppm 7.63 (d, J=9.07 Hz, 2H) 7.50 (d, J=9.07 Hz, 2H) 7.22 (t, J=8.12 Hz, 1H) 6.88-6.93 (m, 2H) 6.79 (d, J=9.07 Hz, 1H) 4.37 (s, 2H) 3.72 (s, 3H) 3.69-3.72 (m, 2H) 2.68 (d, J=11.71 Hz, 2H) 2.14 (s, 3H) 1.95-2.07 (m, 2H) 1.85 (d, J=12.84 Hz, 2H) 1.40 (d, J=11.71 Hz, 2H).

Example 113

Preparation of 3-(4-(1H-pyrazol-4-yl)phenyl)-1-(3-methoxybenzyl)-8-methyl-1,3,8-triazaspiro[4.5]decan-2-one

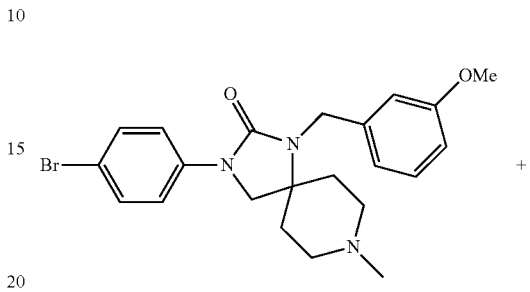

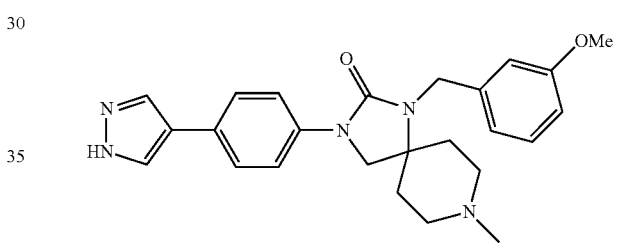

To a solution of 3-(4-bromophenyl)-1-(3-methoxybenzyl)-8-methyl-1,3,8-triazaspiro[4.5]decan-2-one (60 mg, 0.135 mmol) in DMF (4 mL) were added tert-butyl 4-(4,4,5,5-tetramethyl-1,3,2-dioxaborolan-2-yl)-1H-pyrazole-1-carboxylate (55.6 mg, 0.189 mmol), K$_2$CO$_3$ (56 mg, 0.41 mmol) and water (0.4 mL). The reaction mixture was purged with nitrogen for 5 min and charged with 2$^{nd}$ generation XPHOS precatalyst (6.4 mg, 8.1 μmol). The reaction mixture was again purged with nitrogen for 3 min and heated at 90° C. for 16 h. Reaction mixture was cooled to rt, filtered and concentrated. The residue was purified by preparative HPLC to afford 3-(4-(1H-pyrazol-4-yl)phenyl)-1-(3-methoxybenzyl)-8-methyl-1,3,8-triazaspiro[4.5]decan-2-one as a pale yellow solid (9.2 mg, 16% yield), MS(ESI) m/z: 432.2 (M+H)$^+$; $^1$H NMR (400 MHz, DMSO-d$_6$) δ ppm 12.85 (br. s., 1H) 8.11 (br. s., 1H) 7.88 (br. s., 1H) 7.62 (d, J=8.80 Hz, 2H) 7.56 (d, J=8.80 Hz, 2H) 7.17-7.27 (m, 1H) 6.87-6.94 (m, 2H) 6.74-6.83 (m, 1H) 4.37 (s, 2H) 3.74 (s, 2H) 3.73 (s, 3H) 2.70 (br. s., 2H) 2.18 (s, 3H) 2.07 (br. s., 2H) 1.79-1.91 (m, 2H) 1.44 (d, J=11.49 Hz, 2H). LCMS RT=1.22 min, 100.0% (Method E), 1.33 min, 100.0% (Method F).

The following Examples in Table 9 were made by using the same procedure as shown in Example 113.

TABLE 9

| Example | R | Name |
|---|---|---|
| 114 | | 3-(4-(1H-pyrazol-4-yl)phenyl)-1-(3-methoxybenzyl)-8-((tetrahydrofuran-3-yl)methyl)-1,3,8-triazaspiro[4.5]decan-2-one |
| 115 | | 3-(4-(1H-pyrazol-4-yl)phenyl)-8-(cyclopropylmethyl)-1-(3-methoxybenzyl)-1,3,8-triazaspiro[4.5]decan-2-one |
| 116 | | 3-(4-(1H-pyrazol-4-yl)phenyl)-1-(3-methoxybenzyl)-8-propyl-1,3,8-triazaspiro[4.5]decan-2-one |
| 117 | | 3-(4-(1H-pyrazol-4-yl)phenyl)-8-isopentyl-1-(3-methoxybenzyl)-1,3,8-triazaspiro[4.5]decan-2-one |
| 118 | | 3-(4-(1H-pyrazol-4-yl)phenyl)-8-(cyclopentylmethyl)-1-(3-methoxybenzyl)-1,3,8-triazaspiro[4.5]decan-2-one |

TABLE 9-continued

| 120 | 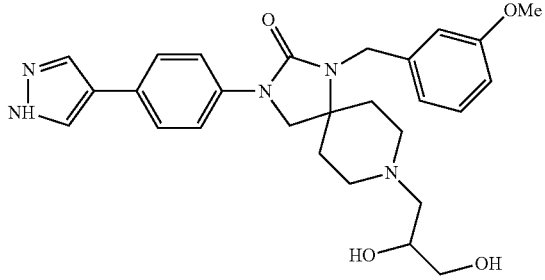 | 3-(4-(1H-pyrazol-4-yl)phenyl)-8-(2,3-dihydroxypropyl)-1-(3-methoxybenzyl)-1,3,8-triazaspiro[4.5]decan-2-one |
| --- | --- | --- |
| 121 | 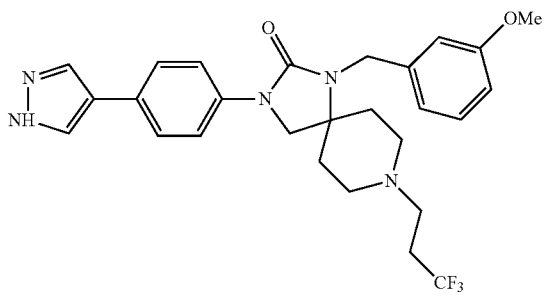 [SMILES: COc1cccc(CN2C(=O)N(c3ccc(-c4cn[nH]c4)cc3)CC23CCN(CCC(F)(F)F)CC3)c1] | 3-(4-(1H-pyrazol-4-yl)phenyl)-1-(3-methoxybenzyl)-8-(3,3,3-trifluoropropyl)-1,3,8-triazaspiro[4.5]decan-2-one |
| 122 | 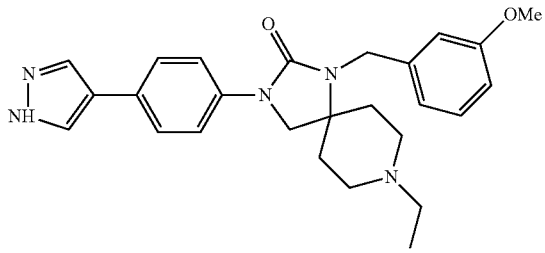 [SMILES: CCN1CCC2(CC1)CN(c1ccc(-c3cn[nH]c3)cc1)C(=O)N2Cc1cccc(OC)c1] | 3-(4-(1H-pyrazol-4-yl)phenyl)-8-ethyl-1-(3-methoxybenzyl)-1,3,8-triazaspiro[4.5]decan-2-one |
| 123 | 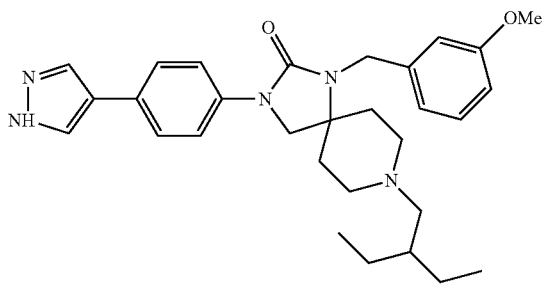 [SMILES: CCC(CC)CN1CCC2(CC1)CN(c1ccc(-c3cn[nH]c3)cc1)C(=O)N2Cc1cccc(OC)c1] | 3-(4-(1H-pyrazol-4-yl)phenyl)-8-(2-ethylbutyl)-1-(3-methoxybenzyl)-1,3,8-triazaspiro[4.5]decan-2-one |
| 124 | 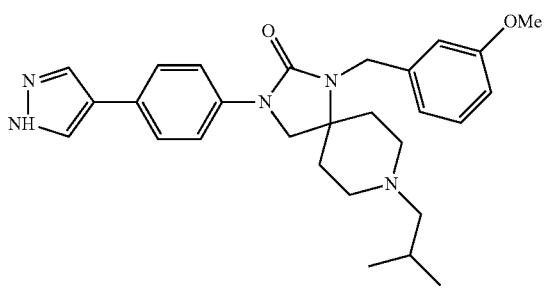 [SMILES: COc1cccc(CN2C(=O)N(c3ccc(-c4cn[nH]c4)cc3)CC23CCN(CC(C)C)CC3)c1] | 3-(4-(1H-pyrazol-4-yl)phenyl)-8-isobutyl-1-(3-methoxybenzyl)-1,3,8-triazaspiro[4.5]decan-2-one |

TABLE 9-continued

| | | |
|---|---|---|
| 125 | 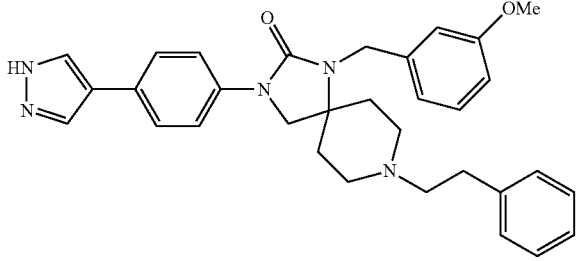 [SMILES: COc1cccc(CN2C(=O)N(c3ccc(-c4cn[nH]c4)cc3)CC23CCN(CCc2ccccc2)CC3)c1] | 3-(4-(1H-pyrazol-4-yl)phenyl)-1-(3-methoxybenzyl)-8-phenethyl-1,3,8-triazaspiro[4.5]decan-2-one |
| 126 | 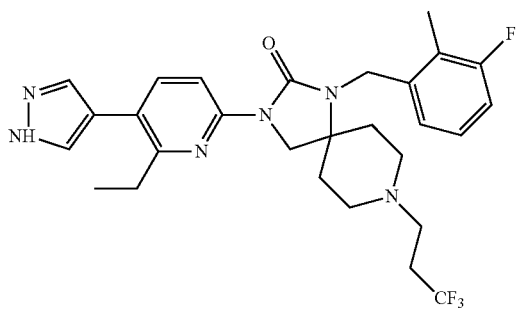 [SMILES: CCc1nc(N2CC3(CCN(CCC(F)(F)F)CC3)N(Cc3cccc(F)c3C)C2=O)ccc1-c1cn[nH]c1] | 3-(6-ethyl-5-(1H-pyrazol-4-yl)pyridin-2-yl)-1-(3-fluoro-2-methylbenzyl)-8-(3,3,3-trifluoropropyl)-1,3,8-triazaspiro[4.5]decan-2-one |
| 127 | 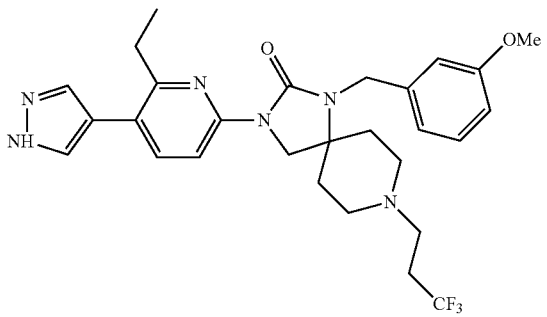 [SMILES: CCc1nc(N2CC3(CCN(CCC(F)(F)F)CC3)N(Cc3cccc(OC)c3)C2=O)ccc1-c1cn[nH]c1] | 3-(6-ethyl-5-(1H-pyrazol-4-yl)pyridin-2-yl)-1-(3-methoxybenzyl)-8-(3,3,3-trifluoropropyl)-1,3,8-triazaspiro[4.5]decan-2-one |
| 128 | 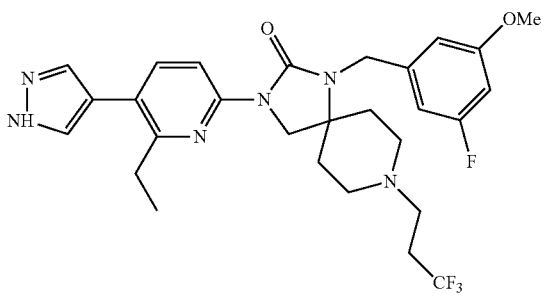 [SMILES: CCc1nc(N2CC3(CCN(CCC(F)(F)F)CC3)N(Cc3cc(F)cc(OC)c3)C2=O)ccc1-c1cn[nH]c1] | 3-(6-ethyl-5-(1H-pyrazol-4-yl)pyridin-2-yl)-1-(3-fluoro-5-methoxybenzyl)-8-(3,3,3-trifluoropropyl)-1,3,8-triazaspiro[4.5]decan-2-one |
| 129 | 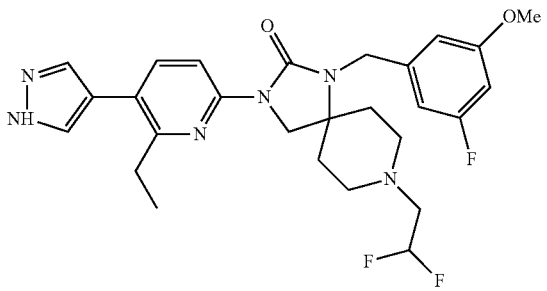 [SMILES: CCc1nc(N2CC3(CCN(CC(F)F)CC3)N(Cc3cc(F)cc(OC)c3)C2=O)ccc1-c1cn[nH]c1] | 8-(2,2-difluoroethyl)-3-(6-ethyl-5-(1H-pyrazol-4-yl)pyridin-2-yl)-1-(3-fluoro-5-methoxybenzyl)-1,3,8-triazaspiro[4.5]decan-2-one |

TABLE 9-continued

| 130 | 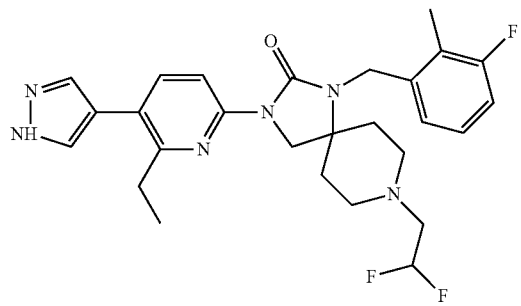 [SMILES: CCc1nc(N2CC3(CCN(CC(F)F)CC3)N(Cc3cccc(F)c3C)C2=O)ccc1-c1cn[nH]c1] | 8-(2,2-difluoroethyl)-3-(6-ethyl-5-(1H-pyrazol-4-yl)pyridin-2-yl)-1-(3-fluoro-2-methylbenzyl)-1,3,8-triazaspiro[4.5]decan-2-one |
| --- | --- | --- |
| 131 | 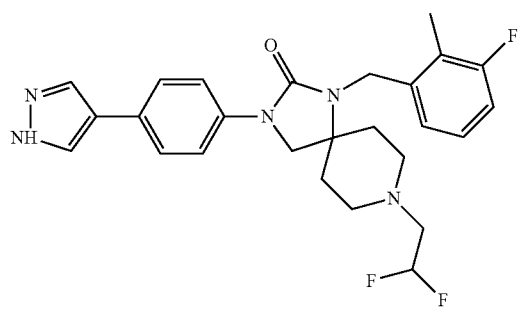 [SMILES: Cc1c(F)cccc1CN1C(=O)N(c2ccc(-c3cn[nH]c3)cc2)CC12CCN(CC(F)F)CC2] | 3-(4-(1H-pyrazol-4-yl)phenyl)-8-(2,2-difluoroethyl)-1-(3-fluoro-2-methylbenzyl)-1,3,8-triazaspiro[4.5]decan-2-one |
| 132 | 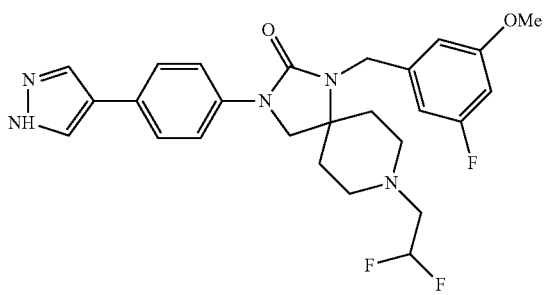 [SMILES: COc1cc(F)cc(CN2C(=O)N(c3ccc(-c4cn[nH]c4)cc3)CC23CCN(CC(F)F)CC3)c1] | 3-(4-(1H-pyrazol-4-yl)phenyl)-8-(2,2-difluoroethyl)-1-(3-fluoro-5-methoxybenzyl)-1,3,8-triazaspiro[4.5]decan-2-one |
| 133 | 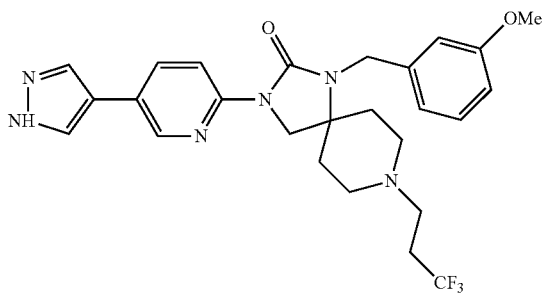 [SMILES: COc1cccc(CN2C(=O)N(c3ccc(-c4cn[nH]c4)cn3)CC23CCN(CCC(F)(F)F)CC3)c1] | 3-(5-(1H-pyrazol-4-yl)pyridin-2-yl)-1-(3-methoxybenzyl)-8-(3,3,3-trifluoropropyl)-1,3,8-triazaspiro[4.5]decan-2-one |
| 134 | 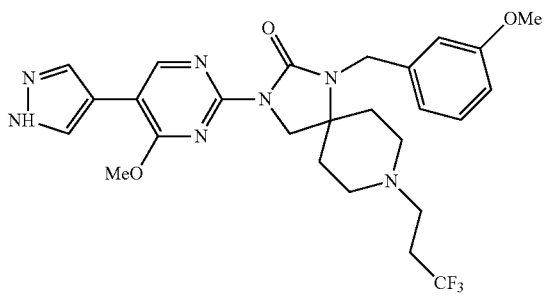 [SMILES: COc1cccc(CN2C(=O)N(c3ncc(-c4cn[nH]c4)c(OC)n3)CC23CCN(CCC(F)(F)F)CC3)c1] | 3-(4-methoxy-5-(1H-pyrazol-4-yl)pyrimidin-2-yl)-1-(3-methoxybenzyl)-8-(3,3,3-trifluoropropyl)-1,3,8-triazaspiro[4.5]decan-2-one |

TABLE 9-continued

| | | | |
|---|---|---|---|
| 135 | | | 8-(2,2-difluoroethyl)-3-(6-methoxy-5-(1H-pyrazol-4-yl)pyridin-2-yl)-1-(3-methoxybenzyl)-1,3,8-triazaspiro[4.5]decan-2-one |
| 136 | | | 3-(6-methoxy-5-(1H-pyrazol-4-yl)pyridin-2-yl)-1-(3-methoxybenzyl)-8-(3,3,3-trifluoropropyl)-1,3,8-triazaspiro[4.5]decan-2-one |
| 137 | | | 8-(2,2-difluoroethyl)-1-(3-fluoro-2-methylbenzyl)-3-(6-methoxy-5-(1H-pyrazol-4-yl)pyridin-triazaspiro[4.5]decan-2-one |

| Example | LCMS (M +H)+ | HPLC Method, RT (min.) & Purity | NMR |
|---|---|---|---|
| 114 | 502.4 | F: 1.48; 99.73% | $^1$H NMR (400 MHz, DMSO-d$_6$) δ ppm 12.86 (br. s., 1 H) 8.13 (br. s., 1 H) 7.88 (br. s., 1 H) 7.63 (m, J = 9.04 Hz, 2 H) 7.56 (m, J = 9.04 Hz, 2 H) 7.22 (t, J = 8.03 Hz, 1 H) 6.86-6.95 (m, 2H) 6.80 (d, J = 9.54 Hz, 1 H) 4.38 (s, 2 H) 3.69-3.78 (m, 5 H) 2.79 (d, J = 9.54 Hz, 2 H) 2.22-2.30 (m, 3 H) 2.07 (s, 2 H) 2.00 (d, J = 11.55 Hz, 2 H) 1.82 (d, J = 10.54 Hz, 2 H) 1.54 (dd, J = 13.55, 7.03 Hz, 2 H) 1.44 (d, J = 12.55 Hz, 2 H) 1.29 (d, J = 7.53 Hz, 2 H) 0.86 (d, J = 6.53 Hz, 7 H) |
| 115 | 472.40 | F: 1.08; 97.9% | $^1$H NMR (400 MHz, DMSO-d$_6$) δ ppm 12.87 (br. s., 1 H) 8.12 (br. s., 1 H) 7.89 (br. s., 1 H) 7.49-7.73 (m, 4 H) 7.24 (t, J = 8.03 Hz, 1 H) 6.86-7.00 (m, 2 H) 6.74-6.84 (m, 1 H) 4.40 (s, 2 H) 3.74 (s, 6 H) 2.93 (br. s., 1 H) 2.18 (d, J = 6.53 Hz, 2 H) 1.99-2.11 (m, 2 H) 1.78-1.93 (m, 2 H) 1.46 (d, J = 12.05 Hz, 2 H) 0.81 (br. s., 1 H) 0.36-0.50 (m, 2 H) 0.01-0.12 (m, 2 H) |
| 116 | 488.40 | F: 1.05; 97.9% | $^1$H NMR (400 MHz, DMSO-d$_6$) δ ppm 12.85 (s, 1 H) 8.14 (s, 1 H) 7.88 (s, 1 H) 7.62 (d, J = 8.53 Hz, 2 H) 7.56 (d, J = 9.04 Hz, 2 H) 7.17-7.28 (m, 1 H) 6.84-6.96 (m, 2 H) 6.80 (d, J = 9.04 Hz, 1 H) 4.38 (s, 2 H) 4.10 (q, J = 5.02 Hz, 2 H) 3.68-3.78 (m, 5 H) 3.17 (d, J = 5.02 Hz, 6 H) 2.22 (br. s., 2 H) 2.02 (br. s., 1 H) 1.82 (br. s., 2 H) 1.42 (br. s., 4 H) 0.77-0.89 (m, 4 H) |
| 117 | 500.40 | F: 1.81; 96.6% | $^1$H NMR (400 MHz, METHANOL-d$_4$) δ ppm 7.95 (br. s., 2 H) 7.52-7.69 (m, 4 H) 7.25 (t, J = 8.03 Hz, 1 H) 6.89-7.03 (m, 2 H) 6.74-6.86 (m, 1 H) 4.50 (s, 2 H) 3.88 (s, 2 H) 3.80 (s, 3 H) 3.07 (br. s., 2 H) 2.55 (br. s., 2 H) 2.37 (d, J = 14.56 Hz, 2 H) 1.94-2.15 (m, 2 H) 1.51-1.73 (m, 4 H) 1.41-1.51 (m, 2 H) 0.88-1.02 (m, 7 H) |
| 118 | 500.40 | F: 1.26; 99.3% | $^1$H NMR (400 MHz, DMSO-d$_6$) δ ppm 12.86 (br. s., 1 H) 8.13 (br. s., 1 H) 7.88 (br. s., 1 H) 7.62 (m, |

TABLE 9-continued

| | | | |
|---|---|---|---|
| | | | J = 8.53 Hz, 2 H) 7.56 (m, J = 9.04 Hz, 2 H) 7.23 (t, J = 7.78 Hz, 1 H) 6.85-6.96 (m, 2 H) 6.76-6.82 (m, 1 H) 4.38 (s, 2 H) 3.68-3.77 (m, 5 H) 2.80 (d, J = 12.05 Hz, 2 H) 2.18 (d, J = 7.53 Hz, 2 H) 1.98-2.08 (m, 3 H) 1.81 (t, J = 13.05 Hz, 2 H) 1.66 (d, J = 7.03 Hz, 2 H) 1.37-1.58 (m, 7 H) 1.14 (dd, J = 12.30, 6.78 Hz, 2 H) |
| 120 | 462.40 | F: 0.91; 96.7% | $^1$H NMR (400 MHz, DMSO-$d_6$) δ ppm 8.00 (br. s., 2 H) 7.64 (m, J = 9.04 Hz, 2 H) 7.57 (m, J = 8.53 Hz, 2 H) 7.17-7.29 (m, 1 H) 6.86-6.98 (m, 2 H) 6.80 (dd, J = 7.28, 1.76 Hz, 1 H) 4.39 (s, 4 H) 3.71-3.82 (m, 6 H) 3.57 (d, J = 5.52 Hz, 1 H) 2.80-2.89 (m, 2 H) 2.35-2.40 (m, 1 H) 2.09-2.28 (m, 2 H) 1.84 (t, J = 12.55 Hz, 2 H) 1.45 (d, J = 12.55 Hz, 2 H) |
| 121 | 514.20 | F: 1.85; 95.1% | $^1$H NMR (400 MHz, DMSO-$d_6$) δ ppm 12.88 (br. s., 1 H) 8.14 (s, 1 H) 7.89 (s, 1 H) 7.64 (m, J = 9.04 Hz, 2 H) 7.58 (m, J = 9.04 Hz, 2 H) 7.23 (t, J = 8.03 Hz, 1 H) 6.86-6.97 (m, 2 H) 6.75-6.85 (m, 1 H) 4.39 (s, 2 H) 3.76 (s, 2 H) 3.73 (s, 3 H) 2.83 (d, J = 10.54 Hz, 2 H) 2.03-2.21 (m, 1 H) 1.82 (br. s., 2 H) 1.46 (d, J = 11.55 Hz, 2 H) |
| 122 | 446.30 | F: 1.25; 95.8% | $^1$H NMR (400 MHz, DMSO-$d_6$) δ ppm 12.87 (s, 1 H) 8.11 (s, 1 H) 7.88 (s, 1 H) 7.63 (m, J = 9.04 Hz, 2 H) 7.56 (m, J = 9.04 Hz, 2 H) 7.22 (t, J = 8.28 Hz, 1 H) 6.85-6.94 (m, 2 H) 6.80 (d, J = 9.04 Hz, 1 H) 4.38 (s, 2 H) 3.69-3.78 (m, 5 H) 2.82 (br. s., 2 H) 2.01 (br. s., 2 H) 1.83 (br. s., 2 H) 1.44 (d, J = 13.55 Hz, 2 H) |
| 123 | 502.40 | F: 1.31; 99.1% | $^1$H NMR (400 MHz, DMSO-$d_6$) δ ppm 12.86 (br. s., 1 H) 8.13 (br. s., 1 H) 7.88 (br. s., 1 H) 7.63 (m, J = 9.04 Hz, 2 H) 7.56 (m, J = 9.04 Hz, 2 H) 7.23 (t, J = 8.03 Hz, 1 H) 6.87-6.97 (m, 2 H) 6.72-6.84 (m, 1 H) 4.39 (s, 2 H) 3.69-3.77 (m, 5 H) 2.76 (d, J = 12.05 Hz, 2 H) 2.11 (d, J = 7.03 Hz, 2 H) 1.96-2.06 (m, 2 H) 1.75-1.87 (m, 2 H) 1.45 (d, J = 12.55 Hz, 2 H) 1.17-1.40 (m, 7 H) 0.81 (t, J = 7.28 Hz, 6 H) |
| 124 | 474.40 | F: 1.12; 98.9% | $^1$H NMR (400 MHz, DMSO-$d_6$) δ ppm 12.86 (br. s., 1 H) 8.13 (br. s., 1 H) 7.88 (br. s., 1 H) 7.63 (m, J = 9.04 Hz, 2 H) 7.56 (m, J = 8.53 Hz, 2 H) 7.23 (t, J = 8.03 Hz, 1 H) 6.86-6.95 (m, 2 H) 6.80 (d, J = 10.04 Hz, 1 H) 4.39 (s, 2 H) 3.70-3.78 (m, 6 H) 2.75 (d, J = 11.55 Hz, 2 H) 1.96-2.07 (m, 4 H) 1.69-1.87 (m, 3 H) 1.45 (d, J = 13.05 Hz, 2 H) 0.84 (d, J = 6.53 Hz, 6 H) |
| 125 | 522.2 | E: 1.48 min, 95.5% F: 2.18 min, 95.8% | $^1$H NMR (400 MHz, DMSO-$d_6$) δ ppm 12.87 (br. s., 1 H) 8.13 (br. s., 1 H) 7.89 (br. s., 1 H) 7.64 (d, J = 8.80 Hz, 2 H) 7.57 (d, J = 8.80 Hz, 2 H) 7.12-7.38 (m, 6 H) 6.88-6.96 (m, 2 H) 6.81 (d, J = 9.05 Hz, 1 H) 4.40 (s, 2 H) 3.77 (br. s., 2 H) 3.74 (s, 3 H) 2.89 (br. s., 2 H) 2.73 (br. s., 1 H) 2.67 (d, J = 1.71 Hz, 1 H) 2.53 (br. s., 2 H) 2.15 (br. s., 2 H) 1.84 (br. s., 2 H) 1.48 (d, J = 10.52 Hz, 2 H) |
| 126 | 545.3 | E: 2.19 min, 94.8% | $^1$H NMR (400 MHz, DMSO-d6) d ppm 13.00 (s, 1 H) 8.01 (d, J = 8.53 Hz, 1 H) 7.93 (br. s., 1 H) 7.68 (d, J = 8.53 Hz, 2 H) 7.17 (d, J = 6.53 Hz, 1 H) 7.08-7.15 (m, 1 H) 6.98-7.08 (m, 1 H) 4.43 (s, 2 H) 3.99 (s, 2 H) 2.79-2.91 (m, 4 H) 2.25 (s, 3 H) 2.06-2.17 (m, 2H) 1.77 (d, J = 11.04 Hz, 2H) 1.57 (d, J = 12.55 Hz, 2 H) 1.20-1.27 (m, 4 H) |
| 127 | 543.3 | E: 1.05 min, 99.1% | $^1$H NMR (400 MHz, DMSO-d6) d ppm 8.04 (d, J = 8.53 Hz, 1 H) 7.68 (d, J = 8.53 Hz, 1 H) 7.24 (t, J = 8.28 Hz, 1 H) 6.86-6.97 (m, 2 H) 6.82 (s, 1 H) 4.42 (s, 2 H) 3.93 (s, 2 H) 3.74 (s, 3 H) 2.83 (d, J = 8.03 Hz, 4 H) 2.04-2.13 (m, 2 H) 1.83 (br. s., 2 H) 1.49 (d, J = 12.05 Hz, 2 H) 1.17-1.30 (m, 4 H) |
| 128 | 561.3 | E: 1.13 min, 91.6% | $^1$H NMR (400 MHz, METHANOL-d4) d ppm 8.05 (d, J = 9.04 Hz, 1 H) 7.77 (s, 2 H) 7.68 (d, J = 8.53 Hz, 1 H) 6.80 (s, 1 H) 6.74 (d, J = 9.04 Hz, 1 H) 6.62 (dt, J = 10.79, 2.38 Hz, 1 H) 4.53 (s, 2 H) 4.19 (s, 2 H) 3.81 (s, 3 H) 2.88 (q, J = 7.53 Hz, 3 H) 2.68 (br. s., 3 H) 2.14 (d, J = 10.54 Hz, 2 H) 1.84 (d, J = 13.05 Hz, 2 H) 1.23-1.35 (m, 6 H) |
| 129 | 529.3 | E: 1.08 min, 91.6% | |
| 130 | 513.3 | F: 1.12 min, 90.2% | $^1$H NMR (400 MHz, METHANOL-d4) d ppm 8.02 (d, J = 8.03 Hz, 1 H) 7.65 (d, J = 8.53 Hz, 3 H) 7.14 (br. s., 2 H) 6.95 (d, J = 8.03 Hz, 1 H) 4.44-4.57 (m, 3 H) 4.08-4.18 (m, 2 H) 2.97 (br. s., 2 H) 2.89 (d, J = 7.03 Hz, 2 H) 2.80 (d, J = 5.02 Hz, 2 H) 2.45 (br. s., 2 H) 2.16-2.36 (m, 3 H) 2.00 (br. s., 2 H) 1.62 (br. s., 3 H) 1.29 (d, J = 7.53 Hz, 9 H) 0.90 (br. s., 2 H) |

TABLE 9-continued

| 131 | 484.3 | F: 1.73 min, 98.2% | $^1$H NMR (400 MHz, DMSO-d$_6$) d ppm 8.02 (s, 2 H) 7.51-7.71 (m, 4 H) 7.00-7.27 (m, 4 H) 6.98 (s, 1 H) 4.41 (s, 2 H) 3.92 (s, 3 H) 2.20-2.32 (m, 3 H) 1.99 (br. s., 2H) 1.73 (d, J = 11.55 Hz, 2H) |
| --- | --- | --- | --- |
| 132 | 500.3 | F: 1.65 mi, 98.1% | $^1$H NMR (400 MHz, DMSO-d6) d ppm 8.02 (br. s., 2 H) 7.54-7.67 (m, 4 H) 6.64-6.82 (m, 3 H) 4.39 (s, 2 H) 3.87 (br. s., 2 H) 3.73-3.78 (m, 4 H) 3.58 (br. s., 4 H) 1.99 (br. s., 2 H) 1.66 (br. s., 2 H) |
| 133 | 515.3 | F: 1.76 min, 97.9% | $^1$H NMR (400 MHz, DMSO-d6) d ppm 8.58 (d, J = 2.51 Hz, 1 H) 8.23 (d, J = 9.04 Hz, 1 H) 8.11 (s, 2 H) 8.01 (dd, J = 8.53, 2.51 Hz, 1 H) 7.18-7.32 (m, 2 H) 7.13 (s, 1 H) 7.00 (s, 1 H) 6.87-6.97 (m, 2 H) 6.84 (dd, J = 8.03, 2.01 Hz, 1 H) 4.42 (s, 2 H) 4.07 (s, 3 H) 3.72-3.78 (m, 3 H) 3.56 (d, J = 13.05 Hz, 2 H) 3.35-3.44 (m, 2 H) 3.25 (t, J = 11.55 Hz, 2 H) 2.86 (dd, J = 16.31, 10.79 Hz, 2 H) 2.55 (s, 4 H) 2.06-2.19 (m, 2 H) 1.82 (d, J = 13.55 Hz, 2 H) |
| 134 | 546.3 | E: 1.67 min, 95.6% | $^1$H NMR (400 MHz, DMSO-d6) d ppm 7.83 (s, 1 H) 7.27 (s, 1 H) 6.41-6.48 (m, 1 H) 6.15-6.19 (m, 2 H) 6.01 (s, 1 H) 3.73 (s, 2 H) 3.37 (s, 3 H) 3.24 (s, 2 H) 2.99 (s, 3 H) 2.16 (s, 2 H) 1.78-1.89 (m, 2 H) 1.61 (d, J = 3.51 Hz, 2 H) 1.41 (d, J = 13.05 Hz, 2 H) 1.22 (br. s., 2 H) 0.80 (d, J = 11.55 Hz, 2 H) |
| 135 | 513.3 | E: 1.13 min, 96.0% | $^1$H NMR (400 MHz, DMSO-d6) d ppm 8.22-8.34 (m, 3 H) 8.02 (d, J = 8.31 Hz, 1 H) 7.48-7.56 (m, 1 H) 7.14-7.24 (m, 2H) 7.08 (dd, J = 7.83, 2.45 Hz, 1 H) 4.68 (s, 2 H) 4.23-4.36 (m, 6 H) 4.00 (s, 4 H) 2.25 (br. s., 2 H) 1.88 (br. s., 2 H) |
| 136 | 545.3 | F: 1.95 min, 98.5% | $^1$H NMR (400 MHz, DMSO-d6) d ppm 8.28 (d, J = 8.31 Hz, 3 H) 8.03 (d, J = 8.31 Hz, 1 H) 7.52 (t, J = 7.70 Hz, 1 H) 7.13-7.24 (m, 2 H) 7.10 (d, J = 8.31 Hz, 1 H) 4.67 (s, 2 H) 4.32 (s, 5 H) 4.00 (s, 3 H) 3.82 (br. s., 2 H) 3.08 (br. s., 2 H) 2.28 (br. s., 2 H) 2.10 (br. s., 2 H) |
| 137 | 515.3 | F: 1.98 min, 95.2% | $^1$H NMR (400 MHz, DMSO-d6) d ppm 8.02 (br. s., 2 H) 7.99 (d, J = 8.03 Hz, 1 H) 7.73 (d, J = 8.03 Hz, 1 H) 7.13-7.23 (m, 1 H) 7.08-7.13 (m, 1 H) 6.97-7.08 (m, 1 H) 4.43 (s, 2 H) 4.04 (s, 5 H) 2.90 (br. s., 3 H) 2.19-2.28 (m, 4 H) 1.86 (br. s., 2 H) 1.61 (br. s., 2 H) |

Example 138

3-(4-(1H-pyrazol-4-yl)phenyl)-8-(2-hydroxy-2-methylpropyl)-1-(3-methoxybenzyl)-1,3,8-triazaspiro[4.5]decan-2-one

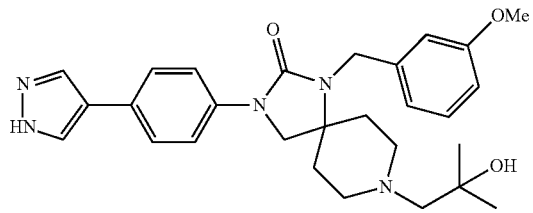 [SMILES: COc1cccc(CN2C(=O)N(c3ccc(-c4cn[nH]c4)cc3)CC23CCN(CC(C)(C)O)CC3)c1]

Example 138a

Preparation of 3-(4-bromophenyl)-8-(2-hydroxy-2-methylpropyl)-1-(3-methoxybenzyl)-1,3,8-triazaspiro[4.5]decan-2-one

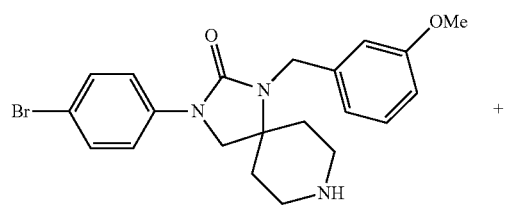

+

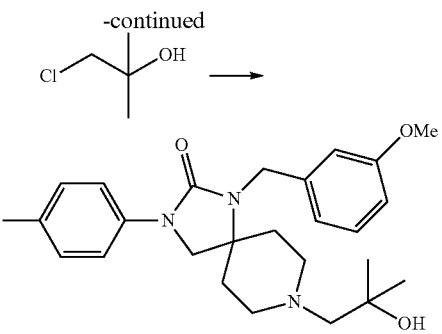

To a solution of 3-(4-bromophenyl)-1-(3-methoxybenzyl)-1,3,8-triazaspiro[4.5]decan-2-one (20 mg, 0.046 mmol) in DMF (1 mL) was added K$_2$CO$_3$ (19.3 mg, 0.139 mmol) and 1-chloro-2-methylpropan-2-ol (10.1 mg, 0.093 mmol). The reaction mixture was heated at 90° C. for 16 h. Reaction mixture was cooled to rt, diluted with water, and extracted with ethyl acetate. The combined ethyl acetate layers were washed with water and brine, dried over Na$_2$SO$_4$, filtered and concentrated to afford 3-(4-bromophenyl)-8-(2-hydroxy-2-methylpropyl)-1-(3-methoxybenzyl)-1,3,8-triazaspiro[4.5]decan-2-one as a yellow gummy solid (25 mg, quant.). MS(ESI) m/z: 503.0 (M+H)$^+$; $^1$H NMR (400 MHz, DMSO-d$_6$) δ ppm 7.63 (d, J=9.54 Hz, 2H) 7.47-7.54 (m, 2H) 7.22 (t, J=8.03 Hz, 1H) 6.86-6.93 (m, 2H) 6.77-6.83 (m, 1H) 4.38 (s, 2H) 3.70-3.76 (m, 5H) 2.83-2.91 (m, 2H) 2.26 (t, J=12.30 Hz, 2H) 2.18 (s, 2H) 1.79-1.89 (m, 2H) 1.39 (d, J=13.55 Hz, 2H) 1.06 (s, 6H).

Example 138

Preparation of 3-(4-(1H-pyrazol-4-yl)phenyl)-8-(2-hydroxy-2-methylpropyl)-1-(3-methoxybenzyl)-1,3,8-triazaspiro[4.5]decan-2-one

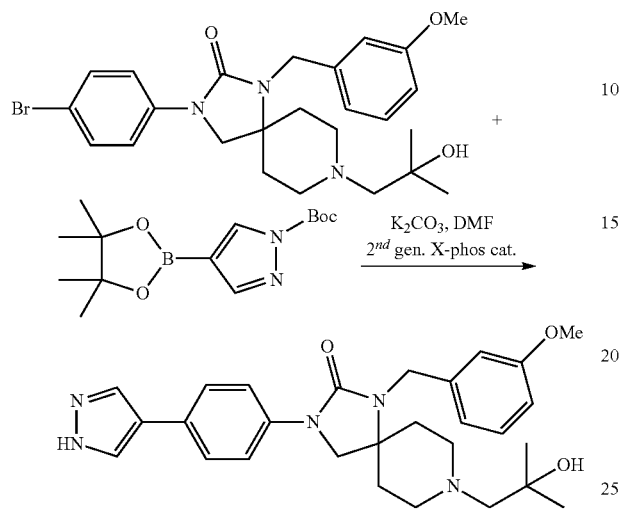

To a solution of 3-(4-bromophenyl)-8-(2-hydroxy-2-methylpropyl)-1-(3-methoxybenzyl)-1,3,8-triazaspiro[4.5]decan-2-one (25 mg, 0.050 mmol) in DMF (1 mL) were added tert-butyl 4-(4,4,5,5-tetramethyl-1,3,2-dioxaborolan-2-yl)-1H-pyrazole-1-carboxylate (20.5 mg, 0.070 mmol), $K_2CO_3$ (20.6 mg, 0.149 mmol) and Water (0.2 mL). The reaction mixture was purged with nitrogen for 5 min and charged with $2^{nd}$ generation XPHOS precatalyst (2.4 mg, 3.0 μmol). The reaction mixture was again purged with nitrogen for 3 min and heated at 90° C. for 16 h. The reaction mixture was cooled to rt, filtered and concentrated. The residue was purified by preparative HPLC to afford 3-(4-(1H-pyrazol-4-yl)phenyl)-8-(2-hydroxy-2-methylpropyl)-1-(3-methoxybenzyl)-1,3,8-triazaspiro[4.5]decan-2-one as a pale yellow solid (1.6 mg, 7% Yield). MS(ESI) m/z: 490.1 $(M+H)^+$; $^1H$ NMR (400 MHz, DMSO-$d_6$) δ ppm 12.85 (br. s., 1H) 8.12 (br. s., 1H) 7.88 (br. s., 1H) 7.62 (d, J=8.80 Hz, 2H) 7.56 (d, J=8.56 Hz, 2H) 7.18-7.27 (m, 1H) 6.86-6.95 (m, 2H) 6.80 (d, J=9.05 Hz, 1H) 4.38 (s, 2H) 4.03 (s, 1H) 3.75 (s, 2H) 3.73 (s, 3H) 2.88 (d, J=11.25 Hz, 2H) 2.22-2.31 (m, 2H) 2.20 (s, 2H) 1.78-1.92 (m, 2H) 1.41 (d, J=12.96 Hz, 2H) 1.06 (s, 6H). LCMS RT=1.17 min, 97.65% (Method E), 1.71 min, 97.10% (Method F).

Example 139 (Enantiomer 1)

3-(4-(1H-pyrazol-4-yl)phenyl)-8-(2-hydroxypropyl)-1-(3-methoxybenzyl)-1,3,8-triazaspiro[4.5]decan-2-one and

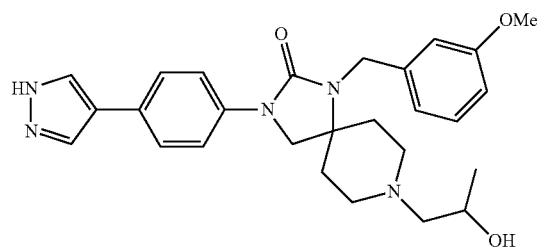 [SMILES: COc1cccc(CN2C(=O)N(c3ccc(-c4cn[nH]c4)cc3)CC23CCN(CC(C)O)CC3)c1]

Example 140 (Enantiomer 2)

3-(4-(1H-pyrazol-4-yl)phenyl)-8-(2-hydroxypropyl)-1-(3-methoxybenzyl)-1,3,8-triazaspiro[4.5]decan-2-one

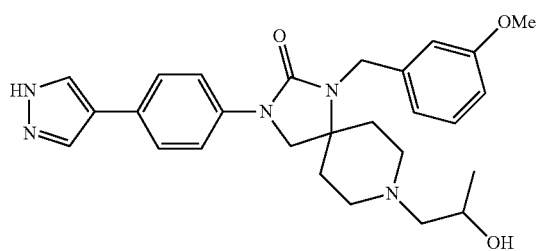 [SMILES: COc1cccc(CN2C(=O)N(c3ccc(-c4cn[nH]c4)cc3)CC23CCN(CC(C)O)CC3)c1]

Example 139a

Preparation of 3-(4-bromophenyl)-8-(2-hydroxypropyl)-1-(3-methoxybenzyl)-1,3,8-triazaspiro[4.5]decan-2-one

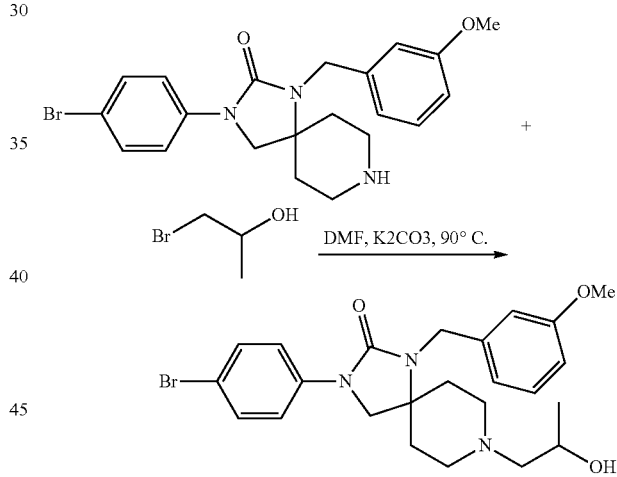

To a solution of 3-(4-bromophenyl)-1-(3-methoxybenzyl)-1,3,8-triazaspiro[4.5]decan-2-one (150 mg, 0.349 mmol) in DMF (5 mL) was added $K_2CO_3$ (145 mg, 1.046 mmol) and 1-bromopropan-2-ol (97 mg, 0.70 mmol). The reaction mixture was heated at 90° C. overnight. The reaction mixture was cooled to rt, diluted with water, and extracted with ethyl acetate (2×). The combined ethyl acetate layers were washed with water and brine, dried over $Na_2SO_4$, filtered and concentrated. The residue was purified by flash chromatography (gradient elution; 0-20% MeOH/$CHCl_3$) to afford 3-(4-bromophenyl)-8-(2-hydroxyethyl)-1-(3-methoxybenzyl)-1,3,8-triazaspiro[4.5]decan-2-one as a yellow gummy solid (170 mg, 100%). MS(ESI) m/z: 488.2 $(M+H)^+$; $^1H$ NMR (300 MHz, DMSO-$d_6$) δ ppm 7.57-7.70 (m, 2H) 7.43-7.53 (m, 2H) 7.22 (t, J=8.12 Hz, 1H) 6.85-6.93 (m, 2H) 6.73-6.83 (m, 1H) 4.38 (s, 2H) 3.69-3.74 (m, 5H) 2.79 (m, 1H) 2.04-2.30 (m, 4H) 1.83 (t, J=11.52 Hz, 2H) 1.42 (d, J=12.84 Hz, 2H) 1.01 (d, J=6.04 Hz, 3H).

Example 139

Example 140

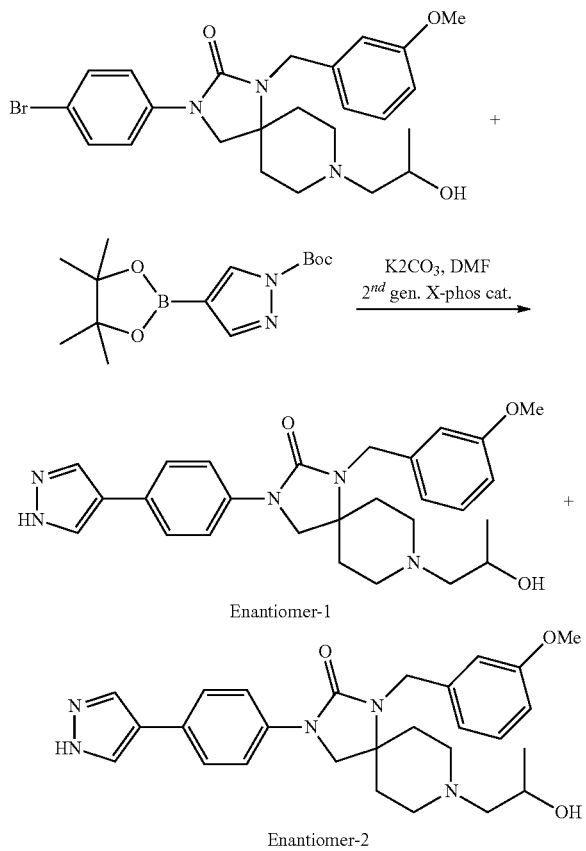

Enantiomer-1

Enantiomer-2

To a solution of 3-(4-bromophenyl)-8-(2-hydroxypropyl)-1-(3-methoxybenzyl)-1,3,8-triazaspiro[4.5]decan-2-one (170 mg, 0.348 mmol) in DMF (4 mL), were added tert-butyl 4-(4,4,5,5-tetramethyl-1,3,2-dioxaborolan-2-yl)-1H-pyrazole-1-carboxylate (143 mg, 0.487 mmol), $K_2CO_3$ (144 mg, 1.04 mmol) and water (0.5 mL). The reaction mixture was purged with nitrogen for 5 min and charged with $2^{nd}$ generation XPHOS precatalyst (16.4 mg, 0.021 mmol). The reaction mixture was again purged with nitrogen for 3 min and heated at 90° C. overnight. The reaction was cooled to rt, filtered and concentrated. The product was purified by preparative HPLC to afford the racemate (45 mg). The enantiomers were separated by SFC [column: Chiralcel OJ-H (250×30 mm, 5u) % $CO_2$: 70%, % Co-solvent: 30% (0.2% DEA in METHANOL), Total Flow: 80.0 g/min, Back Pressure: 100 bar, Temperature: 30° C. UV: 271 nm] to afford 3-(4-(1H-pyrazol-4-yl)phenyl)-8-(2-hydroxypropyl)-1-(3-methoxybenzyl)-1,3,8-triazaspiro[4.5]decan-2-one (Enantiomer-1, 15 mg, 9.0% yield) as an off-white solid. MS(ESI) m/z: 476.4 $(M+H)^+$; $^1H$ NMR (400 MHz, DMSO-$d_6$) δ ppm 8.00 (s, 2H) 7.62 (m, J=9.04 Hz, 2H) 7.56 (m, J=9.04 Hz, 2H) 7.18-7.25 (m, 1H) 6.87-6.94 (m, 2H) 6.75-6.83 (m, 1H) 4.38 (s, 2H) 4.24 (br. s., 1H) 3.75 (s, 2H) 3.73 (s, 4H) 2.80 (d, J=12.05 Hz, 2H) 2.20-2.27 (m, 1H) 2.07-2.19 (m, 3H) 1.78-1.90 (m, 2H) 1.43 (d, J=12.55 Hz, 2H) 1.02 (d, J=6.02 Hz, 3H). HPLC RT=10.54 min, 98.7% (Method M), 10.35 min, 96.3% (Method N). 100% ee with Chiral SFC RT=5.84 min. $[α]^{25.2}_D$=+4.00 (c 0.05, DMSO). And to afford 3-(4-(1H-pyrazol-4-yl)phenyl)-8-(2-hydroxypropyl)-1-(3-methoxybenzyl)-1,3,8-triazaspiro[4.5]decan-2-one (Enantiomer-2, 9.5 mg, 6% yield) as an off-white solid. MS(ESI) m/z: 476.4 $(M+H)^+$; $^1H$ NMR (400 MHz, DMSO-$d_6$) δ ppm 12.84 (br. s., 1H) 8.09 (br. s., 1H) 7.85 (s, 1H) 7.59-7.65 (m, 2H) 7.51-7.58 (m, 2H) 7.18-7.25 (m, 1H) 6.87-6.94 (m, 2H) 6.76-6.83 (m, 1H) 4.38 (s, 2H) 4.24 (d, J=4.02 Hz, 1H) 3.67-3.77 (m, 6H) 2.80 (d, J=12.55 Hz, 2H) 2.20-2.27 (m, 1H) 2.08-2.19 (m, 3H) 1.84 (t, J=12.05 Hz, 2H) 1.43 (d, J=12.55 Hz, 2H) 1.02 (d, J=6.02 Hz 1H, 3H). HPLC RT=10.06 min, 96.3% (Method M), 10.33 min, 95.2% (Method N). 92.6% ee with Chiral SFC RT=7.2 min. $[α]^{25.0}_D$=−4.00 (c 0.05, DMSO).

The following Examples in Table 10 were made by using the same procedure as shown in Example 138.

TABLE 10

| Example | R | Name |
|---|---|---|
| 141 | | 3-(4-(1H-pyrazol-4-yl)phenyl)-8-(2-hydroxyethyl)-1-(3-methoxybenzyl)-1,3,8-triazaspiro[4.5]decan-2-one |
| 142 | | 3-(4-(1H-pyrazol-4-yl)phenyl)-1-(3-methoxybenzyl)-8-(2-methoxyethyl)-1,3,8-triazaspiro[4.5]decan-2-one |

TABLE 10-continued

| 143 | 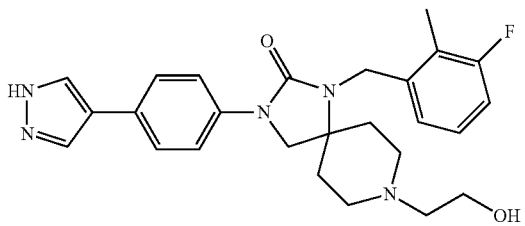 | 3-(4-(1H-pyrazol-4-yl)phenyl)-1-(3-fluoro-2-methylbenzyl)-8-(2-hydroxyethyl)-1,3,8-triazaspiro[4.5]decan-2-one |
| 144 | 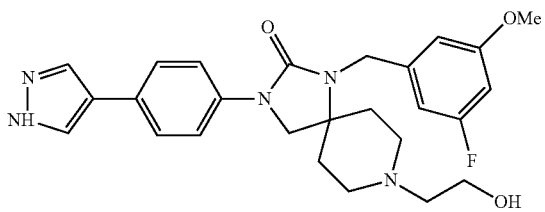 | 3-(4-(1H-pyrazol-4-yl)phenyl)-1-(3-fluoro-5-methoxybenzyl)-8-(2-hydroxyethyl)-1,3,8-triazaspiro[4.5]decan-2-one |
| 145 | 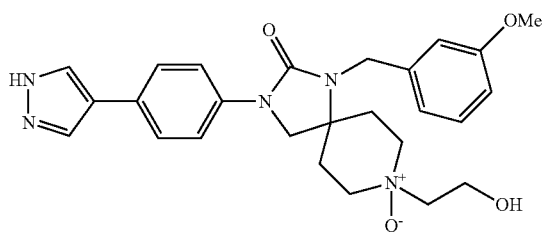 | 3-(4-(1H-pyrazol-4-yl)phenyl)-8-(2-hydroxyethyl)-1-(3-methoxybenzyl)-2-oxo-1,3,8-triazaspiro[4.5]decane 8-oxide |
| 146 | 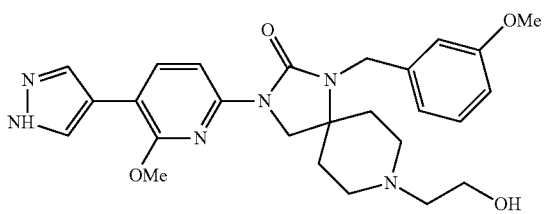 | 8-(2-hydroxyethyl)-3-(6-methoxy-5-(1H-pyrazol-4-yl)pyridin-2-yl)-1-(3-methoxybenzyl)-1,3,8-triazaspiro[4.5]decan-2-one |
| 147 | 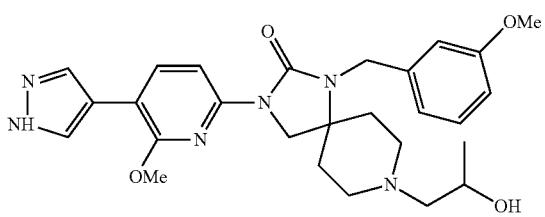 | 8-(2-hydroxypropyl)-3-(6-methoxy-5-(1H-pyrazol-4-yl)pyridin-2-yl)-1-(3-methoxybenzyl)-1,3,8-triazaspiro[4.5]decan-2-one |
| 148 | 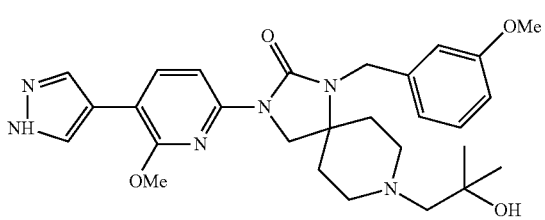 | 8-(2-hydroxy-2-methylpropyl)-3-(6-methoxy-5-(1H-pyrazol-4-yl)pyridin-2-yl)-1-(3-methoxybenzyl)-1,3,8-triazaspiro[4.5]decan-2-one |
| 149 | 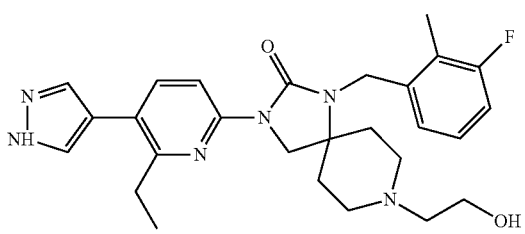 | 3-(6-ethyl-5-(1H-pyrazol-4-yl)pyridin-2-yl)-1-(3-fluoro-2-methylbenzyl)-8-(2-hydroxyethyl)-1,3,8-triazaspiro[4.5]decan-2-one |

TABLE 10-continued

| | | |
|---|---|---|
| 150 | 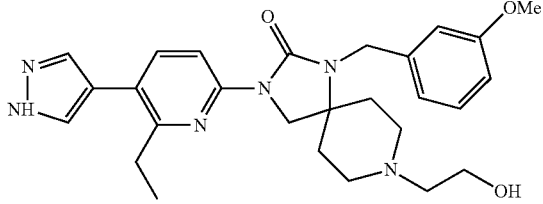 | 3-(6-ethyl-5-(1H-pyrazol-4-yl)pyridin-2-yl)-8-(2-hydroxyethyl)-1-(3-methoxybenzyl)-1,3,8-triazaspiro[4.5]decan-2-one |
| 151 | 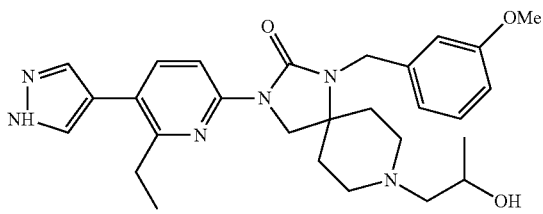 | 3-(6-ethyl-5-(1H-pyrazol-4-yl)pyridin-2-yl)-8-(2-hydroxypropyl)-1-(3-methoxybenzyl)-1,3,8-triazaspiro[4.5]decan-2-one |
| 152 | 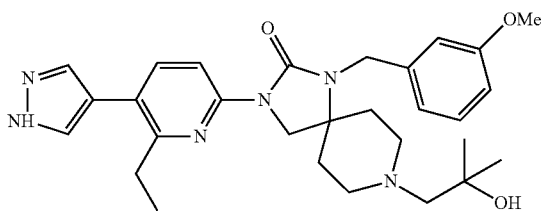 | 3-(6-ethyl-5-(1H-pyrazol-4-yl)pyridin-2-yl)-8-(2-hydroxy-2-methylpropyl)-1-(3-methoxybenzyl)-1,3,8-triazaspiro[4.5]decan-2-one |
| 153 | 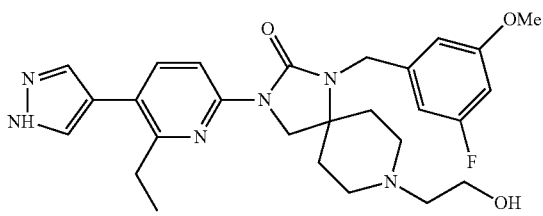 | 3-(6-ethyl-5-(1H-pyrazol-4-yl)pyridin-2-yl)-1-(3-fluoro-5-methoxybenzyl)-8-(2-hydroxyethyl)-1,3,8-triazaspiro[4.5]decan-2-one |
| 154 | 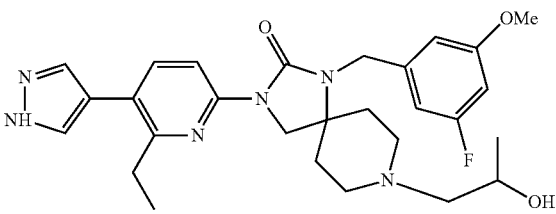 | 3-(6-ethyl-5-(1H-pyrazol-4-yl)pyridin-2-yl)-1-(3-fluoro-5-methoxybenzyl)-8-(2-hydroxypropyl)-1,3,8-triazaspiro[4.5]decan-2-one |
| 155 | 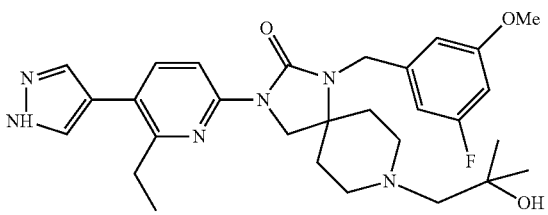 | 3-(6-ethyl-5-(1H-pyrazol-4-yl)pyridin-2-yl)-1-(3-fluoro-5-methoxybenzyl)-8-(2-hydroxy-2-methylpropyl)-1,3,8-triazaspiro[4.5]decan-2-one |
| 156 | 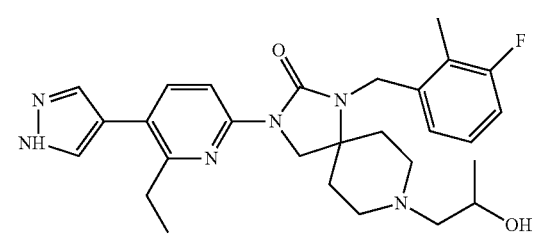 | 3-(6-ethyl-5-(1H-pyrazol-4-yl)pyridin-2-yl)-1-(3-fluoro-2-methylbenzyl)-8-(2-hydroxypropyl)-1,3,8-triazaspiro[4.5]decan-2-one |

TABLE 10-continued

| 157 | 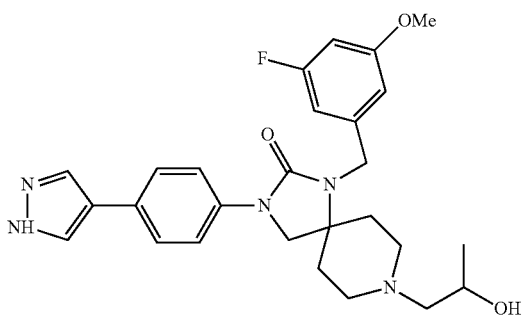 | 3-(4-(1H-pyrazol-4-yl)phenyl)-1-(3-fluoro-5-methoxybenzyl)-8-(2-hydroxypropyl)-1,3,8-triazaspiro[4.5]decan-2-one |
| 158 | 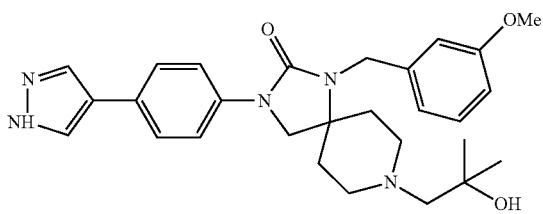 | 3-(4-(1H-pyrazol-4-yl)phenyl)-8-(2-hydroxy-2-methylpropyl)-1-(3-methoxybenzyl)-1,3,8-triazaspiro[4.5]decan-2-one |
| 159 | 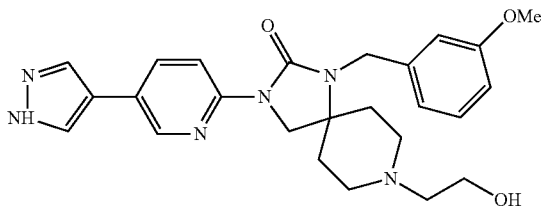 | 3-(5-(1H-pyrazol-4-yl)pyridin-2-yl)-8-(2-hydroxyethyl)-1-(3-methoxybenzyl)-1,3,8-triazaspiro[4.5]decan-2-one |
| 160 | 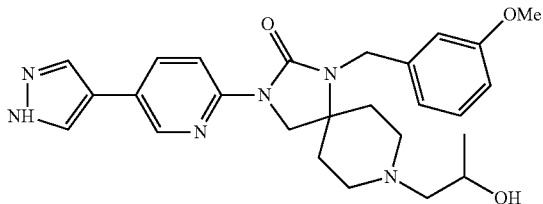 | 3-(5-(1H-pyrazol-4-yl)pyridin-2-yl)-8-(2-hydroxypropyl)-1-(3-methoxybenzyl)-1,3,8-triazaspiro[4.5]decan-2-one |
| 161 | 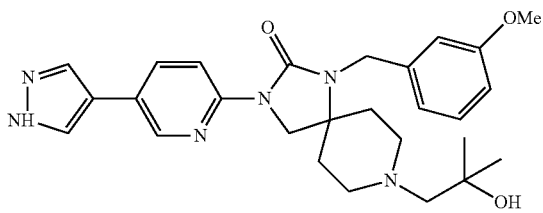 | 3-(5-(1H-pyrazol-4-yl)pyridin-2-yl)-8-(2-hydroxy-2-methylpropyl)-1-(3-methoxybenzyl)-1,3,8-triazaspiro[4.5]decan-2-one |
| 162 | 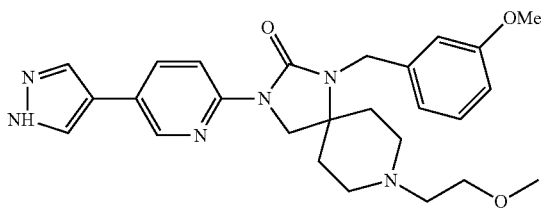 | 3-(5-(1H-pyrazol-4-yl)pyridin-2-yl)-1-(3-methoxybenzyl)-8-(2-methoxyethyl)-1,3,8-triazaspiro[4.5]decan-2-one |
| 163 | 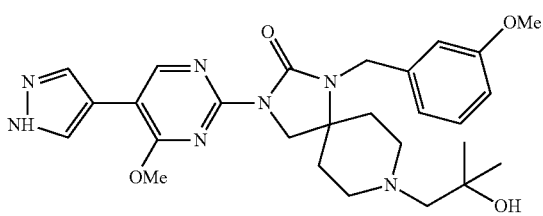 | 8-(2-hydroxy-2-methylpropyl)-3-(4-methoxy-5-(1H-pyrazol-4-yl)pyrimidin-2-yl)-1-(3-methoxybenzyl)-1,3,8-triazaspiro[4.5]decan-2-one |

TABLE 10-continued

| | | | |
|---|---|---|---|
| 165 | 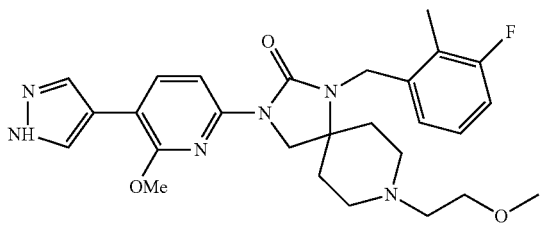 [SMILES: COCCN1CCC2(CC1)CN(c1ccc(-c3cn[nH]c3)c(OC)n1)C(=O)N2Cc1cccc(F)c1C] | | 1-(3-fluoro-2-methylbenzyl)-3-(6-methoxy-5-(1H-pyrazol-4-yl)pyridin-2-yl)-8-(2-methoxyethyl)-1,3,8-triazaspiro[4.5]decan-2-one |
| 166 | 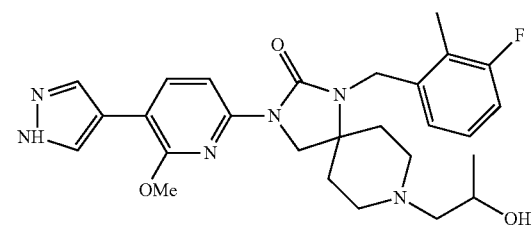 [SMILES: COc1nc(N2CC3(CCN(CC(C)O)CC3)N(Cc3cccc(F)c3C)C2=O)ccc1-c1cn[nH]c1] | | 1-(3-fluoro-2-methylbenzyl)-8-(2-hydroxypropyl)-3-(6-methoxy-5-(1H-pyrazol-4-yl)pyridin-2-yl)-1,3,8-triazaspiro[4.5]decan-2-one |
| 167 | 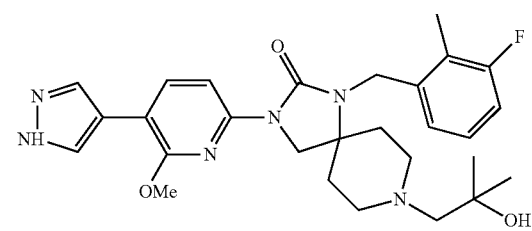 [SMILES: COc1nc(N2CC3(CCN(CC(C)(C)O)CC3)N(Cc3cccc(F)c3C)C2=O)ccc1-c1cn[nH]c1] | | 1-(3-fluoro-2-methylbenzyl)-8-(2-hydroxy-2-methylpropyl)-3-(6-methoxy-5-(1H-pyrazol-4-yl)pyridin-2-yl)-1,3,8-triazaspiro[4.5]decan-2-one |

| Example | LCMS (M + H)+ | HPLC Method, RT (min.) & Purity | NMR |
|---|---|---|---|
| 141 | 462.10 | E: 1.15 min, 97.5%<br>F: 1.31 min, 98.1% | $^1$H NMR (400 MHz, DMSO-d6) δ ppm 12.85 (br. s., 1 H) 8.07 (br. s., 1 H) 7.91 (br. s., 1 H) 7.62 (m, J = 9.05 Hz, 2 H) 7.57 (m, J = 8.56 Hz, 2 H) 7.23 (t, J = 7.95 Hz, 1 H) 6.88-6.95 (m, 2 H) 6.80 (d, J = 8.80 Hz, 1 H) 4.38 (s, 2 H) 3.77 (br. s., 2 H) 3.73 (s, 3 H) 3.50 (br. s., 2 H) 2.82 (br. s., 2 H) 2.33 (s, 2 H) 2.07 (s, 2 H) 1.76-2.01 (m, 2 H) 1.46 (br. s., 2 H) |
| 142 | 476.10 | E: 1.22 min, 100%<br>F: 1.58 min, 100% | $^1$H NMR (400 MHz, DMSO-d6) δ ppm 12.88 (s, 1 H) 8.12 (s, 1 H) 7.90 (s, 1 H) 7.61 (s, 4 H) 7.27 (t, J = 7.95 Hz, 1 H) 6.89-6.98 (m, 2 H) 6.84 (d, J = 7.58 Hz, 1 H) 4.38 (s, 2 H) 3.91 (s, 2 H) 3.75 (s, 3 H) 3.65 (br. s., 2 H) 3.51-3.58 (m., 2 H) 3.18 (s., 3 H) 2.16-2.24 (m, 2 H) 2.0-2.10 (m, 2 H) 1.75 (d, J = 12.72 Hz, 2 H) 1.25 (s, 2 H) |
| 143 | 464.2 | E: 1.25 min, 100%<br>F: 1.43 min, 100% | $^1$H NMR (400 MHz, DMSO-d6) δ ppm 12.88 (br. s., 1 H) 8.06 (br. s., 1 H) 7.95 (br. s., 1 H) 7.63 (m, J = 9.05 Hz, 2 H) 7.57 (m, J = 8.80 Hz, 2 H) 7.13-7.21 (m, 1 H) 7.09 (d, J = 7.34 Hz, 1 H) 6.98-7.05 (m, 1 H) 4.36-4.45 (m, 3 H) 3.81 (s, 2 H) 3.17 (d, J = 5.14 Hz, 2 H) 2.81 (d, J = 11.00 Hz, 2 H) 2.39 (t, J = 6.36 Hz, 2 H) 2.24 (s, 3 H) 2.15 (t, J = 12.10 Hz, 2 H) 1.72-1.86 (m, 2 H) 1.51 (d, J = 11.25 Hz, 2 H). $^{19}$F NMR (376 MHz, DMSO-d6) δ ppm −118.359 |
| 144 | 480.2 | E: 1.21 min, 100%<br>F: 1.38 min, 100% | $^1$H NMR (400 MHz, DMSO-d6) δ ppm 12.86 (br. s., 1 H) 8.13 (br. s., 1 H) 7.88 (br. s., 1 H) 7.63 (d, J = 9.05 Hz, 2 H) 7.57 (d, J = 8.80 Hz, 2 H) 6.65-6.79 (m, 3 H) 4.32-4.42 (m, 3 H) 3.72-3.81 (m, 5 H) 3.48 (q, J = 5.95 Hz, 2 H) 2.83 (d, J = 11.25 Hz, 2 H) 2.40 (t, J = 6.24 Hz, 2 H) 2.14 (t, J = 11.98 Hz, 2 H) 1.73-1.92 (m, 2 H) 1.46 (d, J = 11.74 Hz, 2 H). $^{19}$F NMR (376 MHz, DMSO-d6) δ ppm −111.894 |
| 145 | 478.2 | M: 10.50 min, 88.8%<br>N: 10.74 min, 91.0% | $^1$H NMR (400 MHz, METHANOL-d4) δ ppm 7.93 (s, 2 H) 7.54-7.64 (m, 4 H) 7.23 (t, J = 8.28 Hz, 1 H) 6.95-7.01 (m, 2 H) 6.80 (dd, J = 7.78, 2.26 Hz, 1 H) 4.55 (s, 2 H) 4.03-4.10 (m, 2 H) 3.95 (s, 2 H) 3.76 (s, 3 H) 3.50-3.60 (m, 2 H) 3.33-3.45 (m, 5 H) 2.68-2.79 (m, 2 H) 1.59 (d, J = 13.05 Hz, 2 H) |
| 146 | 493.2 | E: 1.25 min, 100%<br>F: 1.45 min, 100% | $^1$H NMR (400 MHz, DMSO-d6) δ ppm 12.88 (br. s., 1 H), 8.09 (br. s., 1 H), 8.04-7.92 (m, 2 H), 7.76 (d, J = 8.1 Hz, 1 H), 7.23 (t, J = 7.2 Hz, 1 H), 6.96-6.88 (m, 2H), 6.81 (d, J = 8.1 Hz, 1 H), 4.40 (s, 2H), 4.36 (br. s., 1 H), 4.01 (s, 3 H), 3.94 (s., 2 H), 3.73 |

TABLE 10-continued

| | | | |
|---|---|---|---|
| | | | (s, 3 H), 3.48 (br. s., 2 H), 2.84 (br. s., 2 H), 2.39 (br. s., 2H), 2.08 (br. s., 2H), 1.85 (br. s., 2H), 1.47 (br. s., 2 H) |
| 147 | 507.3 | E: 1.25 min, 98.0%<br>F: 1.65 min, 98.2% | $^1$H NMR (400 MHz, DMSO-d6) δ ppm 12.87 (br. s., 1 H), 8.09 (br. s., 1 H), 8.05-7.90 (m, 2 H), 7.76 (d, J = 8.3 Hz, 1 H), 7.23 (t, J = 7.8 Hz, 1 H), 6.96-6.89 (m, 2 H), 6.82 (d, J = 8.3 Hz, 1 H), 4.40 (s, 2 H), 4.24 (br. s., 1 H), 4.01 (s, 3 H), 3.95 (br. s., 2 H), 3.73 (s, 4 H), 2.84 (br. s., 2 H), 2.30-2.04 (m, 4 H), 1.91-1.78 (m, 2 H), 1.53-1.39 (m, 2 H), 1.03 (d, J = 5.1 Hz, 3 H) |
| 148 | 521.3 | E: 1.30 min, 100%<br>F: 1.91 min, 100% | $^1$H NMR (400 MHz, DMSO-d6) δ ppm 12.91 (br. s., 1 H), 8.14-7.93 (m, 3 H), 7.75 (d, J = 8.1 Hz, 1 H), 7.24 (t, J = 7.5 Hz, 1 H), 6.95-6.88 (m, 2 H), 6.81 (d, J = 8.8 Hz, 1 H), 4.41 (s, 2 H), 4.02 (br. s., 4 H), 3.96 (br. s., 2 H), 3.74 (s, 3 H), 2.91 (br. s., 2 H), 2.33-2.15 (m, 3 H), 1.95-1.80 (m, 2 H), 1.50-1.38 (m, 2 H), 1.07 (br. s., 6 H) |
| 149 | 493. | F: 0.97 min, 97.6% | $^1$H NMR (400 MHz, DMSO-d6) d ppm 13.02 (s, 1 H) 8.01 (d, J = 8.53 Hz, 1 H) 7.92 (br. s., 1 H) 7.68 (d, J = 8.53 Hz, 2 H) 7.13-7.21 (m, 1 H) 7.07-7.13 (m, 1 H) 6.97-7.07 (m, 1 H) 4.43 (s, 2 H) 4.34 (t, J = 5.27 Hz, 1 H) 3.98 (s, 2 H) 3.43-3.52 (m, 2 H) 2.84 (q, J = 7.53 Hz, 4 H) 2.40 (t, J = 6.02 Hz, 2 H) 2.25 (s, 3 H) 2.02-2.14 (m, 2 H) 1.74-1.87 (m, 2 H) 1.54 (d, J = 13.05 Hz, 2 H) 1.24 (t, J = 7.28 Hz, 4 H) |
| 150 | 491.3 | F: 0.88 min, 91.4% | $^1$H NMR (400 MHz, DMSO-d6) d ppm 8.04 (d, J = 8.53 Hz, 1 H) 7.68 (d, J = 8.53 Hz, 1 H) 7.24 (t, J = 8.03 Hz, 1 H) 6.87-6.97 (m, 2 H) 6.76-6.84 (m, 1 H) 6.51 (s, 1 H) 4.42 (s, 2 H) 4.37 (br. s., 1 H) 3.92 (s, 2 H) 3.74 (s, 3 H) 3.48 (d, J = 4.52 Hz, 2 H) 2.83 (q, J = 7.53 Hz, 4 H) 2.40 (t, J = 6.27 Hz, 2 H) 2.08 (t, J = 12.55 Hz, 2 H) 1.75-1.90 (m, 2 H) 1.46 (d, J = 10.54 Hz, 2 H) 1.23 (t, J = 7.53 Hz, 3 H) |
| 151 | 505.3 | E: 1.46 min, 98.8% | $^1$H NMR (400 MHz, METHANOL-d4) d ppm 8.02 (d, J = 8.53 Hz, 1 H) 7.82 (br. s., 1 H) 7.70 (br. s., 1 H) 7.65 (d, J = 8.53 Hz, 1 H) 7.10-7.22 (m, 2 H) 6.92-7.01 (m, 1 H) 4.58 (s, 2 H) 4.54 (s, 2 H) 4.13 (s, 2 H) 2.99 (d, J = 12.05 Hz, 2 H) 2.89 (q, J = 7.53 Hz, 2 H) 2.80 (td, J = 15.31, 4.52 Hz, 2 H) 2.45 (t, J = 11.29 Hz, 2 H) 2.33 (d, J = 2.01 Hz, 3 H) 1.92-2.07 (m, 2 H) 1.64 (d, J = 11.55 Hz, 2 H) 1.25-1.40 (m, 6 H) 0.91 (d, J = 7.03 Hz, 1 H) |
| 152 | 519.4 | E: 1.72 min, 98.0% | $^1$H NMR (400 MHz, DMSO-d6) d ppm 8.03 (d, J = 8.53 Hz, 1 H) 7.68 (d, J = 9.04 Hz, 1 H) 7.24 (t, J = 7.78 Hz, 1 H) 6.88-6.97 (m, 2 H) 6.81 (d, J = 8.53 Hz, 1 H) 6.51 (s, 2 H) 6.27 (s, 1 H) 4.42 (s, 2 H) 4.05 (br. s., 1 H) 3.93 (s, 2 H) 3.74 (s, 3 H) 2.91 (br. s., 2 H) 2.83 (q, J = 7.53 Hz, 2 H) 2.22 (br. s., 3 H) 1.78-1.96 (m, 4 H) 1.44 (d, J = 12.05 Hz, 1 H) 1.17-1.32 (m, 4 H) 1.08 (s, 5 H) |
| 153 | 509.3 | E: 1.35 min, 97.0% | $^1$H NMR (400 MHz, DMSO-d6) d ppm 9.05 (s, 1 H) 8.03 (d, J = 8.80 Hz, 1 H) 7.91 (s, 1 H) 7.70 (d, J = 8.80 Hz, 2 H) 6.63-6.86 (m, 3 H) 5.39 (br. s., 1 H) 4.40 (br. s., 2 H) 4.08 (br. s., 2 H) 3.77 (s, 3 H) 3.72 (br. s., 2 H) 3.51 (br. s., 2 H) 3.20 (d, J = 13.94 Hz, 2 H) 2.83 (q, J = 7.25 Hz, 2 H) 2.19 (br. s., 1 H) 1.83 (br. s., 2 H) 1.25 (t, J = 7.46 Hz, 3 H) |
| 154 | 523.3 | F: 0.97 min, 97.6% | $^1$H NMR (400 MHz, DMSO-d6) d ppm 8.95 (s, 1 H) 8.03 (d, J = 8.07 Hz, 1 H) 7.71 (d, J = 8.56 Hz, 2 H) 6.67-6.81 (m, 3 H) 5.51 (s, 1 H) 4.40 (s, 2 H) 4.08 (s, 3 H) 3.77 (s, 4 H) 3.16 (s, 2 H) 2.83 (d, J = 7.83 Hz, 2 H) 1.19-1.31 (m, 5 H) 1.12 (d, J = 5.14 Hz, 3 H) |
| 155 | 537.3 | F: 1.01 min, 95.5% | $^1$H NMR (400 MHz, METHANOL-d4) d ppm 8.04 (d, J = 8.53 Hz, 1 H) 7.76 (br. s., 2 H) 7.67 (d, J = 8.53 Hz, 1 H) 6.80 (s, 1 H) 6.73 (d, J = 9.04 Hz, 1 H) 6.61 (dt, J = 10.79, 2.38 Hz, 1 H) 4.52 (s, 2 H) 4.15 (s, 2 H) 3.81 (s, 3 H) 2.20 (br. s., 2 H) 1.65 (br. s., 2 H) 1.22-1.34 (m, 12 H) |
| 156 | 478.3 | F: 1.34 min, 93.7% | $^1$H NMR (400 MHz, DMSO-d6) d ppm 8.96 (br. s., 1 H) 8.02 (br. s., 2 H) 7.51-7.68 (m, 4 H) 7.15-7.24 (m, 1 H) 7.09-7.15 (m, 1 H) 7.01-7.09 (m, 1 H) 5.52 (br. s., 1 H) 4.39 (br. s., 2 H) 4.04 (d, J = 15.06 Hz, 2 H) 3.93-4.00 (m, 3 H) 3.23 (d, J = 12.55 Hz, 1 H) 3.18 (s, 2 H) 3.13 (d, J = 11.04 Hz, 1 H) 2.94-3.05 (m, 2 H) 2.25-2.30 (m, 3 H) 2.16-2.25 (m, 1 H) 1.97-2.13 (m, 1 H) 1.84 (br. s., 1 H) 1.77 (d, J = 13.55 Hz, 1 H) 1.13 (d, J = 6.53 Hz, 3 H) |

TABLE 10-continued

| | | | |
|---|---|---|---|
| 157 | 494.3 | F: 1.22 min, 95.0% | |
| 158 | 508.3 | F: 1.47 min, 95.2% | $^1$H NMR (400 MHz, DMSO-d6) d ppm 12.89 (br. s., 1 H) 8.58 (br. s., 1 H) 7.99 (br. s., 2 H) 7.51-7.70 (m, 4 H) 6.63-6.79 (m, 3 H) 5.31 (s, 1 H) 4.37 (s, 2 H) 3.96 (s, 2 H) 3.70-3.84 (m, 3 H) 3.60 (d, J = 14.06 Hz, 2 H) 3.09 (d, J = 3.01 Hz, 2 H) 2.25-2.32 (m, 1 H) 1.76 (d, J = 13.55 Hz, 2 H) 1.26 (s, 6 H) |
| 159 | 466.3 | F: 1.01 min, 98.8% | $^1$H NMR (400 MHz, DMSO-d6) d ppm 13.00 (br. s., 1 H) 8.58 (d, J = 2.01 Hz, 1 H) 8.22 (d, J = 9.04 Hz, 2 H) 7.98 (d, J = 6.53 Hz, 2 H) 7.23 (d, J8.03 Hz, 1 H) 6.87-6.97 (m, 2 H) 6.83 (br. s., 1 H) 6.51 (s, 3 H) 4.42 (s, 3 H) 3.91 (br. s., 2 H) 3.74 (s, 4 H) 3.47 (br. s., 2 H) 2.84 (br. s., 2 H) 2.40 (s, 1 H) 2.09 (s, 1 H) 1.85 (br. s., 1 H) 1.50 (s, 1 H) |
| 160 | 477.3 | F: 1.14 min, 97.2% | $^1$H NMR (400 MHz, DMSO-d6) d ppm 13.00 (s, 1 H) 8.58 (d, J = 2.01 Hz, 1 H) 8.21 (m, J = 8.53 Hz, 2 H) 7.98 (m, J = 9.04 Hz, 2 H) 7.25 (t, J = 8.03 Hz, 1 H) 6.89-6.99 (m, 2 H) 6.82 (d, J = 9.04 Hz, 1 H) 6.51 (s, 2 H) 4.42 (s, 2 H) 3.92 (br. s., 2 H) 3.74 (s, 3 H) 2.83 (br. s., 2 H) 2.23 (s, 1 H) 2.09 (br. s., 1 H) 1.92 (s, 1 H) 1.48 (br. s., 2 H) 1.04 (br. s., 3 H) |
| 161 | 491.3 | F: 1.38 min, 97.6% | $^1$H NMR (400 MHz, DMSO-d6) d ppm 12.99 (br. s., 1 H) 8.59 (d, J = 2.01 Hz, 1 H) 8.20 (d, J = 8.53 Hz, 1 H) 7.98 (d, J = 8.03 Hz, 2 H) 7.19-7.31 (m, 1 H) 6.87-7.02 (m, 2 H) 6.82 (d, J = 7.53 Hz, 1 H) 6.51 (s, 2 H) 4.42 (s, 2 H) 4.05 (br. s., 1 H) 4.00 (br. s., 1 H) 3.91 (br. s., 1 H) 3.69-3.80 (m, 3 H) 3.47-3.63 (m, 1 H) 2.99-3.17 (m, 1 H) 2.91 (br. s., 2 H) 2.20 (br. s., 2 H) 1.81-1.94 (m, 1 H) 1.75 (br. s., 1 H) 1.43 (br. s., 1 H) 1.23 (d, J = 12.05 Hz, 3 H) 1.08 (d, J = 5.52 Hz, 3 H) |
| 162 | 477.3 | E: 0.90 min, 94.9% | $^1$H NMR (400 MHz, DMSO-d6) d ppm 12.98 (s, 1 H) 8.54-8.62 (m, 1 H) 8.15-8.27 (m, 2 H) 7.87-8.01 (m, 2 H) 7.24 (t, J = 8.03 Hz, 1 H) 6.88-6.98 (m, 2 H) 6.81 (d, J = 7.03 Hz, 1 H) 6.51 (s, 1 H) 4.42 (s, 2 H) 3.90 (s, 2 H) 3.71-3.77 (m, 3 H) 3.41 (s, 2 H) 3.22 (s, 3 H) 2.84 (d, J = 10.54 Hz, 1 H) 2.09 (br. s., 3 H) 1.84 (br. s., 2 H) 1.45 (d, J = 13.55 Hz, 2 H) |
| 163 | 522.3 | F: 0.77 min, 96.6% | $^1$H NMR (400 MHz, DMSO-d6) d ppm 8.71 (s, 1 H) 8.07 (s, 2H) 7.19-7.28 (m, 1 H) 6.88-6.98 (m, 2 H) 6.81 (d, J = 8.53 Hz, 1 H) 4.41 (s, 2 H) 4.06 (s, 4 H) 3.91 (s, 3 H) 3.74 (s, 5 H) 2.91 (d, J = 9.04 Hz, 2 H) 2.15-2.28 (m, 4 H) 1.87 (s, 17 H) 1.43 (d, J = 13.05 Hz, 2 H) 1.07 (s, 6 H) |
| 165 | 509.3 | F: 1.71 min, 98.1% | $^1$H NMR (400 MHz, DMSO-d6) d ppm 12.87 (br. s., 1 H) 8.09 (br. s., 1 H) 7.98 (d, J = 8.53 Hz, 1 H) 7.95 (br. s., 1 H) 7.73 (d, J = 8.53 Hz, 1 H) 7.13-7.21 (m, 1 H) 7.07-7.12 (m, 1 H) 6.97-7.06 (m, 1 H) 4.42 (s, 2 H) 4.02 (s, 3 H) 4.00 (s, 2 H) 3.40 (t, J = 5.77 Hz, 2 H) 3.21 (s, 3 H) 2.85 (d, J = 11.04 Hz, 2 H) 2.24 (d, J = 1.51 Hz, 3 H) 2.05-2.15 (m, 2 H) 1.74-1.85 (m, 2H) 1.54 (d, J = 11.04 Hz, 2H) |
| 166 | 509.3 | F: 1.55 min, 96.0% | $^1$H NMR (400 MHz, DMSO-d6) d ppm 12.87 (br. s., 1 H) 8.09 (br. s., 1 H) 7.98 (d, J = 8.53 Hz, 1 H) 7.94 (br. s., 1 H) 7.73 (d, J = 8.53 Hz, 1 H) 7.13-7.21 (m, 1 H) 7.07-7.12 (m, 1 H) 6.98-7.06 (m, 1 H) 4.42 (s, 2 H) 4.22 (d, J = 3.51 Hz, 1 H) 4.02 (s, 3 H) 4.00 (s, 2 H) 3.71 (br. s., 1 H) 2.84 (d, J = 11.55 Hz, 2 H) 2.25 (d, J = 1.00 Hz, 4 H) 2.03-2.23 (m, 4 H) 1.82 (br. s., 2 H) 1.53 (d, J = 12.05 Hz, 2 H) 1.01 (d, J = 6.53 Hz, 3 H) |
| 167 | 523.3 | F: 1.82 min, 94.3% | $^1$H NMR (400 MHz, DMSO-d6) d ppm 12.91 (s, 1 H) 8.50 (br. s., 1 H) 8.01 (d, J = 8.03 Hz, 3 H) 7.72 (d, J = 8.53 Hz, 1 H) 7.13-7.24 (m, 1 H) 7.00-7.13 (m, 2 H) 5.30 (s, 1 H) 4.39 (s, 2 H) 4.17 (s, 2 H) 4.03-4.10 (m, 3 H) 3.60 (d, J = 10.04 Hz, 2H) 3.11-3.19 (m, 2H) 2.27 (s, 5 H) 1.85 (d, J = 13.55 Hz, 2H) 1.20-1.29 (m, 6 H) |

Example 168

2-(3-(4-(1H-pyrazol-4-yl)phenyl)-1-(3-methoxybenzyl)-2-oxo-1,3,8-triazaspiro[4.5]decan-8-yl)-N-methylacetamide

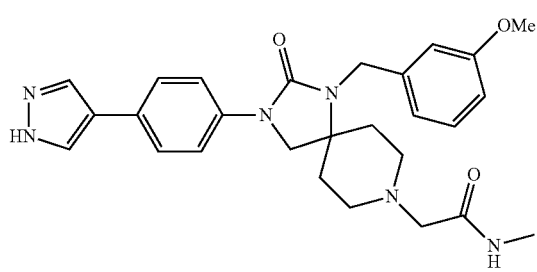 [SMILES: CNC(=O)CN1CCC2(CC1)CN(c1ccc(-c3cn[nH]c3)cc1)C(=O)N2Cc1cccc(OC)c1]

Example 168a

Preparation of 2-(3-(4-bromophenyl)-1-(3-methoxybenzyl)-2-oxo-1,3,8-triazaspiro[4.5]decan-8-yl)-N-methylacetamide

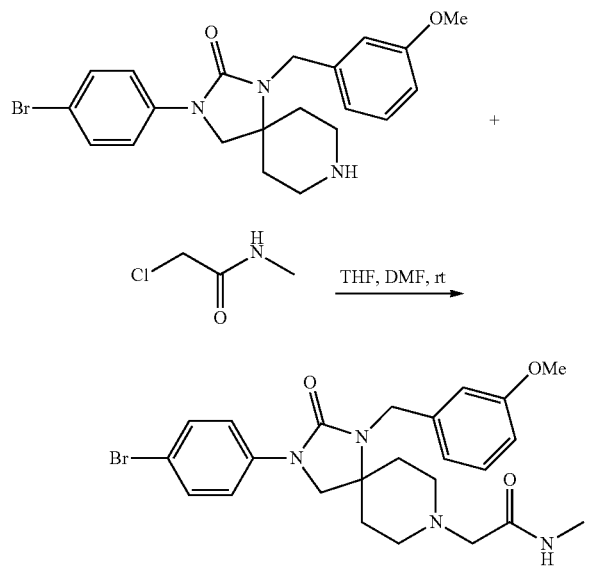

To a solution of 3-(4-bromophenyl)-1-(3-methoxybenzyl)-1,3,8-triazaspiro[4.5]decan-2-one (20 mg, 0.046 mmol) in THF (1.5 mL) and DMF (0.5 mL), were added TEA (0.019 mL, 0.139 mmol) and 2-chloro-N-methylacetamide (10 mg, 0.093 mmol). The reaction mixture was stirred at rt overnight. The reaction mixture was diluted with water and extracted with ethyl acetate. The combined ethyl acetate layers were washed with water and brine, dried over Na$_2$SO$_4$, filtered and concentrated to afford 2-(3-(4-bromophenyl)-1-(3-methoxybenzyl)-2-oxo-1,3,8-triazaspiro[4.5]decan-8-yl)-N-methylacetamide as a yellow gummy solid (20 mg, 86% yield). MS(ESI) m/z: 501.6 (M+H)$^+$; $^1$H NMR (400 MHz, DMSO-d$_6$) δ ppm 7.58-7.65 (m, 2H) 7.45-7.54 (m, 2H) 7.21-7.27 (m, 1H) 6.86-6.95 (m, 2H) 6.80 (dd, J=7.78, 2.26 Hz, 1H) 4.39 (s, 2H) 3.67-3.77 (m, 5H) 2.89 (s, 2H) 2.65-2.84 (m, 2H) 2.61-2.64 (m, 3H) 2.24 (t, J=11.55 Hz, 2H) 1.95 (t, J=13.05 Hz, 2H) 1.45 (d, J=12.55 Hz, 2H).

Example 168

Preparation of 2-(3-(4-(1H-pyrazol-4-yl)phenyl)-1-(3-methoxybenzyl)-2-oxo-1,3,8-triazaspiro[4.5]decan-8-yl)-N-methylacetamide

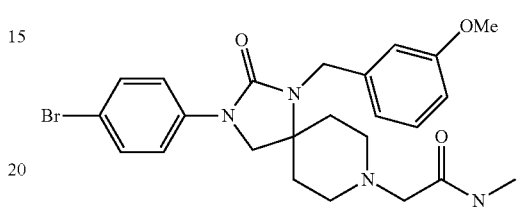

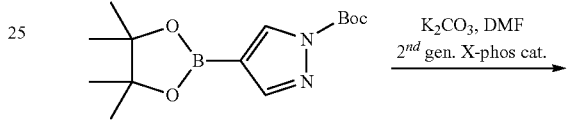

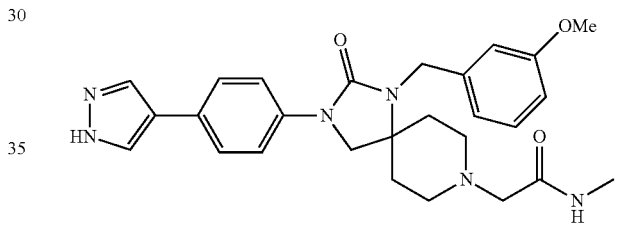

To a solution of 2-(3-(4-bromophenyl)-1-(3-methoxybenzyl)-2-oxo-1,3,8-triazaspiro[4.5]decan-8-yl)-N-methylacetamide (20 mg, 0.040 mmol) in DMF (1 mL) were added tert-butyl 4-(4,4,5,5-tetramethyl-1,3,2-dioxaborolan-2-yl)-1H-pyrazole-1-carboxylate (16.4 mg, 0.056 mmol), K$_2$CO$_3$ (16.5 mg, 0.120 mmol) and Water (0.2 mL). The reaction mixture was purged with nitrogen for 5 min and charged with 2$^{nd}$ generation XPHOS precatalyst (1.9 mg, 2.4 µmol). The reaction mixture was again purged with nitrogen for 3 min and heated at 90° C. for 16 h. The reaction mixture was cooled to rt, filtered and concentrated. The residue was purified by preparative HPLC to afford 2-(3-(4-(1H-pyrazol-4-yl)phenyl)-1-(3-methoxybenzyl)-2-oxo-1,3,8-triazaspiro[4.5]decan-8-yl)-N-methylacetamide as a pale yellow solid (5.5 mg, 27% yield). MS(ESI) m/z: 489.1 (M+H)$^+$; $^1$H NMR (400 MHz, DMSO-d$_6$) δ ppm 12.85 (br. s., 1H) 8.09 (br. s., 1H) 7.90 (br. s., 1H) 7.70 (d, J=4.65 Hz, 1H) 7.62 (m, J=8.80 Hz, 2H) 7.56 (m, J=8.80 Hz, 2H) 7.24 (t, J=7.95 Hz, 1H) 6.87-6.96 (m, 2H) 6.80 (d, J=8.31 Hz, 1H) 4.39 (s, 2H) 3.76 (s, 2H) 3.73 (s, 3H) 2.90 (s, 2H) 2.73 (d, J=10.76 Hz, 2H) 2.62 (d, J=4.65 Hz, 3H) 2.26 (t, J=12.23 Hz, 2H) 1.91-2.01 (m, 2H) 1.47 (d, J=11.98 Hz, 2H). LCMS RT=1.14 min, 97.0% (Method E), 1.51 min, 96.349% (Method F).

The following Examples in Table 11 were made by using the same procedure as shown in Example 168.

TABLE 11

| Example | R | Name |
|---|---|---|
| 169 | | 2-(3-(4-(1H-pyrazol-4-yl)phenyl)-1-(3-methoxybenzyl)-2-oxo-1,3,8-triazaspiro[4.5]decan-8-yl)acetamide |
| 170 | | 2-(3-(4-(1H-pyrazol-4-yl)phenyl)-1-(3-methoxybenzyl)-2-oxo-1,3,8-triazaspiro[4.5]decan-8-yl)-N,N-dimethylacetamide |

| Example | LCMS (M + H)+ | HPLC Method, RT (min.) & Purity | NMR |
|---|---|---|---|
| 169 | 476.30 | E: 0.87 min, 97.8%<br>F: 1.40 min, 95.3% | $^1$H NMR (400 MHz, DMSO-d6) δ ppm 8.00 (br. s., 2 H) 7.62 (d, J = 8.80 Hz, 2 H) 7.56 (d, J = 8.56 Hz, 2 H) 7.19-7.30 (m, 2 H) 7.11 (br. s., 1 H) 6.87-6.96 (m 2 H) 6.80 (d, J = 8.07 Hz, 1 H) 4.39 (s, 2 H) 3.75 (s, 2 H) 3.73 (s, 3 H) 2.86 (s, 2 H) 2.75 (d, J = 11.74 Hz, 2 H) 2.25 (t, J = 12.10 Hz, 2 H) 1.92-2.02 (m, 2 H) 1.45 (d, J = 12.23 Hz, 2 H) |
| 170 | 503.10 | E: 1.17 min, 95.1%<br>F: 1.52 min, 96.3% | $^1$H NMR (400 MHz, DMSO-d6) δ ppm 13.67 (br. s., 1 H) 8.94 (br. s., 1 H) 8.69 (br. s., 1 H) 8.43 (d, J = 9.05 Hz, 2 H) 8.38 (d, J = 8.80 Hz, 2 H) 7.99-8.08 (m, 1 H) 7.68-7.76 (m, 2 H) 7.61 (d, J = 9.78 Hz, 1 H) 5.20 (s, 2 H) 4.56 (s, 2 H) 4.54 (s, 3 H) 3.91-3.99 (m, 2 H) 3.80 (s, 3 H) 3.60 (s, 5 H) 3.07 (d, J = 13.45 Hz, 2 H) 2.63 (br. s., 2 H) 2.26 (d, J = 11.98 Hz, 2 H) |

Example 171

3-(4-(1H-pyrazol-4-yl)phenyl)-8-(4,4-difluorocyclohexanecarbonyl)-1-(3-methoxybenzyl)-1,3,8-triazaspiro[4.5]decan-2-one Example 171a Preparation of 3-(4-bromophenyl)-8-(4,4-difluorocyclohexanecarbonyl)-1-(3-methoxybenzyl)-1,3,8-triazaspiro[4.5]decan-2-one

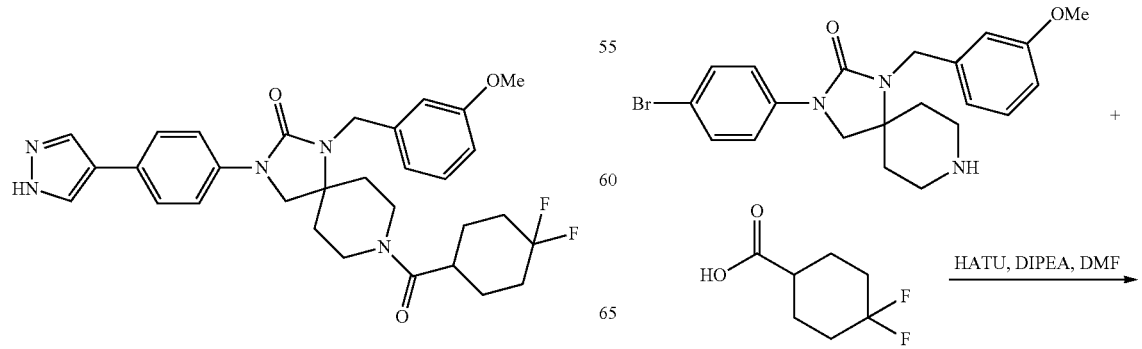

-continued

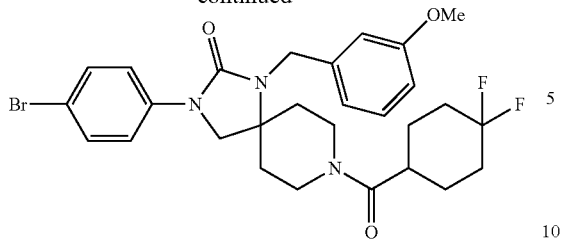

To a solution of 3-(4-bromophenyl)-1-(3-methoxybenzyl)-1,3,8-triazaspiro[4.5]decan-2-one (50 mg, 0.116 mmol) in DMF (1.5 mL), were added 4,4-difluorocyclohexanecarboxylic acid (22.9 mg, 0.139 mmol), DIPEA (0.061 mL, 0.35 mmol) and HATU (66.3 mg, 0.174 mmol). The reaction mixture stirred at rt overnight. The reaction mixture was diluted with water and extracted with ethyl acetate. The combined ethyl acetate layers were washed with water and brine, dried over $Na_2SO_4$, filtered and concentrated. The residue was purified by flash chromatography (gradient elution; 0-100% EtOAc/Hex) to afford 3-(4-bromophenyl)-8-(4,4-difluorocyclohexanecarbonyl)-1-(3-methoxybenzyl)-1,3,8-triazaspiro[4.5]decan-2-one as an off-white solid (49 mg, 73% yield). MS(ESI) m/z: 576.2 (M+H)+; $^1$H NMR (400 MHz, DMSO-$d_6$) δ ppm 7.61-7.66 (m, 2H) 7.49-7.55 (m, 2H) 7.19-7.25 (m, 1H) 6.86-6.92 (m, 2H) 6.77-6.81 (m, 1H) 4.30-4.44 (m, 3H) 3.98 (d, J=14.56 Hz, 1H) 3.87 (s, 2H) 3.72 (s, 3H) 3.12-3.20 (m, 1H) 2.78 (d, J=10.04 Hz, 1H) 2.67 (t, J=2.01 Hz, 1H) 2.01 (br. s., 2H) 1.90 (br. s., 1H) 1.82 (br. s., 1H) 1.49-1.74 (m, 8H). $^{19}$F NMR (376 MHz, DMSO-$d_6$) δ ppm −89.022 and −99.237.

Example 171

Preparation of 3-(4-(1H-pyrazol-4-yl)phenyl)-8-(4,4-difluorocyclohexanecarbonyl)-1-(3-methoxybenzyl)-1,3,8-triazaspiro[4.5]decan-2-one

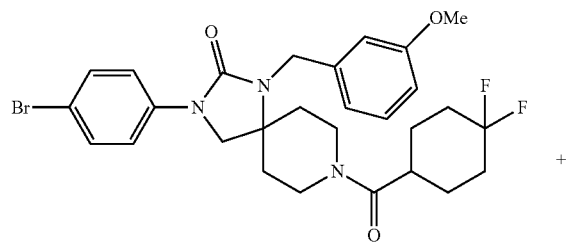

To a solution of 3-(4-bromophenyl)-8-(4,4-difluorocyclohexanecarbonyl)-1-(3-methoxybenzyl)-1,3,8-triazaspiro[4.5]decan-2-one (10 mg, 0.017 mmol) in DMF (4 mL) were added tert-butyl 4-(4,4,5,5-tetramethyl-1,3,2-dioxaborolan-2-yl)-1H-pyrazole-1-carboxylate (7.14 mg, 0.024 mmol), $K_2CO_3$ (7.19 mg, 0.052 mmol) and Water (0.4 mL). The reaction mixture was purged with nitrogen for 5 min and charged with $2^{nd}$ generation XPHOS precatalyst (0.8 mg, 1.0 μmol). The reaction mixture was again purged with nitrogen for 3 min and heated at 90° C. overnight. The reaction mixture was cooled to rt and filtered. The filtrate was concentrated and the residue was purified by preparative HPLC to afford 3-(4-(1H-pyrazol-4-yl)phenyl)-8-(4,4-difluorocyclohexanecarbonyl)-1-(3-methoxybenzyl)-1,3,8-triazaspiro[4.5]decan-2-one as a pale yellow solid (4.0 mg, 41% yield). MS(ESI) m/z: 564.1 (M+H)+; $^1$H NMR (400 MHz, DMSO-$d_6$) δ ppm 8.00 (br. s., 2H) 7.63 (d, J=9.05 Hz, 2H) 7.58 (d, J=8.80 Hz, 2H) 7.19-7.26 (m, 1H) 6.87-6.93 (m, 2H) 4.29-4.47 (m, 3H) 3.98 (d, J=14.67 Hz, 1H) 3.89 (s, 2H) 3.72 (s, 3H) 3.12-3.23 (m, 3H) 2.80 (br. s., 1H) 2.01 (br. s., 2H) 1.78-1.96 (m, 2H) 1.70 (d, J=13.21 Hz, 4H) 1.47-1.63 (m, 4H). $^{19}$F NMR (376 MHz, DMSO-$d_6$) δ ppm peaks at −89.026 and −99.224. LCMS RT=1.92 min, 100% (Method E), 1.96 min, 100% (Method F).

The following Examples in Table 12 were made by using the same procedure as shown in Example 171.

TABLE 12

| Example | R | Name |
|---|---|---|
| 172 | ![structure] | 3-(4-(1H-pyrazol-4-yl)phenyl)-8-(cyclobutanecarbonyl)-1-(3-methoxybenzyl)-1,3,8-triazaspiro[4.5]decan-2-one |

TABLE 12-continued

| 173 | 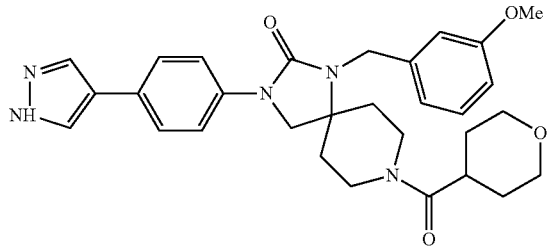 | 3-(4-(1H-pyrazol-4-yl)phenyl)-1-(3-methoxybenzyl)-8-(tetrahydro-2H-pyran-4-carbonyl)-1,3,8-triazaspiro[4.5]decan-2-one, TFA |
| 174 | 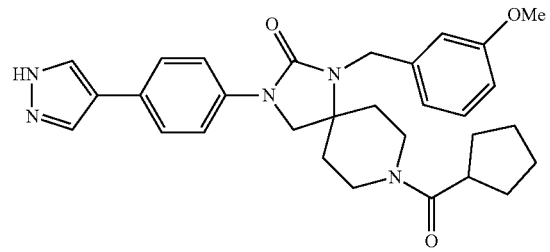 | 3-(4-(1H-pyrazol-4-yl)phenyl)-8-(cyclopentanecarbonyl)-1-(3-methoxybenzyl)-1,3,8-triazaspiro[4.5]decan-2-one |
| 175 | 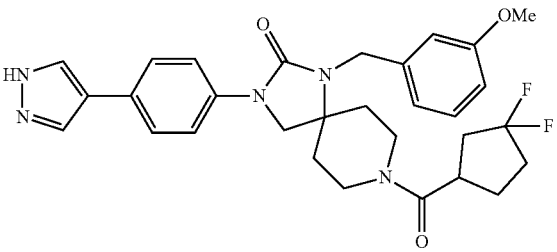 | 3-(4-(1H-pyrazol-4-yl)phenyl)-8-(3,3-difluorocyclopentane-carbonyl)-1-(3-methoxybenzyl)-1,3,8-triazaspiro[4.5]decan-2-one |
| 176 | 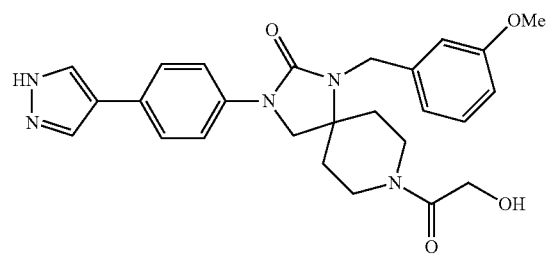 | 3-(4-(1H-pyrazol-4-yl)phenyl)-8-(2-hydroxyacetyl)-1-(3-methoxybenzyl)-1,3,8-triazaspiro[4.5]decan-2-one |
| 177 | 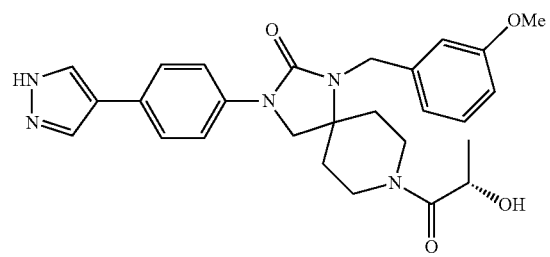 | (S)-3-(4-(1H-pyrazol-4-yl)phenyl)-8-(2-hydroxypropanoyl)-1-(3-methoxybenzyl)-1,3,8-triazaspiro[4.5]decan-2-one |
| 178 | 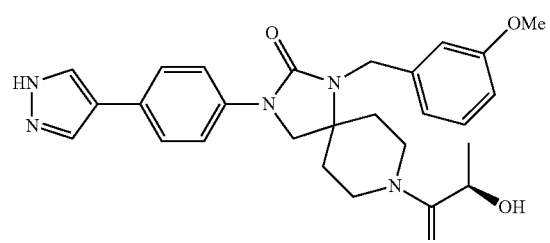 | (R)-3-(4-(1H-pyrazol-4-yl)phenyl)-8-(2-hydroxypropanoyl)-1-(3-methoxybenzyl)-1,3,8-triazaspiro[4.5]decan-2-one |

TABLE 12-continued

| | | |
|---|---|---|
| 179 | 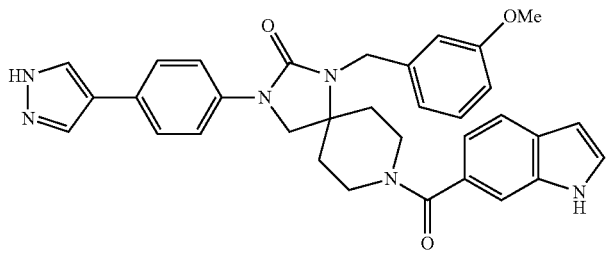 | 3-(4-(1H-pyrazol-4-yl)phenyl)-8-(1H-indole-6-carbonyl)-1-(3-methoxybenzyl)-1,3,8-triazaspiro[4.5]decan-2-one |
| 180 | 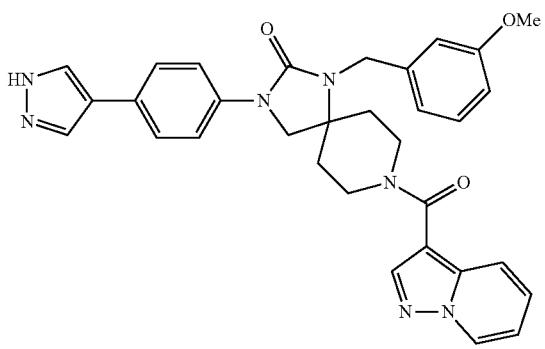 | 3-(4-(1H-pyrazol-4-yl)phenyl)-1-(3-methoxybenzyl)-8-(pyrazolo[1,5-a]pyridine-3-carbonyl)-1,3,8-triazaspiro[4.5]decan-2-one |
| 181 | 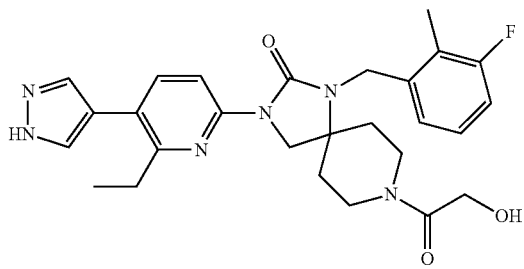 | 3-(6-ethyl-5-(1H-pyrazol-4-yl)pyridin-2-yl)-1-(3-fluoro-2-methylbenzyl)-8-(2-hydroxyacetyl)-1,3,8-triazaspiro[4.5]decan-2-one |
| 182 | 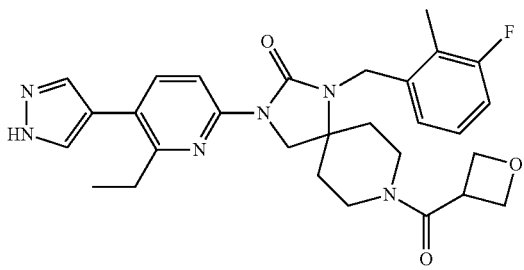 | 3-(6-ethyl-5-(1H-pyrazol-4-yl)pyridin-2-yl)-1-(3-fluoro-2-methylbenzyl)-8-(oxetane-3-carbonyl)-1,3,8-triazaspiro[4.5]decan-2-one |
| 183 | 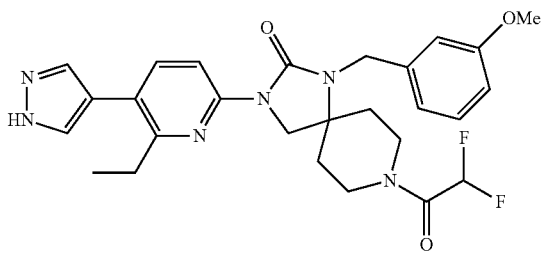 | 8-(2,2-difluoroacetyl)-3-(6-ethyl-5-(1H-pyrazol-4-yl)pyridin-2-yl)-1-(3-methoxybenzyl)-1,3,8-triazaspiro[4.5]decan-2-one |

TABLE 12-continued

| 184 | 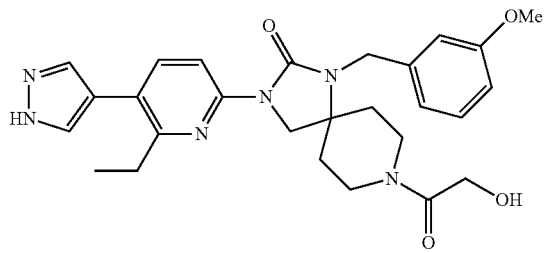 | 3-(6-ethyl-5-(1H-pyrazol-4-yl)pyridin-2-yl)-8-(2-hydroxyacetyl)-1-(3-methoxybenzyl)-1,3,8-triazaspiro[4.5]decan-2-one |
| --- | --- | --- |
| 185 | 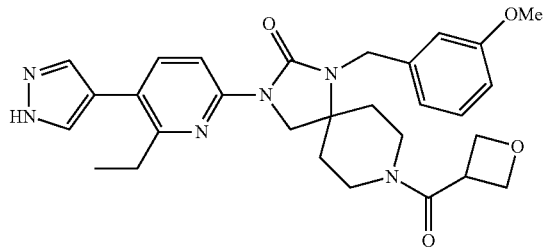 [SMILES: CCc1nc(N2CC3(CCN(C(=O)C4COC4)CC3)N(Cc3cccc(OC)c3)C2=O)ccc1-c1cn[nH]c1] | 3-(6-ethyl-5-(1H-pyrazol-4-yl)pyridin-2-yl)-1-(3-methoxybenzyl)-8-(oxetane-3-carbonyl)-1,3,8-triazaspiro[4.5]decan-2-one |
| 186 | 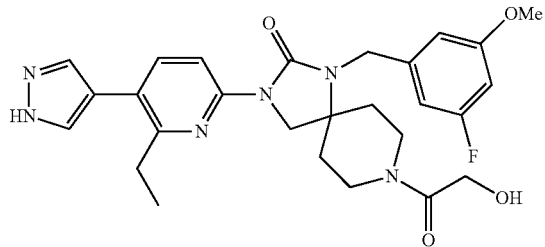 [SMILES: CCc1nc(N2CC3(CCN(C(=O)CO)CC3)N(Cc3cc(F)cc(OC)c3)C2=O)ccc1-c1cn[nH]c1] | 3-(6-ethyl-5-(1H-pyrazol-4-yl)pyridin-2-yl)-1-(3-fluoro-5-methoxybenzyl)-8-(2-hydroxyacetyl)-1,3,8-triazaspiro[4.5]decan-2-one |
| 187 | 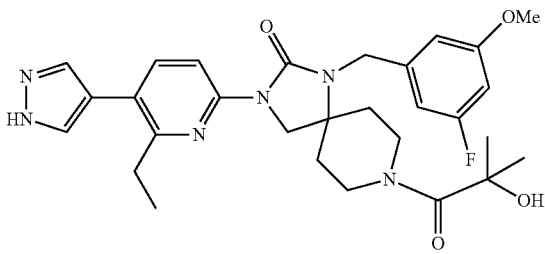 | 3-(6-ethyl-5-(1H-pyrazol-4-yl)pyridin-2-yl)-1-(3-fluoro-5-methoxybenzyl)-8-(2-hydroxy-2-methylpropanoyl)-1,3,8-triazaspiro[4.5]decan-2-one |
| 188 | 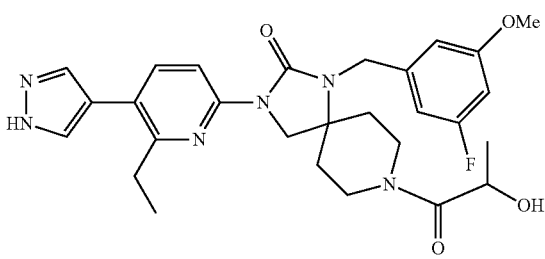 [SMILES: CCc1nc(N2CC3(CCN(C(=O)C(C)O)CC3)N(Cc3cc(F)cc(OC)c3)C2=O)ccc1-c1cn[nH]c1] | 3-(6-ethyl-5-(1H-pyrazol-4-yl)pyridin-2-yl)-1-(3-fluoro-5-methoxybenzyl)-8-(2-hydroxypropanoyl)-1,3,8-triazaspiro[4.5]decan-2-one |
| 189 | 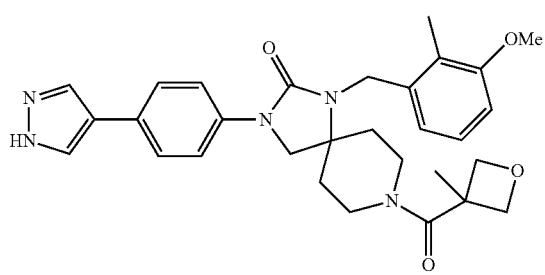 [SMILES: COc1cccc(CN2C(=O)N(c3ccc(-c4cn[nH]c4)cc3)CC23CCN(C(=O)C2(C)COC2)CC3)c1C] | 3-(4-(1H-pyrazol-4-yl)phenyl)-1-(3-fluoro-2-methylbenzyl)-8-(3-methyloxetane-3-carbonyl)-1,3,8-triazaspiro[4.5]decan-2-one |

| | | |
|---|---|---|
| 190 | 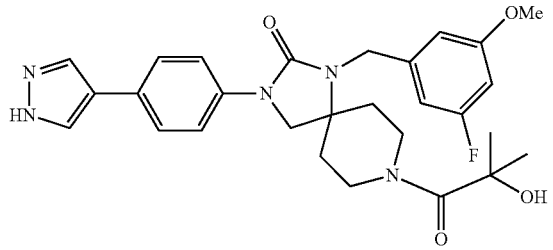 [SMILES: COc1cc(F)cc(CN2C(=O)N(c3ccc(-c4cn[nH]c4)cc3)CC23CCN(C(=O)C(C)(C)O)CC3)c1] | 3-(4-(1H-pyrazol-4-yl)phenyl)-1-(3-fluoro-5-methoxybenzyl)-8-(2-hydroxy-2-methylpropanoyl)-1,3,8-triazaspiro[4.5]decan-2-one |
| 191 | 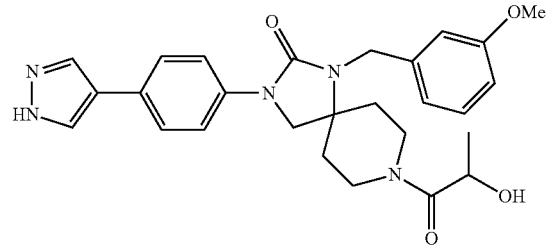 | 3-(4-(1H-pyrazol-4-yl)phenyl)-8-(2-hydroxypropanoyl)-1-(3-methoxybenzyl)-1,3,8-triazaspiro[4.5]decan-2-one |
| 192 | 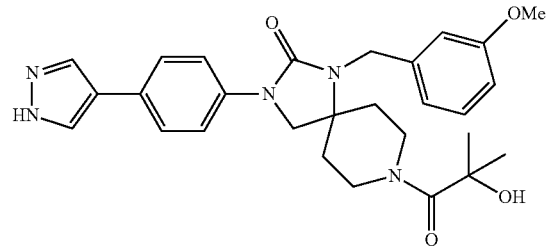 [SMILES: COc1cccc(CN2C(=O)N(c3ccc(-c4cn[nH]c4)cc3)CC23CCN(C(=O)C(C)(C)O)CC3)c1] | 3-(4-(1H-pyrazol-4-yl)phenyl)-8-(2-hydroxy-2-methylpropanoyl)-1-(3-methoxybenzyl)-1,3,8-triazaspiro[4.5]decan-2-one |
| 193 | 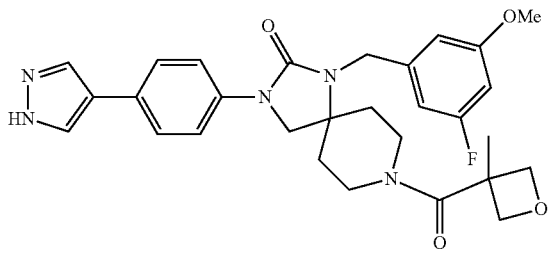 [SMILES: COc1cc(F)cc(CN2C(=O)N(c3ccc(-c4cn[nH]c4)cc3)CC23CCN(C(=O)C2(C)COC2)CC3)c1] | 33-(4-(1H-pyrazol-4-yl)phenyl)-1-(3-fluoro-5-methoxybenzyl)-8-(3-methyloxetane-3-carbonyl)-1,3,8-triazaspiro[4.5]decan-2-one |
| 194 | 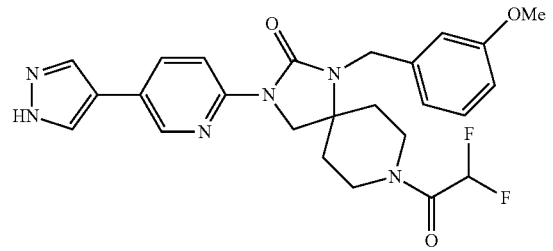 [SMILES: COc1cccc(CN2C(=O)N(c3ccc(-c4cn[nH]c4)cn3)CC23CCN(C(=O)C(F)F)CC3)c1] | 3-(5-(1H-pyrazol-4-yl)pyridin-2-yl)-8-(2,2-difluoroacetyl)-1-(3-methoxybenzyl)-1,3,8-triazaspiro[4.5]decan-2-one |
| 195 | 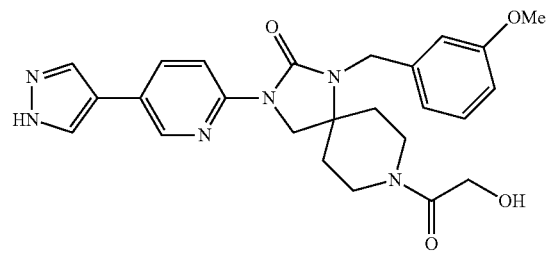 [SMILES: COc1cccc(CN2C(=O)N(c3ccc(-c4cn[nH]c4)cn3)CC23CCN(C(=O)CO)CC3)c1] | 3-(5-(1H-pyrazol-4-yl)pyridin-2-yl)-8-(2-hydroxyacetyl)-1-(3-methoxybenzyl)-1,3,8-triazaspiro[4.5]decan-2-one |

TABLE 12-continued

| 196 | 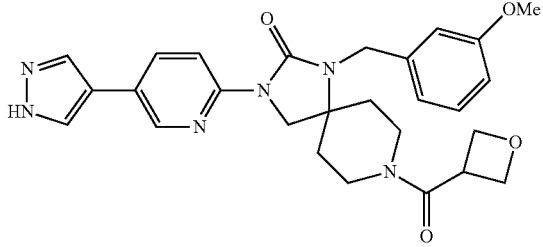 [SMILES: COc1cccc(CN2C(=O)N(c3ccc(-c4cn[nH]c4)cn3)CC23CCN(C(=O)C2COC2)CC3)c1] | 3-(5-(1H-pyrazol-4-yl)pyridin-2-yl)-1-(3-methoxybenzyl)-8-(oxetane-3-carbonyl)-1,3,8-triazaspiro[4.5]decan-2-one |
| 197 | 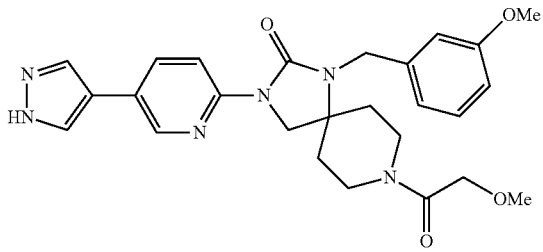 | 3-(5-(1H-pyrazol-4-yl)pyridin-2-yl)-8-(2-methoxyacetyl)-1-(3-methoxybenzyl)-1,3,8-triazaspiro[4.5]decan-2-one |
| 198 | 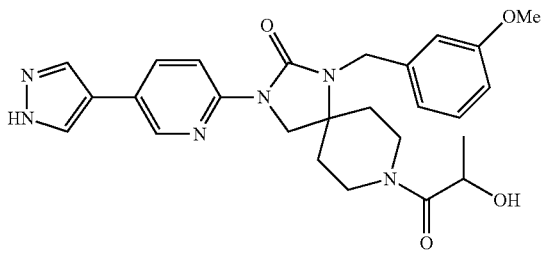 [SMILES: COc1cccc(CN2C(=O)N(c3ccc(-c4cn[nH]c4)cn3)CC23CCN(C(=O)C(C)O)CC3)c1] | 3-(5-(1H-pyrazol-4-yl)pyridin-2-yl)-8-(2-hydroxypropanoyl)-1-(3-methoxybenzyl)-1,3,8-triazaspiro[4.5]decan-2-one |
| 199 | 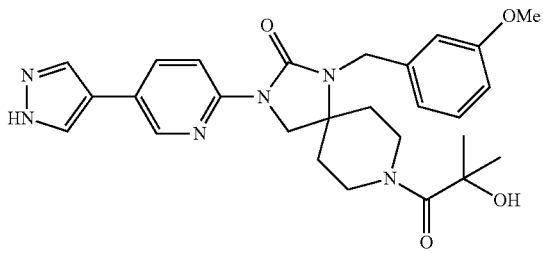 [SMILES: COc1cccc(CN2C(=O)N(c3ccc(-c4cn[nH]c4)cn3)CC23CCN(C(=O)C(C)(C)O)CC3)c1] | 3-(5-(1H-pyrazol-4-yl)pyridin-2-yl)-8-(2-hydroxy-2-methylpropanoyl)-1-(3-methoxybenzyl)-1,3,8-triazaspiro[4.5]decan-2-one |
| 200 | 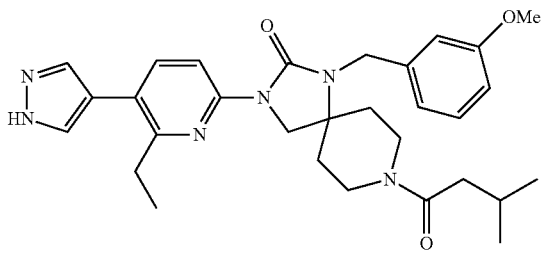 [SMILES: CCc1nc(N2CC3(CCN(C(=O)CC(C)C)CC3)N(Cc3cccc(OC)c3)C2=O)ccc1-c1cn[nH]c1] | 3-(6-ethyl-5-(1H-pyrazol-4-yl)pyridin-2-yl)-1-(3-methoxybenzyl)-8-(3-methylbutanoyl)-1,3,8-triazaspiro[4.5]decan-2-one |
| 201 | 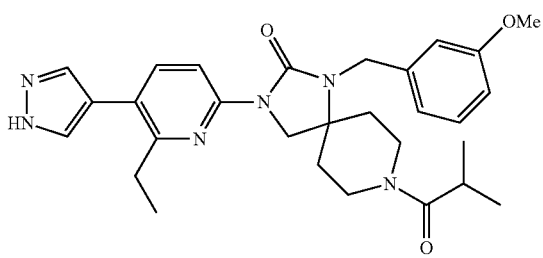 [SMILES: CCc1nc(N2CC3(CCN(C(=O)C(C)C)CC3)N(Cc3cccc(OC)c3)C2=O)ccc1-c1cn[nH]c1] | 3-(6-ethyl-5-(1H-pyrazol-4-yl)pyridin-2-yl)-8-isobutyryl-1-(3-methoxybenzyl)-1,3,8-triazaspiro[4.5]decan-2-one |

TABLE 12-continued

| 202 | 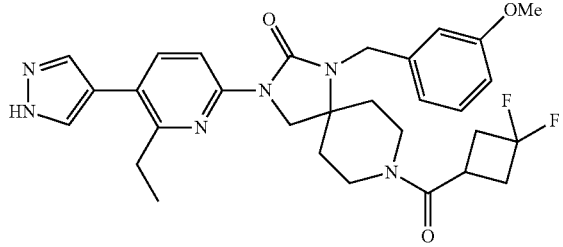 | 8-(3,3-difluorocyclobutane-carbonyl)-3-(6-ethyl-5-(1H-pyrazol-4-yl)pyridin-2-yl)-1-(3-methoxybenzyl)-1,3,8-triazaspiro[4.5]decan-2-one |
| --- | --- | --- |
| 203 | 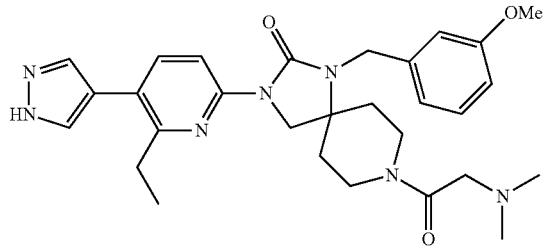 | 8-(2-(dimethylamino)acetyl)-3-(6-ethyl-5-(1H-pyrazol-4-yl)pyridin-2-yl)-1-(3-methoxybenzyl)-1,3,8-triazaspiro[4.5]decan-2-one |
| 204 | 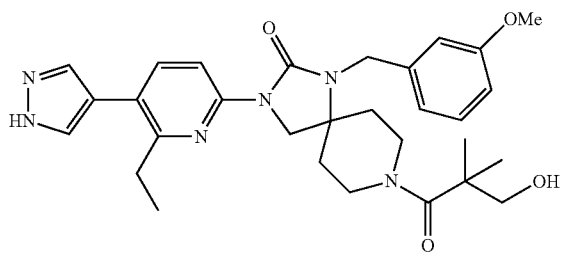 [SMILES: CCc1nc(N2CC3(CCN(C(=O)C(C)(C)CO)CC3)N(Cc3cccc(OC)c3)C2=O)ccc1-c1cn[nH]c1] | 3-(6-ethyl-5-(1H-pyrazol-4-yl)pyridin-2-yl)-8-(3-hydroxy-2,2-dimethylpropanoyl)-1-(3-methoxybenzyl)-1,3,8-triazaspiro[4.5]decan-2-one |
| 205 | 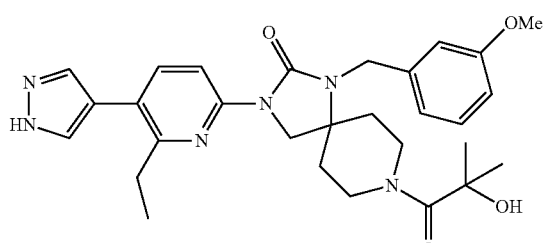 | 3-(6-ethyl-5-(1H-pyrazol-4-yl)pyridin-2-yl)-8-(2-hydroxy-2-methylpropanoyl)-1-(3-methoxybenzyl)-1,3,8-triazaspiro[4.5]decan-2-one |
| 206 | 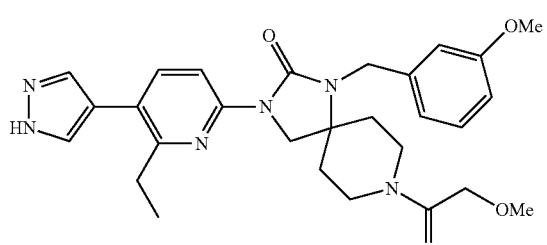 | 3-(6-ethyl-5-(1H-pyrazol-4-yl)pyridin-2-yl)-8-(2-methoxyacetyl)-1-(3-methoxybenzyl)-1,3,8-triazaspiro[4.5]decan-2-one |
| 207 | 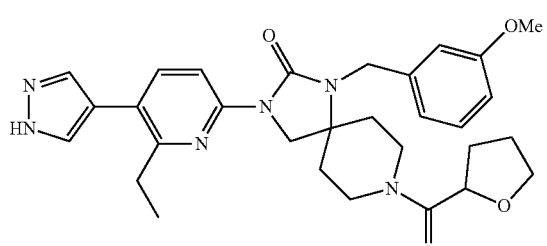 | 3-(6-ethyl-5-(1H-pyrazol-4-yl)pyridin-2-yl)-1-(3-methoxybenzyl)-8-(tetrahydrofuran-2-carbonyl)-1,3,8-triazaspiro[4.5]decan-2-one |

TABLE 12-continued

| | | |
|---|---|---|
| 208 | 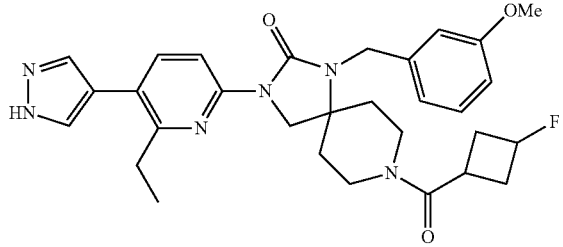 [SMILES: CCc1nc(N2CC3(CCN(C(=O)C4CC(F)C4)CC3)N(Cc3cccc(OC)c3)C2=O)ccc1-c1cn[nH]c1] | 3-(6-ethyl-5-(1H-pyrazol-4-yl)pyridin-2-yl)-8-(3-fluorocyclobutane-carbonyl)-1-(3-methoxybenzyl)-1,3,8-triazaspiro[4.5]decan-2-one |
| 209 | 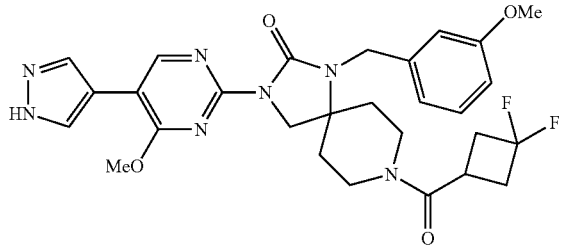 [SMILES: COc1cccc(CN2C(=O)N(c3ncc(-c4cn[nH]c4)c(OC)n3)CC23CCN(C(=O)C2CC(F)(F)C2)CC3)c1] | 8-(3,3-difluorocyclo-butanecarbonyl)-3-(4-methoxy-5-(1H-pyrazol-4-yl)pyrimidin-2-yl)-1-(3-methoxybenzyl)-1,3,8-triazaspiro[4.5]decan-2-one |
| 210 | 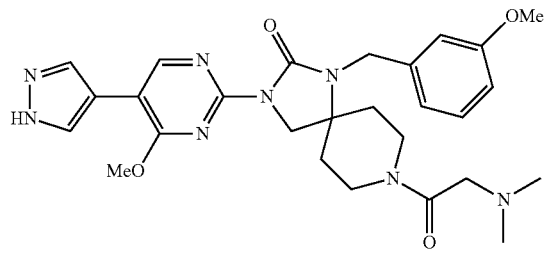 | 8-(2-(dimethylamino)acetyl)-3-(4-methoxy-5-(1H-pyrazol-4-yl)pyrimidin-2-yl)-1-(3-methoxybenzyl)-1,3,8-triazaspiro[4.5]decan-2-one |
| 211 | 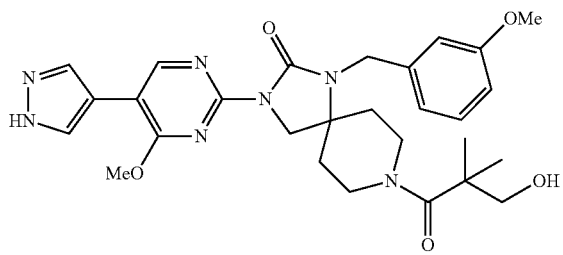 [SMILES: COc1cccc(CN2C(=O)N(c3ncc(-c4cn[nH]c4)c(OC)n3)CC23CCN(C(=O)C(C)(C)CO)CC3)c1] | 8-(3-hydroxy-2,2-dimethylpropanoyl)-3-(4-methoxy-5-(1H-pyrazol-4-yl)pyrimidin-2-yl)-1-(3-methoxybenzyl)-1,3,8-triazaspiro[4.5]decan-2-one |
| 212 | 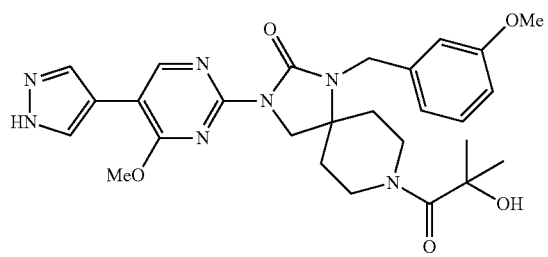 [SMILES: COc1cccc(CN2C(=O)N(c3ncc(-c4cn[nH]c4)c(OC)n3)CC23CCN(C(=O)C(C)(C)O)CC3)c1] | 8-(2-hydroxy-2-methylpropanoyl)-3-(4-methoxy-5-(1H-pyrazol-4-yl)pyrimidin-2-yl)-1-(3-methoxybenzyl)-1,3,8-triazaspiro[4.5]decan-2-one |
| 213 | 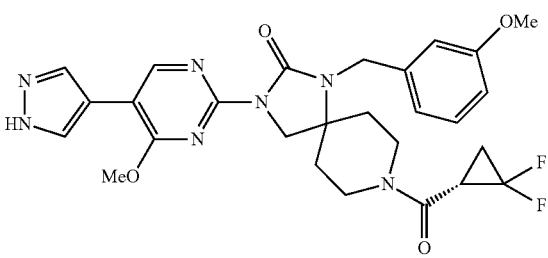 [SMILES: COc1cccc(CN2C(=O)N(c3ncc(-c4cn[nH]c4)c(OC)n3)CC23CCN(C(=O)[C@@H]2CC2(F)F)CC3)c1] | (S)-8-(2,2-difluorocyclopropane-carbonyl)-3-(4-methoxy-5-(1H-pyrazol-4-yl)pyrimidin-2-yl)-1-(3-methoxybenzyl)-1,3,8-triazaspiro[4.5]decan-2-one |

TABLE 12-continued

| | | |
|---|---|---|
| 214 | 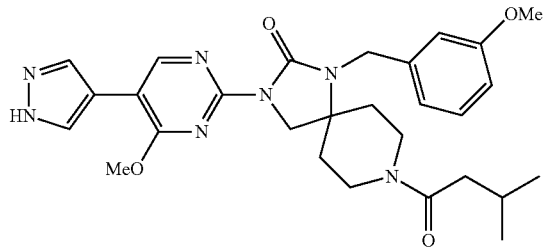 [SMILES: COc1cccc(CN2C(=O)N(c3ncc(-c4cn[nH]c4)c(OC)n3)CC23CCN(C(=O)CC(C)C)CC3)c1] | 3-(4-methoxy-5-(1H-pyrazol-4-yl)pyrimidin-2-yl)-1-(3-methoxybenzyl)-8-(3-methylbutanoyl)-1,3,8-triazaspiro[4.5]decan-2-one |
| 215 | 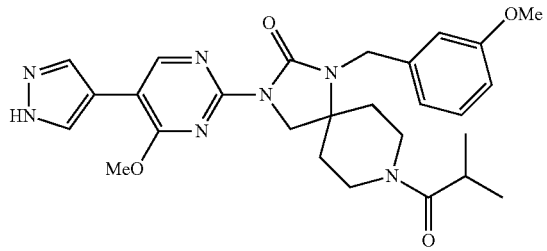 [SMILES: COc1cccc(CN2C(=O)N(c3ncc(-c4cn[nH]c4)c(OC)n3)CC23CCN(C(=O)C(C)C)CC3)c1] | 8-isobutyryl-3-(4-methoxy-5-(1H-pyrazol-4-yl)pyrimidin-2-yl)-1-(3-methoxybenzyl)-1,3,8-triazaspiro[4.5]decan-2-one |
| 216 | 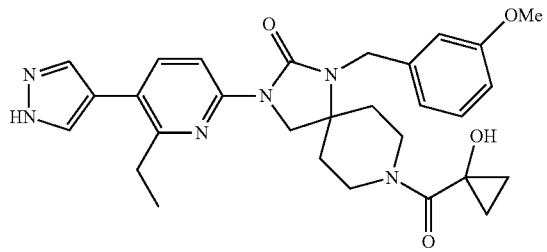 [SMILES: CCc1nc(N2CC3(CCN(C(=O)C4(O)CC4)CC3)N(Cc3cccc(OC)c3)C2=O)ccc1-c1cn[nH]c1] | 3-(6-ethyl-5-(1H-pyrazol-4-yl)pyridin-2-y)-8-(1-hydroxycyclopropane carbonyl)-1-(3-methoxybenzyl)-1,3,8-triazaspiro[4.5]decan-2-one |
| 217 | 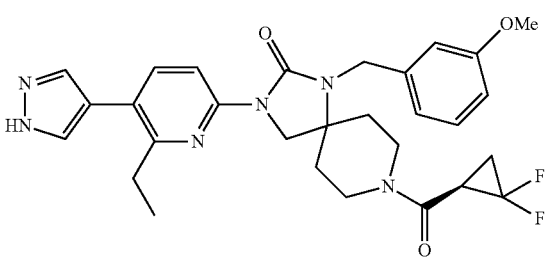 [SMILES: CCc1nc(N2CC3(CCN(C(=O)[C@H]4CC4(F)F)CC3)N(Cc3cccc(OC)c3)C2=O)ccc1-c1cn[nH]c1] | (R)-8-(2,2-difluorocyclopropane-carbonyl)-3-(6-ethyl-5-(1H-pyrazol-4-yl)pyridin-2-yl)-1-(3-methoxybenzyl)-1,3,8-triazaspiro[4.5]decan-2-one |
| 218 | 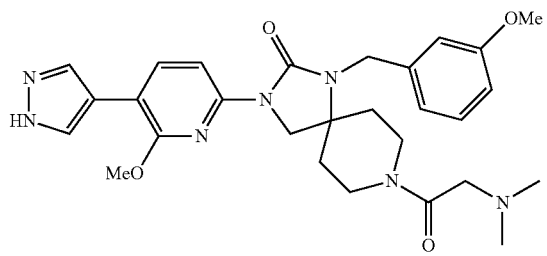 [SMILES: COc1cccc(CN2C(=O)N(c3ccc(-c4cn[nH]c4)c(OC)n3)CC23CCN(C(=O)CN(C)C)CC3)c1] | 8-(2-(dimethylamino)acetyl)-3-(6-methoxy-5-(1H-pyrazol-4-yl)pyridin-2-yl)-1-(3-methoxybenzyl)-1,3,8-triazaspiro[4.5]decan-2-one |
| 219 | 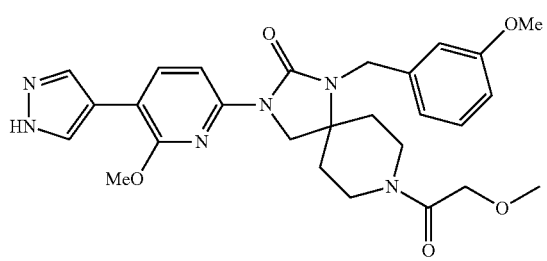 [SMILES: COCC(=O)N1CCC2(CC1)CN(c1ccc(-c3cn[nH]c3)c(OC)n1)C(=O)N2Cc1cccc(OC)c1] | 3-(6-methoxy-5-(1H-pyrazol-4-yl)pyridin-2-yl)-8-(2-methoxyacetyl)-1-(3-methoxybenzyl)-1,3,8-triazaspiro[4.5]decan-2-one |

TABLE 12-continued

| | | |
|---|---|---|
| 220 | 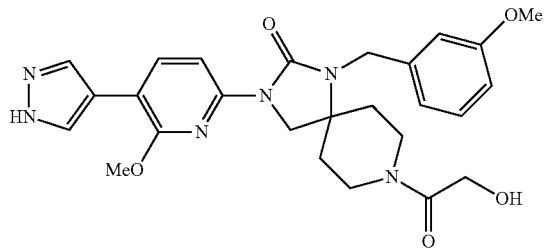 [SMILES: COc1cccc(CN2C(=O)N(c3ccc(-c4cn[nH]c4)c(OC)n3)CC23CCN(C(=O)CO)CC3)c1] | 8-(2-hydroxyacetyl)-3-(6-methoxy-5-(1H-pyrazol-4-yl)pyridin-2-yl)-1-(3-methoxybenzyl)-1,3,8-triazaspiro[4.5]decan-2-one |
| 221 | 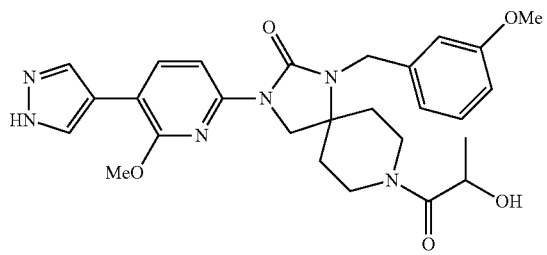 [SMILES: COc1cccc(CN2C(=O)N(c3ccc(-c4cn[nH]c4)c(OC)n3)CC23CCN(C(=O)C(C)O)CC3)c1] | 8-(2-hydroxypropanoyl)-3-(6-methoxy-5-(1H-pyrazol-4-yl)pyridin-2-yl)-1-(3-methoxybenzyl)-1,3,8-triazaspiro[4.5]decan-2-one |
| 222 | 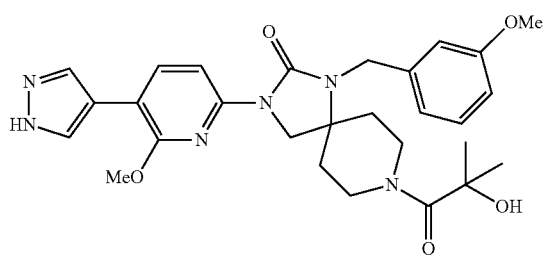 [SMILES: COc1cccc(CN2C(=O)N(c3ccc(-c4cn[nH]c4)c(OC)n3)CC23CCN(C(=O)C(C)(C)O)CC3)c1] | 8-(2-hydroxy-2-methylpropanoyl)-3-(6-methoxy-5-(1H-pyrazol-4-yl)pyridin-2-yl)-1-(3-methoxybenzyl)-1,3,8-triazaspiro[4.5]decan-2-one |
| 223 | 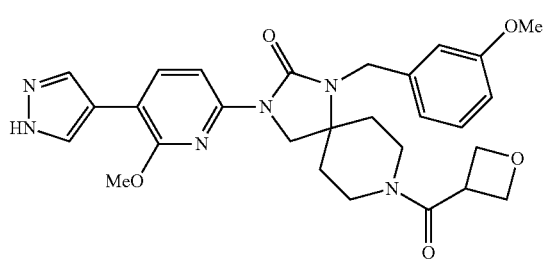 [SMILES: COc1cccc(CN2C(=O)N(c3ccc(-c4cn[nH]c4)c(OC)n3)CC23CCN(C(=O)C2COC2)CC3)c1] | 3-(6-methoxy-5-(1H-pyrazol-4-yl)pyridin-2-yl)-1-(3-methoxybenzyl)-8-(oxetane-3-carbonyl)-1,3,8-triazaspiro[4.5]decan-2-one |
| 224 | 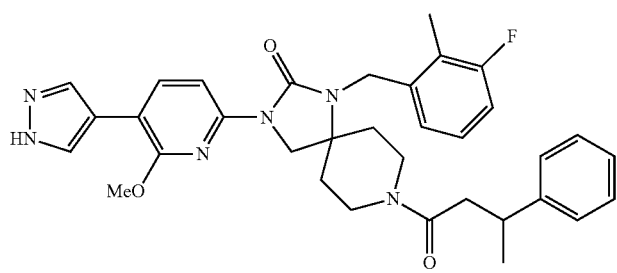 [SMILES: COc1nc(N2CC3(CCN(C(=O)CC(C)c4ccccc4)CC3)N(Cc3cccc(F)c3C)C2=O)ccc1-c1cn[nH]c1] | 1-(3-fluoro-2-methylbenzyl)-3-(6-methoxy-5-(1H-pyrazol-4-yl)pyridin-2-yl)-8-(3-phenylbutanoyl)-1,3,8-triazaspiro[4.5]decan-2-one |
| 225 | 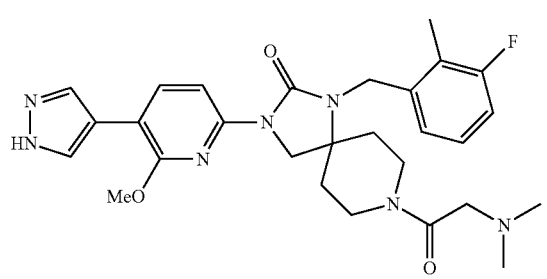 [SMILES: COc1nc(N2CC3(CCN(C(=O)CN(C)C)CC3)N(Cc3cccc(F)c3C)C2=O)ccc1-c1cn[nH]c1] | 8-(2-(dimethylamino)acetyl)-1-(3-fluoro-2-methylbenzyl)-3-(6-methoxy-5-(1H-pyrazol-4-yl)pyridin-2-yl)-1,3,8-triazaspiro[4.5]decan-2-one |

TABLE 12-continued

| | | |
|---|---|---|
| 226 | 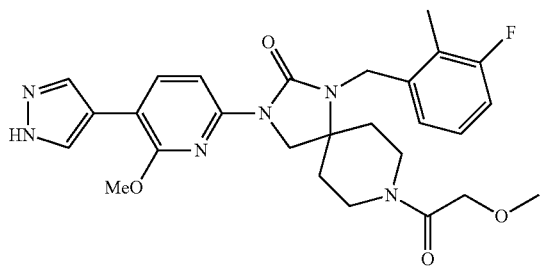 [SMILES: COCC(=O)N1CCC2(CC1)CN(c1ccc(-c3cn[nH]c3)c(OC)n1)C(=O)N2Cc1cccc(F)c1C] | 1-(3-fluoro-2-methylbenzyl)-3-(6-methoxy-5-(1H-pyrazol-4-yl)pyridin-2-yl)-8-(2-methoxyacetyl)-1,3,8-triazaspiro[4.5]decan-2-one |
| 227 | 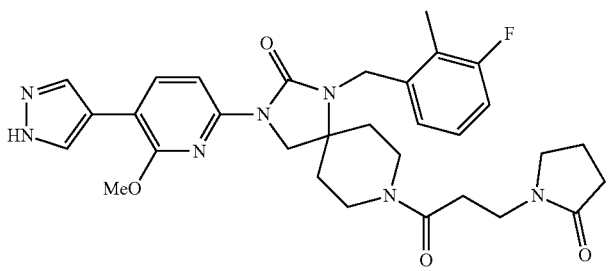 [SMILES: COc1nc(N2CC3(CCN(C(=O)CCN4CCCC4=O)CC3)N(Cc3cccc(F)c3C)C2=O)ccc1-c1cn[nH]c1] | 1-(3-fluoro-2-methylbenzyl)-3-(6-methoxy-5-(1H-pyrazol-4-yl)pyridin-2-yl)-8-(3-(2-oxopyrrolidin-1-yl)propanoyl)-1,3,8-triazaspiro[4.5]decan-2-one |
| 228 | 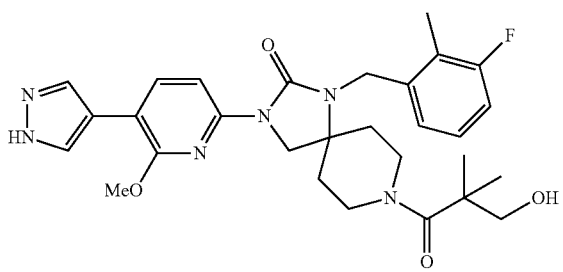 [SMILES: COc1nc(N2CC3(CCN(C(=O)C(C)(C)CO)CC3)N(Cc3cccc(F)c3C)C2=O)ccc1-c1cn[nH]c1] | 1-(3-fluoro-2-methylbenzyl)-8-(3-hydroxy-2,2-dimethylpropanoyl)-3-(6-methoxy-5-(1H-pyrazol-4-yl)pyridin-2-yl)-1,3,8-triazaspiro[4.5]decan-2-one |
| 229 | 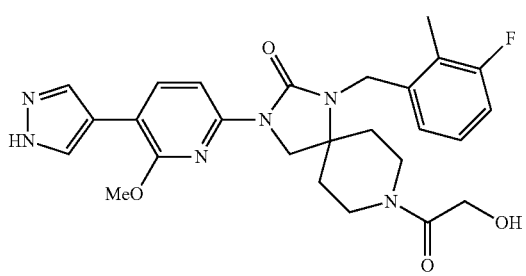 [SMILES: COc1nc(N2CC3(CCN(C(=O)CO)CC3)N(Cc3cccc(F)c3C)C2=O)ccc1-c1cn[nH]c1] | 1-(3-fluoro-2-methylbenzyl)-8-(2-hydroxyacetyl)-3-(6-methoxy-5-(1H-pyrazol-4-yl)pyridin-2-yl)-1,3,8-triazaspiro[4.5]decan-2-one |
| 230 | 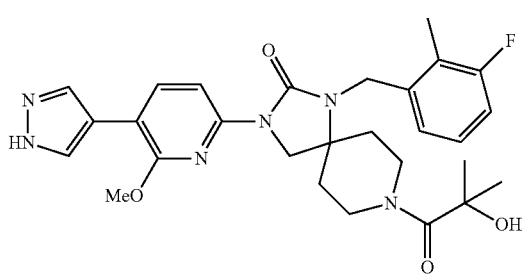 [SMILES: COc1nc(N2CC3(CCN(C(=O)C(C)(C)O)CC3)N(Cc3cccc(F)c3C)C2=O)ccc1-c1cn[nH]c1] | 1-(3-fluoro-2-methylbenzyl)-8-(2-hydroxy-2-methylpropanoyl)-3-(6-methoxy-5-(1H-pyrazol-4-yl)pyridin-2-yl)-1,3,8-triazaspiro[4.5]decan-2-one |

| Example | LCMS (M + H)+ | HPLC Method, RT (min.) & Purity | NMR |
|---|---|---|---|
| 172 | 500.10 | E: 1.81 min, 100%<br>F: 1.86 min, 100% | $^1$H NMR (400 MHz, DMSO-d6) δ ppm 12.87 (br. s., 1 H) 8.15 (br. s., 1 H) 7.89 (br. s., 1 H) 7.64 (m, J = 8.80 Hz, 2 H) 7.58 (m, J = 8.56 Hz, 2 H) 7.23 (t, J = 8.19 Hz, 1 H) 6.87-6.94 (m, 2 H) 6.80 (d, J = 9.05 Hz, 1 H) 4.29-4.46 (m, 3 H) 3.87 (s, 2 H) 3.73 (s, 3 H) 3.67 (d, J = 14.92 Hz, 1 H) 3.02-3.15 (m, 1 H) 2.60-2.75 (m, 2 H) 2.17-2.25 (m, 1 H) 1.95-2.16 (m, 3 H) 1.83-1.94 (m, 1 H) 1.59-1.79 (m, 3 H) 1.52 (br. s., 2 H) |

TABLE 12-continued

| 173 | 530.10 | E: 1.56 min, 100%<br>F: 1.59 min, 100% | ¹H NMR (400 MHz, DMSO-d6) δ ppm 8.02 (s, 2 H) 7.64 (d, J = 9.05 Hz, 2 H) 7.58 (d, J = 8.80 Hz, 2 H) 7.20-7.27 (m, 1 H) 6.87-6.94 (m, 2 H) 6.77-6.83 (m, 1 H) 4.38 (d, J = 9.54 Hz, 3 H) 3.99 (br. s., 2 H) 3.89 (s, 3 H) 3.84 (d, J = 10.52 Hz, 4 H) 3.31-3.43 (m, 2 H) 3.18 (br. s., 1 H) 2.83-2.95 (m, 1 H) 1.66 (d, J = 17.36 Hz, 3 H) 1.42-1.60 (m, 5 H) |
| --- | --- | --- | --- |
| 174 | 514.3 | E: 1.91 min, 99.3%<br>F: 1.92 min, 98.4% | ¹H NMR (400 MHz, DMSO-d6) δ ppm 12.87 (br. s., 1 H) 8.00 (s, 2 H) 7.62-7.68 (m, 2 H) 7.54-7.61 (m, 2 H) 7.23 (t, J = 8.07 Hz, 1 H) 6.88-6.95 (m, 2 H) 6.77-6.83 (m, 1 H) 4.31-4.48 (m, 3 H) 3.96 (s, 1 H) 3.89 (s, 2 H) 3.73 (s, 3 H) 3.10-3.23 (m, 1 H) 2.92-3.03 (m, 1 H) 1.62-1.78 (m, 6 H) 1.42-1.62 (m, 7 H) |
| 175 | 550.3 | E: 1.87 min, 98.8%<br>F: 1.87 min, 98.6% | ¹H NMR (400 MHz, DMSO-d6) δ ppm 12.88 (br. s., 1 H) 8.00 (br. s., 2 H) 7.61-7.68 (m, 2 H) 7.54-7.61 (m, 2 H) 7.23 (t, J = 8.07 Hz, 1 H) 6.88-6.94 (m, 2 H) 6.77-6.83 (m, 1 H) 4.31-4.48 (m, 3 H) 3.89 (s, 3 H) 3.73 (s, 3 H) 3.18 (t, J = 13.21 Hz, 1 H) 2.65-2.78 (m, 1 H) 2.30-2.44 (m, 1 H) 2.18-2.30 (m, 1 H) 1.90-2.17 (m, 3 H) 1.63-1.87 (m, 3 H) 1.50-1.62 (m, 3 H); ¹⁹F NMR (376 MHz, DMSO-d6) δ ppm −89.146 and −91.076 |
| 176 | 476.2 | E: 1.36 min, 97.9%<br>F: 1.37 min, 100% | ¹H NMR (400 MHz, DMSO-d6) δ ppm 12.89 (s, 1 H) 8.02 (br. s., 2 H) 7.64 (d, J = 8.80 Hz, 2 H) 7.58 (d, J = 8.80 Hz, 2 H) 7.19-7.26 (m, 1 H) 6.86-6.94 (m, 2 H) 6.75-6.83 (m, 1 H) 4.54 (br. s., 1 H) 4.37 (s, 2 H) 4.09 (d, J = 9.05 Hz, 2 H) 3.90 (s, 2 H) 3.73 (s, 3 H) 3.08-3.21 (m, 1 H) 2.75 (d, J = 9.29 Hz, 1 H) 1.86 (s, 1 H) 1.68 (br. s., 1 H) 1.60 (s, 2 H) 1.55 (d, J = 10.76 Hz, 2 H) |
| 177 | 490.20 | E: 1.45 min, 100%<br>F: 1.44 min, 100%<br>VII: 4.74, 100% ee | ¹H NMR (400 MHz, DMSO-d6) δ ppm 12.87 (br. s., 1 H) 8.09 (br. s., 1 H) 7.93 (br. s., 1 H) 7.63 (m, J = 8.80 Hz, 2 H) 7.58 (m, J = 8.80 Hz, 2 H) 7.18-7.26 (m, 1 H) 6.86-6.93 (m, 2 H) 6.76-6.82 (m, 1 H) 4.94 (d, J = 7.09 Hz, 1 H) 4.85 (d, J = 7.83 Hz, 1 H) 4.36 (br. s., 2 H) 3.94-4.12 (m, 2 H) 3.89 (s, 2 H) 3.72 (s, 3 H) 3.17 (d, J = 4.65 Hz, 2 H) 2.74 (br. s., 1 H) 1.71-1.86 (m, 1 H) 1.66 (d, J = 12.23 Hz, 1 H) 1.55 (d, J = 12.96 Hz, 2 H) 1.16 (t, J = 5.99 Hz, 3 H) |
| 178 | 490.20 | E: 1.45 min, 100%<br>F: 1.44 min, 100%<br>VII: 5.64, 99.3% ee | ¹H NMR (400 MHz, DMSO-d6) δ ppm 12.87 (br. s., 1 H) 8.14 (br. s., 1 H) 7.89 (br. s., 1 H) 7.63 (m, J = 8.80 Hz, 2 H) 7.58 (m, J = 8.80 Hz, 2 H) 7.18-7.26 (m, 1 H) 6.85-6.93 (m, 2 H) 6.75-6.82 (m, 1 H) 4.85 (d, J = 7.34 Hz, 1 H) 4.36 (br. s., 2 H) 4.01 (t, J = 15.28 Hz, 2 H) 3.89 (s, 2 H) 3.72 (s, 3 H) 3.17 (d, J = 5.14 Hz, 2H) 2.74 (br. s., 1 H) 1.71-1.88 (m, 1 H) 1.68 (br. s., 1 H) 1.55 (d, J = 11.98 Hz, 2H) 1.16 (t, J = 6.11 Hz, 3 H) |
| 179 | 561.3 | E: 1.78 min, 100%<br>F: 1.79 min, 100% | ¹H NMR (400 MHz, DMSO-d6) δ ppm 12.86 (br. s., 1 H) 11.29 (s, 1 H) 8.13 (br. s., 1 H) 7.89 (br. s., 1 H) 7.55-7.67 (m, 5 H) 7.43-7.49 (m, 2 H) 7.21-7.28 (m, 1 H) 7.05 (dd, J = 8.07, 1.47 Hz, 1 H) 6.91-6.99 (m, 2 H) 6.77-6.86 (m, 1 H) 6.48 (s, 1 H) 4.45 (s, 2 H) 3.91 (s, 2 H) 3.75 (s, 3 H) 3.13 (br. s., 2 H) 2.53 (br. s., 2 H) 1.79-1.95 (m, 2 H) 1.56 (br. s., 2 H) |
| 180 | 562.3 | E: 1.62 min, 100%<br>F: 1.65 min, 98.6% | ¹H NMR (400 MHz, DMSO-d6) δ ppm 12.86 (br. s., 1 H) 8.79 (d, J = 7.09 Hz, 1 H) 8.24 (s, 1 H) 8.14 (br. s., 1 H) 7.87 (d, J = 9.05 Hz, 2 H) 7.65 (d, J = 8.56 Hz, 2 H) 7.59 (d, J = 8.80 Hz, 2 H) 7.39-7.48 (m, 1 H) 7.19-7.27 (m, 1 H) 7.06 (t, J = 6.97 Hz, 1 H) 6.91-6.98 (m, 2 H) 6.76-6.85 (m, 1 H) 4.43 (s, 2 H) 4.29 (br. s., 2 H) 3.94 (s, 2 H) 3.73 (s, 3 H) 3.18 (d, J = 5.14 Hz, 2 H) 1.82-1.99 (m, 2 H) 1.61 (d, J = 12.47 Hz, 2H) |
| 181 | 507.3 | F: 1.15 min, 98.4% | ¹H NMR (400 MHz, DMSO-d6) d ppm 13.01 (br. s., 1 H) 7.99 (d, J = 8.53 Hz, 1 H) 7.93 (br. s., 1 H) 7.68 (d, J = 8.53 Hz, 2 H) 7.11-7.21 (m, 1 H) 7.06-7.11 (m, 1 H) 6.95-7.06 (m, 1 H) 4.47 (t, J = 5.52 Hz, 1 H) 4.41 (s, 3 H) 3.97-4.18 (m, 4 H) 3.72 (br. s., 1 H) 3.13 (s, 1 H) 2.84 (q, J = 7.53 Hz, 2 H) 2.23 (d, J = 1.51 Hz, 3 H) 1.81 (br. s., 1 H) 1.67 (br. s., 3 H) 1.25 (t, J = 7.28 Hz, 3 H) |
| 182 | 533.3 | F: 1.21 min, 98.9% | ¹H NMR (400 MHz, DMSO-d6) d ppm 13.02 (s, 1 H) 7.99 (d, J = 8.53 Hz, 1 H) 7.68 (d, J = 8.53 Hz, 2 H) 7.12-7.20 (m, 1 H) 7.09 (d, J = 7.03 Hz, 1 H) 6.99-7.07 (m 1 H) 4.59-4.73 (m, 5 H) 4.39-4.49 (m, 4 H) 4.04-4.14 (m, 4 H) 3.10 (t, J = 13.05 Hz, 1 H) 2.83 (q, J = 7.53 Hz, 2 H) 2.70-2.78 (m, 1 H) 2.23 (d, J = 1.51 Hz, 4 H) 1.73 (br. s., 1 H) 1.65 (d, J = 12.55 Hz, 3 H) 1.25 (t, J = 7.53 Hz, 4 H) |

TABLE 12-continued

| | | | |
|---|---|---|---|
| 183 | 525.3 | E: 1.28 min, 97.5% | |
| 184 | 505.3 | E: 1.33 min, 96.5% | |
| 185 | 531.3 | E: 1.41 min, 99.3% | $^1$H NMR (400 MHz, DMSO-d6) d ppm 13.06 (s, 1 H) 8.02 (d, J = 8.53 Hz, 1 H) 7.69 (d, J = 9.04 Hz, 1 H) 7.23 (t, J = 7.78 Hz, 1 H) 6.86-6.96 (m, 2 H) 6.81 (d, J = 10.04 Hz, 1 H) 6.52 (s, 1 H) 4.59-4.77 (m, 4 H) 4.36-4.49 (m, 3 H) 3.93-4.14 (m, 3 H) 3.73 (s, 3 H) 3.09 (br. s., 1 H) 2.82 (q, J = 7.53 Hz, 2 H) 1.91 (s, 1 H) 1.73 (t, J = 13.05 Hz, 2 H) 1.47-1.61 (m, 2 H) 1.17-1.31 (m, 4 H) |
| 186 | 523.3 | F: 1.41 min, 94.5% | $^1$H NMR (400 MHz, DMSO-d6) d ppm 8.02 (d, J = 8.80 Hz, 1 H) 7.93 (s, 1 H) 7.69 (d, J = 8.80 Hz, 1 H) 6.64-6.79 (m, 2 H) 4.49 (s, 1 H) 4.40 (s, 2 H) 4.07 (s, 3 H) 3.75 (s, 3 H) 2.83 (d, J = 7.34 Hz, 1 H) 1.61 (s, 1 H) 1.24 (t, J = 7.58 Hz, 3 H) |
| 187 | 551.3 | F: 1.25 min, 99.8% | $^1$H NMR (400 MHz, METHANOL-d4) d ppm 8.04 (d, J = 8.53 Hz, 1 H) 7.67 (d, J = 8.53 Hz, 1 H) 6.77 (s, 1 H) 6.71 (d, J = 9.54 Hz, 1 H) 6.53-6.64 (m, 1 H) 4.49 (s, 2 H) 4.21 (s, 2 H) 3.80 (s, 3 H) 2.88 (q, J = 7.36 Hz, 2 H) 1.91 (br. s., 2 H) 1.68 (d, J = 13.55 Hz, 2 H) 1.42-1.48 (m, 6H) 1.26-1.33 (m, 4 H) |
| 188 | 537.6 | E: 1.46 min, 98.7% | $^1$H NMR (400 MHz, DMSO-d6) d ppm 13.00 (s, 1 H) 8.02 (d, J = 8.31 Hz, 1 H) 7.93 (br. s., 1 H) 7.69 (d, J = 8.31 Hz, 2 H) 6.62-6.79 (m, 3 H) 4.40 (br. s., 5 H) 4.07 (s, 3 H) 3.75 (s, 3 H) 2.83 (d, J = 7.09 Hz, 2 H) 1.57-1.65 (m, 2 H) 1.21-1.29 (m, 5 H) 1.18 (br. s., 3 H) |
| 189 | 518.4 | E: 1.28 min, 97.9% | $^1$H NMR (400 MHz, DMSO-d6) d ppm 8.02 (br. s., 2 H) 7.52-7.71 (m, 4 H) 7.11-7.21 (m, 2 H) 6.98-7.08 (m, 1 H) 4.47 (s, 2 H) 3.98 (d, J = 5.52 Hz, 2 H) 3.18 (s, 1 H) 2.93 (s, 3 H) 2.80-2.90 (m, 8 H) 2.25 (d, J = 1.51 Hz, 3 H) 1.90 (br. s., 2 H) 1.72 (br. s., 2 H) |
| 190 | 522.3 | E: 1.30 min, 98.1% | $^1$H NMR (400 MHz, DMSO-d6) d ppm 12.86 (br. s., 1 H) 8.14 (br. s., 1 H) 7.89 (br. s., 1 H) 7.61-7.69 (m, 2 H) 7.49-7.61 (m, 2 H) 6.59-6.80 (m, 3 H) 5.39 (s, 1 H) 4.36 (s, 2 H) 3.91 (s, 2 H) 3.75 (s, 3 H) 1.73 (br. s., 2 H) 1.57 (d, J = 12.05 Hz, 2 H) 1.32 (s, 6 H) |
| 191 | 490.3 | F: 1.19 min, 96.7% | $^1$NMR (400 MHz, DMSO-d6) d ppm 7.98-8.10 (m, 2 H) 7.62-7.69 (m, 3 H) 7.54-7.62 (m, 2 H) 7.18-7.27 (m, 1 H) 6.86-7.03 (m, 3 H) 6.74-6.84 (m, 1 H) 4.40-4.48 (m, 2 H) 4.37 (br. s., 3 H) 4.01 (br. s., 2 H) 3.90 (s, 3 H) 3.73 (s, 4 H) 3.13-3.21 (m, 2 H) 2.75 (br. s., 1 H) 1.62-1.89 (m, 2 H) 1.56 (d, J = 12.05 Hz, 2 H) 1.17 (t, J = 5.27 Hz, 3 H) |
| 192 | 504.3 | E: 1.30 min, 98.9% | $^1$H NMR (400 MHz, DMSO-d6) d ppm 7.96 (br. s., 1 H) 7.61-7.67 (m, 2 H) 7.52-7.61 (m, 2 H) 7.17-7.27 (m, 1 H) 6.84-6.94 (m, 2 H) 6.80 (dd, J = 8.28, 1.76 Hz, 1 H) 4.37 (s, 2 H) 3.90 (s, 2 H) 3.73 (s, 3 H) 1.73 (br. s., 2 H) 1.55 (d, J = 12.05 Hz, 2 H) 1.31 (s, 6 H) |
| 193 | 534.3 | E: 1.24 mm, 95.7% | $^1$H NMR (400 MHz, DMSO-d6) d ppm 8.02 (s, 2 H) 7.54-7.68 (m, 4 H) 6.73-6.83 (m, 2 H) 6.71 (dt, J = 11.04, 2.26 Hz, 1 H) 4.45 (br. s., 2 H) 3.95 (s, 2 H) 3.74-3.78 (m, 3 H) 3.38 (br. s., 4 H) 2.99 (s, 3 H) 2.83-2.93 (m, 9 H) 2.00 (br. s., 1 H) 1.92 (br. s., 1 H) 1.66 (d, J = 13.05 Hz, 2 H) |
| 194 | 497.2 | E: 1.20 min, 98.1% | $^1$H NMR (400 MHz, DMSO-d6) d ppm 12.99 (br. s., 1 H) 8.59 (d, J = 3.01 Hz, 1 H) 8.16-8.28 (m, 2 H) 7.90-8.03 (m, 2 H) 7.23 (t, J = 7.78 Hz, 1 H) 6.86-6.95 (m, 2 H) 6.77-6.83 (m, 1 H) 6.73 (s, 1 H) 6.51 (s, 2 H) 6.27 (s, 1 H) 4.42 (s, 2 H) 4.34 (d, J = 12.55 Hz, 1 H) 4.03-4.10 (m, 2 H) 3.88 (d, J = 14.06 Hz, 1 H) 3.73 (s, 3 H) 3.22-3.28 (m, 1 H) 2.87-2.94 (m, 1 H) 1.87 (s, 1 H) 1.78 (br. s., 1 H) 1.63 (d, J = 11.55 Hz, 2 H) |
| 195 | 477.3 | E: 0.92 min, 98.3% | $^1$H NMR (400 MHz, DMSO-d6) d ppm 12.99 (br. s., 1 H) 8.57-8.65 (m, 1 H) 8.13-8.30 (m, 2 H) 7.98 (dd, J = 8.78, 2.26 Hz, 2 H) 7.18-7.28 (m, 1 H) 6.86-6.98 (m, 2 H) 6.80 (dd, J = 8.28, 1.76 Hz, 1 H) 6.51 (s, 1 H) 4.50 (t, J = 5.52 Hz, 1 H) 4.30-4.45 (m, 3 H) 3.95-4.17 (m, 4 H) 3.63-3.79 (m, 4 H) 3.12 (t, J = 13.05 Hz, 1 H) 2.75 (t, J = 13.55 Hz, 1 H) 2.55 (s, 3 H) 1.89 (d, J = 18.57 Hz, 1 H) 1.62-1.76 (m, 1 H) 1.57 (d, J = 12.05 Hz, 2 H) |
| 196 | 503.3 | E: 1.02 min, 99.4% | $^1$H NMR (400 MHz, DMSO-d6) d ppm 12.99 (br. s., 1 H) 8.58 (d, J = 2.51 Hz, 1 H) 8.20 (d, J = 9.54 Hz, 2 H) 7.91-8.01 (m, 2 H) 7.23 (t, J = 8.03 Hz, 1 H) 6.86-6.95 (m, 2 H) 6.81 (d, J = 9.04 Hz, 1 H) 6.51 (s, 1 H) 4.60-4.74 (m, 4 H) 4.41 (br. s., 4 H) 4.02 |

TABLE 12-continued

| | | | |
|---|---|---|---|
| | | | (d, J = 3.51 Hz, 3 H) 3.73 (s, 4 H) 1.73 (br. s., 1 H) 1.59 (s, 1 H) 1.53 (br. s., 2 H) |
| 197 | 491.3 | F: 1.20 min, 95.8% | ¹H NMR (400 MHz, DMSO-d6) d ppm 12.99 (br. s., 1 H) 8.59 (dd, J = 2.51, 1.00 Hz, 1 H) 8.20 (d, J = 8.03 Hz, 2H) 7.88-8.03 (m, 2H) 7.19-7.29 (m, 1 H) 6.87-6.97 (m, 2 H) 6.76-6.84 (m, 1 H) 6.51 (s, 1 H) 4.41 (s, 2 H) 4.35 (br. s., 1 H) 4.07-4.16 (m, 1 H) 3.97-4.07 (m, 3 H) 3.69-3.82 (m, 4 H) 3.25-3.29 (m, 3 H) 3.11 (d, J = 10.04 Hz, 1 H) 2.70-2.77 (m, 1 H) 1.82 (br. s., 1 H) 1.69 (br. s., 1 H) 1.56 (d, J = 13.55 Hz, 2 H) |
| 198 | 491.3 | F: 1.16 min, 98.6% | ¹H NMR (400 MHz, DMSO-d6) d ppm 12.99 (br. s., 1 H) 8.52-8.65 (m, 1 H) 8.11-8.32 (m, 2 H) 7.84-8.05 (m, 2 H) 7.17-7.28 (m, 1 H) 6.85-6.98 (m, 2 H) 6.76-6.84 (m, 1 H) 6.51 (s, 1 H) 4.77-4.96 (m, 1 H) 4.40 (br. s., 4 H) 4.04 (s, 2 H) 3.98 (br. s., 1 H) 3.73 (s, 3 H) 3.04-3.20 (m, 1 H) 2.73 (br. s., 1 H) 1.84 (br. s., 1 H) 1.68 (d, J = 14.06 Hz, 1 H) 1.58 (d, J = 12.05 Hz, 2H) 1.11-1.23 (m, 3 H) |
| 199 | 505.3 | E: 1.06 min, 96.8% | ¹H NMR (400 MHz, DMSO-d6) d ppm 12.99 (br. s., 1 H) 8.59 (d, J = 2.01 Hz, 1 H) 8.20 (d, J = 9.04 Hz, 2 H) 7.88-8.04 (m, 2 H) 7.24 (t, J = 7.78 Hz, 1 H) 6.85-6.99 (m, 2 H) 6.75-6.84 (m, 1 H) 6.51 (s, 1 H) 5.40 (s, 1 H) 4.40 (s, 2 H) 4.04 (s, 2 H) 3.73 (s, 3H) 1.74 (br. s., 2 H) 1.56 (d, J = 12.55 Hz, 2 H) 1.31 (s, 6 H) |
| 200 | 531.3 | F: 1.79 min, 97.0% | ¹H NMR (400 MHz, DMSO-d6) d ppm 13.00 (br. s., 1 H) 8.02 (d, J = 8.53 Hz, 1 H) 7.93 (br. s., 1 H) 7.69 (d, J = 8.53 Hz, 2 H) 7.18-7.28 (m, 1 H) 6.86-6.95 (m, 2 H) 6.76-6.84 (m, 1 H) 4.30-4.51 (m, 3 H) 4.04 (s, 2 H) 3.89 (d, J = 11.55 Hz, 1 H) 3.73 (s, 3 H) 3.14 (t, J = 13.30 Hz, 1 H) 2.83 (q, J = 7.53 Hz, 2 H) 2.57-2.67 (m, 1 H) 2.19 (dd, J = 7.03, 2.51 Hz, 2 H) 1.97 (dt, J = 13.30, 6.90 Hz, 1 H) 1.73 (d, J = 8.53 Hz, 1 H) 1.67 (br. s., 1 H) 1.57 (br. s., 2 H) 1.24 (t, J = 7.28 Hz, 3 H) 0.90 (d, J = 6.53 Hz, 6 H) |
| 201 | 517.3 | F: 1.29 min, 98.4% | ¹H NMR (400 MHz, DMSO-d6) d ppm 13.00 (br. s., 1 H) 8.03 (d, J = 8.53 Hz, 1 H) 7.93 (br. s., 1 H) 7.69 (d, J = 8.53 Hz, 2 H) 7.23 (t, J = 8.03 Hz, 1 H) 6.85-6.96 (m, 2 H) 6.75-6.84 (m, 1 H) 4.31-4.52 (m, 3 H) 4.05 (s, 2 H) 3.95 (d, J = 13.05 Hz, 1 H) 3.73 (s, 3 H) 3.08-3.24 (m, 1 H) 2.75-2.92 (m, 3 H) 2.57-2.67 (m, 1 H) 1.71 (br. s., 2 H) 1.59 (br. s., 2 H) 1.24 (t, J = 7.28 Hz, 3 H) 0.99 (d, J = 6.53 Hz, 6 H) |
| 202 | 565.3 | F: 1.40 min, 98.3% | ¹H NMR (400 MHz, DMSO-d6) d ppm 12.99 (br. s., 1 H) 8.02 (d, J = 8.53 Hz, 1 H) 7.69 (d, J = 8.53 Hz, 2 H) 7.23 (t, J = 8.28 Hz, 1 H) 6.87-6.96 (m, 2 H) 6.76-6.84 (m, 1 H) 4.33-4.49 (m, 3 H) 4.04 (s, 2 H) 3.69-3.81 (m, 4 H) 3.20-3.30 (m, 1 H) 3.06-3.19 (m, 1 H) 2.70-2.93 (m, 7 H) 1.66-1.83 (m, 2 H) 1.49-1.61 (m, 2 H) 1.24 (t, J = 7.53 Hz, 3 H) |
| 203 | 523.3 | E: 0.91 min, 94.2% | ¹H NMR (400 MHz, DMSO-d6) d ppm 13.02 (s, 1 H) 8.03 (d, J = 9.04 Hz, 1 H) 7.93 (s, 1 H) 7.69 (d, J = 8.53 Hz, 2 H) 7.19-7.27 (m, 1 H) 6.86-6.94 (m, 2 H) 6.82 (d, J = 8.03 Hz, 1 H) 4.40 (s, 3 H) 4.05 (d, J = 4.02 Hz, 2 H) 3.73 (s, 3 H) 3.13 (br. s., 2 H) 2.83 (q, J = 7.53 Hz, 2 H) 1.81 (d, J = 12.05 Hz, 1 H) 1.69 (s, 1 H) 1.59 (d, J = 13.05 Hz, 2 H) 1.20-1.28 (m, 4 H) |
| 204 | 547.3 | E: 1.53 min, 97.3% | ¹H NMR (400 MHz, DMSO-d6) d ppm 13.00 (br. s., 1 H) 8.02 (d, J = 8.53 Hz, 1 H) 7.91 (br. s., 1 H) 7.69 (d, J = 8.53 Hz, 2 H) 7.23 (t, J = 8.03 Hz, 1 H) 6.85-6.95 (m, 2 H) 6.75-6.84 (m, 1 H) 4.55 (t, J = 6.02 Hz, 1 H) 4.41 (s, 2 H) 4.31 (d, J = 12.05 Hz, 2 H) 4.04 (s, 2 H) 3.73 (s, 3 H) 3.42 (d, J = 5.52 Hz, 2 H) 2.86-2.96 (m, 2 H) 2.83 (q, J = 7.53 Hz, 2 H) 1.65-1.81 (m, 2 H) 1.57 (d, J = 12.55 Hz, 2 H) 1.24 (t, J = 7.53 Hz, 3 H) 1.15 (s, 6 H) |
| 205 | 533.3 | E: 1.49 min, 98.7% | ¹H NMR (400 MHz, DMSO-d6) d ppm 13.00 (br. s., 1 H) 8.02 (d, J = 8.53 Hz, 1 H) 7.93 (br. s., 1 H) 7.69 (d, J = 8.53 Hz, 2 H) 7.24 (t, J = 7.78 Hz, 1 H) 6.87-6.97 (m 2 H) 6.81 (dd, J = 8.03, 2.01 Hz, 1 H) 5.39 (s, 1 H) 4.40 (s, 2 H) 4.05 (s, 2 H) 3.73 (s, 3 H) 2.83 (q, J = 7.53 Hz, 2 H) 1.76 (br. s., 2 H) 1.57 (d, J = 12.55 Hz, 2 H) 1.31 (s, 6 H) 1.24 (t, J = 7.28 Hz, 3 H) |
| 206 | 519.3 | F: 1.10 min, 98.3% | ¹H NMR (400 MHz, DMSO-d6) d ppm 13.00 (br. s., 1 H) 8.02 (d, J = 8.53 Hz, 1 H) 7.93 (br. s., 1 H) 7.69 (d, J = 8.53 Hz, 2 H) 7.19-7.28 (m, 1 H) 6.85-6.95 (m, 2 H) 6.77-6.84 (m, 1 H) 4.29-4.46 (m, 3 H) 4.08-4.15 (m, 1 H) 3.99-4.08 (m, 3 H) 3.79 (br. s., 1 H) 3.73 (s, 3 H) 3.28 (s, 3 H) 3.05-3.17 |

TABLE 12-continued

| | | | |
|---|---|---|---|
| | | | (m, 1 H) 2.83 (q, J = 7.53 Hz, 2 H) 2.66-2.74 (m, 1 H) 1.82 (br. s., 1 H) 1.71 (br. s., 1 H) 1.57 (d, J = 12.55 Hz, 2 H) 1.24 (t, J = 7.53 Hz, 3 H) |
| 207 | 545.3 | E: 1.52 min, 98.7% | ¹H NMR (400 MHz, DMSO-d6) d ppm 13.01 (s, 1 H) 8.02 (d, J = 9.04 Hz, 1 H) 7.92 (s, 1 H) 7.69 (d, J = 8.53 Hz, 2 H) 7.19-7.28 (m, 1 H) 6.86-6.96 (m, 2 H) 6.81 (d, J = 9.54 Hz, 1 H) 4.66 (d, J = 8.03 Hz, 1 H) 4.41 (br. s., 3 H) 3.95-4.06 (m, 3 H) 3.69-3.80 (m, 5 H) 2.83 (q, J = 7.53 Hz, 2 H) 2.66-2.72 (m, 1 H) 2.08 (s, 1 H) 1.99 (br. s., 2 H) 1.82 (br. s., 4 H) 1.57 (d, J = 12.55 Hz, 2 H) 1.24 (t, J = 7.53 Hz, 3 H) |
| 208 | 547.3 | F: 1.29 min, 97.8% | ¹H NMR (400 MHz, DMSO-d6) d ppm 13.00 (s, 1 H) 8.02 (d, J = 9.04 Hz, 1 H) 7.92 (br. s., 1 H) 7.69 (d, J = 8.53 Hz, 2 H) 7.19-7.27 (m, 1 H) 6.87-6.96 (m, 2 H) 6.81 (d, J = 8.03 Hz, 1 H) 4.03 (s, 2 H) 3.73 (s, 4 H) 2.80-2.85 (m, 2 H) 1.71 (br. s., 2 H) 1.56 (br. s., 2 H) 1.24 (t, J = 7.53 Hz, 4 H) |
| 209 | 568.3 | E: 1.47 min, 96.2% | ¹H NMR (400 MHz, DMSO-d6) d ppm 13.01 (br. s., 1 H) 8.71 (s, 1 H) 8.16 (br. s., 1 H) 8.00 (br. s., 1 H) 7.17-7.28 (m, 1 H) 6.86-6.97 (m, 2 H) 6.76-6.84 (m, 1 H) 4.31-4.47 (m, 3 H) 4.04-4.11 (m, 3 H) 4.03 (s, 2 H) 3.68-3.79 (m, 4 H) 3.19-3.28 (m, 1 H) 3.09-3.16 (m, 1 H) 2.69-2.93 (m, 5 H) 1.66-1.81 (m, 2 H) 1.56 (t, J = 10.29 Hz, 2 H) |
| 210 | 535.3 | F: 0.98 min, 95.4% | ¹H NMR (400 MHz, METHANOL-d4) d ppm 8.65 (s, 1 H) 8.09 (s, 2 H) 7.26 (t, J = 7.78 Hz, 1 H) 6.90-7.02 (m, 2 H) 6.84 (d, J = 9.54 Hz, 1 H) 4.48-4.64 (m, 3 H) 4.26-4.36 (m, 1 H) 4.15-4.26 (m, 6 H) 3.80 (s, 3 H) 3.68 (br. s., 1 H) 2.85-3.01 (m, 7 H) 2.00 (br. s., 1 H) 1.93 (d, J = 16.56 Hz, 1 H) 1.77 (br. s., 2 H) |
| 211 | 550.3 | F: 1.05 min, 96.0% | ¹H NMR (400 MHz, METHANOL-d4) d ppm 8.08 (br. s., 1 H) 7.25 (br. s., 1 H) 6.97 (br. s., 2 H) 6.83 (d, J = 8.03 Hz, 1 H) 4.56 (d, J = 8.03 Hz, 2 H) 4.46 (br. s., 2 H) 4.19 (br. s., 5 H) 3.77-3.83 (m, 3 H) 3.54-3.61 (m, 2 H) 3.06 (s, 1 H) 3.01 (br. s., 2 H) 1.92 (br. s., 2 H) 1.69 (br. s., 3 H) 1.25-1.27 (m, 6 H) |
| 212 | 536.3 | F: 1.19 min, 97.3% | ¹H NMR (400 MHz, METHANOL-d4) d ppm 8.64 (br. s., 1 H) 8.08 (br. s., 2 H) 7.25 (s, 1 H) 6.96 (br. s., 2 H) 6.83 (d, J = 8.03 Hz, 1 H) 4.20 (br. s., 5 H) 3.79 (s, 3 H) 1.95 (br. s., 2 H) 1.68 (d, J = 12.55 Hz, 2 H) 1.40-1.47 (m, 7 H) |
| 213 | 554.3 | F: 1.19 min, 98.2% | ¹H NMR (400 MHz, DMSO-d6) d ppm 8.72 (s, 1 H) 8.08 (s, 2 H) 7.24 (t, J = 7.53 Hz, 1 H) 6.87 (s, 1 H) 6.91 (s, 1 H) 6.81 (d, J = 8.03 Hz, 1 H) 4.41 (s, 2 H) 4.35 (s, 1 H) 4.04-4.11 (m, 5 H) 3.74 (d, J = 3.01 Hz, 3 H) 1.89 (s, 3 H) |
| 214 | 534.3 | F: 1.25 min, 97.3% | ¹H NMR (400 MHz, DMSO-d6) d ppm 8.71 (s, 1 H) 7.20-7.27 (m, 1 H) 6.86-6.95 (m, 2 H) 6.81 (d, J = 10.54 Hz, 1 H) 4.40 (s, 3 H) 4.07 (s, 3 H) 4.03 (s, 2 H) 3.88 (s, 1 H) 3.74 (s, 3 H) 3.15 (d, J = 13.55 Hz, 1 H) 2.13-2.21 (m, 2 H) 1.96 (d, J = 13.55 Hz, 1 H) 1.73 (s, 1 H) 1.57 (br. s., 2 H) 0.89 (d, J = 6.53 Hz, 6 H) |
| 215 | 520.3 | F: 1.16 min, 97.7% | ¹H NMR (400 MHz, DMSO-d6) d ppm 13.01 (br. s., 1 H) 8.71 (s, 1 H) 8.16 (br. s., 1 H) 8.00 (br. s., 1 H) 7.19-7.28 (m, 1 H) 6.86-6.94 (m, 2 H) 6.81 (d, J = 8.03 Hz, 1 H) 4.40 (d, J = 6.02 Hz, 3 H) 4.07 (s, 3 H) 4.03 (s, 2 H) 3.96 (s, 1 H) 3.73 (s, 3 H) 2.83-2.91 (m, 1 H) 1.73 (s, 2 H) 1.57 (br. s., 2 H) 0.98 (br. s., 7 H) |
| 216 | 531.3 | F: 1.42 min, 97.1% | ¹H NMR (400 MHz, METHANOL-d4) d ppm 8.05 (d, J = 8.53 Hz, 1 H) 7.82 (br. s., 1 H) 7.71 (br. s., 1 H) 7.67 (d, J = 8.53 Hz, 1 H) 7.19-7.29 (m, 1 H) 6.89-7.01 (m, 2 H) 6.77-6.87 (m, 1 H) 4.58 (br. s., 2 H) 4.51 (s, 2 H) 4.20 (s, 2 H) 3.79 (s, 3 H) 2.89 (q, J = 7.53 Hz, 2 H) 1.94 (br. s., 2 H) 1.67 (d, J = 12.05 Hz, 2 H) 1.30 (t, J = 7.53 Hz, 4 H) 1.05 (br. s., 2 H) 0.89 (br. s., 2 H) |
| 217 | 551.3 | E: 1.69 min, 98.0% | ¹H NMR (400 MHz, DMSO-d6) d ppm 13.01 (s, 1 H) 7.99-8.07 (m, 1 H) 7.93 (br. s., 1 H) 7.62-7.74 (m, 2 H) 7.19-7.28 (m, 1 H) 6.85-6.95 (m, 2 H) 6.81 (d, J = 10.04 Hz, 1 H) 4.42 (s, 2 H) 4.37 (br. s., 2 H) 4.02-4.12 (m, 3 H) 3.73 (d, J = 3.01 Hz, 3 H) 2.81-2.86 (m, 2 H) 1.92 (s, 3 H) 1.69 (br. s., 1 H) 1.61 (br. s., 2 H) 1.25 (t, J = 7.53 Hz, 4 H) |
| 218 | 534.3 | E: 1.06 min, 97.2% | ¹H NMR (400 MHz, DMSO-d6) d ppm 13.15 (br. s., 1 H) 8.35 (br. s., 1 H) 8.15-8.28 (m, 2 H) 8.01 (d, J = 8.31 Hz, 1 H) 7.50 (t, J = 7.83 Hz, 1 H) 7.12-7.22 (m, 2 H) 7.07 (dd, J = 7.95, 2.32 Hz, 1 H) 4.65 (s, 3 H) 4.34 (d, J = 6.11 Hz, 2 H) 4.29 (s, 3 H) 3.99 |

TABLE 12-continued

| | | | |
|---|---|---|---|
| | | | (s, 3 H) 3.41 (t, J = 12.72 Hz, 1 H) 3.00 (t, J = 13.08 Hz, 1 H) 2.50-2.65 (m, 6 H) 2.06 (d, J = 13.94 Hz, 1 H) 1.89-2.00 (m, 1 H) 1.84 (d, J = 12.47 Hz, 2 H) |
| 219 | 521.3 | F: 1.38 min, 97.4% | ¹H NMR (400 MHz, DMSO-d6) d ppm 13.14 (br. s., 1 H) 8.36 (br. s., 1 H) 8.26 (d, J = 8.31 Hz, 1 H) 8.21 (br. s., 1 H) 8.01 (d, J = 8.31 Hz, 1 H) 7.44-7.54 (m, 1 H) 7.11-7.21 (m, 2 H) 7.06 (dd, J = 8.31, 1.47 Hz, 1 H) 4.57-4.70 (m, 3 H) 4.31-4.38 (m, 3 H) 4.28 (s, 3 H) 4.03 (d, J = 11.25 Hz, 1 H) 3.99 (s, 3 H) 3.38 (d, J = 16.14 Hz, 1 H) 2.95-3.04 (m, 1 H) 2.08 (br. s., 1 H) 1.96 (br. s., 1 H) 1.82 (d, J = 12.47 Hz, 2 H) |
| 220 | 507.3 | E: 1.24 min, 97.2% | ¹H NMR (400 MHz, DMSO-d6) d ppm 13.14 (br. s., 1 H) 8.36 (s, 1 H) 8.26 (d, J = 8.07 Hz, 1 H) 8.21 (s, 1 H) 8.01 (d, J = 8.31 Hz, 1 H) 7.44-7.54 (m, 1 H) 7.12-7.22 (m, 2 H) 7.06 (dd, J = 7.83, 2.20 Hz, 1 H) 4.73-4.81 (m, 1 H) 4.66 (s, 3 H) 4.37 (d, J = 5.62 Hz, 1 H) 4.34 (s, 3 H) 4.28 (s, 3 H) 3.90-4.03 (m, 4 H) 3.32-3.45 (m, 1 H) 3.02 (t, J = 12.59 Hz, 1 H) 2.11 (d, J = 10.27 Hz, 1 H) 1.96 (br. s., 1 H) 1.82 (d, J = 12.96 Hz, 2 H) |
| 221 | 521.3 | F: 1.34 min, 96.5% | ¹H NMR (400 MHz, DMSO-d6) d ppm 7.96-8.10 (m, 4 H) 7.76 (d, J = 8.53 Hz, 1 H) 7.19-7.28 (m, 1 H) 6.87-6.98 (m, 2 H) 6.76-6.84 (m, 1 H) 4.41 (br. s., 4 H) 4.21 (d, J = 10.04 Hz, 1 H) 4.08 (br. s., 2 H) 4.03 (s, 4H) 3.73 (s, 4H) 3.18 (d, J = 13.55 Hz, 1 H) 2.75 (br. s., 1 H) 1.79 (d, J = 17.57 Hz, 1 H) 1.69 (br. s., 1 H) 1.53-1.62 (m, 2 H) 1.14-1.22 (m, 2 H) |
| 222 | 535.3 | E: 1.45 min, 97.8% | ¹H NMR (400 MHz, DMSO-d6) d ppm 13.14 (br. s., 1 H) 8.36 (br. s., 1 H) 8.25 (d, J = 8.31 Hz, 1 H) 8.21 (br. s., 1 H) 8.01 (d, J = 8.31 Hz, 1 H) 7.44-7.56 (m, 1 H) 7.10-7.24 (m, 2 H) 7.07 (dd, J = 7.83, 2.20 Hz, 1 H) 5.64 (s, 1 H) 4.65 (s, 2 H) 4.34 (s, 2 H) 4.29 (s, 3 H) 3.99 (s, 3 H) 2.01 (br. s., 2 H) 1.82 (d, J = 12.47 Hz, 2 H) 1.57 (s, 6 H) |
| 223 | 533.3 | F: 1.35 min, 97.9% | ¹H NMR (400 MHz, DMSO-d6) d ppm 12.89 (br. s., 1 H) 8.10 (br. s., 1 H) 8.00 (d, J = 8.53 Hz, 1 H) 7.95 (br. s., 1 H) 7.75 (d, J = 8.03 Hz, 1 H) 7.23 (t, J = 8.03 Hz, 1 H) 6.87-6.96 (m, 2 H) 6.77-6.83 (m, 1 H) 4.58-4.76 (m, 4 H) 4.35-4.49 (m, 3 H) 4.08-4.15 (m, 1 H) 4.06 (d, J = 5.52 Hz, 2 H) 4.02 (s, 3 H) 3.73 (s, 3 H) 3.03-3.16 (m, 1 H) 2.74 (t, J = 12.05 Hz, 1 H) 1.66-1.79 (m, 2 H) 1.47-1.61 (m, 2 H) |
| 224 | 597.3 | E: 2.03 min, 98.4% | ¹H NMR (400 MHz, DMSO-d6) d ppm 12.87 (br. s., 1 H) 8.09 (br. s., 1 H) 7.96-8.02 (m, 1 H) 7.94 (br. s., 1 H) 7.71 (t, J = 8.03 Hz, 1 H) 7.19-7.30 (m, 4 H) 6.98-7.18 (m, 4 H) 4.41 (br. s., 2 H) 4.29 (s, 1 H) 4.05-4.14 (m, 2 H) 4.03 (d, J = 1.51 Hz, 3 H) 3.90 (br. s., 1 H) 3.11-3.20 (m, 2 H) 3.06 (d, J = 15.06 Hz, 1 H) 2.55-2.64 (m, 2 H) 2.22 (br. s., 3 H) 1.72 (br. s., 1 H) 1.52-1.68 (m, 3 H) 1.47 (br. s., 1 H) 1.37 (br. s., 1 H) 1.19 (d, J = 6.53 Hz, 3 H) |
| 225 | 536.3 | E: 1.17 min, 97.2% | ¹H NMR (400 MHz, DMSO-d6) d ppm 12.88 (br. s., 1 H) 8.09 (br. s., 1 H) 7.99 (d, J = 8.53 Hz, 1 H) 7.95 (br. s., 1 H) 7.73 (d, J = 8.53 Hz, 1 H) 7.12-7.20 (m, 1 H) 7.07-7.12 (m, 1 H) 6.98-7.07 (m, 1 H) 4.30-4.47 (m, 3 H) 4.06-4.17 (m, 2 H) 4.04 (s, 4 H) 3.05-3.19 (m, 3 H) 2.09-2.27 (m, 9 H) 1.75 (br. s., 1 H) 1.64 (d, J = 9.04 Hz, 1 H) |
| 226 | 523.3 | F: 1.53 min, 98.5% | ¹H NMR (400 MHz, DMSO-d6) d ppm 12.88 (br. s., 1 H) 8.09 (s, 1 H) 7.99 (d, J = 8.03 Hz, 1 H) 7.95 (s, 1 H) 7.72 (d, J = 8.53 Hz, 1 H) 7.12-7.21 (m, 1 H) 7.06-7.12 (m, 1 H) 7.03 (t, J = 8.53 Hz, 1 H) 4.30-4.45 (m, 3 H) 4.04-4.17 (m, 4 H) 4.04 (s, 3 H) 3.77 (d, J = 14.56 Hz, 1 H) 3.26 (s, 3 H) 3.10-3.19 (m, 1 H) 2.68-2.79 (m, 1 H) 2.22 (d, J = 1.51 Hz, 3 H) 1.77 (br. s., 1 H) 1.69 (br. s., 1 H) 1.59-1.67 (m, 2H) |
| 227 | 590.3 | E: 1.44 min, 98.8% | ¹H NMR (400 MHz, DMSO-d6) d ppm 12.87 (br. s., 1 H) 8.09 (br. s., 1 H) 7.97-8.01 (m, 1 H) 7.95 (br. s., 1 H) 7.72 (d, J = 8.53 Hz, 1 H) 7.11-7.21 (m, 1 H) 7.06-7.11 (m, 1 H) 7.02 (t, J = 8.53 Hz, 1 H) 4.42 (s, 3 H) 4.13 (s, 2 H) 4.04 (s, 3 H) 3.88 (d, J = 12.05 Hz, 1 H) 3.33-3.47 (m, 4 H) 3.19 (t, J = 13.80 Hz, 1 H) 2.67-2.72 (m, 1 H) 2.54-2.58 (m, 1 H) 2.19-2.26 (m, 3 H) 2.11-2.19 (m, 2 H) 1.79-1.93 (m, 3 H) 1.64 (d, J = 17.07 Hz, 3 H) |
| 228 | 551.3 | E: 1.58 min, 98.6% | ¹H NMR (400 MHz, DMSO-d6) d ppm 12.88 (br. s., 1 H) 8.10 (br. s., 1 H) 7.99 (d, J = 8.03 Hz, 1 H) 7.95 (br. s., 1 H) 7.73 (d, J = 8.03 Hz, 1 H) 7.15 (dd, J = 7.78, 5.77 Hz, 1 H) 7.08-7.13 (m, 1 H) 6.97-7.07 (m, 1 H) 4.49-4.56 (m, 1 H) 4.41 (s, 2 H) 4.31 |

TABLE 12-continued

| | | | |
|---|---|---|---|
| | | | (d, J = 13.55 Hz, 2 H) 4.12 (s, 2 H) 4.04 (s, 3 H) 3.40 (d, J = 6.02 Hz, 2 H) 2.87-2.99 (m, 2 H) 2.22 (d, J = 1.51 Hz, 3 H) 1.67-1.74 (m, 2 H) 1.58-1.67 (m, 3 H) 1.13 (s, 6 H) |
| 229 | 509.3 | E: 1.38 min, 98.5% | $^1$H NMR (400 MHz, DMSO-d6) d ppm 12.87 (br. s., 1 H) 8.10 (s, 1 H) 7.99 (d, J = 8.53 Hz, 1 H) 7.95 (s, 1 H) 7.72 (d, J = 8.03 Hz, 1 H) 7.12-7.20 (m, 1 H) 7.06-7.12 (m, 1 H) 6.98-7.05 (m, 1 H) 4.48 (t, J = 5.27 Hz, 1 H) 4.40 (s, 3 H) 4.14 (d, J = 5.52 Hz, 2 H) 4.05-4.11 (m, 2 H) 4.04 (s, 3 H) 3.70 (d, J = 14.05 Hz, 1 H) 3.07-3.15 (m, 1 H) 2.78 (br. s., 1 H) 2.22 (d, J = 1.51 Hz, 3 H) 1.81 (br. s., 1 H) 1.59-1.73 (m, 3H) |
| 230 | 537.3 | E: 1.57 min, 96.9% | $^1$H NMR (400 MHz, DMSO-d6) d ppm 12.88 (br. s., 1 H) 8.09 (br. s., 1 H) 7.99 (d, J = 8.03 Hz, 1 H) 7.95 (br. s., 1 H) 7.72 (d, J = 8.03 Hz, 1 H) 7.13-7.21 (m, 1 H) 7.07-7.13 (m, 1 H) 6.97-7.07 (m, 1 H) 5.34 (s, 1 H) 4.40 (s, 2 H) 4.13 (s, 2 H) 4.04 (s, 3 H) 2.23 (d, J = 1.51 Hz, 3 H) 1.59-1.79 (m, 4 H) 1.30 (s, 6 H) |

Example 231

3-(4-(1H-pyrazol-4-yl)phenyl)-8-((4,4-difluorocyclohexyl)methyl)-1-(3-methoxybenzyl)-1,3,8-triazaspiro[4.5]decan-2-one

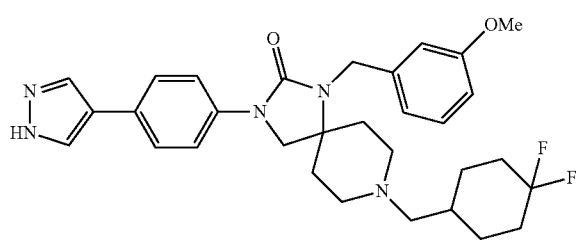 [SMILES: COc1cccc(CN2C(=O)N(c3ccc(-c4cn[nH]c4)cc3)CC23CCN(CC2CCC(F)(F)CC2)CC3)c1]

Example 231a

Preparation of 3-(4-bromophenyl)-8-((4,4-difluorocyclohexyl)methyl)-1-(3-methoxybenzyl)-1,3,8-triazaspiro[4.5]decan-2-one

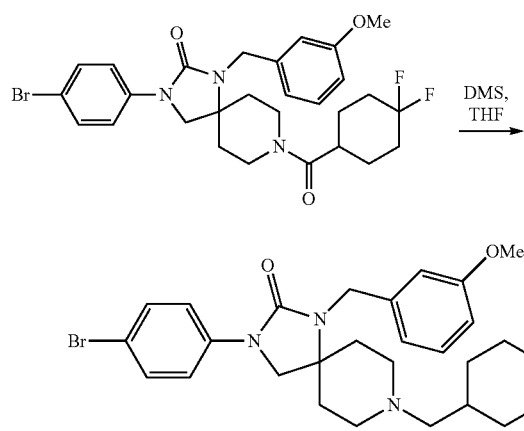

To a solution of 3-(4-bromophenyl)-8-(4,4-difluorocyclohexanecarbonyl)-1-(3-methoxybenzyl)-1,3,8-triazaspiro[4.5]decan-2-one (25 mg, 0.043 mmol) in THF (5 mL) at 0° C., was added borane-methyl sulfide complex (0.021 mL, 0.217 mmol). The reaction mixture was allowed to warm to rt and stir overnight. The reaction mixture was quenched with methanol, then concentrated. The residue was dissolved in THF (2 mL), then 1.5 N HCl (8 mL) was added. The reaction mixture heated at 80° C. for 5 h. The reaction mixture was cooled to rt, basified with 10% NaOH solution, and then extracted with ethyl acetate. The combined ethyl acetate layers were washed with brine, dried over $Na_2SO_4$, filtered and concentrated to afford 3-(4-bromophenyl)-8-((4,4-difluorocyclohexyl)methyl)-1-(3-methoxybenzyl)-1,3,8-triazaspiro[4.5]decan-2-one as a yellow gummy solid (15 mg, 61% yield). MS(ESI) m/z: 564.3 (M+H)$^+$; $^1$H NMR (400 MHz, DMSO-d$_6$) δ ppm 7.61-7.67 (m, 2H) 7.48-7.54 (m, 2H) 7.23 (t, J=8.03 Hz, 1H) 6.86-6.94 (m, 2H) 6.80 (dd, J=6.78, 2.26 Hz, 1H) 4.46 (t, J=5.27 Hz, 2H) 4.39 (s, 2H) 3.97-4.02 (m, 2H) 3.73 (s, 5H) 2.77 (d, J=11.55 Hz, 1H) 2.12 (d, J=7.03 Hz, 1H) 2.02 (br. s., 1H) 1.71-1.85 (m, 8H) 1.49-1.57 (m, 2H) 1.45 (d, J=11.55 Hz, 2H).

Example 231

Preparation of 3-(4-(1H-pyrazol-4-yl)phenyl)-8-((4,4-difluorocyclohexyl)methyl)-1-(3-methoxybenzyl)-1,3,8-triazaspiro[4.5]decan-2-one

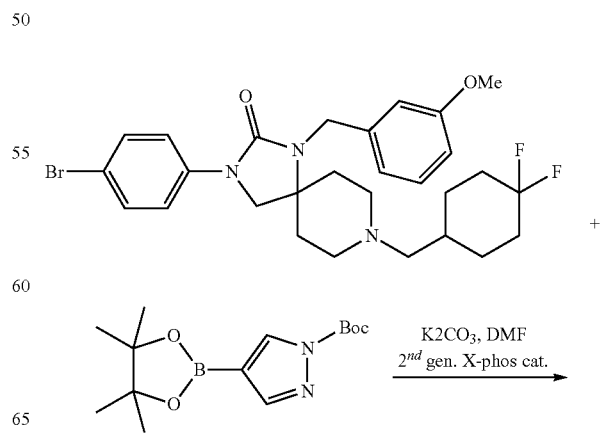

209
-continued

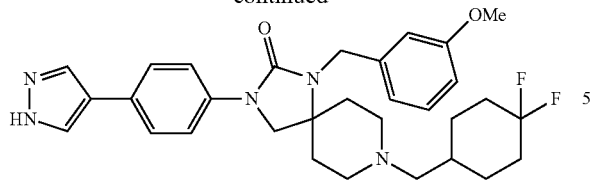

To a solution of 3-(4-bromophenyl)-8-((4,4-difluorocyclohexyl)methyl)-1-(3-methoxybenzyl)-1,3,8-triazaspiro[4.5]decan-2-one (15 mg, 0.027 mmol) in DMF (2 mL), were added tert-butyl 4-(4,4,5,5-tetramethyl-1,3,2-dioxaborolan-2-yl)-1H-pyrazole-1-carboxylate (11.0 mg, 0.037 mmol), K$_2$CO$_3$ (11 mg, 0.080 mmol) and Water (0.4 mL). The reaction mixture was purged with nitrogen for 5 min and charged with 2$^{nd}$ generation XPHOS precatalyst (1.3 mg, 1.6 μmol). The reaction mixture was again purged with nitrogen for 3 min and heated at 90° C. overnight. The reaction mixture was cooled to rt and filtered. The filtrate was concentrated and the residue was purified by preparative HPLC to afford 3-(4-(1H-pyrazol-4-yl)phenyl)-8-((4,4-difluorocyclohexyl)methyl)-1-(3-methoxybenzyl)-1,3,8-triazaspiro[4.5]decan-2-one as a pale yellow solid (2.0 mg, 14% yield). MS(ESI) m/z: 550.1 (M+H)$^+$; $^1$H NMR (400 MHz, DMSO-d$_6$) δ ppm 12.86 (br. s., 1H) 8.13 (br. s., 1H) 7.89 (br. s., 1H) 7.63 (d, J=8.80 Hz, 2H) 7.57 (d, J=8.80 Hz, 2H) 7.24 (t, J=7.95 Hz, 1H) 6.88-6.95 (m, 2H) 6.81 (d, J=9.05 Hz, 1H) 4.39 (s, 2H) 3.76 (s, 2H) 3.74 (s, 3H) 2.78 (d, J=9.78 Hz, 2H) 2.14 (d, J=6.85 Hz, 2H) 2.03 (d, J=12.23 Hz, 4H) 1.81 (br. s., 5H) 1.73 (br. s., 1H) 1.61 (br. s., 1H) 1.46 (d, J=11.98 Hz, 2H) 1.09 (d, J=10.76 Hz, 2H). $^{19}$F NMR (376 MHz, DMSO-d$_6$) δ ppm peaks at −88.717 and −98.986. LCMS RT=1.49 min, 100% (Method E), 2.32 min, 100% (Method F).

The following Examples in Table 13 were made by using the same procedure as shown in Example 231.

210

Example 234

3-(4-(1H-pyrazol-4-yl)phenyl)-1-(3-methoxybenzyl)-8-(methylsulfonyl)-1,3,8-triazaspiro[4.5]decan-2-one

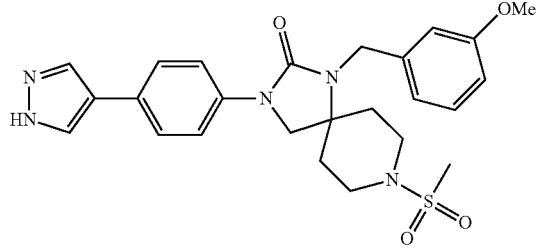 [SMILES: COc1cccc(CN2C(=O)N(c3ccc(-c4cn[nH]c4)cc3)CC23CCN(S(C)(=O)=O)CC3)c1]

Example 234a

Preparation of 3-(4-bromophenyl)-1-(3-methoxybenzyl)-8-(methylsulfonyl)-1,3,8-triazaspiro[4.5]decan-2-one

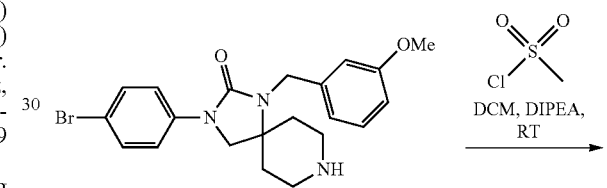

TABLE 13

| Example | R | Name | LCMS (M + H)+ | HPLC Method, RT (min.) & Purity | NMR |
|---|---|---|---|---|---|
| 232 | ![structure] | 3-(4-(1H-pyrazol-4-yl)phenyl)-8-(cyclobutylmethyl)-1-(3-methoxybenzyl)-1,3,8-triazaspiro[4.5]decan-2-one | 486.40 | E: 1.13 min, 100% F: 1.71 min, 100% | $^1$H NMR (400 MHz, DMSO-d6) δ ppm 12.90 (br. s, 1 H) 8.02 (br. s., 2 H) 7.57-7.65 (m, 4 H) 7.23-7.29 (m, 1 H) 6.87-6.95 (m, 2 H) 6.80-6.86 (m, 1 H) 4.37 (s, 2 H) 3.91 (s, 2 H) 3.74 (s, 3 H) 3.34 (s, 2 H), 3.12 (br. s., 4 H) 2.02-2.16 (m, 4 H) 1.90 (d, J = 8.07 Hz, 1 H) 1.70-1.85 (m, 5 H). |
| 233 | ![structure] | 3-(4-(1H-pyrazol-4-yl)phenyl)-1-(3-methoxybenzyl)-8-((tetrahydro-2H-pyran-4-yl)methyl)-1,3,8-triazaspiro[4.5]decan-2-one | 516.40 | E: 1.09 min, 98.0% F: 1.56 min, 97.8% | $^1$H NMR (400 MHz, DMSO-d6) δ ppm 12.85 (br. s., 1 H) 8.12 (br. s., 1 H) 7.88 (br. s., 1 H) 7.63 (d, J = 8.80 Hz, 2 H) 7.57 (d, J = 8.80 Hz, 2 H) 7.23 (t, J = 7.95 Hz, 1 H) 6.88-6.95 (m, 2 H) 6.80 (d, J = 9.54 Hz, 1 H) 4.39 (s, 2 H) 3.82 (d, J = 8.31 Hz, 2 H) 3.76 (s, 2 H) 3.74 (s, 3 H) 3.20-3.29 (m, 2 H) 2.77 (d, J = 12.72 Hz, 2 H) 2.14 (d, J = 7.83 Hz, 2 H) 2.05 (t, J = 11.98 Hz, 2 H) 1.83 (d, J = 11.25 Hz, 2 H) 1.71 (br. s., 1 H) 1.59 (d, J = 11.98 Hz, 2 H) 1.46 (d, J = 11.00 Hz, 2 H) 1.10 (d, J = 8.31 Hz, 2 H) |

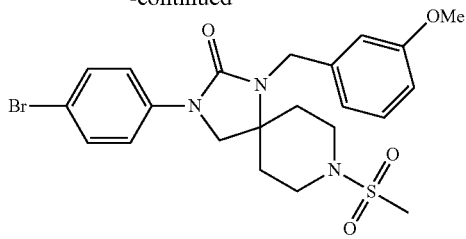

To a solution of 3-(4-bromophenyl)-1-(3-methoxybenzyl)-1,3,8-triazaspiro[4.5]decan-2-one (55 mg, 0.128 mmol) in DCM (4 mL) at 0° C., was added DIPEA (0.056 mL, 0.320 mmol). Methanesulfonyl chloride (0.015 mL, 0.192 mmol) was added dropwise. The reaction mixture was allowed to warm to rt and stir for 2.5 h. The reaction mixture was diluted with DCM, washed with sat. aq. NaHCO$_3$ and brine, dried over Na$_2$SO$_4$, filtered and concentrated to afford 3-(4-bromophenyl)-1-(3-methoxybenzyl)-8-(methylsulfonyl)-1,3,8-triazaspiro[4.5]decan-2-one as a brown gummy solid (65 mg, quant.). MS(ESI) m/z: 508.0 (M+H)$^+$; $^1$H NMR (300 MHz, DMSO-d$_6$) δ ppm 7.63 (d, J=9.07 Hz, 2H) 7.52 (d, J=9.07 Hz, 2H) 7.23 (t, J=8.12 Hz, 1H) 6.89-6.97 (m, 2H) 6.80 (d, J=9.07 Hz, 1H) 4.40 (s, 2H) 3.81 (s, 2H) 3.72 (s, 3H) 3.53 (d, J=11.71 Hz, 2H) 2.80-2.97 (m, 5H) 1.79-1.95 (m, 2H) 1.60 (d, J=13.22 Hz, 2H).

Example 234

Preparation of 3-(4-(1H-pyrazol-4-yl)phenyl)-1-(3-methoxybenzyl)-8-(methylsulfonyl)-1,3,8-triazaspiro[4.5]decan-2-one

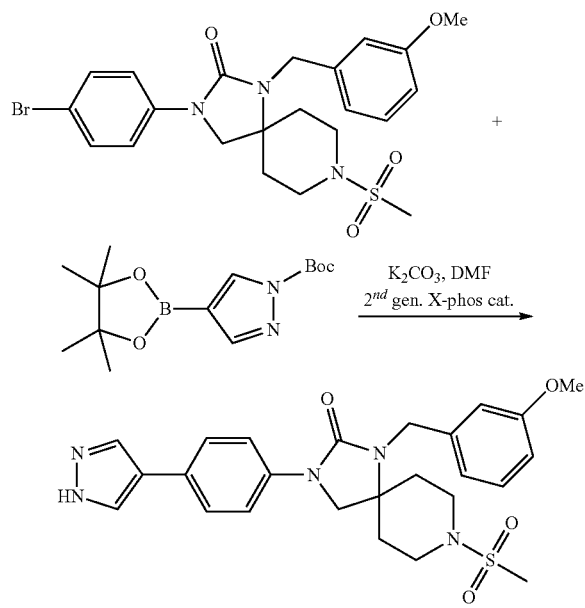

To a solution of 3-(4-bromophenyl)-1-(3-methoxybenzyl)-8-(methylsulfonyl)-1,3,8-triazaspiro[4.5]decan-2-one (65 mg, 0.128 mmol) in DMF (4 mL) were added tert-butyl 4-(4,4,5,5-tetramethyl-1,3,2-dioxaborolan-2-yl)-1H-pyrazole-1-carboxylate (52.6 mg, 0.179 mmol), K$_2$CO$_3$ (53.0 mg, 0.384 mmol) and Water (0.4 mL). The reaction mixture was purged with nitrogen for 5 min and charged with 2$^{nd}$ generation XPHOS precatalyst (6.0 mg, 7.7 μmol). The reaction mixture was again purged with nitrogen for 3 min and heated at 90° C. overnight. The reaction mixture was cooled to rt, filtered and concentrated. The residue was purified by preparative HPLC to afford 3-(4-(1H-pyrazol-4-yl)phenyl)-1-(3-methoxybenzyl)-8-(methylsulfonyl)-1,3,8-triazaspiro[4.5]decan-2-one as a pale yellow solid (14.0 mg, 22% yield). MS(ESI) m/z: 496.2 (M+H)$^+$; $^1$H NMR (400 MHz, DMSO-d$_6$) δ ppm 12.87 (br. s., 1H) 8.13 (br. s., 1H) 7.88 (br. s., 1H) 7.60 (q, J=9.05 Hz, 4H) 7.23 (t, J=8.07 Hz, 1H) 6.86-6.98 (m, 2H) 6.75-6.85 (m, 1H) 4.40 (s, 2H) 3.83 (s, 2H) 3.73 (s, 3H) 3.53 (d, J=12.23 Hz, 2H) 2.90-2.97 (m, 2H) 2.89 (s, 3H) 1.83-1.95 (m, 2H) 1.61 (d, J=12.72 Hz, 2H). LCMS RT=1.58 min, 100% (Method E), 1.51 min, 100% (Method F).

Example 235

3-(4-(1H-pyrazol-4-yl)phenyl)-1-(3-methoxybenzyl)-8-(oxetan-3-yl)-1,3,8-triazaspiro[4.5]decan-2-one

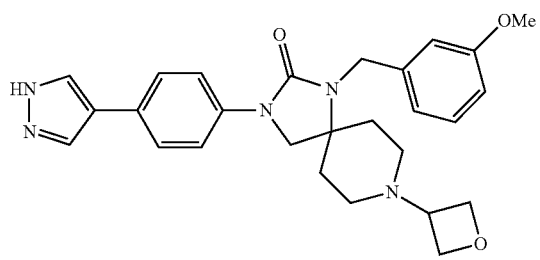 [SMILES: COc1cccc(CN2C(=O)N(c3ccc(-c4cn[nH]c4)cc3)CC23CCN(C2COC2)CC3)c1]

Example 235a

Preparation of 3-(4-bromophenyl)-1-(3-methoxybenzyl)-8-(oxetan-3-yl)-1,3,8-triazaspiro[4.5]decan-2-one

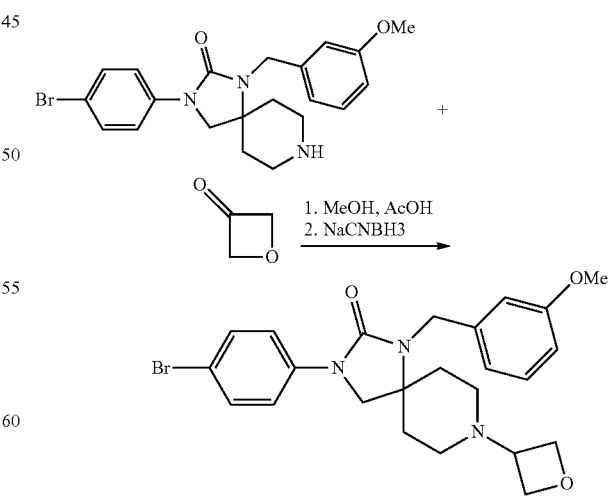

To a solution of 3-(4-bromophenyl)-1-(3-methoxybenzyl)-1,3,8-triazaspiro[4.5]decan-2-one (20 mg, 0.046 mmol) in methanol (1.5 mL) and acetic acid (0.4 mL), was added oxetan-3-one (16.7 mg, 0.232 mmol). The reaction mixture was stirred at rt overnight. The reaction mixture was cooled to 0° C., then sodium cyanoborohydride (8.8 mg, 0.14 mmol) was added. The reaction mixture was stirred at rt for 4 h, then was quenched with sat. solution of NaHCO$_3$ and extracted with ethyl acetate (2×). The combined ethyl acetate layers were washed with brine, dried over Na$_2$SO$_4$, filtered and concentrated to afford 3-(4-bromophenyl)-1-(3-methoxybenzyl)-8-(oxetan-3-yl)-1,3,8-triazaspiro[4.5]decan-2-one as a yellow gummy residue (18 mg, 80% yield). MS(ESI) m/z: 486.2 (M+H)$^+$; $^1$H NMR (400 MHz, DMSO-d$_6$) δ ppm 7.61-7.68 (m, 2H) 7.48-7.54 (m, 2H) 7.23 (t, J=8.28 Hz, 1H) 6.90-6.96 (m, 2H) 6.80 (dd, J=7.28, 1.76 Hz, 1H) 4.58 (s, 2H) 4.56 (s, 2H) 4.37-4.44 (m, 4H) 3.77-3.69 (m, 4H) 3.37-3.44 (m, 2H) 1.89-1.98 (m, 2H) 1.78-1.88 (m, 2H) 1.47 (d, J=12.55 Hz, 2H).

Example 235

Preparation of 3-(4-(1H-pyrazol-4-yl)phenyl)-1-(3-methoxybenzyl)-8-(oxetan-3-yl)-1,3,8-triazaspiro[4.5]decan-2-one

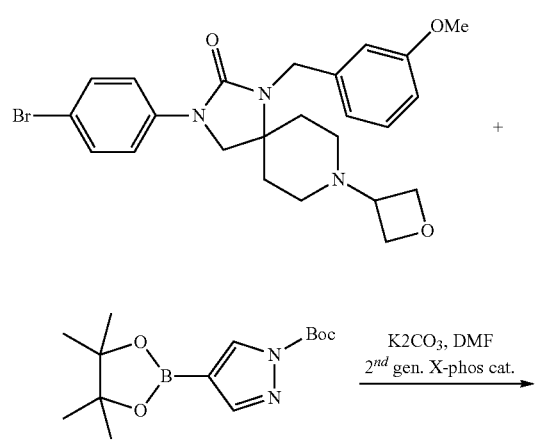

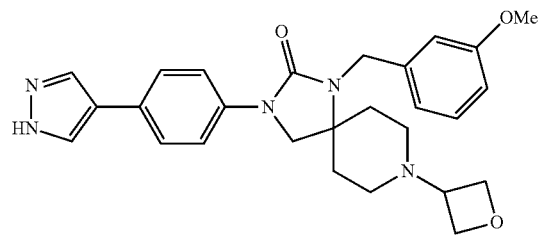

To a solution of 3-(4-bromophenyl)-1-(3-methoxybenzyl)-8-(oxetan-3-yl)-1,3,8-triazaspiro[4.5]decan-2-one (55 mg, 0.113 mmol) in DMF (1 mL), were added tert-butyl 4-(4,4,5,5-tetramethyl-1,3,2-dioxaborolan-2-yl)-1H-pyrazole-1-carboxylate (46.6 mg, 0.158 mmol), K$_2$CO$_3$ (46.9 mg, 0.339 mmol) and water (0.2 mL). The reaction mixture was purged with nitrogen for 5 min and charged with 2$^{nd}$ generation XPHOS precatalyst (5.34 mg, 6.8 μmol). The reaction mixture was again purged with nitrogen for 3 min and heated at 90° C. overnight. The reaction mixture was cooled to rt and filtered. The filtrate was purified via preparative HPLC to afford 3-(4-(1H-pyrazol-4-yl)phenyl)-1-(3-methoxybenzyl)-8-(oxetan-3-yl)-1,3,8-triazaspiro[4.5]decan-2-one as a pale yellow solid (2.1 mg, 4% yield). MS(ESI) m/z: 474.2 (M+H)$^+$; $^1$H NMR (400 MHz, DMSO-d$_6$) δ ppm 12.86 (br. s., 1H) 8.13 (br. s., 1H) 7.88 (br. s., 1H) 7.63 (d, J=8.80 Hz, 2H) 7.57 (d, J=9.05 Hz, 2H) 7.24 (t, J=8.19 Hz, 1H) 6.90-6.98 (m, 2H) 6.81 (d, J=9.54 Hz, 1H) 4.52 (t, J=6.60 Hz, 2H) 4.36-4.45 (m, 4H) 3.75 (s, 2H) 3.74 (s, 3H) 3.43 (d, J=6.36 Hz, 1H) 2.68 (d, J=1.71 Hz, 2H) 1.91-2.01 (m, 2H) 1.78-1.90 (m, 2H) 1.49 (d, J=12.23 Hz, 2H). LCMS RT=1.12 min, 100% (Method E), 1.53 min, 93.0% (Method F).

The following Examples in Table 14 were made by using the same procedure as shown in Example 235.

TABLE 14

| Example | R | Name | LCMS (M + H)+ | HPLC Method, RT (min.) & Purity | NMR |
|---|---|---|---|---|---|
| 236 | ![structure] | 3-(4-(1H-pyrazol-4-yl)phenyl)-1-(3-fluoro-5-methoxybenzyl)-8-(oxetan-3-yl)-1,3,8-triazaspiro[4.5]decan-2-one | 492.2 | E: 1.23 min, 98.6% F: 1.61 min, 97.6% | $^1$H NMR (400 MHz, DMSO-d6) δ ppm 12.86 (br. s., 1 H) 8.13 (s, 1 H) 7.88 (s, 1 H) 7.63 (d, J = 8.80 Hz, 2 H) 7.57 (d, J = 9.05 Hz, 2 H) 6.73-6.82 (m, 2 H) 6.64-6.72 (m, 1 H) 4.53 (t, J = 6.60 Hz, 2 H) 4.38-4.44 (m, 4 H) 3.77 (s, 2 H) 3.76 (s, 3 H) 3.42 (t, J = 6.24 Hz, 1 H) 2.63-2.72 (m, 2 H) 1.91-2.01 (m, 2 H) 1.79-1.89 (m, 2 H) 1.51 (d, J = 12.23 Hz, 2 H); $^{19}$F NMR (376 MHz, DMSO-d6) δ131 ppm −111.888 |

TABLE 14-continued

| Example | R | Name | LCMS (M + H)+ | HPLC Method, RT (min.) & Purity | NMR |
|---|---|---|---|---|---|
| 237 | | 3-(5-(1H-pyrazol-4-yl)pyridin-2-yl)-1-(3-methoxybenzyl)-8-(oxetan-3-yl)-1,3,8-triazaspiro[4.5]decan-2-one | 475.2 | E: 1.03 min, 100% F: 1.47 min, 97.0% | $^1$H NMR (400 MHz, DMSO-d6) δ ppm 12.98 (br. s., 1 H) 8.58 (d, J = 1.71 Hz, 1 H) 8.16-8.27 (m, 2 H) 7.90-8.02 (m, 2 H) 7.24 (t, J = 8.07 Hz, 1 H) 6.92-6.98 (m, 2 H) 6.77-6.83 (m, 1 H) 4.48-4.55 (m, 2 H) 4.35-4.47 (m, 4 H) 3.90 (s, 2 H) 3.74 (s, 3 H) 3.42 (quin, J = 6.30 Hz, 1 H) 2.68 (d, J = 6.85 Hz, 2 H) 1.78-1.95 (m, 4 H) 1.44-1.54 (m, 2 H) |
| 238 | | 3-(6-methoxy-5-(1H-pyrazol-4-yl)pyridin-2-yl)-1-(3-methoxybenzyl)-8-(oxetan-3-yl)-1,3,8-triazaspiro[4.5]decan-2-one | 505.2 | E: 1.17 min, 100% F: 1.68 min, 100% | $^1$H NMR (400 MHz, DMSO-d6) δ ppm 12.87 (br. s., 1 H), 8.09 (br. s., 1 H), 7.99 (d, J = 8.3 Hz, 1 H), 7.95 (br. s., 1 H), 7.76 (d, J = 8.3 Hz, 1 H), 7.24 (t, J = 8.1 Hz, 1 H), 6.97-6.91 (m, 2 H), 6.84-6.77 (m, 1 H), 4.51 (t, J = 6.4 Hz, 2 H), 4.46-4.35 (m, 4 H), 4.00 (s, 3 H), 3.94 (s, 2 H), 3.73 (s, 3 H), 3.46-3.37 (m, 1 H), 2.74-2.67 (m, 2 H), 1.94-1.79 (m, 4 H), 1.54-1.43 (m, 2 H) |
| 239 | | 1-(3-fluoro-2-methylbenzyl)-3-(6-methoxy-5-(1H-pyrazol-4-yl)pyridin-2-yl)-8-(oxetan-3-yl)-1,3,8-triazaspiro[4.5]decan-2-one | 507.2 | E: 1.35 min, 100% F: 1.83 min, 100% | $^1$H NMR (400 MHz, DMSO-d6) δ ppm 12.87 (br. s., 1 H), 8.09 (br. s., 1 H), 7.78 (d, J = 8.4 Hz, 1 H), 7.94 (br. s., 1 H), 7.73 (d, J = 8.3 Hz, 1 H), 7.21-7.14 (m, 1 H), 7.13-7.08 (m, 1 H), 7.03 (t, J = 9.0 Hz, 1 H), 4.51 (t, J = 6.5 Hz, 2 H), 4.44 (s, 2 H), 4.38 (t, J = 6.1 Hz, 2 H), 4.03-3.99 (m, 5 H), 3.47-3.38 (m, 1 H), 2.72-2.64 (m, 2 H), 2.26 (s, 3 H), 1.96-1.77 (m, 4 H), 1.64-1.55 (m, 2 H); $^{19}$F NMR (376 MHz, DMSO-d6) δ ppm −118.39 |

Example 240 tert-butyl 6-(4-(1H-pyrazol-4-yl)phenyl)-8-((3-methoxyphenyl)amino)-7-oxo-2,6-diazaspiro[3.4]octane-2-carboxylate

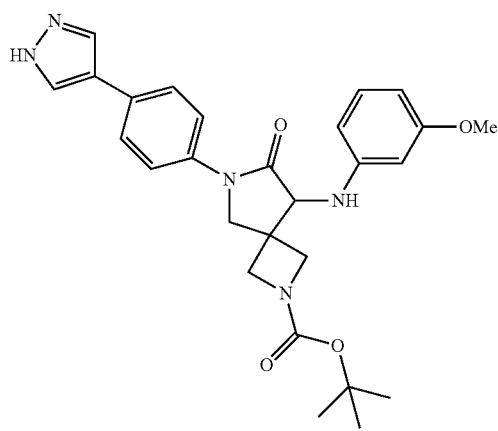 [SMILES: COc1cccc(NC2C(=O)N(c3ccc(-c4cn[nH]c4)cc3)CC23CN(C(=O)OC(C)(C)C)C3)c1]

Example 240a

Preparation of tert-butyl 6-(4-bromophenyl)-8-((3-methoxyphenyl)amino)-7-oxo-2,6-diazaspiro[3.4]octane-2-carboxylate

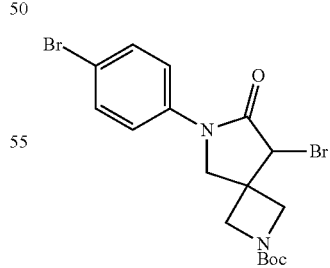

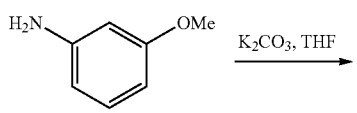

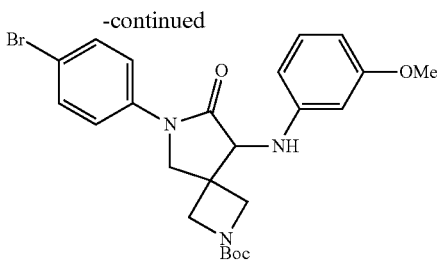

To a solution of tert-butyl 8-bromo-6-(4-bromophenyl)-7-oxo-2,6-diazaspiro[3.4]octane-2-carboxylate (100 mg, 0.217 mmol) and 3-methoxyaniline (0.073 mL, 0.652 mmol) in THF (3 mL) and water (0.5 mL), was added potassium carbonate (90 mg, 0.65 mmol). The reaction mixture was heated at 90° C. overnight. The solvent was concentrated, then the residue was dissolved in ethyl acetate (20 mL). The organic layer was washed with 1.5N HCl, water and brine, dried over $Na_2SO_4$ and concentrated. The crude compound was purified by flash chromatography (20% EtOAc/pet. ether) to afford tert-butyl 6-(4-bromophenyl)-8-((3-methoxyphenyl)amino)-7-oxo-2,6-diazaspiro[3.4]octane-2-carboxylate (25 mg, 23% yield) as a yellow thick gum. MS(ESI) m/z: 503.3 (M+H)+.

Example 240a (tert-butyl 6-(4-bromophenyl)-8-((3-methoxyphenyl)amino)-7-oxo-2,6-diazaspiro[3.4]octane-2-carboxylate) was Also Prepared by Following Procedure To a solution of 3-methoxyaniline (0.488 mL, 4.35 mmol) in THF (3 mL) at −78° C. was added dropwise 1M lithium bis(trimethylsilyl)amide (2.61 mL, 2.61 mmol). The reaction was allowed to come to at rt. After 30 min, the reaction mixture was again cooled to −78° C., then tert-butyl 8-bromo-6-(4-bromophenyl)-7-oxo-2,6-diazaspiro[3.4]octane-2-carboxylate (200 mg, 0.435 mmol) in THF (1 mL) was added dropwise. The reaction was stirred overnight at rt. The reaction was quenched with satd. aq. $NH_4Cl$. The layers were separated and the aqueous layer was extracted with EtOAc (2×15 mL). The combined organic extracts were washed with water and brine, dried over $Na_2SO_4$ and concentrated. The product was purified by flash chromatography (gradient elution, 0-90% EtOAc/petroleum ether) to afford tert-butyl 6-(4-bromophenyl)-8-((3-methoxyphenyl)amino)-7-oxo-2,6-diazaspiro[3.4]octane-2-carboxylate (105 mg, 48% yield) as a dark yellow gummy solid. MS(ESI) m/z: 503.3 (M+H)+.

Example 240

Preparation of tert-butyl 6-(4-(1H-pyrazol-4-yl)phenyl)-8-((3-methoxyphenyl)amino)-7-oxo-2,6-diazaspiro[3.4]octane-2-carboxylate

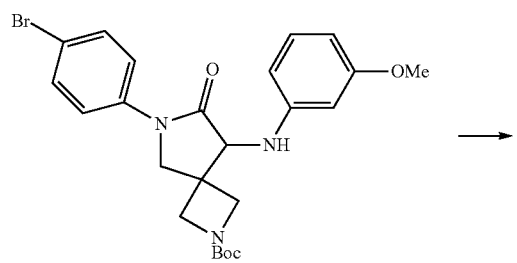

→

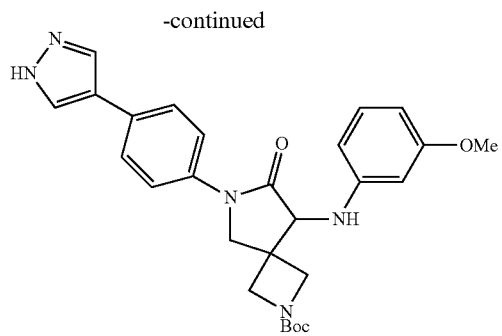

To a solution of tert-butyl 6-(4-bromophenyl)-8-((3-methoxyphenyl)amino)-7-oxo-2,6-diazaspiro[3.4]octane-2-carboxylate (25 mg, 0.050 mmol) in dioxane (1 mL), was added tert-butyl 4-(4,4,5,5-tetramethyl-1,3,2-dioxaborolan-2-yl)-1H-pyrazole-1-carboxylate (17.6 mg, 0.060 mmol), potassium phosphate tribasic (21.1 mg, 0.100 mmol) and water (0.2 mL). The reaction mixture was purged with nitrogen for 5 min. 2$^{nd}$ generation XPHOS precatalyst (2.3 mg, 3.0 μmol) was added to the reaction mixture and was again purged with nitrogen for 5 min. The reaction mixture was heated at 85° C. overnight. Reaction mixture was cooled to rt, diluted with EtOAc and washed with water and brine, dried over $Na_2SO_4$ and concentrated. The crude product was purified by preparative HPLC to afford tert-butyl 6-(4-(1H-pyrazol-4-yl)phenyl)-8-((3-methoxyphenyl)amino)-7-oxo-2,6-diazaspiro[3.4]octane-2-carboxylate (1.1 mg, 5% yield). MS(ESI) m/z: 490.3 (M+H)+; $^1$H NMR (400 MHz, DMSO-$d_6$) δ ppm 12.78 (s, 1H) 9.87 (s, 1H) 7.97 (br. s., 1H) 7.76 (br. s., 1H) 7.43 (m, J=8.56 Hz, 2H) 7.34 (s, 1H) 7.16-7.29 (m, 2H) 6.67 (d, J=8.07 Hz, 1H) 6.45 (m, J=8.56 Hz, 2H) 4.18 (q, J=5.14 Hz, 1H) 4.13 (s, 1H) 3.87 (d, J=6.85 Hz, 1H) 3.72 (s, 3H) 3.00 (br. s., 2H) 3.20 (m, 2H) 1.87 (d, J=13.94 Hz, 1H) 1.77 (br. s., 2H) 1.54 (d, J=9.29 Hz, 1H) 1.37 (s, 9H); HPLC RT=1.93 min, 98.4% (Method E), 1.93 min, 98.6% (Method F).

Example 241 tert-butyl 2-(4-methoxy-5-(1H-pyrazol-4-yl)pyrimidin-2-yl)-4-((3-methoxyphenyl)amino)-3-oxo-2,8-diazaspiro[4.5]decane-8-carboxylate

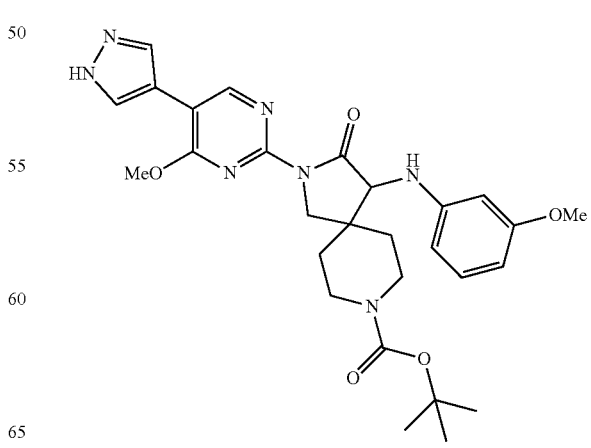

Example 241a

Preparation of afford tert-butyl 2-(5-bromo-4-methoxypyrimidin-2-yl)-4-((3-methoxyphenyl)amino)-3-oxo-2,8-diazaspiro[4.5]decane-8-carboxylate

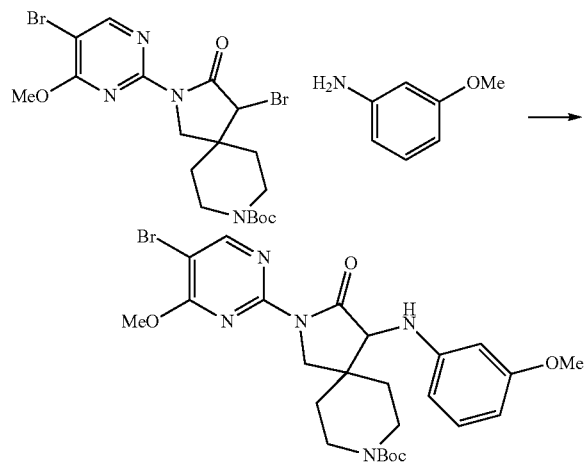

To a stirred solution of 3-methoxyaniline (592 mg, 4.81 mmol) in THF (10 mL) cooled at −78° C., was added 1M LiHMDS (2.40 mL, 2.40 mmol). The reaction was allowed to warm to rt and stir for 30 min. The reaction mixture was again cooled to −78° C. tert-butyl 4-bromo-2-(5-bromo-4-methoxypyrimidin-2-yl)-3-oxo-2,8-diazaspiro[4.5]decane-8-carboxylate (250 mg, 0.481 mmol) in THF (2 mL) was added to the reaction mixture dropwise. The mixture was stirred at rt for 12 h, then was quenched with saturated ammonium chloride solution (100 mL) and extracted with ethyl acetate (50 mL). The organic layer was dried over sodium sulphate and concentrated. The residue was purified by flash chromatography (EtOAc/pet. ether, 1:3) to afford tert-butyl 2-(5-bromo-4-methoxypyrimidin-2-yl)-4-((3-methoxyphenyl)amino)-3-oxo-2,8-diazaspiro[4.5]decane-8-carboxylate (100 mg, 37% yield) as brown semisolid. MS (ESI) m/z: 562.1 (M+H)$^+$.

Example 241

Preparation of tert-butyl 2-(4-methoxy-5-(1H-pyrazol-4-yl)pyrimidin-2-yl)-4-((3-methoxyphenyl)amino)-3-oxo-2,8-diazaspiro[4.5]decane-8-carboxylate

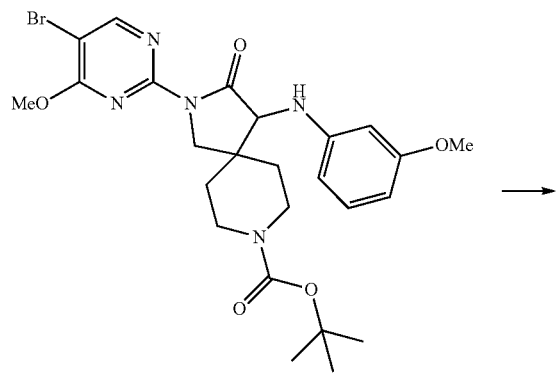

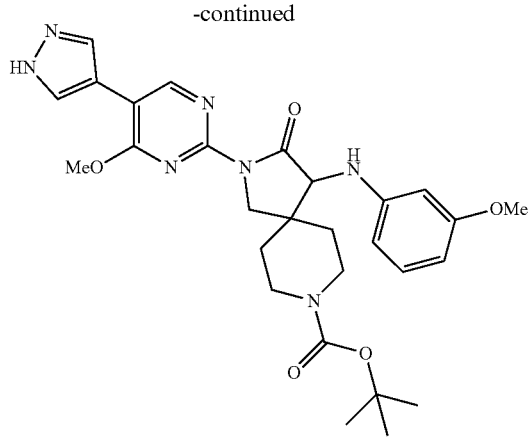

To a solution of tert-butyl 2-(5-bromo-4-methoxypyrimidin-2-yl)-4-((3-methoxyphenyl)amino)-3-oxo-2,8-diazaspiro[4.5]decane-8-carboxylate (30 mg, 0.053 mmol), tert-butyl 4-(4,4,5,5-tetramethyl-1,3,2-dioxaborolan-2-yl)-1H-pyrazole-1-carboxylate (15.7 mg, 0.053 mmol) and K$_2$CO$_3$ (22.1 mg, 0.160 mmol) in a mixture of DMF (1 mL) and water (0.1 mL), was added 2$^{nd}$ generation XPHOS precatalyst (4.2 mg, 5.3 μmol). The reaction mixture was heated to 95° C. for 6 h. The reaction mixture was cooled to rt and diluted with ethyl acetate (10 mL). The black suspension was filtered through celite. The filtrate was concentrated and the residue was purified by preparative HPLC to afford tert-butyl 2-(4-methoxy-5-(1H-pyrazol-4-yl)pyrimidin-2-yl)-4-((3-methoxyphenyl)amino)-3-oxo-2,8-diazaspiro[4.5]decane-8-carboxylate (17.5 mg, 60% yield). MS(ESI) m/z: 550.3 (M+H)$^+$; $^1$H NMR (400 MHz, DMSO-d$_6$) δ ppm 12.68 (br. s, 1H) 9.97 (s, 1H) 8.46 (s, 1H) 7.93 (br. s., 2H) 7.33 (s, 1H) 7.18-7.25 (m, 2H) 6.66 (dt, J=6.85, 2.45 Hz, 1H) 4.50 (s, 1H) 3.81-3.94 (m, 5H) 3.66-3.74 (m, 4H) 3.54 (d, J=12.96 Hz, 1H) 3.00-3.18 (m, 2H) 1.72-1.91 (m, 3H) 1.58 (br. s., 1H) 1.39 (s, 9H). HPLC RT=1.66 min, 100% (Method E), 2.00 min, 99.5% (Method F).

Example 243

2-(4-methoxy-5-(1H-pyrazol-4-yl)pyrimidin-2-yl)-4-((3-methoxyphenyl)amino)-8-(pyrazolo[1,5-a]pyridine-3-carbonyl)-2,8-diazaspiro[4.5]decan-3-one

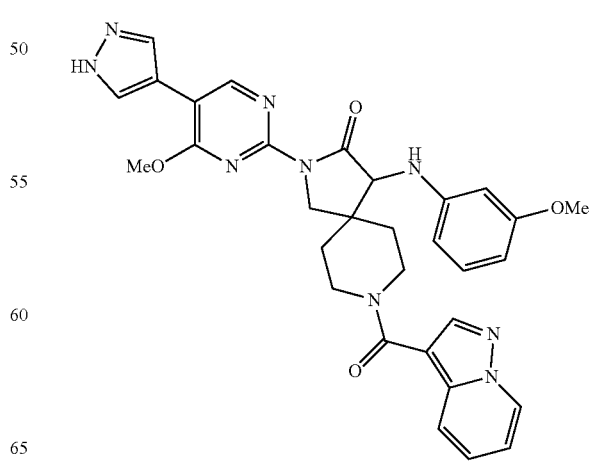

Example 243a

2-(5-bromo-4-methoxypyrimidin-2-yl)-4-((3-methoxyphenyl)amino)-2,8-diazaspiro[4.5]decan-3-one

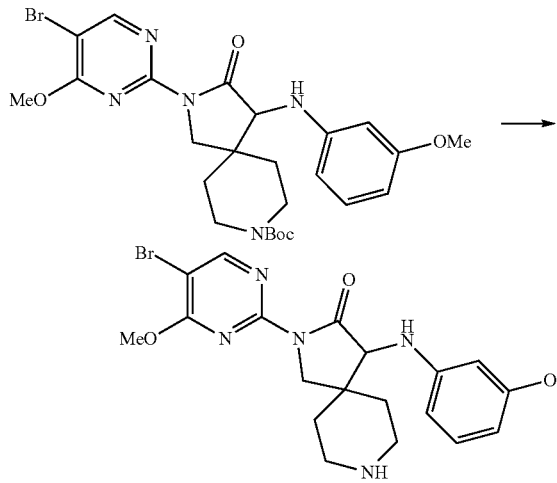

To a solution of tert-butyl 2-(5-bromo-4-methoxypyrimidin-2-yl)-4-((3-methoxyphenyl)amino)-3-oxo-2,8-diazaspiro[4.5]decane-8-carboxylate (130 mg, 0.231 mmol) in DCM (2 mL) cooled at 0° C., was added TFA (0.178 mL, 2.31 mmol). The reaction mixture was stirred at rt for 4 h. The reaction mixture was evaporated and the residue was taken in ethyl acetate (50 mL). The suspension was cooled to 10° C. and basified with saturated sodium carbonate solution (50 mL) and extracted with ethyl acetate (50 mL). The organic layer was separated, dried over sodium sulphate and concentrated to afford 2-(5-bromo-4-methoxypyrimidin-2-yl)-4-((3-methoxyphenyl)amino)-2,8-diazaspiro[4.5]decan-3-one (100 mg, 94% yield) as yellow solid. MS (ESI) m/z: 462.2 (M+H)$^+$.

Example 243b

Preparation of 2-(5-bromo-4-methoxypyrimidin-2-yl)-4-((3-methoxyphenyl)amino)-8-(pyrazolo[1,5-a]pyridine-3-carbonyl)-2,8-diazaspiro[4.5]decan-3-one

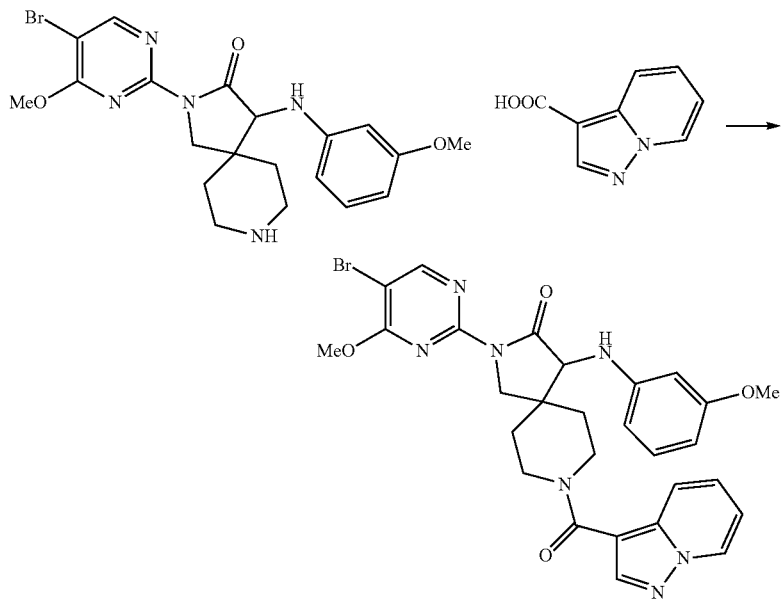

To a solution of 2-(5-bromo-4-methoxypyrimidin-2-yl)-4-((3-methoxyphenyl)amino)-2,8-diazaspiro[4.5]decan-3-one (50 mg, 0.108 mmol), pyrazolo[1,5-a]pyridine-3-carboxylic acid (17.5 mg, 0.108 mmol) and HATU (41.1 mg, 0.108 mmol) in DMF (2 mL), DIPEA (0.057 mL, 0.32 mmol) was added dropwise for 5 min. The reaction mixture was stirred at rt for 12 h. The reaction mixture was partitioned between water (20 mL) and ethyl acetate (25 mL). The organic layer was dried over sodium sulphate and concentrated to afford 2-(5-bromo-4-methoxypyrimidin-2-yl)-4-((3-methoxyphenyl)amino)-8-(pyrazolo[1,5-a]pyridine-3-carbonyl)-2,8-diazaspiro[4.5]decan-3-one as yellow semisolid. MS (ESI) m/z: 606.2 (M+H)$^+$.

Example 243

Preparation of 2-(4-methoxy-5-(1H-pyrazol-4-yl)pyrimidin-2-yl)-4-((3-methoxyphenyl)amino)-8-(pyrazolo[1,5-a]pyridine-3-carbonyl)-2,8-diazaspiro[4.5]decan-3-one

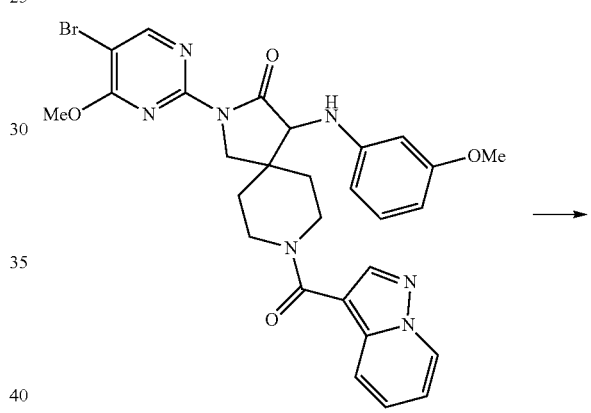

-continued

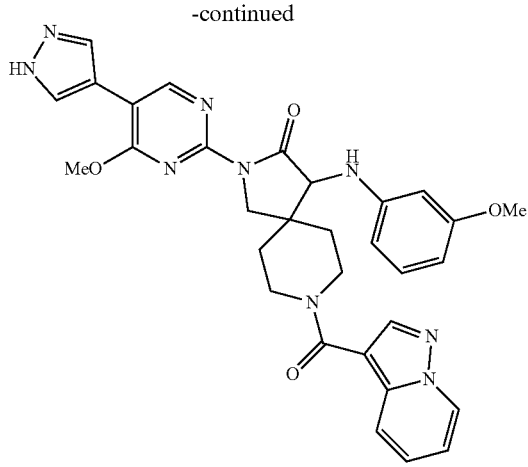

To a solution of 2-(5-bromo-4-methoxypyrimidin-2-yl)-4-((3-methoxyphenyl)amino)-8-(pyrazolo[1,5-a]pyridine-3-carbonyl)-2,8-diazaspiro[4.5]decan-3-one (25 mg, 0.041 mmol), tert-butyl 4-(4,4,5,5-tetramethyl-1,3,2-dioxaborolan-2-yl)-1H-pyrazole-1-carboxylate (12.1 mg, 0.041 mmol) and K$_2$CO$_3$ (17.1 mg, 0.124 mmol) in DMF (1 mL) and water (0.1 mL), was added 2$^{nd}$ generation XPHOS precatalyst (3.2 mg, 4.1 µmol). The reaction mixture was heated to 90° C. for 8 h. The reaction mixture was cooled to rt and diluted with ethyl acetate (10 mL). The black suspension was filtered through celite and the filtrate was concentrated. The residue was purified by preparative HPLC to afford 2-(4-methoxy-5-(1H-pyrazol-4-yl)pyrimidin-2-yl)-4-((3-methoxyphenyl)amino)-8-(pyrazolo[1,5-a]pyridine-3-carbonyl)-2,8-diazaspiro[4.5]decan-3-one (0.7 mg, 3% yield). MS(ESI) m/z: 594.3 (M+H)$^+$; $^1$H NMR (400 MHz, DMSO-d$_6$) δ ppm 12.94 (bs, 1H) 10.01 (s, 1H) 8.77 (d, J=7.09 Hz, 1H) 8.47 (s, 1H) 8.25 (s, 1H) 7.84-8.07 (m, 3H) 7.40-7.46 (m, 1H) 7.34 (s, 1H) 7.18-7.26 (m, 2H) 7.05 (td, J=6.85, 1.22 Hz, 1H) 6.65 (dt, J=7.52, 1.99 Hz, 1H) 4.55 (s, 1H) 3.85-4.07 (m, 7H) 3.44 (br. s., 1H) 1.86-2.04 (m, 3H) 1.69-1.79 (m, 1H). HPLC RT=1.33 min, 96.7% (Method E), 1.54 min, 95.4% (Method F).

The following Examples in Table 15 were made by using the same procedure as shown in Example 243.

TABLE 15

| Example | R | Name | LCMS (M+H)+ | HPLC Method, RT (min.) & Purity | NMR |
|---|---|---|---|---|---|
| 244 | | 6-(4-(1H-pyrazol-4-yl)phenyl)-2-acetyl-8-((3-methoxyphenyl)amino)-2,6-diazaspiro[3.4]octan-7-one | 432.2 | F: 1.13 min, 99.1% | $^1$H NMR (400 MHz, DMSO-d6) d ppm 10.39 (s, 1 H) 8.14 (s, 2 H) 7.67-7.76 (m, 2 H) 7.64 (dt, J = 7.83, 2.20 Hz, 1 H) 7.52-7.59 (m, 1 H) 7.45-7.52 (m, 1 H) 6.95 (dd, J = 8.07, 1.96 Hz, 1 H) 6.67-6.80 (m, 2 H) 4.82 (d, J = 4.16 Hz, 1 H) 4.64 (d, J = 9.78 Hz, 1 H) 4.53-4.58 (m, 1 H) 4.44 (t, J = 7.46 Hz, 1 H) 4.33-4.40 (m, 1 H) 4.21-4.33 (m, 2 H) 4.19 (dd, J = 7.83, 2.93 Hz, 1 H) 4.07 (d, J = 10.52 Hz, 1 H) 3.97-4.03 (m, 3 H) 1.99 (d, J = 13.45 Hz, 3 H) |
| 245 | | 6-(4-(1H-pyrazol-4-yl)phenyl)-8-((3-methoxyphenyl)amino)-2-(oxetane-3-carbonyl)-2,6-diazaspiro[3.4]octan-7-one | 474.3 | E: 1.08 min, 97.8% | $^1$H NMR (400 MHz, DMSO-d6) d ppm 10.34 (d, J = 18.83 Hz, 1 H) 8.14 (s, 2 H) 7.65-7.74 (m, 2 H) 7.62 (q, J = 2.36 Hz, 1 H) 7.47-7.58 (m, 2 H) 6.89-6.98 (m, 1 H) 6.71 (dd, J = 8.56, 3.67 Hz, 2 H) 4.74-4.91 (m, 5 H) 4.53 (br. s., 1 H) 4.31-4.51 (m, 7 H) 4.07-4.23 (m, 7 H) 4.00 (s, 3 H) |

TABLE 15-continued

| Example | R | Name | LCMS (M + H)+ | HPLC Method, RT (min.) & Purity | NMR |
|---|---|---|---|---|---|
| 246 | | 6-(4-(1H-pyrazol-4-yl)phenyl)-2-(2-hydroxy-2-methylpropanoyl)-8-((3-methoxyphenyl)amino)-2,6-diazaspiro[3.4]octan-7-one | 476.3 | E: 1.12 min, 98.1% | $^1$H NMR (400 MHz, DMSO-d6) d ppm 10.33 (d, J = 13.20 Hz, 1 H) 8.14 (s, 2 H) 7.70 (d, J = 7.83 Hz, 2 H) 7.61-7.66 (m, 1 H) 7.53-7.58 (m, 1 H) 7.44-7.53 (m, 1 H) 6.95 (dt, J = 8.07, 1.22 Hz, 1 H) 6.71 (dd, J = 8.56, 3.91 Hz, 2 H) 4.91 (d, J = 10.76 Hz, 1 H) 4.71-4.85 (m, 3 H) 4.66 (d, J = 10.52 Hz, 1 H) 4.40-4.46 (m, 2 H) 4.39 (s, 1 H) 4.31 (s, 1 H) 4.22-4.29 (m, 1 H) 4.18 (d, J = 8.07 Hz, 2 H) 4.09 (d, J = 10.76 Hz, 1 H) 4.00 (s, 3 H) 1.48 (d, J = 3.91 Hz, 5 H) 1.41 (s, 2 H) |
| 247 | | 6-(4-(1H-pyrazol-4-yl)phenyl)-2-(2,2-difluoroethyl)-8-((3-methoxyphenyl)amino)-2,6-diazaspiro[3.4]octan-7-one | 454.3 | E: 1.460 min, 97.3% | $^1$H NMR (400 MHz, DMSO-d6) d ppm 10.29 (s, 1 H) 8.07-8.19 (m, 2 H) 7.59-7.75 (m, 3 H) 7.53-7.58 (m, 1 H) 7.44-7.53 (m, 1 H) 6.94 (ddd, J = 8.19, 2.57, 0.98 Hz, 1 H) 6.69 (d, J = 8.56 Hz, 2 H) 6.19 (t, J = 4.16 Hz, 1 H) 6.05 (t, J = 4.03 Hz, 1 H) 4.68 (s, 2 H) 4.43 (s, 1 H) 4.13 (d, J = 7.34 Hz, 1 H) 4.00 (s, 3 H) 3.68-3.78 (m, 3 H) 3.49 (d, J = 8.07 Hz, 1 H) 2.97-3.09 (m, 2 H) |
| 248 | | methyl 6-(4-(1H-pyrazol-4-yl)phenyl)-8-((3-methoxyphenyl)amino)-7-oxo-2,6-diazaspiro[3.4]octane-2-carboxylate | 448.2 | E: 1.32 min, 98.3% | $^1$H NMR (400 MHz, DMSO-d6) d ppm 10.33 (s, 1 H) 8.14 (s, 2 H) 7.66-7.74 (m, 2 H) 7.63 (t, J = 2.08 Hz, 1 H) 7.52-7.58 (m, 1 H) 7.46-7.52 (m, 1 H) 6.95 (ddd, J = 7.95, 2.57, 1.22 Hz, 1 H) 6.67-6.75 (m, 2 H) 4.81 (s, 1 H) 4.40-4.49 (m, 2 H) 4.28-4.40 (m, 2 H) 4.08-4.20 (m, 3 H) 3.96-4.03 (m, 4 H) 3.76-3.81 (m, 3 H) |

TABLE 15-continued

| Example | R | Name | LCMS (M + H)+ | HPLC Method, RT (min.) & Purity | NMR |
|---|---|---|---|---|---|
| 249 | | -(4-(1H-pyrazol-4-yl)phenyl)-8-acetyl-4-((3-methoxyphenyl)amino)-2,8-diazaspiro[4.5]decan-3-one | 460.3 | E: 1.315 min, 98.30% | $^1$H NMR (400 MHz, DMSO-d6) d ppm 10.13 (d, J = 9.05 Hz, 1 H) 8.25 (br. s., 1 H) 8.03 (br. s., 1 H) 7.70 (d, J = 8.31 Hz, 2 H) 7.59-7.66 (m, 1 H) 7.55 (t, J = 8.19 Hz, 1 H) 7.47 (t, J = 7.95 Hz, 1 H) 6.93 (ddd, J = 8.13, 2.51, 0.86 Hz, 1 H) 6.67-6.77 (m, 2 H) 4.41 (d, J = 2.45 Hz, 1 H) 4.25 (d, J = 13.94 Hz, 1 H) 4.10-4.19 (m, 2 H) 3.99 (s, 3 H) 3.83-3.95 (m, 1 H) 3.78-3.83 (m, 1 H) 3.45-3.51 (m, 1 H) 3.13-3.27 (m, 1 H) 2.16-2.28 (m, 4 H) 2.07-2.15 (m, 1 H) 1.85-2.07 (m, 2 H) |
| 250 | | 2-(4-(1H-pyrazol-4-yl)phenyl)-8-(2-hydroxyacetyl)-4-((3-methoxyphenyl)amino)-2,8-diazaspiro[4.5]decan-3-one | 476.3 | E: 1.32 min, 98.3% | $^1$H NMR (400 MHz, DMSO-d6) d ppm 10.13 (s, 1 H) 8.25 (br. s., 1 H) 8.04 (br. s., 1 H) 7.65-7.73 (m, 2 H) 7.63 (br. s., 1 H) 7.54 (br. s., 1 H) 7.42-7.51 (m, 1 H) 6.93 (ddd, J = 8.25, 2.51, 0.98 Hz, 1 H) 6.71 (m, J = 8.80 Hz, 2 H) 4.67-4.81 (m, 1 H) 4.42 (s, 1 H) 4.20-4.38 (m, 3 H) 4.15 (d, J = 6.85 Hz, 1 H) 3.99 (s, 3 H) 3.82 (d, J = 7.09 Hz, 2 H) 3.57 (s, 9 H) 3.32-3.44 (m, 1 H) 3.28 (d, J = 10.76 Hz, 1 H) 2.17 (br. s., 1 H) 2.10 (br. s., 1 H) 1.88-2.08 (m, 2 H) |
| 251 | | methyl 2-(4-(1H-pyrazol-4-yl)phenyl)-4-((3-methoxyphenyl)amino)-3-oxo-2,8-diazaspiro[4.5]decane-8-carboxylate | 476.3 | E: 1.32 min, 98.3% | $^1$H NMR (400 MHz, DMSO-d6) d ppm 10.12 (s, 1 H) 8.25 (br. s., 1 H) 8.03 (br. s., 1 H) 7.70 (d, J = 8.56 Hz, 2 H) 7.62 (t, J = 2.20 Hz, 1 H) 7.50-7.57 (m, 1 H) 7.42-7.50 (m, 1 H) 6.93 (ddd, J = 8.07, 2.45, 0.98 Hz, 1 H) 6.71 (d, J = 8.56 Hz, 2 H) 4.41 (s, 1 H) 4.13 (d, J = 6.85 Hz, 1 H) 3.86-4.04 (m, 6 H) 3.81-3.86 (m, 3 H) 3.80 (d, J = 6.85 Hz, 1 H) 3.57 (s, 11 H) 3.34 (br. s., 2 H) 1.96-2.20 (m, 3 H) 1.79-1.89 (m, 1 H) |

TABLE 15-continued

| Example | R | Name | LCMS (M + H)+ | HPLC Method, RT (min.) & Purity | NMR |
|---|---|---|---|---|---|
| 252 | | 2-(4-(1H-pyrazol-4-yl)phenyl)-8-(2-hydroxyethyl)-4-((3-methoxyphenyl)amino)-2,8-diazaspiro[4.5]decan-3-one | 462.3 | F: 1.00 min, 96.8% | ¹H NMR (400 MHz, DMSO-d6) d ppm 9.37 (br. s., 1 H) 8.24 (br. s., 1 H) 8.07 (br. s., 1 H) 7.72 (m, J = 8.56 Hz, 2 H) 7.63 (t, J = 2.08 Hz, 1 H) 7.44-7.59 (m, 2 H) 6.95 (d, J = 7.34 Hz, 1 H) 6.71 (m, J = 8.56 Hz, 2 H) 5.55 (br. s., 1 H) 4.47 (s, 1 H) 4.17 (d, J = 7.09 Hz, 1 H) 3.99 (s, 5 H) 3.72-3.88 (m, 3 H) 3.39 (br. s., 2 H) 3.33 (br. s., 1 H) 3.24 (br. s., 1 H) 2.29-2.50 (m, 3 H) 2.04-2.16 (m, 1 H) |
| 253 | | 2-(4-(1H-pyrazol-4-yl)phenyl)-8-(2-hydroxy-2-methylpropyl)-4-((3-methoxyphenyl)amino)-2,8-diazaspiro[4.5]decan-3-one | 490.3 | F: 1.31 min, 97.4% | ¹H NMR (400 MHz, DMSO-d6) d ppm 10.18 (s, 1 H) 8.90 (br. s., 1 H) 8.09 (br. s., 2 H) 7.72 (d, J = 8.31 Hz, 2 H) 7.65 (t, J = 2.08 Hz, 1 H) 7.52-7.60 (m, 1 H) 7.43-7.52 (m, 1 H) 6.95 (d, J = 7.58 Hz, 1 H) 6.62-6.79 (m, 2 H) 5.41-5.53 (m, 1 H) 4.46 (s, 1 H) 4.08-4.23 (m, 1 H) 3.96-4.04 (m, 3 H) 3.72-3.92 (m, 3 H) 3.43 (br. s., 1 H) 3.21-3.40 (m, 3 H) 2.52 (d, J = 15.16 Hz, 1 H) 2.40 (br. s., 2 H) 2.32 (d, J = 13.94 Hz, 2 H) 1.49 (s, 6 H) |
| 254 | | 2-(5-(1H-pyrazol-4-yl)pyridin-2-yl)-4-((3-methoxyphenyl)amino)-8-(3-phenylbutanoyl)-2,8-diazaspiro[4.5]decan-3-one | 565.3 | F: 1.36 min, 98.3% | ¹H NMR (400 MHz, DMSO-d6) d ppm 12.87 (br. s., 1 H) 9.83-9.95 (m, 1 H) 8.37 (d, J = 2.01 Hz, 1 H) 8.08 (br. s., 1 H) 7.83 (br. s., 1 H) 7.79 (d, J = 8.53 Hz, 1 H) 7.36 (d, J = 13.05 Hz, 1 H) 7.09-7.31 (m, 7 H) 6.66 (d, J = 6.02 Hz, 1 H) 6.47 (d, J = 8.03 Hz, 1 H) 4.28-4.42 (m, 1 H) 3.77-4.01 (m, 2 H) 3.56-3.77 (m, 5 H) 3.05-3.26 (m, 2 H) 2.82-3.04 (m, 1 H) 2.56-2.64 (m, 2 H) 1.68-1.86 (m, 3 H) 1.66 (br. s., 1 H) 1.14-1.27 (m, 4 H) |

TABLE 15-continued

| Example | R | Name | LCMS (M + H)+ | HPLC Method, RT (min.) & Purity | NMR |
|---|---|---|---|---|---|
| 255 | | -(5-(1H-pyrazol-4-yl)pyridin-2-yl)-4-((3-methoxyphenyl)amino)-8-(3-(4-methoxyphenyl)propanoyl)-2,8-diazaspiro[4.5]decan-3-one | 581.3 | F: 1.55 min, 94.1% | ¹H NMR (400 MHz, DMSO-d6) d ppm 12.87 (br. s., 1 H) 9.89 (br. s., 1 H) 8.38 (d, J = 2.01 Hz, 1 H) 8.08 (s, 1 H) 7.75-7.87 (m, 2 H) 7.37 (br. s., 1 H) 7.25 (s, 1 H) 7.17-7.23 (m, 1 H) 7.14 (t, J = 9.04 Hz, 2 H) 6.82 (t, J = 9.04 Hz, 2 H) 6.66 (d, J = 8.53 Hz, 1 H) 6.47 (d, J = 8.03 Hz, 1 H) 4.38 (s, 1 H) 3.88 (d, J = 7.03 Hz, 2 H) 3.67-3.75 (m, 9 H) 3.21 (s, 1 H) 2.99 (s, 1 H) 2.73 (d, J = 9.04 Hz, 2 H) 1.80 (br. s., 3 H) |
| 256 | | 2-(5-(1H-pyrazol-4-yl)pyridin-2-yl)-4-((3-methoxyphenyl)amino)-8-(3-(3-methyl-1H-indol-1-yl)propanoyl)-2,8-diazaspiro[4.5]decan-3-one | 604.3 | F: 1.77 min, 97.1% | ¹H NMR (400 MHz, DMSO-d6) d ppm 12.86 (br. s., 1 H) 9.87 (d, J = 3.51 Hz, 1 H) 8.37 (d, J = 2.01 Hz, 1 H) 8.07 (s, 1 H) 7.83 (br. s., 1 H) 7.78 (dd, J = 8.53, 2.01 Hz, 1 H) 7.31-7.49 (m, 3 H) 7.16-7.28 (m, 2 H) 7.04-7.15 (m, 2 H) 6.93-7.02 (m, 1 H) 6.66 (d, J = 7.53 Hz, 1 H) 6.45 (dd, J = 8.53, 2.51 Hz, 1 H) 4.22-4.41 (m, 3 H) 3.97 (d, J = 13.05 Hz, 1 H) 3.77-3.91 (m, 1 H) 3.73 (d, J = 3.01 Hz, 3 H) 3.54-3.68 (m, 1 H) 3.48 (d, J = 14.06 Hz, 1 H) 2.94-3.18 (m, 2 H) 2.70-2.87 (m, 2 H) 2.22 (d, J = 9.54 Hz, 3 H) 1.75 (br. s., 1 H) 1.59-1.72 (m, 2 H) 1.45-1.59 (m, 1 H) |
| 257 | | 2-(5-(1H-pyrazol-4-yl)pyridin-2-yl)-4-((3-methoxyphenyl)amino)-8-(2-(2-methylthiazol-4-yl)acetyl)-2,8-diazaspiro[4.5]decan-3-one | 558.2 | F: 1.25 min, 95.2% | ¹H NMR (400 MHz, DMSO-d6) d ppm 12.86 (br. s., 1 H) 9.88 (s, 1 H) 8.30-8.44 (m, 1 H) 8.07 (br. s., 1 H) 7.84 (br. s., 1 H) 7.79 (dd, J = 8.53, 2.01 Hz, 1 H) 7.31-7.40 (m, 1 H) 7.09-7.29 (m, 3 H) 6.59-6.71 (m, 1 H) 6.47 (dd, J = 8.53, 4.52 Hz, 1 H) 4.38 (d, J = 3.51 Hz, 1 H) 4.04 (d, J = 12.55 Hz, 1 H) 3.84-3.94 (m, 2 H) 3.76-3.83 (m, 2 H) 3.66-3.76 (m, 5 H) 3.17-3.30 (m, 1 H) 2.91-3.07 (m, 1 H) 2.59-2.65 (m, 2 H) 1.82 (br. s., 2 H) 1.74 (d, J = 9.54 Hz, 1 H) 1.58 (t, J = 9.54 Hz, 1 H) 1.16-1.34 (m, 1 H) 1.07 (d, J = 6.53 Hz, 1 H) |

TABLE 15-continued

| Example | R | Name | LCMS (M + H)+ | HPLC Method, RT (min.) & Purity | NMR |
|---|---|---|---|---|---|
| 258 | | 2-(5-(1H-pyrazol-4-yl)pyridin-2-yl)-4-((3-methoxyphenyl)amino)-8-(3-(5-phenyl-1,3,4-oxadiazol-2-yl)propanoyl)-2,8-diazaspiro[4.5]decan-3-one | 619.2 | F: 1.26 min, 98.2% | ¹H NMR (400 MHz, DMSO-d6) d ppm 12.87 (br. s., 1 H) 9.91 (d, J = 6.53 Hz, 1 H) 8.39 (s, 1 H) 8.08 (br. s., 1 H) 7.98 (dd, J = 7.78, 1.76 Hz, 2 H) 7.84 (br. s., 1 H) 7.80 (d, J = 8.53 Hz, 1 H) 7.52-7.67 (m, 3 H) 7.37 (d, J = 11.55 Hz, 1 H) 7.27 (t, J = 8.78 Hz, 1 H) 7.21 (td, J = 8.03, 3.01 Hz, 1 H) 6.66 (d, J = 6.02 Hz, 1 H) 6.48 (d, J = 8.53 Hz, 1 H) 4.41 (d, J = 5.52 Hz, 1 H) 4.01 (d, J = 13.55 Hz, 1 H) 3.91 (t, J = 6.53 Hz, 2 H) 3.62-3.80 (m, 5 H) 3.19-3.30 (m, 1 H) 2.88-3.16 (m, 5 H) 1.91 (br. s., 1 H) 1.84 (d, J = 13.05 Hz, 1 H) 1.74 (d, J = 9.04 Hz, 1 H) 1.59 (br. s., 1 H) |
| 259 | | 2-(5-(1H-pyrazol-4-yl)pyridin-2-yl)-4-((3-methoxyphenyl)amino)-8-(3-(2-oxopyrrolidin-1-yl)propanoyl)-2,8-diazaspiro[4.5]decan-3-one | 558.3 | F: 0.99, 96.3% | ¹H NMR (400 MHz, DMSO-d6) d ppm 12.87 (br. s., 1 H) 9.90 (d, J = 5.02 Hz, 1 H) 8.38 (d, J = 2.01 Hz, 1 H) 8.08 (br. s., 1 H) 7.84 (br. s., 1 H) 7.80 (dd, J = 8.78, 2.26 Hz, 1 H) 7.37 (d, J = 10.04 Hz, 1 H) 7.24-7.30 (m, 1 H) 7.15-7.24 (m, 1 H) 6.61-6.70 (m, 1 H) 6.48 (d, J = 8.53 Hz, 1 H) 4.40 (d, J = 4.02 Hz, 1 H) 4.00 (s, 1 H) 3.80-3.95 (m, 2 H) 3.66-3.76 (m, 5 H) 3.61 (br. s., 1 H) 3.33-3.41 (m, 3 H) 3.22 (d, J = 13.05 Hz, 1 H) 2.90-3.03 (m, 1 H) 2.09-2.22 (m, 2 H) 1.78-1.95 (m, 5 H) 1.73 (br. s., 1 H) 1.65 (br. s., 1 H) |

What is claimed is:
1. A compound according to Formula (I):

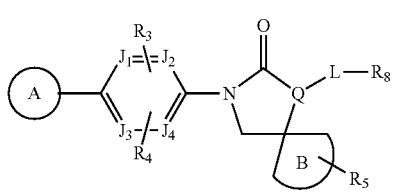

or an enantiomer, a diastereomer, a stereoisomer, a tautomer, a pharmaceutically acceptable salt thereof, wherein Ring A is independently selected from

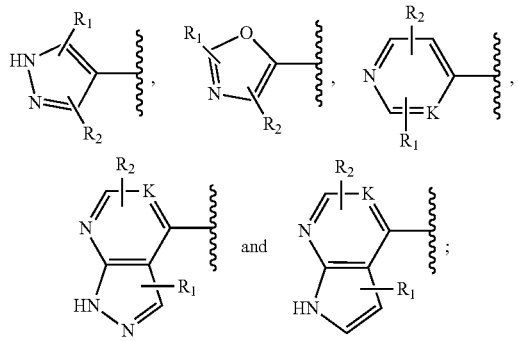

Ring B is independently selected from cycloalkyl and heterocyclyl, each substituted with 1-3 $R_5$;
$J_1$, $J_2$, $J_3$, and $J_4$ are independently selected from N, $CR_3$, and $CR_4$; provided no more than two of $J_1$, $J_2$, $J_3$, and $J_4$ are N;
Q is independently selected from N and $CR_{10}$;
L is independently selected from $-(CR_6R_7)_r-$ and $NR_{10}$; provided when Q is N, L is $-(CR_6R_7)_n-$ and when Q is $CR_{10}$, L is $NR_{10}$;
K, at each occurrence, is independently selected from N, $CR_1$, and $CR_2$;
$R_1$, at each occurrence, is independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;
$R_2$, at each occurrence, is independently selected from H, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rC(=O)NR_aR_a$, $-(CH_2)_rNR_aC(=O)R_b$, $-(CH_2)_rNR_aC(=O)$ $NR_aR_a$, $-(CH_2)_rNR_aC(=O)OR_b$, $-(CH_2)_rOC(=O)$ $NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;
$R_3$ is independently selected from H, F, Cl, Br, CN, $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rCN$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)r-C_{3-6}$ carbocyclyl substituted with 0-3 $R_e$, and $-(CH_2)r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;
$R_5$ is independently selected from H, $C_{1-4}$alkyl substituted with 0-4 $R_e$, $-(CH_2)_rOR_b$, $(CH_2)_rS(O)_pR_c$, $-(CH_2)_r$ $C(=O)R_b$, $-(CH_2)_rNR_aR_a$, $-(CH_2)_rCN$, $-(CH_2)_rC(=O)NR_aR_a$, $-(CH_2)_rNR_aC(=O)R_b$, $-(CH_2)_rNR_aC(=O)NR_aR_a$, $-(CH_2)_rNR_aC(=O)OR_b$, $-(CH_2)_rOC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, $-C(=O)$-heterocyclyl substituted with 0-3 $R_e$, and $-(CH_2)_r$-heterocyclyl substituted with 0-3 $R_e$;
$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;
$R_8$ is independently selected from $C_{3-6}$ cycloalkyl, heterocyclyl, aryl and heteroaryl, each substituted with 0-5 $R_9$;
$R_9$, at each occurrence, is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_r$ CN, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)$ $OR_b$, $-(CHR_d)_rC(=O)R_b$, $-(CHR_d)_rC(=O)NR_aR_a$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;
$R_{10}$ is independently selected from H and $C_{1-4}$alkyl substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_d$, at each occurrence, is independently selected from H and $C_{1-4}$alkyl substituted with 0-5 $R_e$;
$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r$-heterocyclyl, $-(CH_2)_r$-aryl, $-(CH_2)_r$-heteroaryl, F, Cl, Br, CN, $NO_2$, $=O$, $-(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)$ $OR_d$, $OC(=O)NR_fR_f$, and $-(CH_2)_rNR_fR_f$;

$R_f$, at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2;

r, at each occurrence, is independently selected from zero, 1, 2, 3, and 4;

provided (1) when $R_9$ is —C(=O)$NR_aR_a$, one of $R_a$ is H or $C_{1-6}$ alkyl, then the other $R_a$ is not —(CH$_2$)$_r$-5-tetrazolyl or —(CH$_2$)$_r$-5-(2-oxo-1,3,4-oxadiazolyl);

(2) when $R_9$ is —C(=O)$NR_aR_a$, one of $R_a$ is H or $C_{1-6}$ alkyl, and the other $R_a$ is $C_{1-6}$ alkyl substituted with 1 $R_e$, then $R_e$ is not -5-tetrazolyl or 5-(2-oxo-1,3,4-oxadiazolyl).

2. The compound of claim 1 or an enantiomer, a diastereomer, a stereoisomer, a tautomer, a pharmaceutically acceptable salt thereof, wherein $R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

$R_3$ is independently selected from H, F, Cl, Br, CN, $C_{1-4}$ alkyl substituted with 0-3 $R_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—C$_{3-6}$ carbocyclyl substituted with 0-3 $R_e$, and —(CH$_2$)$_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_5$ is independently selected from H, $C_{1-4}$alkyl substituted with 0-4 $R_e$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 $R_e$, —C(=O)-heterocyclyl substituted with 0-3 $R_e$, and —(CH$_2$)$_r$-heterocyclyl substituted with 0-3 $R_e$;

$R_6$ and $R_7$ are independently selected from H, $C_{1-4}$alkyl substituted with 0-4 $R_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 $R_e$, and —(CH$_2$)$_r$-heterocyclyl substituted with 0-3 $R_e$;

$R_8$ is independently selected from

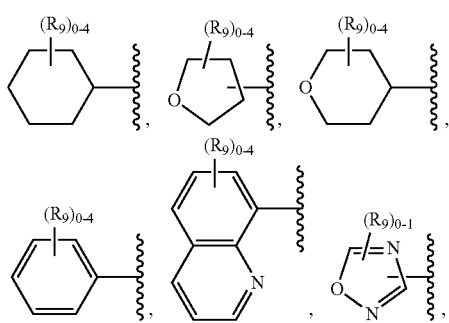

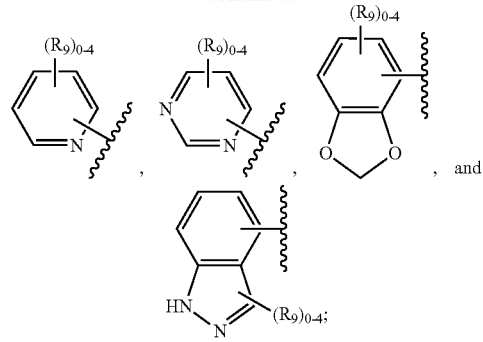

$R_9$, at each occurrence, is independently selected from F, Cl, Br, $C_{1-4}$ alkyl, $C_{2-4}$ alkenyl, $C_{2-4}$ alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —C(=O)NR$_a$R$_a$—(CHR$_d$)$_r$ OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 $R_e$.

3. The compound of claim 2, having Formula (II):

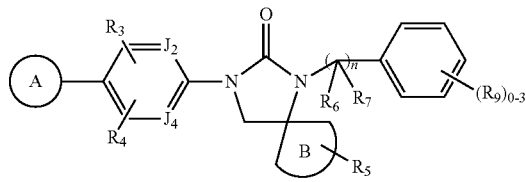

or an enantiomer, a diastereomer, a stereoisomer, a tautomer, a pharmaceutically acceptable salt thereof, wherein Ring A is independently selected from

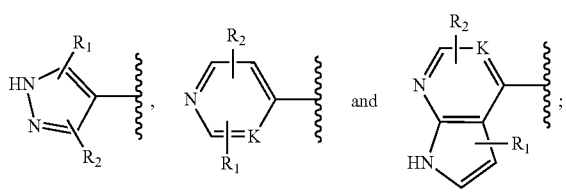

Ring B is independently selected from $C_{3-6}$ cycloalkyl and 4-, 5-, 6-, 7-membered heterocyclyl comprising carbon atoms and 1 heteroatom selected from N and O, and substituted with 1-3 $R_5$;

$J_2$, and $J_4$ are independently selected from N, $CR_3$, and $CR_4$;

$R_1$, at each occurrence, is independently selected from H, F, Cl, Br, CN, NR$_a$R$_a$, and $C_{1-4}$alkyl substituted with 0-4 $R_e$;

$R_2$, at each occurrence, is independently selected from H, F, Cl, Br, OH, CN, NR$_a$R$_a$, and $C_{1-4}$alkyl substituted with 0-4 $R_e$;

239

R$_3$ is independently selected from H, F, Cl, Br, CN, C$_{1-4}$ alkyl substituted with 0-3 R$_e$, —(CH$_2$)$_r$OR$_b$, and —C$_{3-6}$ cycloalkyl;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, C$_{1-4}$alkyl substituted with 0-4 R$_e$, —(CH$_2$)$_r$S(O)$_p$R$_c$, —(CH$_2$)$_r$C(=O)R$_b$, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$R$_c$, (CH$_2$)$_r$C$_{3-6}$ carbocyclyl substituted with 0-3 R$_e$, —C(=O)-heterocyclyl substituted with 0-3 R$_e$, and —(CH$_2$)$_r$heterocyclyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 R$_e$, and —(CH$_2$)$_r$-heterocyclyl substituted with 0-3 R$_e$;

R$_8$ is independently selected from

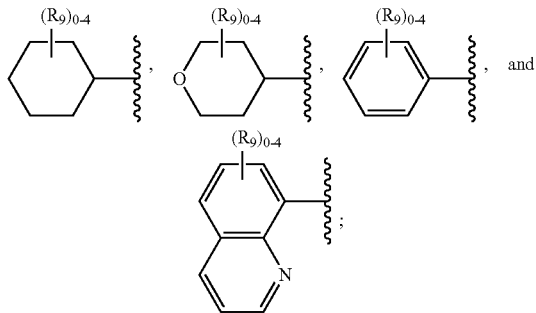

R$_9$, at each occurrence, is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

240

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-heterocyclyl, —(CH$_2$)$_r$-aryl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1 and 2;

p, at each occurrence, is independently selected from zero, 1, and 2; and r, at each occurrence, is independently selected from zero, 1, 2, 3, and 4.

4. The compound of claim 3, having Formula (III):

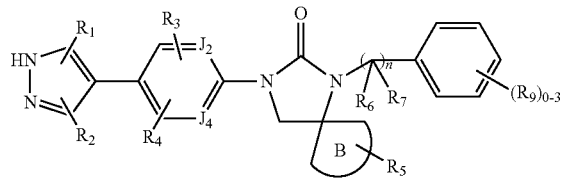

(III)

or an enantiomer, a diastereomer, a stereoisomer, a tautomer, a pharmaceutically acceptable salt thereof, wherein Ring B is independently selected from cyclopropyl and 6-membered heterocyclyl comprising carbon atoms and 1 heteoatom selected from NR$_5$ and O;

J$_2$, and J$_4$ are independently selected from N, CR$_3$, and CR$_4$;

R$_1$ is independently selected from H, F, Cl, Br, CN, NR$_a$R$_a$, and C$_{1-4}$alkyl substituted with 0-4 R$_e$;

R$_2$ is independently selected from H and C$_{1-4}$alkyl substituted with 0-4 R$_e$;

R$_3$ is independently selected from H, F, Cl, Br, CN, C$_{1-4}$ alkyl substituted with 0-3 R$_e$, —(CH$_2$)$_r$OR$_b$, and —C$_{3-6}$ cycloalkyl;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, C$_{1-4}$alkyl substituted with 0-4 R$_e$, —(CH$_2$)$_r$S(O)$_p$R$_c$, —(CH$_2$)$_r$C(=O)R$_b$, —(CH$_2$)$_r$C(=O)NR$_a$R$_a$, —(CH$_2$)$_r$C(=O)OR$_b$, —(CH$_2$)$_r$S(O)$_p$NR$_a$R$_a$, (CH$_2$)$_r$—C$_{3-6}$ carbocyclyl substituted with 0-3 R$_e$, —C(=O)-heterocyclyl substituted with 0-3 R$_e$, and —(CH$_2$),heterocyclyl substituted with 0-3 R$_e$;

R$_6$ is independently selected from H, C$_{1-4}$alkyl substituted with 0-4 R$_e$, —CH$_2$OR$_b$, —C(=O)R$_b$, NR$_a$C(=O)R$_b$, —CH$_2$NR$_a$R$_a$, —C(=O)NR$_a$R$_a$, -$_r$C(=O)OR$_b$, and heterocyclyl substituted with 0-3 R$_e$;

R$_7$ is independently selected from H and C$_{1-4}$alkyl;

R$_9$, at each occurrence, is independently selected from F, Cl, Br, C$_{1-4}$ alkyl, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$C(=O)NR$_a$R$_a$, —(CH$_2$)$_r$-cycloalkyl, —(CH$_2$)$_r$-heterocyclyl, —(CH$_2$),aryl, and —(CH$_2$)$_r$- heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-heterocyclyl, —$(CH_2)_r$-aryl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

5. The compound of claim 4, having Formula (IV):

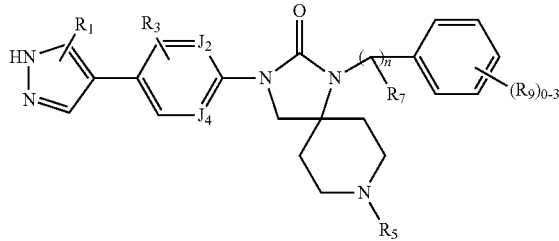

(IV)

or enantiomer, a diastereomer, a stereoisomer, a tautomer, a pharmaceutically acceptable salt thereof, wherein $J_2$, and $J_4$ are independently selected from N and $CR_3$;
$R_1$ is independently selected from H and $CF_3$;
$R_3$ is independently selected from H, CN, $C_{1-4}$ alkyl, —$OC_{1-3}$ alkyl, and —$C_{3-6}$ cycloalkyl;
$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ carbocyclyl substituted with 0-3 $R_e$, —$C(=O)$—$C_{3-6}$ carbocyclyl, —$(CH_2)_r$-heterocyclyl substituted with 0-3 $R_e$, and —$C(=O)$-heterocyclyl substituted with 0-3 $R_e$;
$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, $C(=O)NR_aR_a$, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

6. The compound of claim 5, or enantiomer, a diastereomer, a stereoisomer, a tautomer, a pharmaceutically acceptable salt thereof, wherein $R_1$ is H;
$R_3$ is independently selected from H, $C_{1-4}$ alkyl, —$OC_{1-3}$ alkyl, and —$C_{3-6}$ cycloalkyl;
$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ cycloalkyl substituted with 0-3 $R_e$, —$C(=O)$—$C_{3-6}$ cycloalkyl, —$(CH_2)_r$-heterocyclyl substituted with 0-3 $R_e$, and —$C(=O)$-heterocyclyl substituted with 0-3 $R_e$; wherein the heterocyclyl is selected from

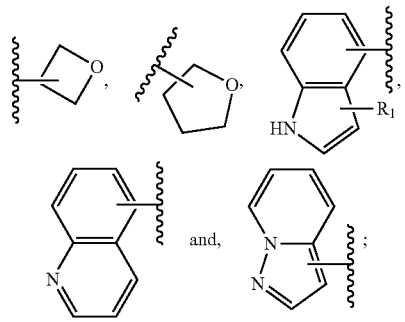

$R_7$ is independently selected from H and $C_{1-4}$alkyl;
$R_9$, at each occurrence, is independently selected from F, Cl, $CH_3$, $CF_3$, —OH, $OCHF_2$, $OCF_3$, CN, —$C(=O)NH_2$, —$C(=O)NHC_{1-4}$alkyl, substituted with 0-5 $R_e$—$C(=O)N(C_{1-4}$alkyl substituted with 0-5 $R_e)_2$, —$C(=O)NH$—$C_{3-6}$cycloalkyl, $C(=O)NH$-heterocyclyl substituted with 0-5 $R_e$, $C(=O)N$-heterocyclyl substituted with 0-5 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, and OC$_{1-4}$alkyl and NR$_f$R$_f$;

$R_f$, at each occurrence, is independently selected from H, F, Cl, Br, CN, OH, $C_{1-5}$ alkyl, $C_{3-6}$ cycloalkyl, and phenyl;

n is 1; and r, at each occurrence, is independently selected from zero, 1, 2, and 3.

7. The compound of claim 5, having Formula (V):

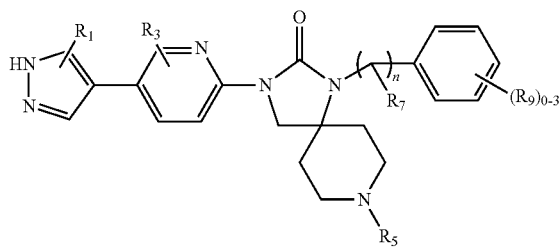

(V)

or enantiomer, a diastereomer, a stereoisomer, a tautomer, a pharmaceutically acceptable salt thereof, wherein $R_1$ is independently selected from H and CF$_3$;

$R_3$ is independently selected from H, CN, $C_{1-4}$ alkyl, —OC$_{1-3}$ alkyl, and —C$_{3-6}$ cycloalkyl;

$R_5$ is independently selected from H, $C_{1-4}$alkyl substituted with 0-4 $R_e$, —S(O)$_p$R$_c$, —(CH$_2$)$_r$C(=O)R$_b$, —(CH$_2$)$_r$C(=O)NR$_a$R$_a$, —(CH$_2$)$_r$C(=O)OR$_b$, —S(O)$_p$NR$_a$R$_a$, —(CH$_2$)$_r$—C$_{3-6}$ carbocyclyl substituted with 0-3 $R_e$, —C(=O)—C$_{3-6}$ carbocyclyl, —(CH$_2$)$_r$-heterocyclyl substituted with 0-3 $R_e$, and —C(=O)-heterocyclyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —OR$_b$, CN, C(=O)NR$_a$R$_a$, and heterocyclyl substituted with 0-3 $R_e$;

$R_a$, at each occurrence, is independently selected from H, $C_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, and —(CH$_2$)$_r$heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, OC$_{1-4}$alkyl, and NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

8. The compound of claim 5, having Formula (VI):

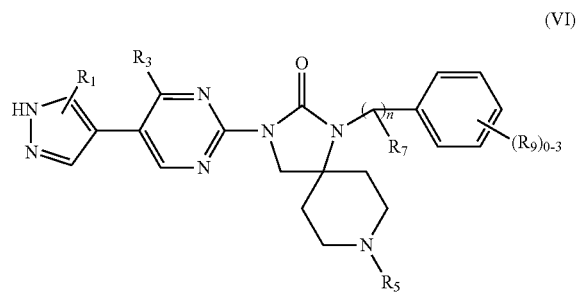

(VI)

or enantiomer, a diastereomer, a stereoisomer, a tautomer, a pharmaceutically acceptable salt thereof, wherein $R_1$ is independently selected from H and CF$_3$;

$R_3$ is independently selected from H, CN, $C_{1-4}$ alkyl, —OC$_{1-3}$ alkyl, and —C$_{3-6}$ cycloalkyl;

$R_5$ is independently selected from H, $C_{1-4}$alkyl substituted with 0-4 $R_e$, —S(O)$_p$R$_c$, —(CH$_2$)$_r$C(=O)R$_b$, —(CH$_2$)$_r$C(=O)NR$_a$R$_a$, —(CH$_2$)$_r$C(=O)OR$_b$, —S(O)$_p$NR$_a$R$_a$, —(CH$_2$)$_r$—C$_{3-6}$ carbocyclyl substituted with 0-3 $R_e$, —C(=O)—C$_{3-6}$ carbocyclyl, —(CH$_2$)$_r$-heterocyclyl substituted with 0-3 $R_e$, and —C(=O)-heterocyclyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —OR$_b$, CN, C(=O)NR$_a$R$_a$, and heterocyclyl substituted with 0-3 $R_e$;

$R_a$, at each occurrence, is independently selected from H, $C_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, and —(CH$_2$)$_r$heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, OC$_{1-4}$alkyl, and NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2; and r, at each occurrence, is independently selected from zero, 1, 2, and 3.

9. The compound of claim 4, having Formula (VII):

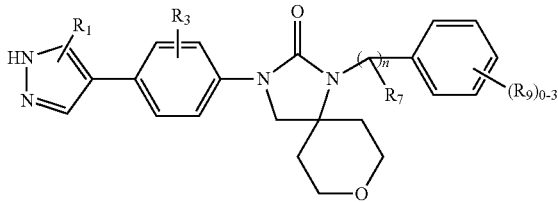

(VII)

or enantiomer, a diastereomer, a stereoisomer, a tautomer, a pharmaceutically acceptable salt thereof, wherein
$R_1$ is independently selected from H and $CF_3$;
$R_3$ is independently selected from H, CN, $C_{1-4}$ alkyl, —$OC_{1-3}$ alkyl, and —$C_{3-6}$ cycloalkyl;
$R_5$ is independently selected from H, $C_{1-4}$alkyl substituted with 0-4 $R_e$, —$S(O)_pR_c$, —$(CH_2)_rC(=O)R_b$, —$(CH_2)_rC(=O)NR_aR_a$, —$(CH_2)_rC(=O)OR_b$, —$S(O)_pNR_aR_a$, —$(CH_2)_r$—$C_{3-6}$ carbocyclyl substituted with 0-3 $R_e$, —C(=O)—$C_{3-6}$ carbocyclyl, —$(CH_2)_r$-heterocyclyl substituted with 0-3 $R_e$, and —C(=O)-heterocyclyl substituted with 0-3 $R_e$;
$R_7$ is independently selected from H and $C_{1-4}$alkyl;
$R_9$, at each occurrence, is independently selected from F, Cl, $C_{1-4}$ alkyl substituted with 0-3 $R_e$, —$OR_b$, CN, —C(=O)$OR_b$, —C(=O)$R_b$, —C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
n is independently selected from 1 and 2; and
r, at each occurrence, is independently selected from zero, 1, 2, and 3.

10. The compound of claim 4, having Formula (VIII):

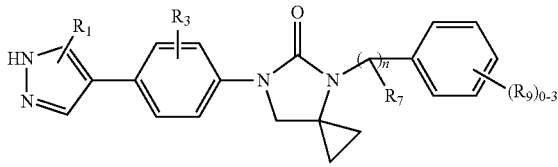

(VIII)

or enantiomer, a diastereomer, a stereoisomer, a tautomer, a pharmaceutically acceptable salt thereof, wherein
$R_1$ is independently selected from H and $CF_3$;
$R_3$ is independently selected from H, CN, $C_{1-4}$ alkyl, —$OC_{1-3}$ alkyl, and —$C_{3-6}$ cycloalkyl;
$R_7$ is independently selected from H and $C_{1-4}$alkyl;
$R_9$, at each occurrence, is independently selected from F, Cl, $C_{1-4}$ alkyl substituted with 0-3 $R_e$, —$OR_b$, CN, —C(=O)$OR_b$, —C(=O)$R_b$, —C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
n is independently selected from 1 and 2; and
r, at each occurrence, is independently selected from zero, 1, 2, and 3.

11. The compound of claim 2, having Formula (IX):

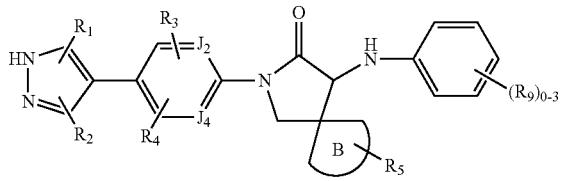

(IX)

or an enantiomer, a diastereomer, a stereoisomer, a tautomer, a pharmaceutically acceptable salt thereof, wherein
Ring B is independently selected from $C_{3-6}$ cycloalkyl and 4-, 5-, 6-, 7-membered heterocyclyl comprising carbon atoms and 1 heteroatom selected from N and O, and substituted with 1-3 $R_5$;
$J_2$, and $J_4$ are independently selected from N, $CR_3$, and $CR_4$;
$R_1$ is independently selected from H, F, Cl, Br, CN, $NR_aR_a$, and $C_{1-4}$alkyl substituted with 0-4 $R_e$;
$R_2$ is independently selected from H and $C_{1-4}$alkyl substituted with 0-4 $R_e$;
$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, $C_{1-4}$alkyl substituted with 0-4 $R_e$, —$(CH_2)_rS(O)_pR_c$, —$(CH_2)_rC(=O)R_b$, —$(CH_2)_rC(=O)NR_aR_a$, —$(CH_2)_rC(=O)OR_b$, —$(CH_2)_rS(O)_pNR_aR_a$, $(CH_2)_r$—$C_{3-6}$ carbocyclyl substituted with 0-3 $R_e$, —C(=O)-heterocyclyl substituted with 0-3 $R_e$, and —$(CH_2)_r$heterocyclyl substituted with 0-3 $R_e$;
$R_9$, at each occurrence, is independently selected from F, Cl, Br, $C_{1-4}$ alkyl, —$(CH_2)_rOR_b$, —$(CH_2)_rCN$, —$(CH_2)_rNR_aR_a$, —$(CH_2)_rNR_aC(=O)R_b$, —$(CH_2)_rN$-

$R_aC(=O)NR_aR_a$, —$(CH_2)_rC(=O)OR_b$, —$(CH_2)_rC(=O)R_b$, —$C(=O)NR_aR_a$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, F, Cl, Br, CN, $NO_2$, =O, $CO_2H$, —$(CH_2)_rOR_f$, $S(O)_pR_f$, $S(O)_pNR_fR_f$ and —$(CH_2)_rNR_fR_f$;

$R_f$ at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

12. The compound of claim 11, having Formula (X):

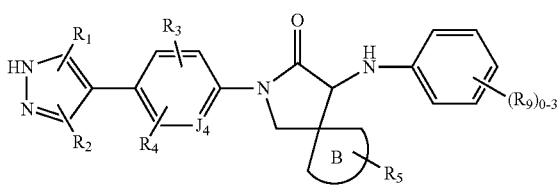

(X)

or an enantiomer, a diastereomer, a stereoisomer, a tautomer, a pharmaceutically acceptable salt thereof, wherein Ring B is independently selected from 4- and 6-membered heterocyclyl comprising carbon atoms and one nitrogen atom;

$J_4$ is independently selected from N and CH;

$R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, $C_{1-4}$alkyl substituted with 0-4 $R_e$, —$C(=O)R_b$, —$C(=O)NR_aR_a$, and —$C(=O)OR_b$;

$R_9$, at each occurrence, is independently selected from F, Cl, $C_{1-4}$ alkyl substituted with 0-3 $R_e$, —$OR_b$, CN, —$C(=O)OR_b$, —$C(=O)R_b$, —$C(=O)NR_aR_a$, and heterocyclyl substituted with 0-3 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, F, Cl, Br, CN, $NO_2$, =O, $CO_2H$, —$(CH_2)_rOR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4.

13. A pharmaceutical composition comprising one or more compounds according to claim 1 and a pharmaceutically acceptable carrier or diluent.

* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```